United States Patent
Beight et al.

(10) Patent No.: US 6,605,626 B2
(45) Date of Patent: Aug. 12, 2003

(54) ANTITHROMBOTIC AGENTS

(75) Inventors: Douglas Wade Beight, Indianapolis, IN (US); Trelia Joyce Craft, Indianapolis, IN (US); Jeffry Bernard Franciskovich, Indianapolis, IN (US); Theodore Goodson Jr., Indianapolis, IN (US); Steven Edward Hall, Chapel Hill, NC (US); David Kent Herron, Indianapolis, IN (US); Valentine Joseph Klimkowski, Carmel, IN (US); Jeffrey Alan Kyle, Fishers, IN (US); John Joseph Masters, Fishers, IN (US); David Mendel, Indianapolis, IN (US); Guy Milot, Chapel Hill, NC (US); Jason Scott Sawyer, Indianapolis, IN (US); Robert Theodore Shuman, Sedona, AZ (US); Gerald Floyd Smith, Indianapolis, IN (US); Anne Louise Tebbe, Indianapolis, IN (US); Jennifer Marie Tinsley, Martinsville, IN (US); Leonard Crayton Weir, Raleigh, NC (US); James Howard Wikel, Greenwood, IN (US); Michael Robert Wiley, Indianapolis, IN (US); Ying Kwong Yee, Carmel, IN (US)

(73) Assignee: Eli Lilly and Company, Indianapolis, IN (US)

(*) Notice: Subject to any disclaimer, the term of this patent is extended or adjusted under 35 U.S.C. 154(b) by 33 days.

(21) Appl. No.: 09/961,164

(22) Filed: Sep. 21, 2001

(65) Prior Publication Data

US 2002/0120007 A1 Aug. 29, 2002

Related U.S. Application Data

(62) Division of application No. 09/445,972, filed as application No. PCT/US98/13427 on Jun. 26, 1998, now Pat. No. 6,313,122.
(60) Provisional application No. 60/050,894, filed on Jun. 26, 1997.

(51) Int. Cl.$^7$ .................. A61K 31/44; A61K 31/426; A61K 31/4545; A61K 31/5375; A61K 31/381; A61K 31/165; C07D 401/04; C07D 213/56; C07D 211/32; C07D 277/38; C07D 233/164

(52) U.S. Cl. ................ 514/352; 514/330; 514/318; 514/327; 514/326; 514/417; 514/411; 514/357; 514/370; 514/237.5; 514/343; 514/443; 514/469; 514/616; 514/603; 514/465; 546/308; 546/194; 546/221; 546/234; 546/213; 546/214; 546/209; 548/473; 548/450; 548/451; 548/332.1; 548/195; 548/194; 544/165; 549/439; 549/58; 549/467; 564/155; 564/157; 564/86

(58) Field of Search .................. 546/194, 308, 546/221, 234, 213, 214, 209, 335, 278.4; 548/473, 195, 450, 194, 451, 332.1; 549/439, 58, 467; 544/165; 564/155, 157, 86; 514/330, 318, 327, 326, 417, 411, 357, 370, 237.5, 343, 443, 469, 616, 603, 465, 352

(56) References Cited

U.S. PATENT DOCUMENTS

| | | | | |
|---|---|---|---|---|
| 3,931,195 A | * | 1/1976 | Dykstra | ................. 260/293.58 |
| 5,518,735 A | | 5/1996 | Stürzebecher et al. | |
| 6,140,351 A | | 10/2000 | Arnaiz et al. | |
| 6,380,221 B1 | * | 4/2002 | Arnaiz | ....................... 514/337 |

FOREIGN PATENT DOCUMENTS

| | | |
|---|---|---|
| WO | WO 98/57951 | 12/1998 |
| WO | WO 99/00126 | 1/1999 |
| WO | WO 99/00127 | 1/1999 |
| WO | WO 99/00128 | 1/1999 |
| WO | WO 99/32477 | 7/1999 |
| WO | WO 99/42439 | 8/1999 |
| WO | WO 99/48878 | 9/1999 |
| WO | WO 00/39092 | 7/2000 |
| WO | WO 00/39111 | 7/2000 |
| WO | WO 00/39117 | 7/2000 |
| WO | WO 00/39118 | 7/2000 |

OTHER PUBLICATIONS

U.S. patent application Ser. No. 08/994,284, Priority for WO99/32477, filed Dec. 1997.

U.S. patent application Ser. No. 09/187,459, Priority for WO99/32477, filed Nov. 1998.

Ramana et al. Mass Spectrometer as a Probe in the Synthesis of 2–Substituted Benzimidazoles. Tetrahedron. 1994, vol. 50, No. 8, pp. 2485–2496, especially p. 2486, scheme 1, compounds 2, 3, 4.

DeLuca et al. The *para*–Toluenesulfonic Acid–Promoted Synthesis of 2–Substituted Benzoxazoles and Benzimidazoles from Diacylated Precursors. Tetrahedron. Jan. 1997, vol. 53, No. 2, pp. 457–464, especially p. 459, Table 1, compound b.

(List continued on next page.)

*Primary Examiner*—Evelyn Mei Huang
(74) *Attorney, Agent, or Firm*—Thomas E. Jackson

(57) ABSTRACT

This application relates to a compound of formula I (or a prodrug thereof or a pharmaceutically acceptable salt of the compound or prodrug thereof) as defined herein, pharmaceutical compositions thereof, and its use as an inhibitor of factor Xa, as well as a process for its preparation and intermediates therefor.

17 Claims, No Drawings

OTHER PUBLICATIONS

Ismail et al. The Role of Steric and Electronic Factors on the Mode of Reaction of Amines with 2–Substituted–6,8–Dibromo–3,1–Benzoxazin–4–Ones. Egypt. J. Chem. 1989, vol. 32, No. 6, pp. 651–660, especially p. 653, compound g.

Wallis, R.B. Inhibitors of Coagulation Factor Xa: From Macromolecular Beginnings to Small Molecules. Current Opinion in Therapeutic Patents. 1993, vol. 3, No. 8, pp. 1173–1179.

Fahmy et al. Acid Azides: Part X. New Synthesis & Decomposition Reactions of Phthalimido–benzoic Acid Azides. Indian J. Chem. Mar. 1986, vol. 25B, No. 3, pp. 308–311, especially p. 309, Table 1, compounds IIIb, IIIc, IIId.

Mohamed et al. Synthesis & Some Reactions of 2–(•/β–Naphthyl)–3,1–benzoxazin–4(H)–ones & 3–Amino–2–(β–naphthyl)quinazolin–4(3H)–one. Indian J. Chem. Feb. 1986, vol. 25b, No. 2, pp. 207–211, especially p. 208, scheme 2, compound IIIa.

Edmunds, Jeremy J. and Rapundalo, Stephen T., (Doherty, Annette M. Section Editor), *Annual Reports in Medicinal Chemistry*, (1996), 31, 51–60.

Myers, H. V., et al., *Molecular Diversity*, (1995), 1, 13–20.

* cited by examiner

ANTITHROMBOTIC AGENTS

This application claims the benefit of U.S. Provisional Application No. 60/050,894, filed Jun. 26, 1997.

This invention relates to antithrombotic aromatic compounds which demonstrate activity as inhibitors of factor Xa and, accordingly, which are useful anticoagulants in mammals. In particular it relates to aromatic compounds having high anticoagulant activity, and antithrombotic activity. Thus, this invention relates to new inhibitors of factor Xa, pharmaceutical compositions containing the compounds as active ingredients, and the use of the compounds as anticoagulants for prophylaxis and treatment of thromboembolic disorders such as venous thrombosis, pulmonary embolism, arterial thrombosis, in particular myocardial ischemia, myocardial infarction and cerebral thrombosis, general hypercoagulable states and local hypercoagulable states, such as following angioplasty and coronary bypass operations, and generalized tissue injury as it relates to the inflammatory process. In addition, the antithrombotic agents are useful as anticoagulants in in vitro applications.

The process of blood coagulation, thrombosis, is triggered by a complex proteolytic cascade leading to the formation of thrombin. Thrombin proteolytically removes activation peptides from the Aα-chains and the Bβ-chains of fibrinogen, which is soluble in blood plasma, initiating insoluble fibrin formation. The formation of thrombin from prothrombin is catalyzed by factor Xa.

Anticoagulation currently is achieved by the administration of heparins and coumarins. Parenteral pharmacological control of coagulation and thrombosis is based on inhibition of thrombin through the use of heparins. Heparins act indirectly on thrombin by accelerating the inhibitory effect of endogenous antithrombin III (the main physiological inhibitor of thrombin). Because antithrombin III levels vary in plasma and because clot-bound thrombin seems resistant to this indirect mechanism, heparins can be an ineffective treatment. Because coagulation assays are believed to be associated with efficacy and with safety, heparin levels must be monitored with coagulation assays (particularly the activated partial thromboplastin time (APTT) assay). Coumarins impede the generation of thrombin by blocking the posttranslational gamma-carboxylation in the synthesis of prothrombin and other proteins of this type. Because of their mechanism of action, the effect of coumarins can only develop slowly, 6–24 hours after administration. Further, they are not selective anticoagulants. Coumarins also require monitoring with coagulation assays (particularly the prothrombin time (PT) assay).

Recently, interest has grown in small synthetic molecules which demonstrate potent direct inhibition of thrombin and factor Xa. See, Jeremy J. Edmunds and Stephen T. Rapundalo (Annette M. Doherty Section Editor), *Annual Reports in Medicinal Chemistry*, (1996), 31, 51–60.

Although the heparins and coumarins are effective anticoagulants, no commercial drug has yet emerged from the small synthetic molecules; and despite the continuing promise for this class of compounds, there still exists a need for anticoagulants which act selectively on factor Xa or thrombin, and which, independent of antithrombin III, exert inhibitory action shortly after administration, preferably by an oral route, and do not interfere with lysis of blood clots, as required to maintain hemostasis.

The present invention is directed to the discovery that the compounds of the present invention, as defined below, are potent inhibitors of factor Xa which may have high bioavailability following oral administration.

According to the invention there is provided a method of inhibiting factor Xa comprising using an effective amount of a factor Xa inhibiting compound of formula I

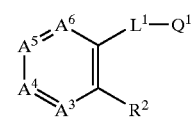

wherein $A^3, A^4, A^5$ and $A^6$, together with the two carbons to which they are attached, complete a substituted benzene in which $A^3$ is $CR^3$, $A^4$ is $CR^4$, $A^5$ is $CR^5$, and $A^6$ is $CR^6$; wherein $R^3$ is hydrogen, hydroxy, [(1–2C)alkyl]carbonyloxy (which may bear an ω-carboxy substituent), benzoyloxy (which may bear one or more halo, hydroxy, methoxy or methyl substituents), methyl or methoxy;

one of $R^4$ and $R^5$ is hydrogen, methyl, halo, trifluoromethyl, nitro, amino(imino)methyl, amino (hydroxyimino)-methyl, $R^fO$—, $R^fO_2C$—, $R^fO_2C$—$CH_2$—, $R^fO_2C$—$CH_2$—$O$—, 3-methoxycarbonyl-1-oxopropyl, $R^gNH$— or bis(methylsulfonyl)amino;

the other of $R^4$ and $R^5$ is hydrogen, halo or methyl; and $R^6$ is hydrogen, fluoro, hydroxy, [(1–2C)alkyl]-carbonyloxy (which may bear an ω-carboxy substituent), benzoyloxy (which may bear one or more halo, hydroxy, methoxy or methyl substituents), methyl or methoxy;

in which $R^f$ is hydrogen, (1–4C)alkyl or benzyl; $R^g$ is hydrogen, [(1–4C)alkyl]carbonyl, acetyl, trifluoroacetyl, methoxyacetyl, dimethylaminoacetyl, phenylalanyl, 2-(t-butoxycarbonylamino)-4-methylsulfinyl-1-oxobutyl, 3-[[(1–2C)alkoxy] carbonyl]-1-oxopropyl or $R^hSO_h$— (wherein h is 1 or 2); and $R^h$ is (1–4C)alkyl, trifluoromethyl, phenyl, 3,5-dimethylisoxazol-4-yl or dimethylamino; or two adjacent residues selected from $R^3$, $R^4$, $R^5$ and $R^6$ together form a benz ring; and the other two are each hydrogen;

$L^1$ is —NH—CO—, —O—CO— or —CO—NH— such that —$L^1$—$Q^1$ is —NH—CO—$Q^1$, —O—CO—$Q^1$ or —CO—NH—$Q^1$;

$Q^1$ is phenyl, 2-furanyl, 2-thienyl, 4-thiazolyl, 2-pyridyl, 2-naphthyl, 1,2-dihydrobenzofuran-5-yl, 1,2-dihydrobenzofuran-6-yl or 1,2-benzisoxazol-6-yl in which the phenyl may bear one, two or three substituents at the 3-, 4- or 5-position(s) independently selected from halo, cyano, carbamoyl, aminomethyl, methyl, methoxy, difluoromethoxy, hydroxymethyl, formyl, vinyl, amino, hydroxy and 3,4-methylenedioxy, and in addition the phenyl may bear a 2-chloro or 2-fluoro substituent, the 2-furanyl or 2-thienyl may bear a chloro or methyl substituent at the 5-position, the 4-thiazolyl may bear an amino substituent at the 2-position, the 2-pyridyl may bear an amino substituent at the 6-position, and the 1,2-benzisoxazol-6-yl may bear a chloro or methyl substituent at the 3-position; or —CO—$Q^1$ is cyclopentenylcarbonyl or cyclohexenylcarbonyl;

$R^2$ is —$L^{2A}$—$Q^{2A}$, —$L^{2B}$—$Q^{2B}$, —$L^{2C}$—$Q^{2C}$, —$L^{2D}$—$Q^{2D}$ or —$L^{2E}$—$Q^{2E}$ wherein $L^{2A}$ is a direct bond; and
$Q^{2A}$ is

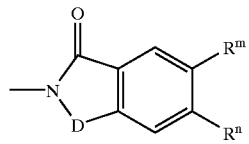

in which D is carbonyl or —CHR$^k$— in which R$^k$ is hydrogen, hydroxy, (1–6C)alkoxy, or —CH$_2$—R$^j$ in which R$^j$ is carboxy, [(1–4C)alkoxy]carbonyl or carbamoyl which may bear one or two (1–2C)alkyl substituents on the nitrogen; and one of R$^m$ and R$^n$ is hydrogen and the other is amino, bromo, (1–4C)alkyl or (1–4C)alkoxy, or R$^m$ and R$^n$ together form a benz ring;

$L^{2B}$ is —NH—CO—, —O—CO—, —CH$_2$—O— or —O—CH$_2$— such that —L$^{2B}$—Q$^{2B}$ is —NH—CO—Q$^{2B}$, —O—CO—Q$^{2B}$, —CH$_2$—O—Q$^{2B}$ or —O—CH$_2$—Q$^{2B}$; and
$Q^{2B}$ is

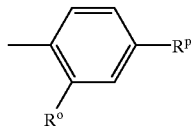

in which R$^o$ is hydrogen, halo, (1–6C)alkyl, (1–4C) alkoxy, benzyloxy or (1–4C)alkylthio; and R$^p$ is 1-hydroxyethyl, 1-hydroxy-1-methylethyl, 1-methoxy-1-methylethyl, 4-piperidinyl, 4-pyridinyl, dimethylaminosulfonyl or —J—R$^q$ in which J is a single bond, methylene, carbonyl, oxo, —S(O)$_q$— (wherein q is 0, 1 or 2), or —NR$^r$— (wherein R$^r$ is hydrogen or methyl); and R$^q$ is (1–6C)alkyl, phenyl, 3-pyridyl or 4-pyridyl;

$L^{2C}$ is —NR$^v$—CO—X—, —NR$^v$—CS—Y—, —CH$_2$—CO—NR$^w$—CH$_2$—, —O—CO—, —O—CH$_2$—, —S—CH$_2$— or —CH$_2$—NR$^x$—CH$_2$— such that —L$^{2C}$—Q$^{2C}$ is —NR$^v$—CO—X—Q$^{2C}$, —NR$^v$—CS—Y—Q$^{2C}$, —CH$_2$—CO—NR$^w$—CH$_2$—Q$^{2C}$, —O—CO—Q$^{2C}$, —O—CH$_2$—Q$^{2C}$, —S—CH$_2$—Q$^{2C}$ or —CH$_2$—NR$^x$—CH$_2$—Q$^{2C}$ in which X is —(CH$_2$)$_x$— (wherein x is 0, 1 or 2), —NR$^w$—, —NR$^w$—CH$_2$—, —O—, —O—CH$_2$— or —S—CH$_2$—; Y is —NR$^w$—CH$_2$— or —O—CH$_2$—; each of R$^v$ and R$^w$ is independently hydrogen, benzyl or (1–6C)alkyl which is not branched at the α-position; and R$^x$ is hydrogen, benzyloxycarbonyl or [(1–4C)alkoxy]carbonyl; and $Q^{2C}$ is 1-(4-pyridyl)piperidin-4-yl, 1-(4-pyridyl)piperidin-3-yl or 1-(4-pyridyl)pyrrolidin-3-yl in which the pyridyl may bear a substituent at its 2-position selected from cyano, aminomethyl, carboxy, hydroxymethyl and (1–2C)alkyl;

$L^{2D}$ is —NH—CO— such that —L$^{2D}$—Q$^{2D}$ is —NH—CO—Q$^{2D}$; and $Q^{2D}$ is selected from 4-(4-pyridinyl)benzyloxy, 9-oxo-9H-fluoren-3-yl, benzo[b]thiophen-2-yl (which may bear a chloro, methyl or methoxy substituent), benzofuran-2-yl (which may bear a chloro, methyl or methoxy substituent), 4-(4-morpholinyl)-4-oxobutyl, and 4-piperidinyl or 3,4-didehydropiperidin-4-yl (either one bearing a substituent at the 1-position selected from methylsulfonyl, phenylsulfonyl, (1–5C)alkyl, (4–7C)cycloalkyl, tetrahydropyran-4-yl, 4-thiacyclohexyl and —CH$_2$—R$^z$ in which R$^z$ is isopropyl, cyclopropyl, phenyl, pentafluorophenyl, furyl, thienyl, 2-thiazolyl, or pyridyl in which the phenyl may bear one or two substituents independently selected from halo, cyano, hydroxy, methoxy, acetoxy, benzyloxy, amino, acetylamino, nitro and 3,4-methylenedioxy, and the thienyl or furyl may bear a methyl or nitro substituent);

$L^{2E}$ is —NH—CO—O—(CH$_2$)$_n$— (wherein n is 0, 1 or 2) or —NH—CO—O—(CH$_2$)$_2$—O— such that —L$^{2E}$—Q$^{2E}$ is —NH—CO—O—(CH$_2$)$_n$—Q$^{2E}$ or —NH—CO—O—(CH$_2$)$_2$—O—Q$^{2E}$; and $Q^{2E}$ is 4-piperidinyl or 1-benzylpiperidin-4-yl;

or a prodrug of the compound of formula I;

or a pharmaceutically acceptable salt of the compound of formula I or prodrug thereof.

A particular factor Xa inhibiting compound of formula I is one wherein

A$^3$, A$^4$, A$^5$ and A$^6$, together with the two carbons to which they are attached, complete a substituted benzene in which A$^3$ is CR$^3$, A$^4$ is CR$^4$, A$^5$ is CR$^5$, and A$^6$ is CR$^6$; wherein R$^3$ is hydrogen, hydroxy, [(1–2C)alkyl]carbonyloxy (which may bear an ω-carboxy substituent), benzoyloxy (which may bear one or more halo, hydroxy, methoxy or methyl substituents), methyl or methoxy;

one of R$^4$ and R$^5$ is hydrogen, methyl, halo, trifluoromethyl, nitro, amino(imino)methyl, amino (hydroxyimino)-methyl, R$^f$O—, R$^f$O$_2$C—, R$^f$O$_2$C—CH$_2$—, R$^f$O$_2$C—CH$_2$—O—, 3-methoxycarbonyl-1-oxopropyl, R$^g$NH— or bis(methylsulfonyl)amino;

the other of R$^4$ and R$^5$ is hydrogen, halo or methyl; and

R$^6$ is hydrogen, hydroxy, [(1–2C)alkyl]carbonyloxy (which may bear an ω-carboxy substituent), benzoyloxy (which may bear one or more halo, hydroxy, methoxy or methyl substituents), methyl or methoxy;

in which R$^f$ is hydrogen, (1–4C)alkyl or benzyl; R$^g$ is hydrogen, acetyl, trifluoroacetyl, phenylalanyl, 2-(t-butoxycarbonylamino)-4-methylsulfinyl-1-oxobutyl, 3-[[(1–2C)alkoxy]carbonyl]-1-oxopropyl or R$^h$SO$_2$—; and R$^h$ is (1–4C)alkyl, trifluoromethyl, phenyl, 3,5-dimethylisoxazol-4-yl or dimethylamino; or two adjacent residues selected from R$^3$, R$^4$, R$^5$ and R$^6$ together form a benz ring; and the other two are each hydrogen;

$L^1$ is —NH—CO—, —O—CO— or —CO—NH— such that —L$^1$—Q$^1$ is —NH—CO—Q$^1$, —O—CO—Q$^1$ or —CO—NH—Q$^1$;

$Q^1$ is phenyl, 2-thienyl, 4-thiazolyl, 2-pyridyl, 2-naphthyl or 1,2-benzisoxazol-6-yl in which the phenyl may bear one, two or three substituents at the 3-, 4- or 5-position (s) independently selected from halo, cyano, carbamoyl, aminomethyl, methyl, methoxy, hydroxymethyl, formyl, vinyl, amino, hydroxy and 3,4-methylenedioxy, the 2-thienyl may bear a chloro or methyl substituent at the 5-position, the 4-thiazolyl may bear an amino substituent at the 2-position, the 2-pyridyl may bear an amino substituent at the 6-position, and the 1,2-benzisoxazol-6-yl may bear a chloro or methyl substituent at the 3-position;

R$^2$ is —L$^{2A}$—Q$^{2A}$, —L$^{2B}$—Q$^{2B}$, —L$^{2C}$—Q$^{2C}$, —L$^{2D}$—Q$^{2D}$ or —L$^{2E}$—Q$^{2E}$ wherein $L^{2A}$ is a direct bond; and $Q^{2A}$ is

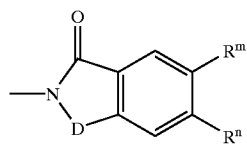

in which D is carbonyl or —CHR$^k$— in which R$^k$ is hydrogen, hydroxy, (1–6C)alkoxy, or —CH$_2$—R$^j$ in which R$^j$ is carboxy, [(1–4C)alkoxy]carbonyl or carbamoyl which may bear one or two (1–2C)alkyl substituents on the nitrogen; and one of R$^m$ and R$^n$ is hydrogen and the other is amino, bromo, (1–4C)alkyl or (1–4C)alkoxy, or R$^m$ and R$^n$ together form a benz ring;

L$^{2B}$ is —NH—CO—, —O—CO—, —CH$_2$—O— or —O—CH$_2$— such that —L$^{2B}$—Q$^{2B}$ is —NH—CO—Q$^{2B}$, —O—CO—Q$^{2B}$, —CH$_2$—O—Q$^{2B}$ or —O—CH$_2$—Q$^{2B}$; and Q$^{2B}$ is

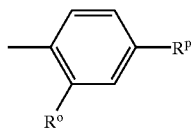

in which R$^o$ is hydrogen, halo, (1–6C)alkyl, (1–4C)alkoxy, benzyloxy or (1–4C)alkylthio; and R$^p$ is 1-hydroxyethyl, 1-hydroxy-1-methylethyl, 1-methoxy-1-methylethyl, 4-piperidinyl, 4-pyridinyl, dimethylaminosulfonyl or —J—R$^q$ in which J is a single bond, methylene, carbonyl, oxo, —S(O)$_q$— (wherein q is 0, 1 or 2), or —NR$^r$— (wherein R$^r$ is hydrogen or methyl); and R$^q$ is (1–6C)alkyl, phenyl, 3-pyridyl or 4-pyridyl;

L$^{2C}$ is —NR$^v$—CO—X—, —NR$^v$—CS—Y—, —CH$_2$—CO—NR$^w$—CH$_2$—, —O—CO—, —O—CH$_2$—, —S—CH$_2$— or —CH$_2$—NR$^x$—CH$_2$— such that —L$^{2C}$—Q$^{2C}$ is NR$^v$—CO—X—Q$^{2C}$, —NR$^v$—CS—Y—Q$^{2C}$, —CH$_2$—CO—NR$^w$—CH$_2$—Q$^{2C}$, —O—CO—Q$^{2C}$, —O—CH$_2$—Q$^{2C}$, —S—CH$_2$—Q$^{2C}$ or —CH$_2$—NR$^x$—CH$_2$—Q$^{2C}$ in which X is —(CH$_2$)$_x$— (wherein x is 0, 1 or 2), —NR$^w$—CH$_2$—, —O—CH$_2$— or —S—CH$_2$—; Y is —NR$^w$—CH$_2$— or —O—CH$_2$—; each of R$^v$ and R$^w$ is independently hydrogen, benzyl or (1–6C)alkyl which is not branched at the α-position; and R$^x$ is hydrogen, benzyloxycarbonyl or [(1–4C)alkoxy]carbonyl; and Q$^{2C}$ is 1-(4-pyridyl)piperidin-4-yl in which the pyridyl may bear a substituent at its 2-position selected from cyano, aminomethyl, carboxy, hydroxymethyl and (1–2C)alkyl;

L$^{2D}$ is —NH—CO— such that —L$^{2D}$—Q$^{2D}$ is —NH—CO—Q$^{2D}$; and

Q$^{2D}$ is selected from 4-(4-pyridinyl)benzyloxy, 9-oxo-9H-fluoren-3-yl, benzo[b]thiophen-2-yl (which may bear a chloro, methyl or methoxy substituent), benzofuran-2-yl (which may bear a chloro, methyl or methoxy substituent), 4-(4-morpholinyl)-4-oxobutyl, and 4-piperidinyl bearing a substituent at the 1-position selected from methylsulfonyl, phenylsulfonyl and —CH$_2$—R$^z$ in which R$^z$ is isopropyl, cyclopropyl, phenyl, pentafluorophenyl, furyl, thienyl, 2-thiazolyl, or pyridyl in which the phenyl may bear one or two substituents independently selected from halo, cyano, hydroxy, methoxy, acetoxy, benzyloxy, amino, acetylamino, nitro and 3,4-methylenedioxy, and the thienyl or furyl may bear a methyl or nitro substituent;

L$^{2E}$ is —NH—CO—O—(CH$_2$)$_n$— (wherein n is 0, 1 or 2) or —NH—CO—O—(CH$_2$)$_2$—O— such that —L$^{2E}$—Q$^{2E}$ is —NH—CO—O—(CH$_2$)$_n$—Q$^{2E}$ or —NH—CO—O—(CH$_2$)$_2$—O—Q$^{2E}$; and Q$^{2E}$ is 4-piperidinyl or 1-benzylpiperidin-4-yl;

or a prodrug of the compound of formula I;

or a pharmaceutically acceptable salt of the compound of formula I or prodrug thereof.

In addition, there is provided the use of a factor Xa inhibiting compound of formula I (or prodrug or salt) as described herein as an active ingredient in the manufacture of a medicament for use in producing an anticoagulant or antithrombotic effect.

The present invention also provides a method of inhibiting coagulation in a mammal comprising administering to a mammal in need of treatment, a coagulation inhibiting dose of a factor Xa inhibiting compound of formula I having any of the definitions herein.

The present invention further provides a method of inhibiting factor Xa comprising administering to a mammal in need of treatment, a factor Xa inhibiting dose of a factor Xa inhibiting compound of formula I having any of the definitions herein.

Further, the present invention provides a method of treating a thromboembolic disorder comprising administering to a mammal in need of treatment, an effective dose of a factor Xa inhibiting compound of formula I having any of the definitions herein.

In addition, there is provided the use of a factor Xa inhibiting compound of formula I having any of the definitions herein for the manufacture of a medicament for treatment of a thromboembolic disorder.

As an additional feature of the invention there is provided a pharmaceutical formulation comprising in association with a pharmaceutically acceptable carrier, diluent or excipient, a prodrug of a factor Xa inhibiting compound of formula I (or of a pharmaceutically acceptable salt thereof) as provided in any of the descriptions herein.

In general, the factor Xa inhibiting compounds of formula I are believed to be novel and, thus, to constitute an additional aspect of the invention. However, certain compounds of formula I have been disclosed. The phthalimides of formula I wherein each of A$^3$, A$^4$, A$^5$ and A$^6$ is CH, R$^2$ is phthalimido, and —L$^1$—Q$^1$ is —NH—CO—Q$^1$, in which Q$^1$ is phenyl bearing a 4-chloro, 4-methyl or 4-methoxy substituent, or —L$^1$—Q$^1$ is —CO—NH—Q$^1$ in which Q$^1$ is phenyl or phenyl bearing a 4-chloro, 4-methyl or 4-methoxy substituent are found in the Chemical Abstracts Registry. Also, compounds of formula I wherein each of A$^3$, A$^5$ and A$^6$ is CH, A$^4$ is C—OH, —L$^1$—Q$^1$ is —NH—CO—Q$^1$, and R$^2$ is —NH—CO—Q$^{2B}$ in which, selected together, Q$^1$ is phenyl or phenyl bearing a 3-chloro, 4-fluoro or 4-methoxy substituent and Q$^{2B}$ is 4-methylphenyl, 4-ethylphenyl or 4-methoxyphenyl or Q$^1$ is phenyl or phenyl bearing a 4-methoxy, 4-chloro, 3,4-dichloro, 3,5-dihydroxy, 3,4-dihydroxy or 3-hydroxy substituent(s) and Q$^{2B}$ is 4-methylphenyl or 4-methoxyphenyl are disclosed in H. V. Meyers, et al., *Molecular Diversity*, (1995), 1, 13–20.

Thus, according to the invention there is provided a novel compound of formula I

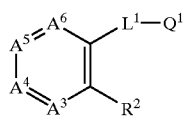

I wherein $A^3$, $A^4$, $A^5$ and $A^6$; together with the two carbons to which they are attached, complete a substituted benzene in which $A^3$ is $CR^3$, $A^4$ is $CR^4$; $A^5$ is $CR^5$, and $A^6$ is $CR^6$; wherein $R^3$ is hydrogen, hydroxy, [(1–2C)alkyl]carbonyloxy (which may bear an ω-carboxy substituent), benzoyloxy (which may bear one or more halo, hydroxy, methoxy or methyl substituents), methyl or methoxy;

one of $R^4$ and $R^5$ is hydrogen, methyl, halo, trifluoromethyl, nitro, amino(imino)methyl, amino (hydroxyimino)methyl, $R^fO$—, $R^fO_2C$—, $R^fO_2C$—$CH_2$—, $R^fO_2C$—$CH_2$—O—, 3-methoxycarbonyl-1-oxopropyl, $R^gNH$— or bis(methylsulfonyl)amino;

the other of $R^4$ and $R^5$ is hydrogen, halo or methyl; and $R^6$ is hydrogen, fluoro, hydroxy, [(1–2C)alkyl]-carbonyloxy (which may bear an ω-carboxy substituent), benzoyloxy (which may bear one or more halo, hydroxy, methoxy or methyl substituents), methyl or methoxy;

in which $R^f$ is hydrogen, (1–4C)alkyl or benzyl; $R^g$ is hydrogen, [(1–4C)alkyl]carbonyl, acetyl, trifluoroacetyl, methoxyacetyl, dimethylaminoacetyl, phenylalanyl, 2-(t-butoxycarbonylamino)-4-methylsulfinyl-1-oxobutyl, 3-[[(1–2C)alkoxy]carbonyl]-1-oxopropyl or $R^hSO_h$— (wherein h is 1 or 2); and $R^h$ is (1–4C)alkyl, trifluoromethyl, phenyl, 3,5-dimethylisoxazol-4-yl or dimethylamino; or two adjacent residues selected from $R^3$, $R^4$, $R^5$ and $R^6$ together form a benz ring; and the other two are each hydrogen;

$L^1$ is —NH—CO—, —O—CO— or —CO—NH— such that —$L^1$—$Q^1$ is —NH—CO—$Q^1$, —O—CO—$Q^1$ or —CO—NH—$Q^1$;

$Q^1$ is phenyl, 2-furanyl, 2-thienyl, 4-thiazolyl, 2-pyridyl, 2-naphthyl, 1,2-dihydrobenzofuran-5-yl, 1,2-dihydrobenzofuran-6-yl or 1,2-benzisoxazol-6-yl in which the phenyl may bear one, two or three substituents at the 3-, 4- or 5-position(s) independently selected from halo, cyano, carbamoyl, aminomethyl, methyl, methoxy, difluoromethoxy, hydroxymethyl, formyl, vinyl, amino, hydroxy and 3,4-methylenedioxy, and in addition the phenyl may bear a 2-chloro or 2-fluoro substituent, the 2-furanyl or 2-thienyl may bear a chloro or methyl substituent at the 5-position, the 4-thiazolyl may bear an amino substituent at the 2-position, the 2-pyridyl may bear an amino substituent at the 6-position, and the 1,2-benzisoxazol-6-yl may bear a chloro or methyl substituent at the 3-position; or —CO—$Q^1$ is cyclopentenylcarbonyl or cyclohexenylcarbonyl;

$R^2$ is —$L^{2A}$—$Q^{2A}$, —$L^{2B}$—$Q^{2B}$, —$L^{2C}$—$Q^{2C}$, —$L^{2D}$—$Q^{2D}$ or —$L^{2E}$—$Q^{2E}$ wherein $L^{2A}$ is a direct bond; and $Q^{2A}$ is

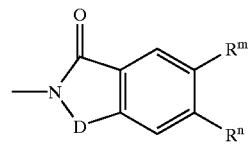

in which D is carbonyl or —$CHR^k$— in which $R^k$ is hydrogen, hydroxy, (1–6C)alkoxy, or —$CH_2$—$R^j$ in which $R^j$ is carboxy, [(1–4C)alkoxy]carbonyl or carbamoyl which may bear one or two (1–2C)alkyl substituents on the nitrogen; and one of $R^m$ and $R^n$ is hydrogen and the other is amino, bromo, (1–4C)alkyl or (1–4C)alkoxy, or $R^m$ and $R^n$ together form a benz ring;

$L^{2B}$ is —NH—CO—, —O—CO—, —$CH_2$—O— or —O—$CH_2$— such that —$L^{2B}$—$Q^{2B}$ is —NH—CO—$Q^{2B}$, —O—CO—$Q^{2B}$, —$CH_2$—O—$Q^{2B}$ or —O—$CH_2$—$Q^{2B}$; and $Q^{2B}$ is

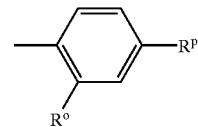

in which $R^o$ is hydrogen, halo, (1–6C)alkyl, (1–4C)alkoxy, benzyloxy or (1–4C)alkylthio; and $R^p$ is 1-hydroxyethyl, 1-hydroxy-1-methylethyl, 1-methoxy-1-methylethyl, 4-piperidinyl, 4-pyridinyl, dimethylaminosulfonyl or —J—$R^q$ in which J is a single bond, methylene, carbonyl, oxo, —$S(O)_q$— (wherein q is 0, 1 or 2), or —$NR^r$— (wherein $R^r$ is hydrogen or methyl); and $R^q$ is (1–6C)alkyl, phenyl, 3-pyridyl or 4-pyridyl;

$L^{2C}$ is —$NR^v$—CO—X—, —$NR^v$—CS—Y—, —$CH_2$—CO—$NR^w$—$CH_2$—, —O—CO—, —O—$CH_2$—, —S—$CH_2$— or —$CH_2$—$NR^x$—$CH_2$— such that —$L^{2C}$—$Q^{2C}$ is —$NR^v$—CO—X—$Q^{2C}$, —$NR^v$—CS—Y—$Q^{2C}$, —$CH_2$—CO—$NR^w$—$CH_2$—$Q^{2C}$, —O—CO—$Q^{2C}$, —O—$CH_2Q^{2C}$, —S—$CH_2$—$Q^{2C}$ or —$CH_2$—$NR^x$—$CH_2$—$Q^{2C}$ in which X is —$(CH_2)_x$— (wherein x is 0, 1 or 2), —$NR^w$—, —$NR^w$—$CH_2$—, —O—, —O—$CH_2$— or —S—$CH_2$—; Y is —$NR^w$—$CH_2$— or —O—$CH_2$—; each of $R^v$ and $R^w$ is independently hydrogen, benzyl or (1–6C)alkyl which is not branched at the α-position; and $R^x$ is hydrogen, benzyloxycarbonyl or [(1–4C)alkoxy]carbonyl; and $Q^{2C}$ is 1-(4-pyridyl)piperidin-4-yl, 1-(4-pyridyl)piperidin-3-yl or 1-(4-pyridyl)pyrrolidin-3-yl in which the pyridyl may bear a substituent at its 2-position selected from cyano, aminomethyl, carboxy, hydroxymethyl and (1–2C)alkyl;

$L^{2D}$ is —NH—CO— such that —$L^{2D}$—$Q^{2D}$ is —NH—CO—$Q^{2D}$; and $Q^{2D}$ is selected from 4-(4-pyridinyl)benzyloxy, 9-oxo-9H-fluoren-3-yl, benzo[b]thiophen-2-yl (which may bear a chloro, methyl or methoxy substituent), benzofuran-2-yl (which may bear a chloro, methyl or methoxy substituent), 4-(4-morpholinyl)-4-oxobutyl, and 4-piperidinyl or 3,4-didehydropiperidin-4-yl (either one bearing a substituent at the 1-position selected from methylsulfonyl, phenylsulfonyl, (1–5C)

alkyl, (4–7C)cycloalkyl, tetrahydropyran-4-yl, 4-thiacyclohexyl and —CH$_2$—R$^z$ in which R$^z$ is isopropyl, cyclopropyl, phenyl, pentafluorophenyl, furyl, thienyl, 2-thiazolyl, or pyridyl in which the phenyl may bear one or two substituents independently selected from halo, cyano, hydroxy, methoxy, acetoxy, benzyloxy, amino, acetylamino, nitro and 3,4-methylenedioxy, and the thienyl or furyl may bear a methyl or nitro substituent);

L$^{2E}$ is —NH—CO—O—(CH$_2$)$_n$— (wherein n is 0, 1 or 2) or —NH—CO—O—(CH$_2$)$_2$—O— such that —L$^{2E}$—Q$^{2E}$ is —NH—CO—O—(CH$_2$)$_n$—Q$^{2E}$ or —NH—CO—O—(CH$_2$)$_2$—O—Q$^{2E}$; and Q$^{2E}$ is 4-piperidinyl or 1-benzylpiperidin-4-yl;

or a prodrug of the compound of formula I;

or a pharmaceutically acceptable salt of the compound of formula I or prodrug thereof;

provided that the compound is not one wherein each of A$^3$, A$^4$, A$^5$ and A$^6$ is CH, R$^2$ is phthalimido, and —L$^1$—Q$^1$ is —NH—CO—Q$^1$, in which Q$^1$ is phenyl bearing a 4-chloro, 4-methyl or 4-methoxy substituent, or —L$^1$—Q$^1$ is —CO—NH—Q$^1$ in which Q$^1$ is phenyl or phenyl bearing a 4-chloro, 4-methyl or 4-methoxy substituent;

nor one wherein each of A$^3$, A$^5$ and A$^6$ is CH, A$^4$ is C—OH, —L$^1$—Q$^1$ is —NH—CO—Q$^1$, and R$^2$ is —NH—CO—Q$^{2B}$ in which, selected together, Q$^1$ is phenyl or phenyl bearing a 3-chloro, 4-fluoro or 4-methoxy substituent and Q$^{2B}$ is 4-methylphenyl, 4-ethylphenyl or 4-methoxyphenyl or Q$^1$ is phenyl or phenyl bearing a 4-methoxy, 4-chloro, 3,4-dichloro, 3,5-dihydroxy, 3,4-dihydroxy or 3-hydroxy substituent(s) and Q$^{2B}$ is 4-methylphenyl or 4-methoxyphenyl.

A particular novel compound of formula I is one wherein A$^3$, A$^4$, A$^5$ and A$^6$, together with the two carbons to which they are attached, complete a substituted benzene in which A$^3$ is CR$^3$, A$^4$ is CR$^4$, A$^5$ is CR$^5$, and A$^6$ is CR$^6$; wherein R$^3$ is hydrogen, hydroxy, [(1–2C)alkyl]carbonyloxy (which may bear an ω-carboxy substituent), benzoyloxy (which may bear one or more halo, hydroxy, methoxy or methyl substituents), methyl or methoxy;

one of R$^4$ and R$^5$ is hydrogen, methyl, halo, trifluoromethyl, nitro, amino(imino)methyl, amino(hydroxyimino)-methyl, R$^f$O—, R$^f$O$_2$C—, R$^f$O$_2$C—CH$_2$—, R$^f$O$_2$C—CH$_2$—O—, 3-methoxycarbonyl-1-oxopropyl, R$^g$NH— or bis(methylsulfonyl)amino;

the other of R$^4$ and R$^5$ is hydrogen, halo or methyl; and

R$^6$ is hydrogen, hydroxy, [(1–2C)alkyl]carbonyloxy (which may bear an ω-carboxy substituent), benzoyloxy (which may bear one or more halo, hydroxy, methoxy or methyl substituents), methyl or methoxy;

in which R$^f$ is hydrogen, (1–4C)alkyl or benzyl; R$^g$ is hydrogen, acetyl, trifluoroacetyl, phenylalanyl, 2-(t-butoxycarbonylamino)-4-methylsulfinyl-1-oxobutyl, 3-[[(1–2C)alkoxy]carbonyl]-1-oxopropyl or R$^h$SO$_2$—; and R$^h$ is (1–4C)alkyl, trifluoromethyl, phenyl, 3,5-dimethylisoxazol-4-yl or dimethylamino; or two adjacent residues selected from R$^3$, R$^4$, R$^5$ and R$^6$ together form a benz ring; and the other two are each hydrogen;

L$^1$ is —NH—CO—, —O—CO— or —CO—NH— such that —L$^1$—Q$^1$ is —NH—CO—Q$^1$, —O—CO—Q$^1$ or —CO—NH—Q$^1$;

Q$^1$ is phenyl, 2-thienyl, 4-thiazolyl, 2-pyridyl, 2-naphthyl or 1,2-benzisoxazol-6-yl in which the phenyl may bear one, two or three substituents at the 3-, 4- or 5-position(s) independently selected from halo, cyano, carbamoyl, aminomethyl, methyl, methoxy, hydroxymethyl, formyl, vinyl, amino, hydroxy and 3,4-methylenedioxy, the 2-thienyl may bear a chloro or methyl substituent at the 5-position, the 4-thiazolyl may bear an amino substituent at the 2-position, the 2-pyridyl may bear an amino substituent at the 6-position, and the 1,2-benzisoxazol-6-yl may bear a chloro or methyl substituent at the 3-position;

R$^2$ is —L$^{2A}$—Q$^{2A}$, —L$^{2B}$—Q$^{2B}$, —L$^{2C}$—Q$^{2C}$, —L$^{2D}$—Q$^{2D}$ or —L$^{2E}$—Q$^{2E}$ wherein L$^{2A}$ is a direct bond; and Q$^{2A}$ is

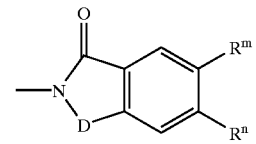

in which D is carbonyl or —CHR$^k$— in which R$^k$ is hydrogen, hydroxy, (1–6C)alkoxy, or —CH$_2$—R$^j$ in which R$^j$ is carboxy, [(1–4C)alkoxy]carbonyl or carbamoyl which may bear one or two (1–2C)alkyl substituents on the nitrogen; and one of R$^m$ and R$^n$ is hydrogen and the other is amino, bromo, (1–4C)alkyl or (1–4C)alkoxy, or R$^m$ and R$^n$ together form a benz ring;

L$^{2B}$ is —NH—CO—, —O—CO—, —CH$_2$—O— or —O—CH$_2$— such that —L$^{2B}$—Q$^{2B}$ is —NH—CO—Q$^{2B}$, —O—CO—Q$^{2B}$, —CH$_2$—O—Q$^{2B}$ or —O—CH$_2$—Q$^{2B}$; and Q$^{2B}$ is

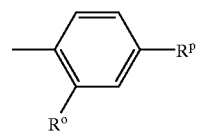

in which R$^o$ is hydrogen, halo, (1–6C)alkyl, (1–4C)alkoxy, benzyloxy or (1–4C)alkylthio; and R$^p$ is 1-hydroxyethyl, 1-hydroxy-1-methylethyl, 1-methoxy-1-methylethyl, 4-piperidinyl, 4-pyridinyl, dimethylaminosulfonyl or —J—R$^q$ in which J is a single bond, methylene, carbonyl, oxo, —S(O)$_q$— (wherein q is 0, 1 or 2), or —NR$^r$— (wherein R$^r$ is hydrogen or methyl); and R$^q$ is (1–6C)alkyl, phenyl, 3-pyridyl or 4-pyridyl;

L$^{2C}$ is —NR$^v$—CO—X—, —NR$^v$—CS—Y—, —CH$_2$—CO—NR$^w$—CH$_2$—, —O—CO—, —O—CH$_2$—, —S—CH$_2$— or —CH$_2$—NR$^x$—CH$_2$— such that —L$^{2C}$—Q$^{2C}$ is —NR$^v$—CO—X—Q$^{2C}$, —NR$^v$—CS—Y—Q$^{2C}$, —CH$_2$—CO—NR$^w$—CH$_2$—Q$^{2C}$, —O—CO—Q$^{2C}$, —O—CH$_2$—Q$^{2C}$, —S—CH$_2$—Q$^{2C}$ or —CH$_2$—NR$^x$—CH$_2$—Q$^{2C}$ in which X is —(CH$_2$)$_x$— (wherein x is 0, 1 or 2), —NR$^w$—CH$_2$—, —O—CH$_2$— or —S—CH$_2$—; Y is —NR$^w$—CH$_2$— or —O—CH$_2$—; each of R$^v$ and R$^w$ is independently hydrogen, benzyl or (1–6C)alkyl which is not branched at the α-position; and R$^x$ is hydrogen, benzyloxycarbonyl or [(1–4C)alkoxy]carbonyl; and Q$^{2C}$ is 1-(4-pyridyl)piperidin-4-yl in which the pyridyl may bear a substituent at its 2-position selected from cyano, aminomethyl, carboxy, hydroxymethyl and (1–2C)alkyl;

$L^{2D}$ is —NH—CO— such that —$L^{2D}$—$Q^{2D}$ is —NH—CO—$Q^{2D}$; and $Q^{2D}$ is selected from 4-(4-pyridinyl)benzyloxy, 9-oxo-9H-fluoren-3-yl, benzo[b]thiophen-2-yl (which may bear a chloro, methyl or methoxy substituent), benzofuran-2-yl (which may bear a chloro, methyl or methoxy substituent), 4-(4-morpholinyl)-4-oxobutyl, and 4-piperidinyl bearing a substituent at the 1-position selected from methylsulfonyl, phenylsulfonyl and —CH$_2$—R$^z$ in which R$^z$ is isopropyl, cyclopropyl, phenyl, pentafluorophenyl, furyl, thienyl, 2-thiazolyl, or pyridyl in which the phenyl may bear one or two substituents independently selected from halo, cyano, hydroxy, methoxy, acetoxy, benzyloxy, amino, acetylamino, nitro and 3,4-methylenedioxy, and the thienyl or furyl may bear a methyl or nitro substituent;

$L^{2E}$ is —NH—CO—O—(CH$_2$)$_n$— (wherein n is 0, 1 or 2) or —NH—CO—O—(CH$_2$)$_2$—O— such that —$L^{2E}$—$Q^{2E}$ is —NH—CO—O—(CH$_2$)$_n$—$Q^{2E}$ or —NH—CO—O—(CH$_2$)$_2$—O—$Q^{2E}$; and $Q^{2E}$ is 4-piperidinyl or 1-benzylpiperidin-4-yl;

or a prodrug of the compound of formula I;

or a pharmaceutically acceptable salt of the compound of formula I or prodrug thereof;

provided that the compound is not one wherein each of $A^3$, $A^4$, $A^5$ and $A^6$ is CH, $R^2$ is phthalimido, and —$L^1$—$Q^1$ is —NH—CO—$Q^1$, in which $Q^1$ is phenyl bearing a 4-chloro, 4-methyl or 4-methoxy substituent, or —$L^1$—$Q^1$ is —CO—NH—$Q^1$ in which $Q^1$ is phenyl or phenyl bearing a 4-chloro, 4-methyl or 4-methoxy substituent;

nor one wherein each of $A^3$, $A^5$ and $A^6$ is CH, $A^4$ is C—OH, —$L^1$—$Q^1$ is —NH—CO—$Q^1$, and $R^2$ is —NH—CO—$Q^{2B}$ in which, selected together, $Q^1$ is phenyl or phenyl bearing a 3-chloro, 4-fluoro or 4-methoxy substituent and $Q^{2B}$ is 4-methylphenyl, 4-ethylphenyl or 4-methoxyphenyl or $Q^1$ is phenyl or phenyl bearing a 4-methoxy, 4-chloro, 3,4-dichloro, 3,5-dihydroxy, 3,4-dihydroxy or 3-hydroxy substituent(s) and $Q^{2B}$ is 4-methylphenyl or 4-methoxyphenyl.

A pharmaceutically acceptable salt of an antithrombotic agent of the instant invention includes one which is an acid-addition salt made from a basic compound of formula I and an acid which provides a pharmaceutically acceptable anion, as well as a salt which is made from an acidic compound of formula I and a base which provides a pharmaceutically acceptable cation. Thus, a salt of a novel compound of formula I as provided herein made with an acid or base which affords a pharmaceutically acceptable counterion provides a particular aspect of the invention. Examples of such acids and bases are provided hereinbelow.

As an additional aspect of the invention there is provided a pharmaceutical formulation comprising in association with a pharmaceutically acceptable carrier, diluent or excipient, a novel compound of formula I (or a pharmaceutically acceptable salt thereof) as provided in any of the descriptions herein.

In this specification, the following definitions are used, unless otherwise described: Halo is fluoro, chloro, bromo or iodo. Alkyl, alkoxy, etc. denote both straight and branched groups; but reference to an individual radical such as "propyl" embraces only the straight chain ("normal") radical, a branched chain isomer such as "isopropyl" being specifically denoted. When two adjacent residues form a (fused) benz ring, they form a cis, cis-buta-1,3-dien-1,4-diyl divalent radical.

It will be appreciated that certain compounds of formula I (or salts or prodrugs, etc.) may exist in, and be isolated in, isomeric forms, including tautomeric forms, cis- or trans-isomers, as well as optically active, racemic, or diastereomeric forms. It is to be understood that the present invention encompasses a compound of formula I in any of the tautomeric forms or as an a mixture thereof; or as a mixture of diastereomers, as well as in the form of an individual diastereomer, and that the present invention encompasses a compound of formula I as a mixture of enantiomers, as well as in the form of an individual enantiomer, any of which mixtures or form possesses inhibitory properties against factor Xa, it being well known in the art how to prepare or isolate particular forms and how to determine inhibitory properties against factor Xa by standard tests including those described below.

In addition, a compound of formula I (or salt or prodrug, etc.) may exhibit polymorphism or may form a solvate with water or an organic solvent. The present invention also encompasses any such polymorphic form, any solvate or any mixture thereof.

Particular values are listed below for radicals, substituents, and ranges, for illustration only, and they do not exclude other defined values or other values within defined ranges for the radicals and substituents.

For an alkyl group or the alkyl portion of an alkyl containing group such as, for example alkoxy, a particular value for (1–2C)alkyl is methyl or ethyl, and more particularly is methyl; for (1–4C)alkyl is methyl, ethyl, propyl, isopropyl, butyl, isobutyl, or t-butyl, and more particularly is methyl, isopropyl, butyl or t-butyl; for (1–6C)alkyl is methyl, ethyl, propyl, butyl, pentyl or hexyl, and more particularly is methyl, butyl, or hexyl. A particular value for halo is bromo or chloro, and more particularly is chloro.

A further particular compound of formula I is one of formula Ia

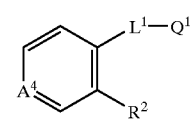

Ia wherein $A^4$, $L^1$, $Q^1$ and $R^2$ have any of the values defined herein.

A particular value for $Q^1$ is 4-chlorophenyl or 4-methoxyphenyl.

A particular value for $R^2$ is —$L^{2A}$—$Q^{2A}$.
A particular value for $R^2$ is —$L^{2B}$—$Q^{2B}$.
A particular value for $R^2$ is —$L^{2C}$—$Q^{2C}$.
A particular value for $R^2$ is —$L^{2D}$—$Q^{2D}$.
A particular value for $R^2$ is —$L^{2E}$—$Q^{2E}$.

A more particular value for $R^2$ is, for example, (4-t-butylbenzoyl)amino, (4-methoxybenzoyl)amino, or [1-(4-pyridyl)piperidin-4-yl]methoxycarbonylamino.

One particular compound of formula I as described herein is one in which $L^1$—$Q^1$ is —NH—CO—$Q^1$.

Another particular compound of formula I as described herein is one in which $L^1$—$Q^1$ is —CO—NH—$Q^1$.

A prodrug of a compound of formula I may be one formed in a conventional manner with a functional group of the compound, such as with an amino, hydroxy or carboxy group.

A compound of formula I may be prepared by processes which include processes known in the chemical art for the production of any known compounds of formula I or of structurally analogous compounds or by a novel process described herein. A process for the preparation of a novel compound of formula I (or a pharmaceutically acceptable salt thereof), novel processes for the preparation of a compound of formula I and novel intermediates for the manufacture of a compound of formula I as defined above provide further features of the invention and are illustrated by the following procedures in which the meanings of the generic radicals are as defined above, unless otherwise specified. It will be recognized that it may be preferred or necessary to prepare a compound of formula I in which a functional group is protected using a conventional protecting group, then to remove the protecting group to provide the compound of formula I.

Thus, there is provided a process for preparing a novel compound of formula I (or a pharmaceutically acceptable salt thereof) as provided in any of the above descriptions which is selected from any of those described in the examples, including the following.

(A) For a compound of formula I in which the linkage of $R^2$ to the ring terminates in —NH—CO—, —$NR^v$—CO— or —$NR^v$—CS—, acylating an amine of formula II,

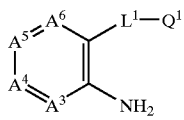

II or a corresponding amine in which the nitrogen bears the group $R^v$, using a corresponding acid which terminates with the group HO—CO— or HO—CS—, or an activated derivative thereof. Typical activated derivatives include the acid halides, activated esters, including 4-nitrophenyl esters and those derived from coupling reagents, as well as (when the product is a urea or thiourea) isocyanates and isothiocyanates.

(B) For a compound of formula I in which —$L^1$—$Q^1$ is —NH—CO—$Q^1$, acylating an amine of formula III

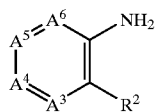

III using an acid of formula HO—CO—$Q^1$, or an activated derivative thereof.

(C) For a compound of formula I in which —$L^1$—$Q^1$ is —CO—NH—$Q^1$ and $R^2$ is of the form —NH—CO—$Q^2$, acylating an amine of formula $H_2N$—$Q^1$ using a [1,3] oxazine of formula IV,

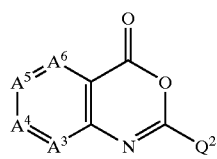

IV wherein $Q^2$ represents, for example, $Q^{2B}$, $Q^{2C}$ or $Q^{2D}$.

(D) For a compound of formula I in which $R^2$ is —$L^{2A}$—$Q^{2A}$ and D is carbonyl, diacylating a compound of formula II using an anhydride of formula V.

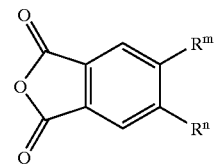

V (E) For a compound of formula I in which $R^2$ is —O—CO—$Q^{2B}$, acylating an alcohol of formula VI

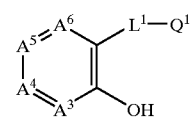

VI using an acid of formula Ho—CO—$Q^{2B}$, or an activated derivative thereof.

(F) For a compound of formula I in which $R^4$ or $R^5$ is amino, reducing the nitro group of a corresponding compound of formula I in which $R^4$ or $R^5$ is nitro.

(G) For a compound of formula I in which $R^4$ or $R^5$ is $R^gNH$— and $R^g$ is $R^hSO_2$—, substituting the amino group of a corresponding compound of formula I in which $R^4$ or $R^5$ is amino using an activated derivative of the sulfonic acid $R^hSO_2$—OH.

Whereafter, for any of the above procedures, when a functional group is protected using a protecting group, removing the protecting group.

Whereafter, for any of the above procedures, when a pharmaceutically acceptable salt of a compound of formula I is required, it is obtained by reacting the basic form of a basic compound of formula I with an acid affording a physiologically acceptable counterion or the acidic form of an acidic compound of formula I with a base affording a physiologically acceptable counterion or by any other conventional procedure.

A novel intermediate or starting material compound such as, for example, a novel compound of formula II, III, IV or VI, etc., provides a further aspect of the invention.

As mentioned above, a compound corresponding to a compound of formula I but in which a functional group is protected may serve as an intermediate for a compound of formula I. Accordingly, such a protected intermediate for a novel compound of formula I provides a further aspect of the invention. Thus, as one particular aspect of the invention, there is provided a compound corresponding to a novel compound of formula I as defined above in which $R^4$ is hydroxy, but in which the corresponding substituent is —$OP^p$ in place of hydroxy, wherein $P^p$ is a phenol protecting group other than (1–4C)alkyl or benzyl. Phenol protecting groups are well known in the art, for example as described in T. W. Greene and P. G. M. Wuts, "Protecting Groups in Organic Synthesis" (1991). Further, $P^p$ may denote a functionalized resin, for example as disclosed in H. V. Meyers, et al., *Molecular Diversity*, (1995), 1, 13–20.

As mentioned above, the invention includes a pharmaceutically acceptable salt of the factor Xa inhibiting compound defined by the above formula I. A basic compound of this invention possesses one or more functional groups sufficiently basic to react with any of a number of inorganic and organic acids affording a physiologically acceptable counterion to form a pharmaceutically acceptable salt. Acids commonly employed to form pharmaceutically acceptable acid addition salts are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromobenzenesulfonic acid, carbonic acid, succinic acid, citric acid, benzoic acid, acetic acid, and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycollate, tartrate, methanesulfonate, propanesulfonate, naphthalene-1-sulfonate, naphthalene-2-sulfonate, mandelate, and the like. Preferred pharmaceutically acceptable acid addition salts include those formed with mineral acids such as hydrochloric acid, hydrobromic acid and sulfuric acid.

For a compound of formula I which bears an acidic moiety, such as a carboxy group, a pharmaceutically acceptable salt may be made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as triethylamine, morpholine, piperidine and triethanolamine.

If not commercially available, a necessary starting material for the preparation of a compound of formula I may be prepared by a procedure which is selected from standard techniques of organic chemistry, including aromatic and heteroaromatic substitution and transformation, from techniques which are analogous to the syntheses of known, structurally similar compounds, and techniques which are analogous to the above described procedures or procedures described in the Examples. It will be clear to one skilled in the art that a variety of sequences is available for the preparation of the starting materials. Starting materials which are novel provide another aspect of the invention.

Selective methods of substitution, protection and deprotection are well known in the art for preparation of a compound such as one of formula II, III, IV or VI discussed above.

Generally, a basic compound of the invention is isolated best in the form of an acid addition salt. A salt of a compound of formula I formed with an acid such as one of those mentioned above is useful as a pharmaceutically acceptable salt for administration of the antithrombotic agent and for preparation of a formulation of the agent. Other acid addition salts may be prepared and used in the isolation and purification of the compounds.

As noted above, the optically active isomers and diastereomers of the compounds of formula I are also considered part of this invention. Such optically active isomers may be prepared from their respective optically active precursors by the procedures described above, or by resolving the racemic mixtures. This resolution can be carried out by derivatization with a chiral reagent followed by chromatography or by repeated crystallization. Removal of the chiral auxiliary by standard methods affords substantially optically pure isomers of the compounds of the present invention or their precursors. Further details regarding resolutions can be obtained in Jacques, et al., *Enantiomers, Racemates, and Resolutions*, John Wiley & sons, 1981.

The compounds of the invention are believed to selectively inhibit factor Xa over other proteinases and nonenzyme proteins involved in blood coagulation without appreciable interference with the body's natural clot lysing ability (the compounds have a low inhibitory effect on fibrinolysis). Further, such selectivity is believed to permit use with thrombolytic agents without substantial interference with thrombolysis and fibrinolysis.

The invention in one of its aspects provides a method of inhibiting factor Xa in mammals comprising administering to a mammal in need of treatment an effective (factor Xa inhibiting) dose of a compound of formula I.

In another of its aspects, the invention provides a method of treating a thromboembolic disorder comprising administering to a mammal in need of treatment an effective (thromboembolic disorder therapeutic and/or prophylactic amount) dose of a compound of formula I.

The invention in another of its aspects provides a method of inhibiting coagulation in a mammal comprising administering to a mammal in need of treatment an effective (coagulation inhibiting) dose of a compound of formula I.

The factor Xa inhibition, coagulation inhibition and thromboembolic disorder treatment contemplated by the present method includes both medical therapeutic and/or prophylactic treatment as appropriate.

In a further embodiment the invention relates to treatment, in a human or animal, of a condition where inhibition of factor Xa is required. The compounds of the invention are expected to be useful in mammals, including man, in treatment or prophylaxis of thrombosis and hypercoagulability in blood and tissues. Disorders in which the compounds have a potential utility are in treatment or prophylaxis of thrombosis and hypercoagulability in blood and tissues. Disorders in which the compounds have a potential utility, in treatment and/or prophylaxis, include venous thrombosis and pulmonary embolism, arterial thrombosis, such as in myocardial ischemia, myocardial infarction, unstable angina, thrombosis-based stroke and peripheral arterial thrombosis. Further, the compounds have expected utility in the treatment or prophylaxis of atherosclerotic disorders (diseases) such as coronary arterial disease, cerebral arterial disease and peripheral arterial disease. Further, the compounds are expected to be useful together with thrombolytics in myocardial infarction. Further, the compounds have expected utility in prophylaxis for reocclusion after thrombolysis, percutaneous transluminal angioplasty (PTCA) and coronary bypass operations. Further, the compounds have expected utility in prevention of rethrombosis after microsurgery. Further, the compounds are expected to be useful in anticoagulant treatment in connection with artificial organs and cardiac valves. Further, the compounds have expected utility in anticoagulant treatment in hemodialysis and disseminated intravascular coagulation. A further expected utility is in rinsing of catheters and mechanical devices used in patients in viva, and as an anticoagulant for preservation of blood, plasma and other blood products in vitro. Still further, the compounds have expected utility in other diseases where blood coagulation could be a fundamental contributing process or a source of secondary pathology, such as cancer, including metastasis, inflammatory diseases, including arthritis, and diabetes. The anti-coagulant compound is administered orally or parenterally, e.g. by intravenous infusion (iv), intramuscular injection (im) or subcutaneously (sc).

The specific dose of a compound administered according to this invention to obtain therapeutic and/or prophylactic effects will, of course, be determined by the particular circumstances surrounding the case, including, for example, the compound administered, the rate of administration, the route of administration, and the condition being treated.

A typical daily dose for each of the above utilities is between about 0.01 mg/kg and about 1000 mg/kg. The dose regimen may vary e.g. for prophylactic use a single daily dose may be administered or multiple doses such as 3 or 5 times daily may be appropriate. In critical care situations a compound of the invention is administered by iv infusion at a rate between about 0.01 mg/kg/h and about 20 mg/kg/h and preferably between about 0.1 mg/kg/h and about 5 mg/kg/h.

The method of this invention also is practiced in conjunction with a clot lysing agent e.g. tissue plasminogen activator (t-PA), modified t-PA, streptokinase or urokinase. In cases when clot formation has occurred and an artery or vein is blocked, either partially or totally, a clot lysing agent is usually employed. A compound of the invention can be administered prior to or along with the lysing agent or subsequent to its use, and preferably further is administered along with aspirin to prevent the reoccurrence of clot formation.

The method of this invention is also practiced in conjunction with a platelet glycoprotein receptor (IIb/IIIa) antagonist, that inhibits platelet aggregation. A compound of the invention can be administered prior to or along with the IIb/IIIa antagonist or subsequent to its use to prevent the occurrence or reoccurrence of clot formation.

The method of this invention is also practiced in conjunction with aspirin. A compound of the invention can be administered prior to or along with aspirin or subsequent to its use to prevent the occurrence or reoccurrence of clot formation. As stated above, preferably a compound of the present invention is administered in conjunction with a clot lysing agent and aspirin.

This invention also provides a pharmaceutical composition for use in the above described therapeutic method. A pharmaceutical composition of the invention comprises an effective factor Xa inhibiting amount of a compound of formula I in association with a pharmaceutically acceptable carrier, excipient or diluent.

The active ingredient in such formulations comprises from 0.1 percent to 99.9 percent by weight of the formulation. By "Pharmaceutically acceptable" it is meant the carrier, diluent or excipient must be compatible with the other ingredients of the formulation and not deleterious to the recipient thereof.

For oral administration the antithrombotic compound is formulated in gelatin capsules or tablets which may contain excipients such as binders, lubricants, disintegration agents and the like. For parenteral administration the antithrombotic is formulated in a pharmaceutically acceptable diluent e.g. physiological saline (0.9 percent), 5 percent dextrose, Ringer's solution and the like.

The compound of the present invention can be formulated in unit dosage formulations comprising a dose between about 0.1 mg and about 1000 mg. Preferably the compound is in the form of a pharmaceutically acceptable salt such as for example the sulfate salt, acetate salt or a phosphate salt. An example of a unit dosage formulation comprises 5 mg of a compound of the present invention as a pharmaceutically acceptable salt in a 10 mL sterile glass ampoule. Another example of a unit dosage formulation comprises about 10 mg of a compound of the present invention as a pharmaceutically acceptable salt in 20 mL of isotonic saline contained in a sterile ampoule.

The compounds can be administered by a variety of routes including oral, rectal, transdermal, subcutaneous, intravenous, intramuscular, and intranasal. The compounds of the present invention are preferably formulated prior to administration.

The present pharmaceutical compositions are prepared by known procedures using well known and readily available ingredients. The compositions of this invention may be formulated so as to provide quick, sustained, or delayed release of the active ingredient after administration to the patient by employing procedures well known in the art. In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols, (as a solid or in a liquid medium), soft and hard gelatin capsules, suppositories, sterile injectable solutions, sterile packaged powders, and the like.

The following formulation examples are illustrative only and are not intended to limit the scope of the invention in any way. "Active ingredient," of course, means a compound according to formula I or a pharmaceutically acceptable salt or solvate thereof.

Formulation 1: Hard gelatin capsules are prepared using the following ingredients:

|  | Quantity (mg/capsule) |
| --- | --- |
| Active ingredient | 250 |
| Starch, dried | 200 |
| Magnesium stearate | 10 |
| Total | 460 mg |

Formulation 2: A tablet is prepared using the ingredients below:

|  | Quantity (mg/tablet) |
| --- | --- |
| Active ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3: An aerosol solution is prepared containing the following components:

|                                         | Weight |
|-----------------------------------------|--------|
| Active ingredient                       | 0.25   |
| Ethanol                                 | 29.75  |
| Propellant 22 (Chlorodifluoromethane)   | 70.00  |
| Total                                   | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4: Tablets, each containing 60 mg of active ingredient, are made as follows:

| Active ingredient                          | 60 mg  |
|--------------------------------------------|--------|
| Starch                                     | 45 mg  |
| Microcrystalline cellulose                 | 35 mg  |
| Polyvinylpyrrolidone (as 10% solution in water) | 4 mg   |
| Sodium carboxymethyl starch                | 4.5 mg |
| Magnesium stearate                         | 0.5 mg |
| Talc                                       | 1 mg   |
| Total                                      | 150 mg |

The active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. Sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5: Capsules, each containing 80 mg of active ingredient, are made as follows:

| Active ingredient          | 80 mg  |
|----------------------------|--------|
| Starch                     | 59 mg  |
| Microcrystalline cellulose | 59 mg  |
| Magnesium stearate         | 2 mg   |
| Total                      | 200 mg |

The active ingredient, cellulose, starch, and magnesium stearate are blended, passed through a No. 45 mesh U.S. sieve, and filled into hard gelatin capsules in 200 mg quantities.

Formulation 6: Suppositories, each containing 225 mg of active ingredient, are made as follows:

| Active ingredient              | 225 mg   |
|--------------------------------|----------|
| Saturated fatty acid glycerides| 2,000 mg |
| Total                          | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7: Suspensions, each containing 50 mg of active ingredient per 5 mL dose, are made as follows:

| Active ingredient              | 50 mg   |
|--------------------------------|---------|
| Sodium carboxymethyl cellulose | 50 mg   |
| Syrup                          | 1.25 mL |
| Benzoic acid solution          | 0.10 mL |
| Flavor                         | q.v.    |
| Color                          | q.v.    |
| Purified water to total        | 5 mL    |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8: An intravenous formulation may be prepared as follows:

| Active ingredient | 100 mg   |
|-------------------|----------|
| Isotonic saline   | 1,000 mL |

The solution of the above ingredients generally is administered intravenously to a subject at a rate of 1 mL per minute.

The ability of a compound of the present invention to be an effective and orally active factor Xa inhibitor may be evaluated in one or more of the following assays or in other standard assays known to those in the art.

The inhibition by a compound of the inhibition of a serine protease of the human blood coagulation system or of the fibrinolytic system, as well as of trypsin, is determined in vitro for the particular enzyme by measuring its inhibitor binding affinity in an assay in which the enzyme hydrolyzes a particular chromogenic substrate, for example as described in Smith, G. F.; Gifford-Moore, D.; Craft, T. J.; Chirgadze, N.; Ruterbories, K. J.; Lindstrom, T. D.; Satterwhite, J. H. Efegatran: A New Cardiovascular Anticoagulant. *New Anticoagulants for the Cardiovascular Patient*; Pifarre, R., Ed.; Hanley & Belfus, Inc.: Philadelphia, 1997; pp. 265–300. The inhibitor binding affinity is measured as apparent association constant Kass which is the hypothetical equilibrium constant for the reaction between enzyme and the test inhibitor compound (I).

$$\text{Enzyme} + I \rightleftharpoons \text{Enzyme} - I$$

$$\text{Kass} = \frac{[\text{Enzyme} - I]}{[(\text{Enzyme}) \times (I)]}$$

Conveniently, enzyme inhibition kinetics are performed in 96-well polystyrene plates and reaction rates are determined from the rate of hydrolysis of appropriate p-nitroanilide substrates at 405 nm using a Thermomax plate reader from Molecular Devices (San Francisco, Calif.). The same protocol is followed for all enzymes studied: 50 µL buffer (0.03 M Tris, 0.15 M NaCl pH 7) in each well, followed by 25 µL of inhibitor solution (in 100% methanol, or in 50% v:v aqueous methanol) and 25 µL enzyme solution; within two minutes, 150 µL aqueous solution of chromogenic substrate (0.25 mg/mL) is added to start the enzymatic reaction. The rates of chromogenic substrate hydrolysis reactions provide a linear relationship with the enzymes studied such that free enzyme can be quantitated in reaction mixtures. Data is analyzed directly as rates by the Softmax program to produce [free enzyme] calculations for tight-binding Kass determinations. For apparent Kass determinations, 1.34 nM human factor Xa is used to hydrolyze 0.18 mM BzIle-Glu-Gly-Arg-pNA; 5.9 nM human thrombin or 1.4 nM bovine trypsin is used to hydrolyze 0.2 mM BzPhe-Val-Arg-pNA; 3.4 nM human plasmin is used with 0.5 mM HD-Val-Leu-Lys-pNA; 1.2 nK human nt-PA is used with 0.81 mM HD-Ile-Pro-Arg-pNA; and 0.37 nM urokinase is used with 0.30 mm pyro-gfsGlu-Gly-Arg-pNA.

Kass is calculated for a range of concentrations of test compounds and the mean value reported in units of liter per mole. In general, a factor Xa inhibiting compound of formula I of the instant invention exhibits a Kass of 0.1 to $0.5 \times 10^6$ L/mole or much greater.

The factor Xa inhibitor preferably should spare fibrinolysis induced by urokinase, tissue plasminogen activator (t-PA) and streptokinase. This would be important to the therapeutic use of such an agent as an adjunct to streptokinase, tp-PA or urokinase thrombolytic therapy and to the use of such an agent as an endogenous fibrinolysis-sparing (with respect to t-PA and urokinase) antithrombotic agent. In addition to the lack of interference with the amidase activity of the fibrinolytic proteases, such fibrinolytic system sparing can be studied by the use of human plasma clots and their lysis by the respective fibrinolytic plasminogen activators.

Materials

Dog plasma is obtained from conscious mixed-breed hounds (either sex Butler Farms, Clyde, N.Y., U.S.A.) by venipuncture into 3.8 percent citrate. Fibrinogen is prepared from fresh dog plasma and human fibrinogen is prepared from in-date ACD human blood at the fraction I-2 according to previous procedures and specification. Smith, *Biochem. J.*, 185, 1–11 (1980; and Smith, et al., *Biochemistry*, 11, 2958–2967, (1972). Human fibrinogen (98 percent pure/ plasmin free) is from American Diagnostica, Greenwich, Conn. Radiolabeling of fibrinogen I-2 preparations is performed as previously reported. Smith, et al., *Biochemistry*, 11, 2958–2967, (1972). Urokinase is purchased from Leo Pharmaceuticals, Denmark, as 2200 Ploug units/vial. Streptokinase is purchased from Hoechst-Roussel Pharmaceuticals, Somerville, N.J.

Methods—Effects on Lysis of Human Plasma Clots by t-PA

Human plasma clots are formed in micro test tubes by adding 50 µL thrombin (73 NIH unit/mL) to 100 µL human plasma which contains 0.0229 µCi 125-iodine labeled fibrinogen. Clot lysis is studied by overlaying the clots with 50 µL of urokinase or streptokinase (50, 100, or 1000 unit/mL) and incubating for 20 hours at room temperature. After incubation the tubes are centrifuged in a Beckman Microfuge. 25 µL of supernate is added into 1.0 mL volume of 0.03 M tris/0.15 M NaCl buffer for gamma counting. Counting controls 100 percent lysis are obtained by omitting thrombin (and substituting buffer). The factor Xa inhibitors are evaluated for possible interference with fibrinolysis by including the compounds in the overlay solutions at 1, 5, and 10 µg/mL concentrations. Rough approximations of $IC_{50}$ values are estimated by linear extrapolations from data points to a value which would represent 50 percent of lysis for that particular concentration of fibrinolytic agent.

Anticoagulant Activity

Materials

Dog plasma and rat plasma are obtained from-conscious mixed-breed hounds (either sex, Butler Farms, Clyde, N.Y., U.S.A.) or from anesthetized male Sprague-Dawley rats (Harlan Sprague-Dawley, Inc., Indianapolis, Ind., U.S.A.) by venipuncture into 3.8 percent citrate. Fibrinogen is prepared from in-date ACD human blood as the fraction 1–2 according to previous procedures and specifications. Smith, *Biochem. J.*, 185, 1–11 (1980); and Smith, et al., *Biochemistry*, 11, 2958–2967 (1972). Human fibrinogen is also purchased as 98 percent pure/plasmin free from American Diagnostica, Greenwich, Conn. Coagulation reagents Actin, Thromboplastin, Innovin and Human plasma are from Baxter Healthcare Corp., Dade Division, Miami, Fla. Bovine thrombin from Parke-Davis (Detroit, Mich.) is used for coagulation assays in plasma.

Methods

Anticoagulation Determinations

Coagulation assay procedures are as previously described. Smith, et al., *Thrombosis Research*, 50, 163–174 (1988). A CoAScreener coagulation instrument (American LABor, Inc.) is used for all coagulation assay measurements. The prothrombin time (PT) is measured by adding 0.05 mL saline and 0.05 mL Thromboplastin-C reagent or recombinant human tissue factor reagent (Innovin) to 0.05 mL test plasma. The activated partial thromboplastin time (APTT) is measured by incubation of 0.05 mL test plasma with 0.05 mL Actin reagent for 120 seconds followed by 0.05 mL $CaCl_2$ (0.02 M). The thrombin time (TT) is measured by adding 0.05 mL saline and 0.05 mL thrombin (10 NIH units/mL) to 0.05 mL test plasma. The compounds of formula I are added to human or animal plasma over a wide range of concentrations to determine prolongation effects on the APTT, PT, and TT assays. Linear extrapolations are performed to estimate the concentrations required to double the clotting time for each assay.

Animals

Male Sprague Dawley rats (350–425 gm, Harlan Sprague Dawley Inc., Indianapolis, Ind.) are anesthetized with xylazine (20 mg/kg, s.c.) and ketamine (120 mg/kg, s.c.) and maintained on a heated water blanket (37° C.). The jugular vein(s) is cannulated to allow for infusions.

Arterio-Venous Shunt Model

The left jugular vein and right carotid artery are cannulated with 20 cm lengths of polyethylene PE 60 tubing. A 6 cm center section of larger tubing (PE 190) with a cotton thread (5 cm) in the lumen, is friction fitted between the longer sections to complete the arterio-venous shunt circuit. Blood is circulated through the shunt for 15 min before the thread is carefully removed and weighed. The weight of a wet thread is subtracted from the total weight of the thread and thrombus (see J. R. Smith, *Br J Pharmacol*, 77:29, 1982).

$FeCl_3$ Model of Arterial Injury

The carotid arteries are isolated via a midline ventral cervical incision. A thermocouple is placed under each artery and vessel temperature is recorded continuously on a strip chart recorder. A cuff of tubing (0.058 ID×0.077 OD×4 mm, Baxter Med. Grade Silicone), cut longitudinally, is placed around each carotid directly above the thermocouple. $FeCl_3$ hexahydrate is dissolved in water and the concentration (20 percent) is expressed in terms of the actual weight of $FeCl_3$ only. To injure the artery and induce thrombosis, 2.85 $\mu$L is pipetted into the cuff to bathe the artery above the thermocouple probe. Arterial occlusion is indicated by a rapid drop in temperature. The time to occlusion is reported in minutes and represents the elapsed time between application of $FeCl_3$ and the rapid drop in vessel temperature (see K. D. Kurz, Thromb. Res., 60:269, 1990).

Coagulation Parameters

Plasma thrombin time (TT) and activated partial thromboplastin time (APTT) are measured with a fibrometer. Blood is sampled from a jugular catheter and collected in syringe containing sodium citrate (3.8 percent, 1 part to 9 parts blood). To measure TT, rat plasma (0.1 mL) is mixed with saline (0.1 mL) and bovine thrombin (0.1 mL, 30 U/mL in TRIS buffer; Parke Davis) at 37° C. For APTT, plasma (0.1 mL) and APTT solution (0.1 mL, Organon Teknika) are incubated for 5 minutes (37° C.) and $CaCl_2$ (0.1 mL, 0.025 M) is added to start coagulation. Assays are done in duplicate and averaged.

Index of Bioavailability

Bioavailability studies may be conducted as follows. Compounds are administered as aqueous solutions to male Fisher rats, intravenously (iv) at 5 mg/kg via tail vein injection and orally (po) to fasted animals at 20 mg/kg by gavage. Serial blood samples are obtained at 5, 30, 120, and 240 minutes postdose following intravenous administration and at 1, 2, 4, and 6 hours after oral dosing. Plasma is analyzed for drug concentration using an HPLC procedure involving C8 Bond Elute (Varion) cartridges for sample preparation and a methanol/30 n ammonium acetate buffer (pH 4) gradient optimized for each compound. % Oral bioavailability is calculated by the following equation:

$$\% \text{ Oral bioavailability} = \frac{AUC \, po}{AUC \, iv} \times \frac{Dose \, iv}{Dose \, po} \times 100$$

where AUC is area under the curve calculated from the plasma level of compound over the time course of the experiment following oral (AUC po) and intravenous (AUC iv) dosing.

Compounds

Compound solutions are prepared fresh daily in normal saline and are injected as a bolus or are infused starting 15 minutes before and continuing throughout the experimental perturbation which is 15 minutes in the arteriovenous shunt model and 60 minutes in the $FeCl_3$ model of arterial injury and in the spontaneous thrombolysis model. Bolus injection volume is 1 mL/kg for i.v., and 5 mL/kg for p.o., and infusion volume is 3 mL/hr.

Statistics

Results are expressed as means +/−SEM. One-way analysis of variance is used to detect statistically significant differences and then Dunnett's test is applied to determine which means are different. Significance level for rejection of the null hypothesis of equal means is $P<0.05$.

Animals

Male dogs (Beagles; 18 months-2 years; 12–13 kg, Marshall Farms, North Rose, N.Y. 14516) are fasted overnight and fed Purina certified Prescription Diet (Purina Mills, St. Louis, Mo.) 240 minutes after dosing. Water is available ad libitum. The room temperature is maintained between 66–74° F.; 45–50 percent relative humidity; and lighted from 0600–1800 hours.

Pharmacokinetic Model

Test compound is formulated immediately prior to dosing by dissolving in sterile 0.9 percent saline to a 5 mg/mL preparation. Dogs are given a single 2 mg/kg dose of test compound by oral gavage. Blood samples (4.5 mL) are taken from the cephalic vein at 0.25, 0.5, 0.75, 1, 2, 3, 4 and 6 hours after dosing. Samples are collected in citrated Vacutainer tubes and kept on ice prior to reduction to plasma by centrifugation. Plasma samples are analyzed by HPLC MS. Plasma concentration of test compound is recorded and used to calculate the pharmacokinetic-parameters: elimination rate constant, Ke; total clearance, Clt; volume of distribution, $V_D$; time of maximum plasma test compound concentration, Tmax; maximum concentration of test compound of Tmax, Cmax; plasma half-life, t0.5; and area under the curve, A.U.C.; fraction of test compound absorbed, F.

Canine Model of Coronary Artery Thrombosis

Surgical preparation and instrumentation of the dogs are as described in Jackson, et al., Circulation, 82, 930–940 (1990). Mixed-breed hounds (aged 6–7 months, either sex, Butler Farms, Clyde, N.Y., U.S.A.) are anesthetized with sodium pentobarbital (30 mg/kg intravenously, i.v.), intubated, and ventilated with room air. Tidal volume and respiratory rates are adjusted to maintain blood $PO_2$, $PCO_2$, and pH within normal limits. Subdermal needle electrodes are inserted for the recording of a lead II ECG.

The left jugular vein and common carotid artery are isolated through a left mediolateral neck incision. Arterial blood pressure (ABP) is measured continuously with a precalibrated Millar transducer (model (MPC-500, Millar Instruments, Houston, Tex., U.S.A.) inserted into the carotid artery. The jugular vein is cannulated for blood sampling during the experiment. In addition, the femoral veins of both hindlegs are cannulated for administration of test compound.

A left thoracotomy is performed at the fifth intercostal space, and the heart is suspended in a pericardial cradle. A 1- to 2-cm segment of the left-circumflex coronary artery (LCX) is isolated proximal to the first major diagonal ventricular branch. A 26-gauge needle-tipped wire anodal electrode (Teflon-coated, 30-gauge silverplated copper wire) 3–4 mm long is inserted into the LCX and placed in contact with the intimal surface of the artery (confirmed at the end of the experiment). The stimulating circuit is completed by placing the cathode in a subcutaneous (s.c.) site. An adjustable plastic occluder is placed around the LCX, over the region of the electrode. A precalibrated electromagnetic flow probe (Carolina Medical Electronics, King, N.C., U.S.A.) is placed around the LCX proximal to the anode for measurement of coronary blood flow (CBF). The occluder is adjusted to produce a 40–50 percent inhibition of the hyperemic blood flow response observed after 10-s mechanical occlusion of the LCX. All hemodynamic and ECG measurements are recorded and analyzed with a data acquisition system (model M3000, Modular Instruments, Malvern, Pa. U.S.A.).

Thrombus Formation and Compound Administration Regimens

Electrolytic injury of the intima of the LCX is produced by applying 100-$\mu$A direct current (DC) to the anode. The current is maintained for 60 min and then discontinued whether the vessel has occluded or not. Thrombus formation proceeds spontaneously until the LCX is totally occluded (determined as zero CBF and an increase in the S-T segment). Compound administration is started after the occluding thrombus is allowed to age for 1 hour. A 2-hour infusion of the compounds of the present invention at doses of 0.5 and 1 mg/kg/hour is begun simultaneously with an infusion of thrombolytic agent (e.g. tissue plasminogen activator, streptokinase, APSAC). Reperfusion is followed for 3 hour after administration of test compound. Reocclusion of coronary arteries after successful thrombolysis is defined as zero CBF which persisted for at least 30 minutes.

Hematology and Template Bleeding Time Determinations

Whole blood cell counts, hemoglobin, and hematocrit values are determined on a 40-µL sample of citrated (3.8 percent) blood (1 part citrate:9 parts blood) with a hematology analyzer (Cell-Dyn 900, Sequoia-Turner. Mount View, Calif., U.S.A.). Gingival template bleeding times are determined with a Simplate II bleeding time device (Organon Teknika Durham, N.C., U.S.A.). The device is used to make 2 horizontal incisions in the gingiva of either the upper or lower left jaw of the dog. Each incision is 3 mm wide×2 mm deep. The incisions are made, and a stopwatch is used to determine how long bleeding occurs. A cotton swab is used to soak up the blood as it oozes from the incision.

Template bleeding time is the time from incision to stoppage of bleeding. Bleeding times are taken just before administration of test compound (0 min), 60 min into infusion, at conclusion of administration of the test compound (120 min), and at the end of the experiment.

All data are analyzed by one-way analysis of variance (ANOVA) followed by Student-Neuman-Kuels post hoc t test to determine the level of significance. Repeated-measures ANOVA are used to determine significant differences between time points during the experiments. Values are determined to be statistically different at least at the level of $p<0.05$. All values are mean ±SEM. All studies are conducted in accordance with the guiding principles of the American Physiological Society. Further details regarding the procedures are described in Jackson, et al., *J. Cardiovasc. Pharmacol.*, (1993), 21, 587–599.

The following Examples are provided to further describe the invention and are not to be construed as limitations thereof.

The abbreviations, symbols and terms used in the examples have the following meanings.

Ac=acetyl
AIBN=azobisisobutyronitrile
Anal.=elemental analysis
aq=aqueous
Bn or Bzl=benzyl
Boc=t-butyloxycarbonyl
Bu=butyl
n-BuLi=butyllithium
Calc=calculated
conc=concentrated
DCC=dicyclohexylcarbodiimide
DMAP=4-dimethylaminopyridine
DM=dimethylformamide
DMSO=dimethylsulfoxide
EDC=1-(3-dimethylaminopropyl)-3-ethyl-carbodiimide hydrochloride
eq=(molar) equivalent
Et=ethyl
EtOAc=ethyl acetate
Et3N=triethylamine
Et2O=diethyl ether
EtOH=ethanol
Hex=hexanes
HoAt=1-hydroxy-7-azabenzotriazole
HOBT=1-hydroxybenzotriazole
HPLC=High Performance Liquid Chromatography
HRMS=high resolution mass spectrum
i-PrOH=isopropanol
IR=Infrared Spectrum
Me=methyl
MeI=methyl iodide
MeOH=methanol
MS-FAB=fast atom bombardment mass spectrum
MS-FIA=flow injection analysis mass spectrum
MS-FD=field desorption mass spectrum
MS-IS=ion spray mass spectrum
NBS=N-bromosuccinimide
NMR=Nuclear Magnetic Resonance
Ph=phenyl
i-Pr=isopropyl
RPHPLC=Reversed Phase High Performance Liquid Chromatography
satd=saturated
$SiO_2$=silica gel
SCX=strong cation exchange (resin)
TBS=tert-butyldimethylsilyl
TFA=trifluoroacetic acid
THF=tetrahydrofuran
TIPS=triisopropylsilyl
TLC=thin layer chromatography
tosyl=p-toluenesulfonyl
triflic acid=trifluoromethanesulfonic acid Unless otherwise stated, pH adjustments and work up are with aqueous acid or base solutions. $^1$H-NMR indicates a satisfactory NMR spectrum was obtained for the compound described. IR indicates a satisfactory infra red spectrum was obtained for the compound described.

For consistency and clarity, a number of compounds are named as substituted diamine derivatives.

The following conditions were used for reverse phase HPLC purification in some of the title compounds described in the examples below.

Solvents: A=0.05% conc. HCl in water, B=acetonitrile
Column: Vydac C18—5×25 cm
Method A: 90/10 (A/B) through 50/50 (A/B), linear gradient over 180 min.
Method B: 80/20 (A/B) through 50/50 (A/B), linear gradient over 180 min.
Method C: 85/15 (A/B) through 40/60 (A/B), linear gradient over 120 min.
Method D: 90/10 (A/B) through 70/30 (A/B), linear gradient over 300 min.

EXAMPLE 1

Preparation of $N^1$-(4-Methoxybenzoyl)-$N^2$-(1-benzylpiperidin-4-ylcarbonyl)-1,2-benzenediamine

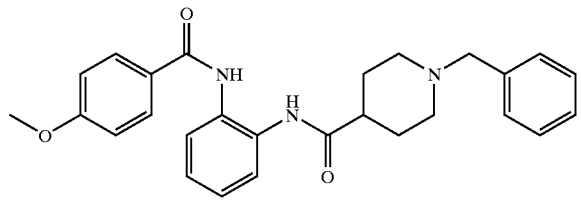

A. N-Benzylisonipecotate

A solution of ethyl N-benzylisonipecotate (1.70 g, 6.88 mmol) in ethanol (15 mL) was treated with 1 N aqueous sodium hydroxide (7.0 mL). After 2.5 days, the mixture was treated with 1 N aqueous hydrochloric acid (20 mL), concentrated, and dried under high vacuum to yield a pasty solid which was used without further purification.

B. $N^1$-(4-Methoxybenzoyl)-$N^2$-(1-benzylpiperidin-4-ylcarbonyl)-1,2-benzenediamine

General Procedure for Acylation

A suspension N-benzylisonipecotate (383 mg, 1.50 mmol) in methylene chloride was treated with oxalyl chloride (0.65 mL, 7.5 mmol) followed by dimethylformamide (0.01 mL). After 0.75 h, the mixture was concentrated in vacuo. The residue was dissolved in methylene chloride (2 mL) and added dropwise to a solution of $N^1$-(4-methoxybenzoyl)-1,2-benzenediamine (327 mg, 1.35 mmol) and pyridine in methylene chloride (7 mL) and tetrahydrofuran (2 mL). After 16 h, the mixture was poured into a mixture of ethyl acetate and 1 N aqueous sodium hydroxide. The organic layer was washed once with 1 N aqueous sodium hydroxide, once with saturated sodium chloride solution, dried (potassium carbonate), and filtered. The residue was purified by flash chromatography (silica gel, ethyl acetate/hexanes) to yield 322 mg (54%) of the title compound.

$^1$H-NMR, IR MS-FD m/e 443 (p) Analysis for $C_{27}H_{29}N_3O_3$: Calc: C, 73.11; H, 6.59; N, 9.47; Found: C, 73.35; H, 6.81; N, 9.57.

EXAMPLE 2

Preparation of $N^1$-(4-Methoxybenzoyl)-$N^2$-[1-(4-cyanobenzyl)piperidin-4-ylcarbonyl]-1,2-benzenediamine

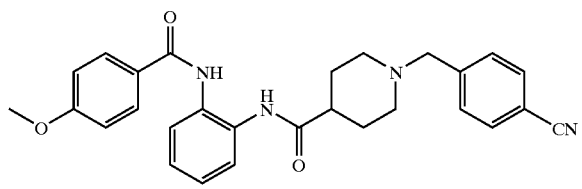

A. $N^1$-(4-Methoxybenzoyl)-$N^2$-(piperidin-4-ylcarbonyl)-1,2-benzenediamine A solution of $N^1$-(4-methoxybenzoyl)-$N^2$-(1-benzylpiperidin-4-ylcarbonyl)-1,2-benzenediamine (1.02 g, 2.30 †mmol), 1 N aqueous hydrochloric acid (5 mL), and 5% palladium-on-carbon (1.06 g) in ethanol (100 mL) was placed under a hydrogen atmosphere (1 bar). After 16 h, the mixture was filtered through diatomaceous earth and the filtrate concentrated in vacuo. The residue was treated with 1 N aqueous sodium hydroxide followed by ethyl acetate. The aqueous layer was extracted twice with ethyl acetate and the combined organics were washed with 1 N aqueous sodium hydroxide, saturated sodium chloride solution, and dried (potassium carbonate). Concentration and recrystallization yielded 656 mg (81%) of the title compound.

$^1$H-NMR, IR MS-FD m/e (p) Analysis for $C_{20}H_{23}N_3O_3$: Calc: C, 67.97; H, 6.56; N, 11.89; Found: C, 67.13; H, 6.67; N, 11.51.

B. $N^1$-(4-Methoxybenzoyl)-$N^2$-[1-(4-cyanobenzyl)piperidin-4-ylcarbonyl]-1,2-benzenediamine A solution of $N^1$-(4-methoxybenzoyl)-$N^2$-(piperidin-4-ylcarbonyl)-1,2-benzenediamine (180 mg, 0.510 mmol) and α-bromo-p-tolunitrile (104 mg, 0.530 mmol) in acetonitrile (5 mL) was treated with potassium carbonate and the resulting mixture was heated at reflux for 2 h. The mixture was poured into a mixture of ethyl acetate and water. The organic layer was concentrated in vacuo, the residue dissolved in 10% acetic acid/methanol, and the resulting solution loaded onto an ion exchange resin (SCX, Varian). Elution with methanol (4 column volumes) followed by 2 N ammonia in methanol (2 column volumes) and concentration of the appropriate fractions yielded 214 mg (90%) of the title compound.

$^1$H-NMR MS-FD m/e 468 (p)

EXAMPLE 3

Preparation of $N^1$-(4-Methoxybenzoyl)-$N^2$-[1-(4-hydroxybenzyl)piperidin-4-ylcarbonyl]-1,2-benzenediamine

General Procedure for Examples 4–22

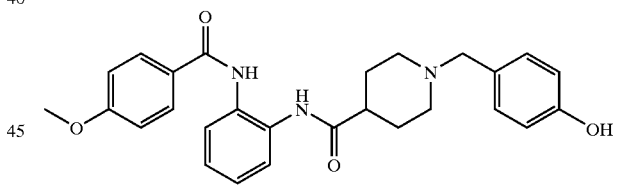

To a solution of $N^1$-(4-methoxybenzoyl)-$N^2$-(piperidin-4-ylcarbonyl)-1,2-benzenediamine (15 mg, 0.045 mmol), in 10–20% acetic acid in anhydrous methanol (0.20 mL) was added p-hydroxybenzaldehyde (16 mg, 0.14 mmol) and a freshly prepared solution of sodium cyanoborohydride (4.0 mg, 0.060 †mmol) in anhydrous methanol (0.24 mL). The mixture was shaken at room temperature for 14–18 h and then loaded onto an ion exchange resin (SCX, Varian). Elution with methanol (4 column volumes) followed by 2 N ammonia in methanol (2 column volumes) and concentration of the appropriate fractions provided the crude product. After drying the sample under vacuum for 12–20 h, the residue was dissolved in methanol and treated with hydrochloric acid (1–2 eq). The mixture was then concentrated in vacuo to give the title compound as the hydrochloride salt.

$^1$H-NMR MS-FD m/e 460 (p+1)

EXAMPLE 4

Preparation of $N^1$-(4-Methoxybenzoyl)-$N^2$-[1-(2-chloro-4-hydroxybenzyl)piperidin-4-ylcarbonyl]-1,2-benzenediamine

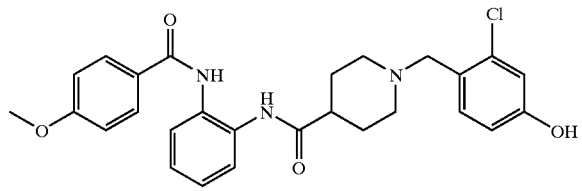

Using the general procedure described in Example 3, $N^1$-(4-methoxybenzoyl)-$N^2$-(piperidin-4-ylcarbonyl)-1,2-benzenediamine (0.045 mmol) was reacted with 2-chloro-4-hydroxybenzaldehyde to provide 22 mg of the title product as the free base. Treatment with hydrochloric acid and concentration in vacuo yielded the salt of the title compound.

$^1$H-NMR MS-FD m/e 494 (p)

EXAMPLE 5

Preparation of $N^1$-(4-Methoxybenzoyl)-$N^2$-[1-(3-chloro-4-hydroxybenzyl)piperidin-4-ylcarbonyl]-1,2-benzenediamine

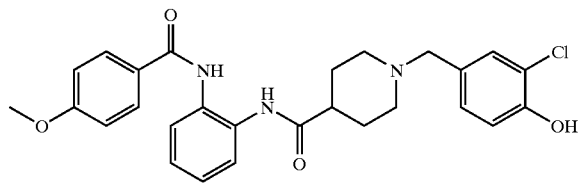

Using the general procedure described in Example 3, $N^1$-(4-methoxybenzoyl)-$N^2$-(piperidin-4-ylcarbonyl)-1,2-benzenediamine (0.045 mmol) was reacted with 3-chloro-4-hydroxybenzaldehyde to provide 22 mg of the title product as the free base. Treatment with hydrochloric acid and concentration in vacuo yielded the salt of the title compound.

$^1$H-NMR MS-FD m/e 494 (p)

EXAMPLE 6

Preparation of $N^1$-(4-Methoxybenzoyl)-$N^2$-[1-(3,4-methylenedioxybenzyl)piperidin-4-ylcarbonyl]-1,2-benzenediamine

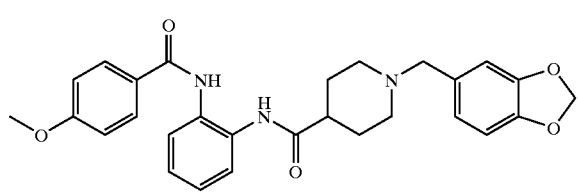

Using the general procedure described in Example 3, $N^1$-(4-methoxybenzoyl)-$N^2$-(piperidin-4-ylcarbonyl)-1,2-benzenediamine (0.045 mmol) was reacted with piperonal to provide 21 mg of the title product as the free base. Treatment with hydrochloric acid and concentration in vacuo yielded the salt of the title compound.

$^1$H-NMR MS-FD m/e 487 (p)

EXAMPLE 7

Preparation of $N^1$-(4-Methoxybenzoyl)-$N^2$-[1-(4-acetamidobenzyl)piperidin-4-ylcarbonyl]-1,2-benzenediamine

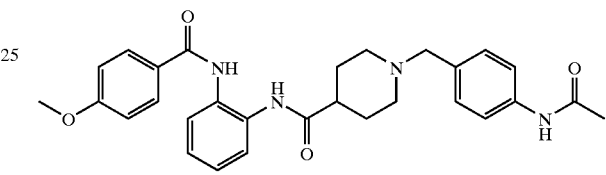

Using the general procedure described in Example 3, $N^1$-(4-methoxybenzoyl)-$N^2$-(piperidin-4-ylcarbonyl)-1,2-benzenediamine (0.045 mmol) was reacted with 4-acetamidobenzaldehyde to provide 23 mg of the title product as the free base. Treatment with hydrochloric acid and concentration in vacuo yielded the salt of the title compound.

$^1$H-NMR MS-FD m/e 501 (p+1)

EXAMPLE 8

Preparation of $N^1$-(4-Methoxybenzoyl)-$N^2$-[1-(2-methoxybenzyl)piperidin-4-ylcarbonyl]-1,2-benzenediamine

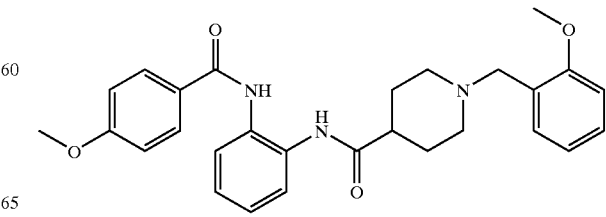

Using the general procedure described in Example 3, $N^1$-(4-methoxybenzoyl)-$N^2$-(piperidin-4-ylcarbonyl)-1,2-benzenediamine (0.045 mmol) was reacted with 2-methoxybenzaldehyde to provide 21 mg of the title product as the free base. Treatment with hydrochloric acid and concentration in vacuo yielded the salt of the title compound.

$^1$H-NMR MS-FD m/e 473 (p)

EXAMPLE 9

Preparation of $N^3$-(4-Methoxybenzoyl)-$N^2$-[1-(3-methylthiophen-2-ylmethyl)piperidin-4-ylcarbonyl]-1,2-benzenediamine

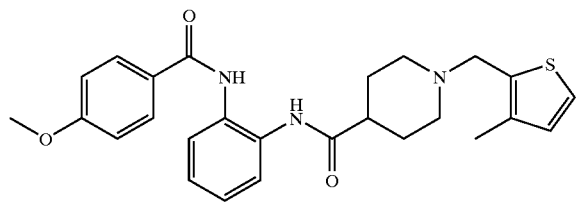

Using the general procedure described in Example 3, $N^1$-(4-methoxybenzoyl)-$N^2$-(piperidin-4-ylcarbonyl)-1,2-benzenediamine (0.045 mmol) was reacted with 3-methyl-2-thiophenecarboxaldehyde to provide 20 mg of the title product as the free base. Treatment with hydrochloric acid and concentration in vacuo yielded the salt of the title compound.

$^1$H-NMR MS-FD m/e 463 (p)

EXAMPLE 10

Preparation of $N^1$-(4-Methoxybenzoyl)-$N^2$-[1-(3-furylmethyl)piperidin-4-ylcarbonyl]-1,2-benzenediamine

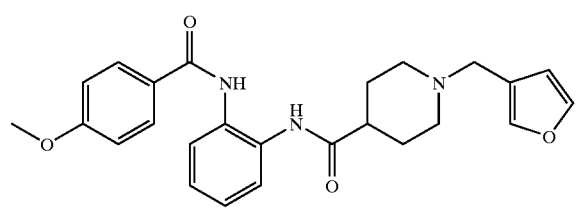

Using the general procedure described in Example 3, $N^1$-(4-methoxybenzoyl)-$N^2$-(piperidin-4-ylcarbonyl)-1,2-benzenediamine (0.045 mmol) was reacted with 3-furaldehyde to provide 19 mg of the title product as the free base. Treatment with hydrochloric acid and concentration in vacuo yielded the salt of the title compound.

$^1$H-NMR MS-FD m/e 433 (p)

EXAMPLE 11

Preparation of $N^1$-(4-methoxybenzoyl)-$N^2$-(1-pentafluorobenzylpiperidin-4-ylcarbonyl)-1,2-benzenediamine

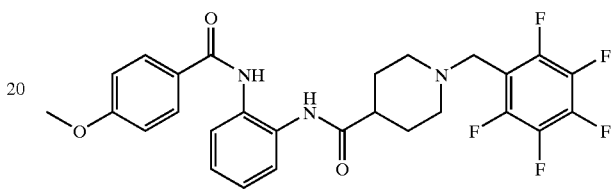

Using the general procedure described in Example 3, $N^1$-(4-methoxybenzoyl)-$N^2$-(piperidin-4-ylcarbonyl)-1,2-benzenediamine (0.070 mmol) was reacted with pentafluorobenzaldehyde to provide 30 mg of the title product as the free base. Treatment with hydrochloric acid and concentration in vacuo yielded the salt of the title compound.

$^1$H-NMR MS-FD m/e 533 (p)

EXAMPLE 12

Preparation of $N^1$-(4-Methoxybenzoyl)-$N^2$-[1-(4-benzyloxybenzyl)piperidin-4-ylcarbonyl]-1,2-benzenediamine

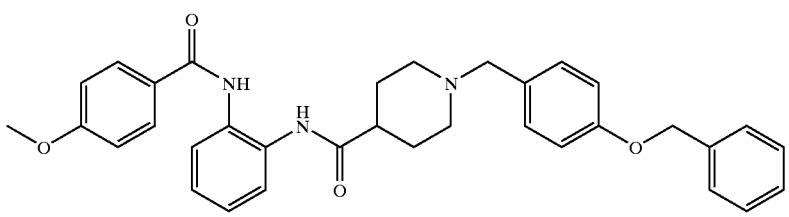

Using the general procedure described in Example 3, $N^1$-(4-methoxybenzoyl)-$N^2$-(piperidin-4-ylcarbonyl)-1,2-benzenediamine (0.070 mmol) was reacted with 4-benzyloxybenzaldehyde to provide 40 mg of the title product as the free base. Treatment with hydrochloric acid and concentration in vacuo yielded the salt of the title compound.

$^1$H-NMR MS-FD m/e 549 (p)

EXAMPLE 13

Preparation of $N^1$-(4-Methoxybenzoyl)-$N^2$-[1-(2-pyridylmethyl)piperidin-4-ylcarbonyl]-1,2-benzenediamine

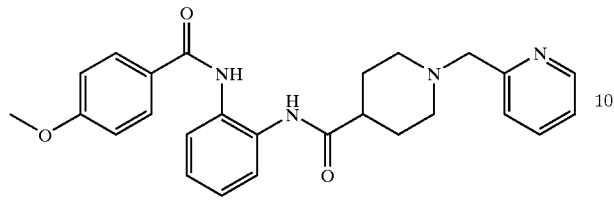

Using the general procedure described in Example 3, $N^1$-(4-methoxybenzoyl)-$N^2$-(piperidin-4-ylcarbonyl)-1,2-benzenediamine (0.070 mmol) was reacted with 2-pyridinecarboxaldehyde to provide 44 mg of the title product as the free base. Treatment with hydrochloric acid and concentration in vacuo yielded the salt of the title compound.

$^1$H-NMR MS-FD m/e 445 (p+1)

EXAMPLE 14

Preparation of $N^1$-(4-Methoxybenzoyl)-$N^2$-[1-(3-pyridylmethyl)piperidin-4-ylcarbonyl]-1,2-benzenediamine

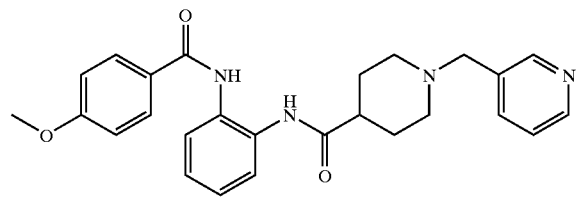

Using the general procedure described in Example 3, $N^1$-(4-methoxybenzoyl)-$N^2$-(piperidin-4-ylcarbonyl)-1,2-benzenediamine (0.070 mmol) was reacted with 3-pyridinecarboxaldehyde to provide 47 mg of the title product as the free base. Treatment with hydrochloric acid and concentration in vacuo yielded the salt of the title compound.

$^1$H-NMR MS-FD m/e 444 (p)

EXAMPLE 15

Preparation of $N^1$-(4-Methoxybenzoyl)-$N^2$-[1-(4-pyridylmethyl)piperidin-4-ylcarbonyl]-1,2-benzenediamine

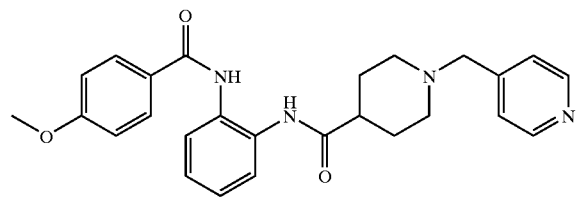

Using the general procedure described in Example 3, $N^1$-(4-methoxybenzoyl)-$N^2$-(piperidin-4-ylcarbonyl)-1,2-benzenediamine (0.070 mmol) was reacted with 4-pyridinecarboxaldehyde to provide 45 mg of the title product as the free base. Treatment with hydrochloric acid and concentration in vacuo yielded the salt of the title compound.

$^1$H-NMR MS-FD m/e 444 (p)

EXAMPLE 16

Preparation of $N^1$-(4-Methoxybenzoyl)-$N^2$-[1-(4-nitrobenzyl)piperidin-4-ylcarbonyl]-1,2-benzenediamine

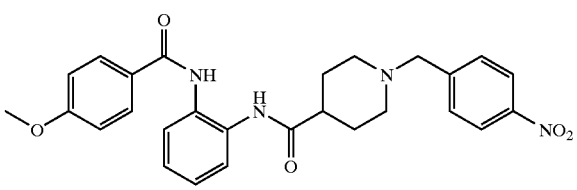

Using the general procedure described in Example 3, $N^1$-(4-methoxybenzoyl)-$N^2$-(piperidin-4-ylcarbonyl)-1,2-benzenediamine (0.14 mmol) was reacted with 4-nitrobenzaldehyde to provide 36 mg of the title product as the free base. Treatment with hydrochloric acid and concentration in vacuo yielded the salt of the title compound.

$^1$H-NMR MS-FD, m/e 488 (p)

EXAMPLE 17

Preparation of $N^1$-(4-Methoxybenzoyl)-$N^2$-[1-(4-iodobenzyl)piperidin-4-ylcarbonyl]-1,2-benzenediamine

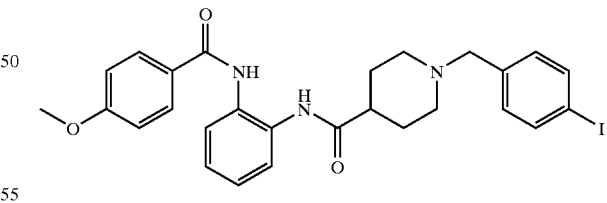

Using the general procedure described in Example 3, $N^1$-(4-methoxybenzoyl)-$N^2$-(piperidin-4-ylcarbonyl)-1,2-benzenediamine (0.070 mmol) was reacted with 4-iodobenzaldehyde to provide 28 mg of the title product as the free base. Treatment with hydrochloric acid and concentration in vacuo yielded the salt of the title compound.

$^1$H-NMR MS-FD, m/e 569 (p)

EXAMPLE 18

Preparation of $N^1$-(4-Methoxybenzoyl)-$N^2$-[1-(2-nitrobenzyl)piperidin-4-ylcarbonyl]-1,2-benzenediamine

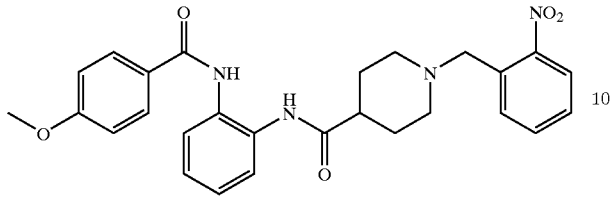

Using the general procedure described in Example 3, $N^1$-(4-methoxybenzoyl)-$N^2$-(piperidin-4-ylcarbonyl)-1,2-benzenediamine (0.070 mmol) was reacted with 2-nitrobenzaldehyde to provide 32 mg of the title product as the free base. Treatment with hydrochloric acid and concentration in vacuo yielded the salt of the title compound.

$^1$H-NMR MS-FD, m/e 489 (p+1)

EXAMPLE 19

Preparation of $N^1$-(4-Methoxybenzoyl)-$N^2$-[1-(5-nitrofuran-2-ylmethyl)piperidin-4-ylcarbonyl]-1,2-benzenediamine

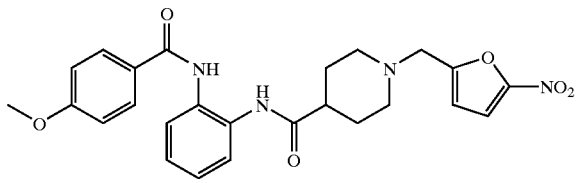

Using the general procedure described in Example 3, $N^1$-(4-methoxybenzoyl)-$N^2$-(piperidin-4-ylcarbonyl)-1,2-benzenediamine (0.14 mmol) was reacted with 5-nitro-2-furaldehyde to provide 30 mg of the title product as the free base. Treatment with hydrochloric acid and concentration in vacuo yielded the salt of the title compound.

$^1$H-NMR MS-FD, m/e 478 (p)

EXAMPLE 20

Preparation of $N^1$-(4-Methoxybenzoyl)-$N^2$-[1-(2-thiazolylmethyl)piperidin-4-ylcarbonyl]-1,2-benzenediamine

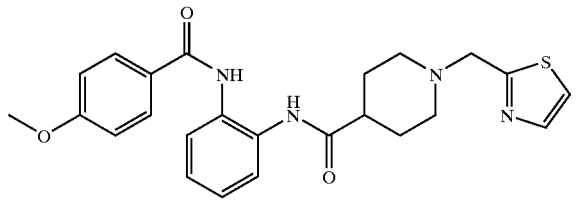

Using the general procedure described in Example 3, $N^1$-(4-methoxybenzoyl)-$N^2$-(piperidin-4-ylcarbonyl)-1,2-benzenediamine (0.070 mmol) was reacted with 2-thiazolecarboxaldehyde to provide 28 mg of the title product as the free base. Treatment with hydrochloric acid and concentration in vacuo yielded the salt of the title compound.

$^1$H-NMR

MS-FD, m/e 451 (p+1)

EXAMPLE 21

Preparation of $N^1$-(4-Methoxybenzoyl)-$N^2$-(1-cyclopropylmethylpiperidin-4-ylcarbonyl]-1,2-benzenediamine

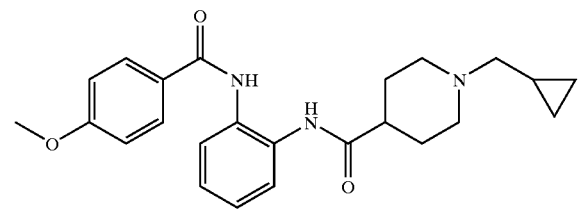

Using the general procedure described in Example 3, $N^1$-(4-methoxybenzoyl)-$N^2$-(piperidin-4-ylcarbonyl)-1,2-benzenediamine (0.070 mmol) was reacted with cyclopropanecarboxaldehyde to provide 30 mg of the title product as the free base. Treatment with hydrochloric acid and concentration in vacuo yielded the salt of the title compound.

$^1$H-NMR MS-FD, m/e 407 (p)

EXAMPLE 22

Preparation of $N^1$-(4-Methoxybenzoyl)-$N^2$-(1-isobutylpiperidin-4-ylcarbonyl)-1,2-benzenediamine

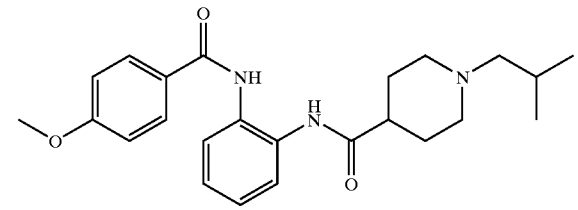

Using the general procedure described in Example 3, $N^1$-(4-methoxybenzoyl)-$N^2$-(piperidin-4-ylcarbonyl)-1,2-benzenediamine (0.070 mmol) was reacted with isobutyraldehyde to provide 32 mg of the title product as the free base. Treatment with hydrochloric acid and concentration in vacuo yielded the salt of the title compound.

$^1$H-NMR MS-FD, m/e 409 (p)

EXAMPLE 23

Preparation of $N^1$-(4-methoxybenzoyl)-$N^2$-(1-phenylsulfonylpiperidin-4-ylcarbonyl)-1,2-benzenediamine

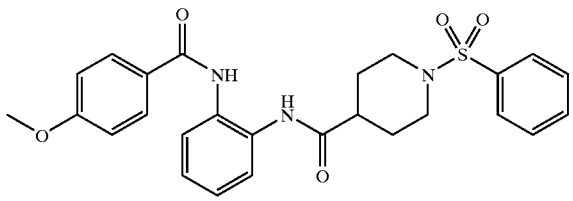

A solution of $N^1$-(4-methoxybenzoyl)-$N^2$-(piperidin-4-ylcarbonyl)-1,2-benzenediamine (41 mg, 0.12 mmol) and pyridine (0.05 mL) in methylene chloride (3 mL) was treated with benzenesulfonyl chloride (0.014 mL, 0.11 mmol). After 20 h, the mixture was treated with silica gel (3 cm$^3$) and concentrated in vacuo. The residue was chromatographed (silica gel, 50% hexanes/50% ethyl acetate to 30% hexanes/70% ethyl acetate). Recrystallization of the residue from hexanes/ethyl acetate yielded 39 mg (68%) of the title compound.

$^1$H-NMR, IR MS-FD m/e 493 (p) Analysis for $C_{26}H_{27}N_3O_5S$: Calc: C, 63.27; H, 5.51; N, 8.51. Found: C, 63.05; H, 5.65; N, 8.35.

EXAMPLE 24

Preparation of $N^1$-(4-methoxybenzoyl)-$N^2$-(4-piperidinylmethoxycarbonyl)-1,2-benzenediamine

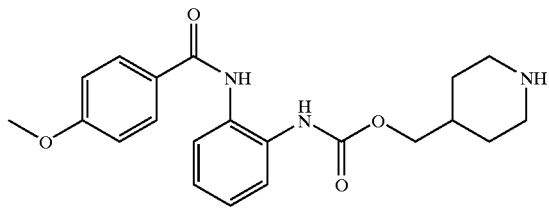

A. $N^1$-(4-Methoxybenzoyl)-$N^2$-[1-(tert-butoxycarbonyl)piperidin-4-ylmethoxycarbonyl]-1,2-benzenediamine A solution of 1.9 M phosgene in toluene (2.0 mL) was treated with 1-(tert-butoxycarbonyl)-4-hydroxymethylpiperidine (200 mg, 0.930 mmol). After 1 h, the mixture was concentrated in vacuo and the residue dried under high vacuum for 4 h. The residue was dissolved in methylene chloride (2.5 mL) and then added dropwise to a solution of $N^1$-(4-methoxybenzoyl)-1,2-benzenediamine (230 mg, 0.950 mmol) and pyridine (0.4 mL) in methylene chloride (5 mL) and tetrahydrofuran (1 mL). After 16 h, the mixture was poured into a mixture of water and ethyl acetate. The organic layer was washed once with 1.0 N aqueous hydrochloric acid, once with saturated sodium chloride solution, dried (potassium carbonate), and filtered. Concentration and purification of the residue by flash chromatography (silica gel, ethyl acetate/hexanes) yielded 416 mg (93%) of the title compound.

$^1$H-NMR, IR MS-FD m/e 483 (p) Analysis for $C_{26}H_{33}N_3O_6$. Calc: C, 64.58; H, 6.88; N, 8.69; Found: C, 64.46; H, 7.16; N, 8.41.

B. $N^1$-(4-Methoxybenzoyl)-$N^2$-(4-piperidinylmethoxycarbonyl)-1,2-benzenediamine A solution of $N^1$-(4-methoxybenzoyl)-$N^2$-[1-(tert-butoxycarbonyl)piperidin-4-ylmethoxycarbonyl]-1,2-benzenediamine (180 mg, 0.373 mmol) in methylene chloride (10 mL) was treated with trifluoroacetic acid (5 mL). After 2 h, the mixture was concentrated in vacuo yielding the trifluoroacetic acid salt of the title compound.

$^1$H-NMR, IR MS-FD m/e 384 (p+1) Analysis for $C_{21}H_{26}N_3O_4 \cdot C_2F_3O_2$: Calc: C, 55.53; H, 5.27; N, 8.45; Found: C, 56.84; H, 5.49; N, 8.87.

EXAMPLE 25

Preparation of $N^1$-(4-Methoxybenzoyl)-$N^2$-[2-(4-piperidinyl)ethoxycarbonyl]-1,2-benzenediamine

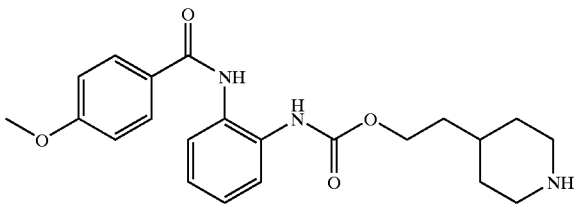

A. $N^1$-(4-Methoxybenzoyl)-$N^2$-[2-[1-(tert-butoxycarbonyl)piperidin-4-yl]ethoxycarbonyl]-1,2-benzenediamine Using the general procedure in Example 24, Part A, 2-[1-(tert-butoxycarbonyl)piperidin-4-yl]ethanol (1.31 mmol) yielded 352 mg (54%) of the title compound.

$^1$H-NMR, IR MS-FD, m/e 497 (p) Analysis for $C_{27}H_{35}N_3O_6$: Calc: C, 65.17; H, 7.09; N, 8.45; Found: C, 65.23; H, 7.33; N, 8.43.

B. $N^1$-(4-Methoxybenzoyl)-$N^2$-[2-(4-piperidinyl)ethoxycarbonyl]-1,2-benzenediamine A solution of $N^1$-(4-methoxybenzoyl)-$N^2$-[2-[1-(tert-butoxycarbonyl)piperidin-4-yl]ethoxycarbonyl]-1,2-benzenediamine (312 mg, 0.627 mmol) in methylene chloride (3 mL) was treated with trifluoroacetic acid (0.48 mL). After 0.5 h, the mixture was concentrated in vacuo. The residue was treated with 1 N aqueous sodium hydroxide followed by ethyl acetate. The aqueous phase was extracted twice with ethyl acetate and the combined organic layers were dried and concentrated in vacuo. The residue was taken up in methanol and treated with hydrochloric acid (gas, 1–2 eq) and concentrated in vacuo to yield the hydrochloride salt of the title compound (270 mg).

$^1$H-NMR, IR MS-FD m/e 398 (p) Analysis for $C_{22}H_{27}N_3O_4 \cdot HCl$: Calc: C, 60.90; H, 6.50; N, 9.68; Found: C, 60.65; H, 6.71; N, 9.71.

EXAMPLE 26

Preparation of $N^1$-(4-Methoxybenzoyl)-$N^2$-[2-(4-piperidinyloxy)ethoxycarbonyl]-1,2-benzenediamine

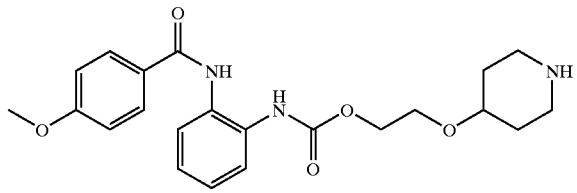

A. $N^1$-(4-Methoxybenzoyl)-$N^2$-[2-[1-(tert-butoxycarbonyl)piperidin-4-yloxy]ethoxycarbonyl]-1,2-benzenediamine Using the general procedure in Example 24, Part A, 2-[1-(tert-butoxycarbonyl)piperidin-4-yloxy]ethanol (0.57 mmol) yielded 210 mg (72%) of the title compound.

$^1$H-NMR, IR MS-FD m/e 513 (p) Analysis for $C_{27}H_{35}N_3O_7$: Calc: C, 63.08; H, 6.81; N, 8.18; Found: C, 64.93; H, 7.07; N, 8.52.

B. $N^1$-(4-Methoxybenzoyl)-$N^2$-[2-(4-piperidinyloxy)ethoxycarbonyl]-1,2-benzenediamine A solution of $N^1$-(4-methoxybenzoyl)-$N^2$-[2-[1-(tert-butoxycarbonyl)piperidin-4-yloxy]ethoxycarbonyl]-1,2-benzenediamine (180 mg, 0.362 mmol) in methylene chloride (2 mL) was treated with trifluoroacetic acid (0.30 mL). After 0.5 h, the mixture was concentrated in vacuo. The residue was treated with 1 N aqueous sodium hydroxide followed by ethyl acetate. The aqueous phase was extracted twice with ethyl acetate and the combined organic phases were dried (sodium sulfate), filtered, and concentrated in vacuo. The residue was taken up in methanol and treated with hydrochloric acid (gas,1–2 eq) and concentrated in vacuo yielding the hydrochloride salt of the title compound (270 mg).

$^1$H-NMR, IR MS-FD m/e 414 (p) Analysis for $C_{22}H_{28}ClN_3O_5$: Calc: C, 58.68; H, 6.22; N, 9.33; Found: C, 58.56; H, 6.17; N, 9.20.

EXAMPLE 27

Preparation of $N^1$-(4-Methoxybenzoyl)-$N^2$-(1-benzylpiperidin-4-yloxycarbonyl)-1,2-benzenediamine

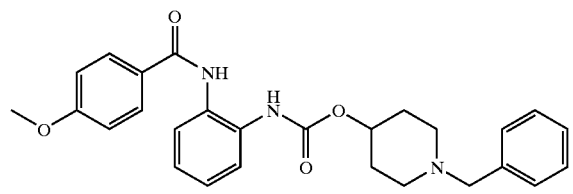

A. $N^1$-(4-Methoxybenzoyl)-$N^2$-(4-piperidinyloxycarbonyl)-1,2-benzenediamine

Using the general procedure in Example 24, Part A, 1-(tert-butoxycarbonyl)piperdin-4-ol (1.17 mmol) yielded 218 mg (40%) of $N^1$-(4-methoxybenzoyl)-$N^2$-[1-(tert-butoxycarbonyl)piperidin-4-yloxycarbonyl)-1,2-benzenediamine. A portion of this material (106 mg) was then treated with methylene chloride (5 mL) and trifluoroacetic acid (3 mL) for 3 h. The mixture was concentrated in vacuo and the residue treated with 1 N aqueous sodium hydroxide, followed by ethyl acetate. The aqueous layer was extracted twice with ethyl acetate and the combined organic extracts were washed with saturated sodium chloride solution, dried (potassium carbonate), filtered, and concentrated in vacuo to yield the title compound. Treatment of an acetonitrile solution of this material with hydrochloric acid (gas, 1–2 eq), followed by concentration and drying yielded the hydrochloride salt.

$^1$H-NMR

B. $N^1$-(4-Methoxybenzoyl)-$N^2$-(1-benzylpiperidin-4-yloxycarbonyl)-1,2-benzenediamine General Procedure for Benzylation A solution of $N^1$-(4-methoxybenzoyl)-$N^2$-(4-piperidinyloxycarbonyl)-1,2-benzenediamine (50 mg, 0.12 mmol) and triethylamine (0.040 mL, 0.26 mmol) in methylene chloride was treated with benzyl bromide (0.015 mL, 0.12 mmol). After 1 h, the mixture was poured into a mixture of ethyl acetate and 1 N aqueous sodium hydroxide. The organic layer was washed with saturated sodium chloride solution, dried (potassium carbonate), and filtered. Concentration and purification of the residue by flash chromatography (silica gel, 90% chloroform/10% ammonium hydroxide in methanol) afforded the free base. Treatment of the free base with hydrochloric acid (gas, 1–2 eq.) in methanol and drying yielded the hydrochloride salt of the title compound (30 mg).

$^1$H-NMR MS-FD m/e 459 (p) Analysis for $C_{27}H_{29}N_3O_4$·HCl: Calc: C, 65.38; H, 6.10; N, 8.47; Found: C, 64.33; H, 6.25; N, 7.95.

EXAMPLE 28

Preparation of $N^1$-(4-methoxybenzoyl)-$N^2$-(1-benzylpiperidin-4-ylmethoxycarbonyl)-1,2-benzenediamine

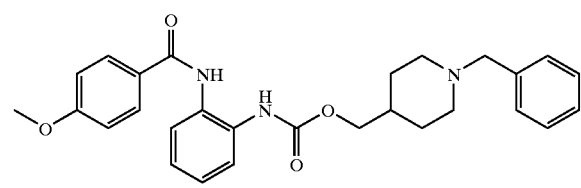

Using the general procedure described in Example 27, Part A, $N^1$-(4-methoxybenzoyl)-$N^2$-(4-piperidinylmethoxycarbonyl)-1,2-benzenediamine (0.096 mmol) yielded the hydrochloride salt of the title compound (30 mg). MS-FD m/e 473 (p) Analysis for $C_{28}H_{31}N_3O_4$·HCl: Calc: C, 65.94; H, 6.32; N, 8.24; Found: C, 65.67; H, 6.49; N, 8.01.

EXAMPLE 29

Preparation of N[1]-(4-Methoxybenzoyl)-N[2]-[2-(1-benzylpiperidin-4-yloxy)ethoxycarbonyl]-1,2-benzenediamine

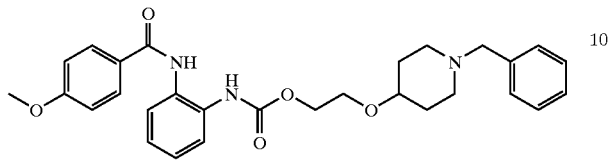

Using the procedure described in Example 27, Part A, N[1]-(4-methoxybenzoyl)-N[2]-(2-(4-piperidinyloxy)ethoxycarbonyl]-1,2-benzenediamine (0.21 mmol) yielded the hydrochloride salt of the title compound (75 mg).

$^1$H-NMR MS-FD m/e 503 (p) Analysis for $C_{28}H_{32}ClN_3O_4$: Calc: C, 64.50; H, 6.35; N, 7.78; Found: C, 64.59; H, 6.20; N, 7.67.

EXAMPLE 30

Preparation of N-(4-Methoxybenzoyl)-2-(5-tert-butyl-1,3-dihydro-1,3-dioxo-2H-isoindol-2-yl)benzeneamine

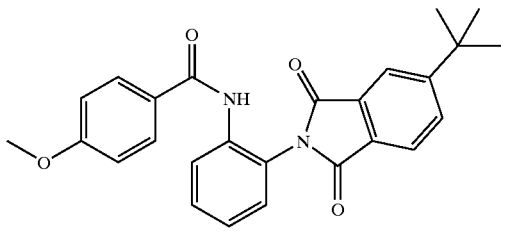

A slurry of N[1]-(4-methoxybenzoyl)-1,2-benzenediamine (100 mg, 0.413 mmol) and 4-tert-butylphthalic anhydride (84.3 mg, 0.413 mmol) in toluene (1.5 mL) was placed in a bath heated to 110° C. After 16 h, the mixture was concentrated in vacuo and the residue purified by flash chromatography (silica gel, hexanes/ethyl acetate) to afford 149 mg (85%) of the title compound. The material was further purified by recrystallization from hexanes/ethyl acetate.

$^1$H-NMR MS-FD m/e 428 (p) Analysis for $C_{26}H_{24}N_2O_4$: Calc: C, 72.88; H, 5.65; N, 6.54; Found: C, 73.09; H, 5.87; N, 6.61.

EXAMPLE 31

Preparation of N-(4-Methoxybenzoyl)-2-(5-amino-1,3-dihydro-1,3-dioxo-2H-isoindol-2-yl)benzeneamine

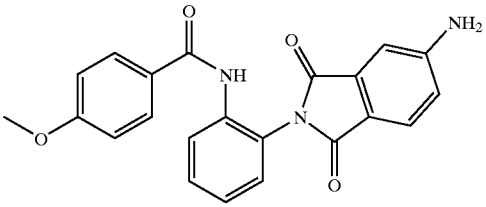

A. N-(4-Methoxybenzoyl)-2-(5-nitro-1,3-dihydro-1,3-dioxo-2H-isoindol-2-yl)benzeneamine Using the procedure described in Example 30, 4-nitrophthalic anhydride (997 mg, 5.17 mmol) was reacted in toluene (40 mL) and tetrahydrofuran (10 mL) to yield, after recrystallization from hexanes/ethyl acetate, 1.56 g (73%) of the title compound.

$^1$H-NMR MS-FD m/e 417 (p) Analysis for $C_{22}H_{15}N_3O_6$: Calc: C, 63.31; H, 3.62; N, 10.07; Found: C, 64.06; H, 3.64; N, 10.08.

B. N-(4-Methoxybenzoyl)-2-(5-amino-1,3-dihydro-1,3-dioxo-2H-isoindol-2-yl)benzeneamine A solution of N-(4-methoxybenzoyl)-2-(5-nitro-1,3-dihydro-1,3-dioxo-2H-isoindol-2-yl)benzeneamine (1.11 g, 2.66 mmol) and 5% palladium-on-carbon (1.21 g) in 2:1 ethanol:ethyl acetate (200 mL) was placed under 1 atmosphere of hydrogen. After consumption of the starting material (about 2–3 h), the mixture was filtered through diatomaceous earth and the resulting filtrate concentrated in vacuo. Recrystallization from hexanes/ethyl acetate yielded 596 mg (58% of the title-compound.

$^1$H-NMR, IR MS-FD m/e 387 (p) Analysis for $C_{22}H_{17}N_3O_4$: Calc: C, 68.21; H, 4.42; N, 10.85; Found: C, 68.19; H, 4.58; N, 10.66.

EXAMPLE 32

Preparation of N-(4-Methoxybenzoyl)-2-(1,3-dihydro-1,3-diazo-2n-benz[f]inoindol-2-yl)benzeneamine

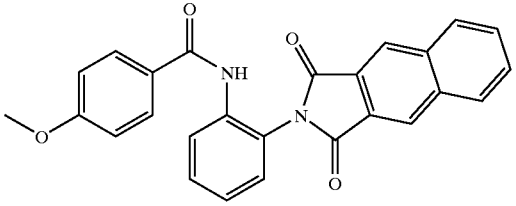

A pressure tube was charged with N[1]-(4-methoxybenzoyl)-1,2-benzenediamine (1.00 g, 4.13 mmol), 2,3-napthalenedicarboxylic anhydride (820 mg, 4.13 mmol), and tetrahydrofuran (16 mL). The resultant slurry was then placed in a bath heated to 110° C. for 16 h. After cooling to ambient temperature and standing for 3 h, the mixture was further cooled to −10° C. for 20 h. The resulting solid was collected by filtration and washed with cold ethyl acetate. The solid was then pulverized and dried under vacuum at 50° C. for 20 h to yield 1.45 g (83%) of the title compound.
$^1$H-NMR, IR MS-FD m/e 422 (p) Analysis for $C_{26}H_{18}N_2O_4$: Calc: C, 73.93; H, 4.30; N, 6.63; Found C, 73.94; H, 4.56; N, 6.60.

EXAMPLE 33

Preparation of N-(4-Methoxybenzoyl)-2-(5-bromo-1,3-dihydro-1,3-diazo-2H-isoindol-2-yl) benzeneamine

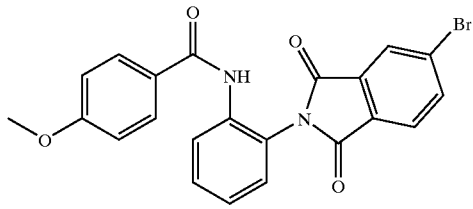

A pressure tube was charged with $N^1$-(4-methoxybenzoyl)-1,2-benzenediamine (2.00 g, 8.26 mmol), 4-bromophthalic anhydride (1.88 g, 8.26 mmol), and tetrahydrofuran (8 mL). The resultant slurry was then placed in a bath heated to 110° C. for 16 h. After cooling to ambient temperature, the product was triturated with ethyl acetate/hexanes and collected by filtration. Recrystallization from ethyl acetate/hexanes yielded 3.48 g (93%) of the title compound.

$^1$H-NMR, IR MS-FD m/e (p) Analysis for $C_{26}H_{18}N_2O_4$: Calc: C, 73.93; H, 4.30; N, 6.63; Found: C, 73.64; H, 4.56; N, 6.60.

EXAMPLE 34

Preparation of N-(4-Methoxybenzoyl)-2-(1-ethoxy-1,3-dihydro-3-ozo-2H-benz[f]isoindol-2-yl) benzeneamine

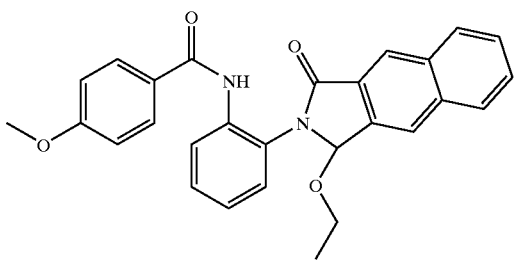

A slurry of N-(4-methoxybenzoyl)-2-(1,3-dihydro-1,3-dioxo-2H-benz[f]isoindol-2-yl)benzeneamine (3.44 g, 8.15 mmol) in anhydrous ethanol (330 mL) was treated with sodium borohydride (620 mg, 16.3 mmol). After 2 h, the mixture was slowly treated with 1 M hydrochloric acid in diethyl ether (17.0 mL 17.0 mmol), stirred at room temperature for 0.5 h, filtered through diatomaceous earth, and concentrated in vacuo. The residue was purified by flash chromatography (silica gel, hexanes/ethyl acetate) to yield 1.61 g (44%) of the title compound. An analytical sample was obtained by recrystallization from ethyl acetate/hexanes.

$^1$H-NMR, IR MS-FD m/e 452 (p) Analysis for $C_{28}H_{24}N_2O_4$: Calc: C, 74.32; H, 5.35; N, 6.19; Found: C, 74.27; H, 5.48; N, 6.18.

EXAMPLE 35

Preparation of N-(4-Methoxybenzoyl)-2-[1-(ethoxycarbonylmethyl)-1,3-dihydro-3-oxo-2H-benz[f]isoindol-2-yl]-benzeneamine

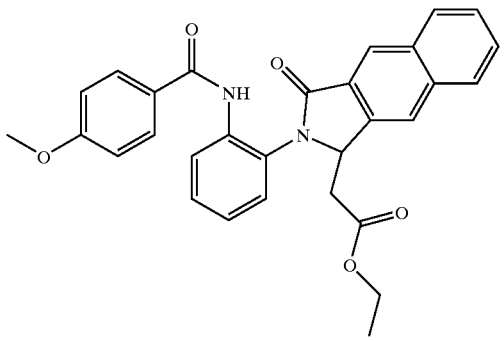

A solution of N-(4-methoxybenzoyl)-2-(1-ethoxy-1,3-dihydro-3-oxo-2H-benz [f]isoindol-2-yl)benzeneamine (0.75 g, 1.7 mmol) and 1-ethoxy-1-trimethylsilyloxyethylene (0.80 g, 5.0 mmol) in methylene chloride at −78° C. was treated dropwise with boron trifluoride etherate (0.23 mL, 1.8 mmol). Upon complete addition, the cooling bath was removed and the mixture was allowed to warm for 0.5 h. The mixture was poured into a mixture of ethyl acetate and aqueous saturated sodium bicarbonate solution. The organic layer was washed with water, saturated sodium chloride solution, dried (potassium carbonate), and filtered. Concentration and purification of the residue by radial chromatography (silica gel, hexanes/ethyl acetate) yielded 428 mg (44%) of the title compound. An analytical sample was obtained by recrystallization from ethyl acetate/hexanes.

$^1$H-NMR, IR MS-FD m/e 494 (p) Analysis for $C_{30}H_{26}N_2O_5$: Calc: C, 72.86; H, 5.30; N, 5.66; Found: C, 72.77; H, 5.51; N, 5.62.

EXAMPLE 36

Preparation of N-(4-Methoxybenzoyl)-2-[1-(carboxymethyl)-1,3-dihydro-3-ozo-2H-benz[f] isoindol-2-yl]benzeneamine

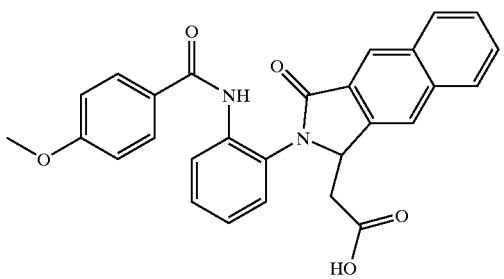

A solution of N-(4-methoxybenzoyl)-2-[1-(ethoxycarbonylmethyl)-1,3-dihydro-3-oxo-2H-benz[f] isoindol-2-yl]-benzeneamine (78.1 mg, 0.158 mmol) and lithium hydroxide hydrate (7.0 mg, 0.16 mmol) in 9:1 tetrahydrofuran/water (2 mL) was rapidly stirred for 18 h. The mixture was poured into ethyl acetate and 1 N aqueous hydrochloric acid. The aqueous layer was extracted three times with ethyl acetate and the combined organic extracts were washed with saturated sodium chloride solution, dried (magnesium sulfate), filtered, and concentrated in vacuo. Recrystallization from hexanes/ethyl acetate yielded 49.6 mg (67%) of the title compound.

$^1$H-NMR, IR MS-FD m/e 466 (p) Analysis for $C_{28}H_{22}N_2O_5$: Calc: C, 72.09; H, 4.75; N, 6.01; Found: C, 72.19; H, 4.93; N, 5.75.

EXAMPLE 37

Preparation of $N^1$-(4-methoxybenzoyl)-$N^2$-(2-naphthoyl) benzenediamine

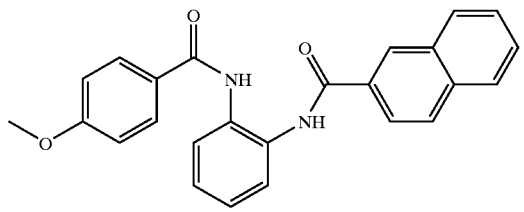

A solution of $N^1$-(4-methoxybenzoyl)-1,2-benzenediamine (200 mg, 0.826 mmol) and pyridine (0.25 mL) in chloroform (5 mL) was treated with 2-naphthoyl chloride (158 mg, 0.826 mmol). After 20 h, the mixture was poured into a mixture of ethyl acetate and 1 N aqueous hydrochloric acid. The organic layer was washed with water, saturated sodium chloride solution, and dried (potassium carbonate), filtered, and concentrated in vacuo. Recrystallization from hexanes/ethyl acetate yielded 211 mg (65%) of the title compound.

$^1$H-NMR, IR MS-FD m/e 396 (p) Analysis for $C_{25}H_{20}N_2O_3$: Calc: C, 75.74; H, 5.09; N, 7.07; Found: C, 75.56; H, 5.10; N, 6.97.

EXAMPLE 38

Preparation of N-(4-Methoxybenzoyl)-2-(1,3-dihydro-1,3-dioxo-2H-benz[f]isoindol-2-yl)-4-hydroxybenzeneamine

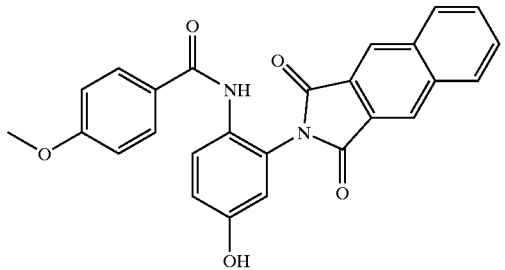

A. N-(4-Methoxybenzoyl)-2-(1,3-dihydro-1,3-dioxo-2H-benz[f]isoindol-2-yl)-4-(tert-butyldimethylsiloxy) benzeneamine Using a similar procedure to that Example 32, $N^1$-(4-methoxybenzoyl)-4-(tert-butyldimethylsiloxy)-1,2-benzenediamine (197 mg, 0.529 mmol) yielded, after purification by flash chromatography (silica gel, hexanes/ethyl acetate), 228 mg (78%) of the title compound.

$^1$H-NMR, IR MS-FD m/e 552 (p) Analysis for $C_{32}H_{32}N_2O_5Si$: Calc: C, 69.54; H, 5.84; N, 5.07; Found: C, 69.81; H, 5.92; N, 5.24.

B. N-(4-Methoxybenzoyl)-2-(1,3-dihydro-1,3-dioxo-2H-benz[f]isoindol-2-yl)-4-hydroxybenzeneamine A solution of N-(4-methoxybenzoyl)-2-(1,3-dihydro-1,3-dioxo-2H-benz[f]isoindol-2-yl)-4-(tert-butyldimethylsiloxy)benzeneamine (48.6 mg, 0.088 mmol) in 2:1 dioxane:methanol (6 mL) was treated with 12 M aqueous hydrochloric acid (0.010 mL). After 6 h, the mixture was concentrated in vacuo and the residue purified by flash chromatography (silica gel; ethyl acetate/hexanes) to yield 24.6 mg (64%) of the title compound.

$^1$H-NMR, IR MS-FD m/e 438 (p) Analysis for $C_{26}H_{18}N_2O_5$: Calc: C, 71.23; H, 4.14; N, 6.39; Found: C, 69.54; H, 4.78; N, 5.63.

EXAMPLE 39

Preparation of N-(4-Methoxyphenyl)-2-(1,3-dihydro-1,3-dioxo-2H-benz[f]isoindol-2-yl)benzamide

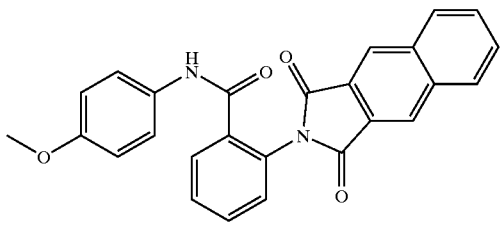

A pressure tube was charged with N-(4-methoxyphenyl)-2-aminobenzamide (500 mg, 2.07 mmol), 2,3-napthalenedicarboxylic anhydride (409 mg, 2.07 mmol), and tetrahydrofuran (10 mL). The resultant slurry was then placed in a bath heated to 110 C for 16 h. After cooling to ambient temperature and concentration to ½ of the solution volume, the product was triturated with 50% hexanes/50% ethyl acetate and the resulting solid collected by filtration. Recrystallization from hexanes/ethyl acetate yielded 476 mg (55%) of the title compound.

$^1$H-NMR, IR MS-FD m/e 422 (p) Analysis for $C_{26}H_{18}N_2O_4$: Calc: C, 73.92; H, 4.29; N, 6.63; Found: C, 73.66; H, 4.35; N, 6.42.

EXAMPLE 40

Preparation of $N^1$-(4-Methoxybenzoyl)-$N^2$-(4-phenylbenzoyl)-1,2-benzenediamine

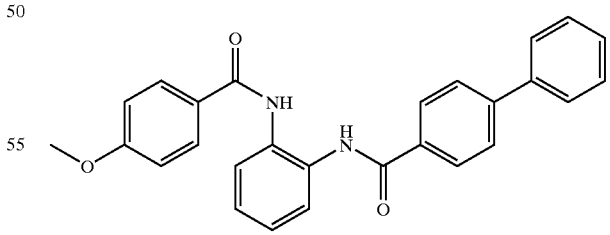

Using a similar procedure to that described for Example 1, Part B, 4-phenylbenzoic acid (200 mg, 1.01 mmol) yielded 75 mg (18%) of the title compound.

$^1$H-NMR, IR MS-FD m/e 422 (p) Analysis for $C_{27}H_{22}N_2O_3$: Calc: C, 76.76; H, 5.25; N, 6.63; Found: C, 76.86; H, 5.46; N, 6.64.

EXAMPLE 41

Preparation of N¹-(4-Methoxybenzoyl)-N²-[1-(4-pyridyl)piperidin-4-ylcarbonyl]-1,2-benzenediamine

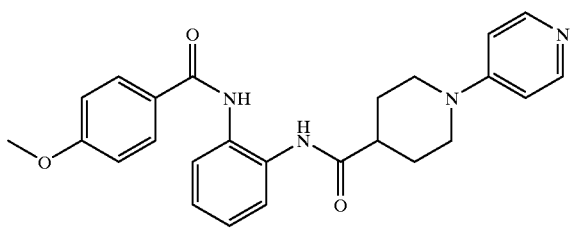

Using a similar procedure to that described for Example 1, Part B, N-(4-pyridyl)isonepicotic acid (400 mg, 1.93 mmol) yielded 114 mg (14%) of the title compound.

¹H-NMR, IR MS-FD m/e 430 (p) Analysis for $C_{25}H_{26}N_4O_3$: Calc: C, 69.75; H, 6.09; N, 13.01; Found: C, 69.23; H, 5.75; N, 12.63.

EXAMPLE 42

Preparation of N¹-(4-Methoxybenzoyl)-N²-[4-(4-piperidinyl)benzoyl]-1,2-benzenediamine

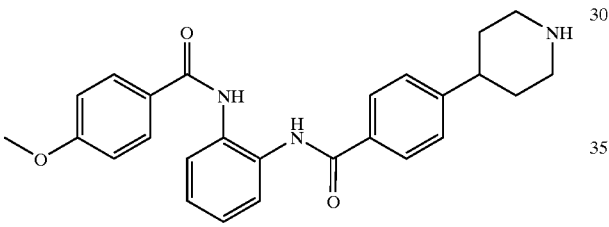

A. 4-[1-(N-tert-butoxycarbonyl)piperidin-4-yl]benzoic acid

A solution of sodium 4-(4-pyridyl)benzoate (1.00 g, 4.52 mmol) and platinum(IV) oxide (200 mg) in 1:1 ethanol/acetic acid was placed under hydrogen gas (4.1 bar). After 6 h, the mixture was filtered and the resulting filtrate concentrated in vacuo. The residue was treated with toluene and concentrated. The residue was dissolved in 1:1 tetrahydrofuran/water (30 mL) and treated with potassium carbonate (1.26 g) and di-tert-butyl dicarbonate (990 mg, 4.54 mmol). After 2 h, the pH of the mixture was adjusted to about 4 by addition of 2 M potassium hydrogen sulfate. The mixture was poured into ethyl acetate. The aqueous layer was separated and extracted several times with a mixture of ethyl acetate and tetrahydrofuran. The combined organic extracts were dried (magnesium sulfate), filtered, and concentrated in vacuo. The residue was purified by reverse phase chromatography (C18, water/acetonitrile) to yield 50 mg (4%) of the title compound.

¹H-NMR

B. N¹-(4-Methoxybenzoyl)-N²-[4-[1-(N-tert-butoxycarbonyl)piperidin-4-yl]benzoyl]-1,2-benzenediamine Using a similar procedure to that described for Example 1, part B, 4-[1-(N-tert-butoxycarbonyl)piperidin-4-yl] benzoic acid (55 mg, 0.18 mmol) yielded 25 mg of the title compound (unpure) which was used in the next reaction without further purification.

¹H-NMR

C. N¹-(4-Methoxybenzoyl)-N²-[4-(4-piperidinyl)benzoyl]-1,2-benzenediamine

A solution of N¹-(4-methoxybenzoyl)-N²-[4-[1-(N-tert-butoxycarbonyl)piperidin-4-yl]benzoyl]-1,2-benzenediamine (25 mg) in trifluoroacetic acid (1 mL) was stirred at room temperature for 0.25 h. Concentration, purification of the residue by ion exchange (SCX resin, Varian), and salt formation by treatment with hydrochloric acid in methanol, followed by trituration with diethyl ether, yielded 6 mg (27%) of the title compound.

¹H-NMR MS-FD m/e 429 (p)

EXAMPLE 43

Preparation of N¹-(4-Methoxybenzoyl)-N²-[4-(4-pyridyl)benzoyl]-1,2-benzenediamine

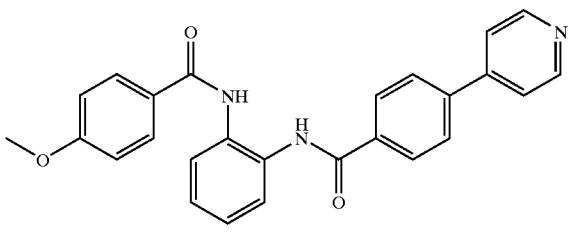

Using a similar procedure to that described for Example 1, Part B, sodium 4-(4-pyridyl)benzoate (300 mg, 1.36 mmol) yielded 6.2 mg (1%) of the title compound.

¹H-NMR MS-FD m/e 424 (p)

EXAMPLE 44

Preparation of N¹-(4-Methoxybenzoyl)-N²-[4-(benzoyl)benzoyl]-1,2-benzenediamine

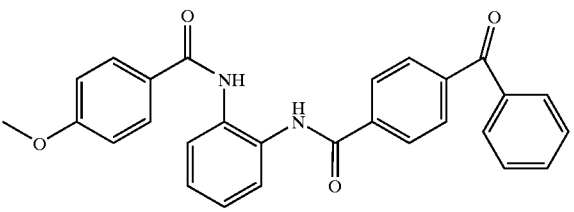

Using a similar procedure to that described for Example 1, Part B, 4-benzoylbenzoic acid (200 mg, 0.88 mmol) yielded 131 mg (33%) of the title compound.

¹H-NMR, IR MS-FD m/e 450 (p) Analysis for $C_{28}H_{22}N_2O_4$: Calc: C, 74.65; H, 4.92; N, 6.22; Found: C, 74.57; H, 4.99; N, 6.20.

EXAMPLE 45

Preparation of N[1]-(4-Methoxybenzoyl)-N[2]-(9-oxo-9-H-fluoren-2-ylcarbonyl)-1,2-benzenediamine

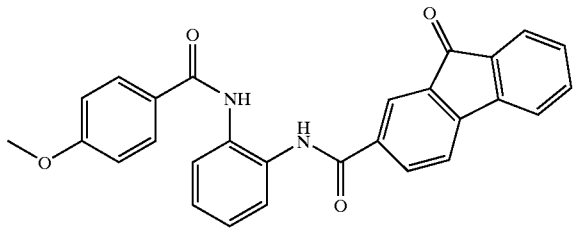

Using a similar procedure to that described for Example 1, Part B, 9-fluorenone-2-carboxylic acid (250 mg, 1.12 mmol) yielded 107 mg (21%) of the title compound.

$^1$H-NMR, IR MS-FD m/e 448 (p) Analysis for $C_{28}H_{20}N_2O_4$: Calc: C, 74.99; H, 4.50; N, 6.25; Found: C, 74.75; H, 4.50; N, 6.52.

EXAMPLE 46

Preparation of N[1]-(4-Methoxybenzoyl)-N[2]-[4-(4-pyridyl)benzyloxycarbonyl]-1,2-benzenediamine

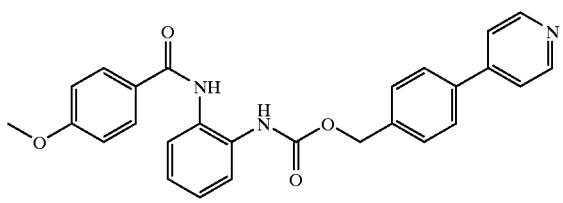

A. 4-(4-Pyridyl)benzyl Alcohol

A solution of sodium 4-(4-pyridyl)benzoate (500 mg, 2.26 mmol), and N-methylmorpholine (0.250 mL, 2.26 mmol) in tetrahydrofuran (12 mL) was treated with ethyl chloroformate (0.216 mL, 2.26 mmol). After 0.25 h, the mixture was treated with sodium borohydride (256 mg, 6.79 mmol) followed by methanol (24 mL) dropwise. After 0.5 h, the mixture was treated with 10% aqueous acetic acid and concentrated in vacuo. The residue was partitioned between ethyl acetate and 1 N aqueous sodium hydroxide. The aqueous layer was extracted twice with ethyl acetate and the combined extracts were dried (magnesium sulfate), filtered, and concentrated in vacuo to yield 140 mg of the title compound which was used without further purification.

$^1$H-NMR

B. N[1]-(4-Methoxybenzoyl)-N[2]-[4-(4-pyridyl)benzyloxycarbonyl]-1,2-benzenediamine Using a similar procedure to that described for Example 24, Part A, 4-(4-pyridyl)benzyl alcohol (140 mg, 0.76 mmol) yielded 25 mg (7%) of the title compound.

$^1$H-NMR MS-FD m/e 453 (p)

EXAMPLE 47

Preparation of N[1]-(4-Methoxybenzoyl)-N[2]-[1-(4-pyridyl)piperidin-4-ylmethoxycarbonyl]-1,2-benzenediamine

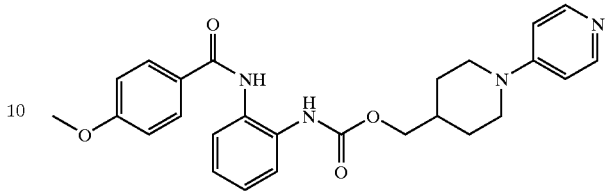

A. 1-(4-Pyridyl)piperidine-4-methanol

A solution of methyl N-(4-pyridyl)isonipecotate (600 mg, 2.72 mmol) in tetrahydrofuran was added to solution of lithium aluminum hydride (100 mg) in tetrahydrofuran (14 mL) cooled to 0° C. Upon consumption of the starting material (0.5–2 h), the mixture was treated with water (0.10 mL), 15% aqueous sodium hydroxide (0.10 mL), and water (0.30 mL). After 0.25 h, the mixture was sonicated for 0.25 h, then poured into a mixture of ethyl acetate, water, sodium tartrate, and potassium tartrate. The aqueous layer was extracted twice with ethyl acetate and the combined extracts were dried (magnesium sulfate), filtered, and concentrated in vacuo to yield 357 mg (68%) of the title compound, which was used without further purification.

$^1$H-NMR,

B. N[1]-(4-Methoxybenzoyl)-N[2]-[1-(4-pyridyl)piperidin-4-ylmethoxycarbonyl)-1,2-benzenediamine Using a similar procedure to that described for Example 24, Part A, 1-(4-pyridyl)piperidine-4-methanol (270 mg, 1.40 mmol) yielded 55 mg (9%) of the title compound.

$^1$H-NMR, IR MS-FD m/e 461 (p+1) Analysis for $C_{26}H_{28}N_4O_4$: Calc: C, 67.81; H, 6.13; N, 12.17; Found: C, 68.03; H, 6.16; N, 12.19.

EXAMPLE 48

Preparation of N[1]-(4-Bromobenzoyl)-N[2]-[1-(4-pyridyl)piperidin-4-ylmethoxycarbonyl)-1,2-benzenediamine

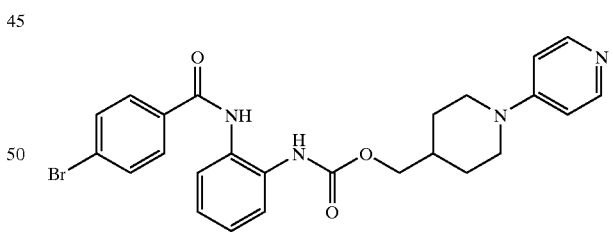

A. 2-Nitro-N-[1-(4-pyridyl)piperidin-4-ylmethoxycarbonyl] benzeneamine

A solution of 2-nitrophenyl isocyanate (4.25 g, 25.9 mmol) and 1-(4-pyridyl)piperidine-4-methanol (4.13 g, 21.5 mmol) in methylene chloride (100 mL) was stirred at room temperature for 18 h. The mixture was concentrated in vacuo and the residue purified by flash chromatography (silica gel, 5% methanol/1% triethylamine/94% chloroform) to yield 7.55 g (96%) of the title compound.

$^1$H-NMR, IR MS-FD m/e 357 (p+1) Analysis for $C_{18}H_{20}N_4O_4$: Calc: C, 60.67; H, 5.66; N, 15.72; Found: C, 60.43; H, 5.55; N, 15.69.

B. $N^1$-[1-(4-Pyridyl)piperidin-4-ylmethoxycarbonyl)-1,2-benzenediamine

A solution of 2-nitro-N-[1-(4-pyridyl)piperidin-4-ylmethoxycarbonyl)benzeneamine (7.55 g, 21.2 mmol) and 5% palladium-on-carbon (4.00 g) in ethanol (250 mL) was placed under an atmosphere of hydrogen (1 bar). After consumption of the starting material (16–20 h), the mixture was filtered through diatomaceous earth. Hot ethyl acetate was used to wash the filter cake. Concentration of the filtrate in vacuo yielded 6.58 g (96%) of the title compound.

$^1$H-NMR, IR MS-FD m/e 326 (p) Analysis for $C_{18}H_{22}N_4O_2$: Calc: C, 66.24; H, 6.79; N, 17.17; Found: C, 66.36; H, 6.81; N, 17.43.

C. $N^1$-(4-Bromobenzoyl)-$N^2$-[1-(4-pyridyl)piperidin-4-ylmethoxycarbonyl]-1,2-benzenediamine A solution of $N^1$-[1-(4-pyridyl)piperidin-4-ylmethoxycarbonyl]-1,2-benzenediamine (300 mg, 0.920 mmol) and pyridine (0.74 mL) in chloroform (5 mL) was treated with 4-bromobenzoyl chloride (405 mg, 1.84 mmol). After 20 h, the mixture was concentrated and the residue partitioned between water and ethyl acetate. The aqueous layer was extracted three times with ethyl acetate and the combined organics were washed with 1 N aqueous sodium hydroxide, water, saturated sodium chloride solution. The solution was dried (potassium carbonate), filtered, and concentrated in vacuo. Recrystallization (methanol/chloroform and hexanes) yielded 200 mg (43%) of the title compound.

$^1$H-NMR, IR MS-FD m/e 509 (p) Analysis for $C_{25}H_{25}BrN_4O_3$: Calc: C, 58.95; H, 4.95; N, 11.00; Found: C, 58.93; H, 4.97; N, 10.79.

EXAMPLE 49

Preparation of $N^1$-(4-Iodobenzoyl)-$N^2$-[1-(4-pyridyl)piperidin-4-ylmethoxycarbonyl]-1,2-benzenediamine

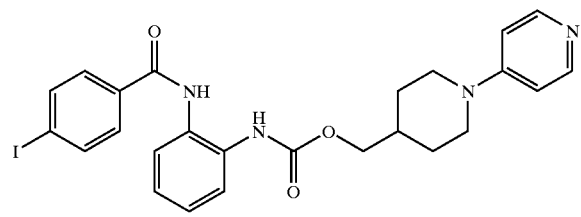

Using a similar procedure to that described in Example 48, Part C, $N^1$-[1-(4-pyridyl)piperidin-4-ylmethoxycarbonyl]-1,2-benzenediamine (300 mg, 0.920 mmol) yielded 379 mg (74%) of the title compound.

$^1$H-NMR, IR MS-FD m/e 556 (p) Analysis for $C_{25}H_{25}IN_4O_3$: Calc: C, 53.97; H, 4.53; N, 10.07; Found: C, 54.15; H, 4.53; N, 9.99.

EXAMPLE 50

Preparation of $N^1$-(3-Methoxybenzoyl)-$N^2$-[1-(4-pyridyl)piperidin-4-ylmethoxycarbonyl]-1,2-benzenediamine

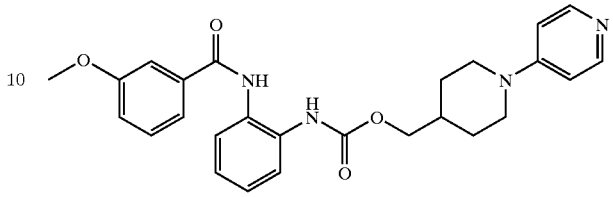

Using a similar procedure to that described in Example 48, Part C, $N^1$-[1-(4-pyridyl)piperidin-4-ylmethoxycarbonyl]-1,2-benzenediamine (300 mg, 0.920 mmol) yielded 300 mg (71%) of the title compound.

$^1$H-NMR, IR MS-FD m/e 461 (p+1) Analysis for $C_{26}H_{28}N_4O_4$: Calc: C, 67.81; H, 6.13; N, 12.17; Found: C, 68.02; H, 5.94; N, 11.95.

EXAMPLE 51

Preparation of $N^1$-(3-Aminobenzoyl)-$N^2$-[1-(4-pyridyl)piperidin-4-ylmethoxycarbonyl]-1,2-benzenediamine

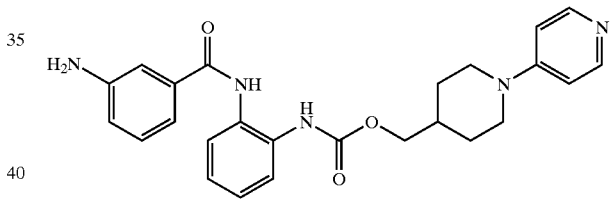

A. $N^1$-(3-Nitrobenzoyl)-$N^2$-[1-(4-pyridyl)piperidin-4-ylmethoxycarbonyl]-1,2-benzenediamine Using a similar procedure to that described in Example 48, Part C, $N^1$-[1-(4-pyridyl)piperidin-4-ylmethoxycarbonyl]-1,2-benzenediamine (300 mg, 0.920 mmol) yielded 200 mg (47%) of the title compound.

$^1$H-NMR, IR MS-FD m/e 465 (p) Analysis for $C_{25}H_{25}ClN_4O_3$: Calc: C, 64.58; H, 5.42; N, 12.05; Found: C, 62.95; H, 5.19; N, 11.31.

B. $N^1$-(3-Aminobenzoyl)-$N^2$-[1-(4-pyridyl)piperidin-4-ylmethoxycarbonyl)-1,2-benzenediamine 4-ylmethoxycarbonyl)-1,2-benzenediamine (370 mg, 0.78 mmol) and 5% palladium-on-carbon (200 mg) in ethanol (10 mL) was placed under an atmosphere of hydrogen (1 atm). After consumption of the starting material, the mixture was filtered through diatomaceous earth and the filtrate concentrated in vacuo. Recrystallization (methanol/diethyl ether) yielded 40 mg (12%) of the title compound.

$^1$H-NMR, IR MS-FD m/e 446 (p+1) Analysis for $C_{25}H_{27}N_5O_3$: Calc: C, 67.40; H, 6.11; N, 15.72; Found: C, 61.81; H, 5.95; N, 14.12.

EXAMPLE 52

Preparation of N¹-(4-Chlorobenzoyl)-N²-[1-(4-pyridyl)piperidin-4-ylmethoxycarbonyl)-1,2-benzenediamine

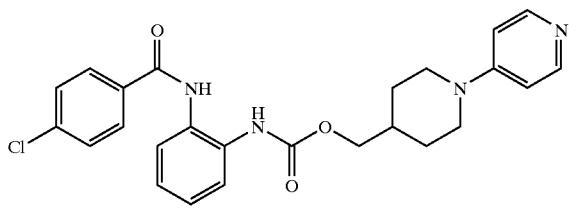

Using a similar procedure to that described in Example 48, Part C, N¹-[1-(4-pyridyl)piperidin-4-ylmethoxycarbonyl)-1,2-benzenediamine (300 mg, 0.920 mmol) yielded 200 mg (47%) of the title compound.

¹H-NMR, IR MS-FD m/e 465 (p) Analysis for $C_{25}H_{25}ClN_4O_3$: Calc: C, 64.58; H, 5.42; N, 12.05; Found: C, 62.95; H, 5.19; N, 11.31.

EXAMPLE 53

Preparation of N¹-(4-Cyanobenzoyl)-N²-[1-(4-pyridyl)piperidin-4-ylmethoxycarbonyl)-1,2-benzenediamine

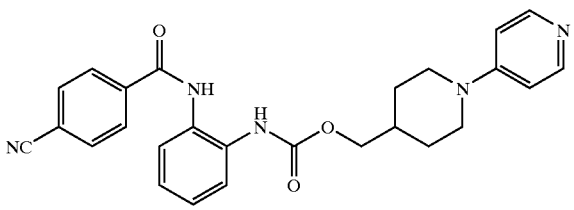

Using a similar procedure to that described in Example 48, Part C, N¹-[1-(4-pyridyl)piperidin-4-ylmethoxycarbonyl)-1,2-benzenediamine (500 mg, 1.53 mmol) yielded 295 mg (42%) of the title compound.

¹H-NMR, IR MS-FD m/e 456 (p+1) Analysis for $C_{26}H_{25}N_5O_3$: Calc: C, 68.56; H, 5.53; N, 15.37; Found: C, 68.37; H, 5.50; N, 15.21.

EXAMPLE 54

Preparation of 2-[(4-t-Butylbenzoyl)amino]-N-(3,4-methylenedioxyphenyl)-5-[(methylsulfonyl)amino]benzamide

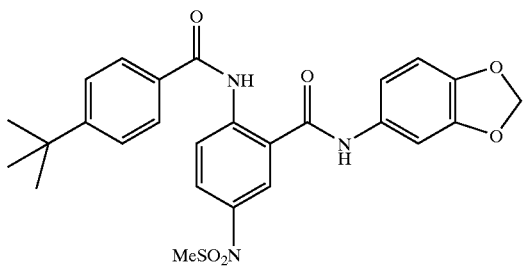

A. 2-[(4-t-Butylbenzoyl)amino]-N-(3,4-methylenedioxyphenyl)-5-nitrobenzamide

By methods substantially equivalent to those described in Example 59-C, 2-[(4-t-butylbenzoyl)amino]-N-(3,4-methylenedioxyphenyl)-5-nitrobenzamide (75%) was prepared from 6-nitro-2-(4-t-butylphenyl)-4H-3,1-benzoxazin-4-one and 3,4-methylenedioxyaniline.

¹H-NMR FD-MS, m/e 461.3 (M⁺) Analysis for $C_{25}H_{23}N_3O_6$: Calc: C, 65.07; H, 5.02; N, 9.11; Found: C, 65.17; H, 5.12; N, 9.06.

B. 5-Amino-2-[(4-t-butylbenzoyl)amino]-N-(3,4-methylenedioxyphenyl)benzamide

By methods substantially equivalent to those described in Example 59-D, 5-amino-2-[(4-t-butylbenzoyl)amino]-N-(3,4-methylenedioxyphenyl)benzamide (100%) was prepared from 2-[(4-t-butylbenzoyl)amino]-N-(3,4-methylenedioxyphenyl)-5-nitrobenzamide.

¹H-NMR FD-MS, m/e 431.2 (M⁺) Analysis for $C_{25}H_{25}N_3O_4 \cdot 0.25H_2O$: Calc: C, 68.87; X, 5.90; N, 9.64; Found: C, 68.87; H, 6.16; N, 9.36.

C. 2-[(4-t-Butylbenzoyl)amino]-N-(3,4-methylenedioxyphenyl)-5-[(methylsulfonyl)amino]benzamide By methods substantially equivalent to those described in Example 59-E, 2-[(4-t-butylbenzoyl)amino]-N-(3,4-methylenedioxyphenyl)-5-[(methylsulfonyl)amino]benzamide (66%) was prepared from 5-amino-2-[(4-t-butylbenzoyl)amino]-N-(3,4-methylenedioxyphenyl)benzamide.

¹H-NMR FD-MS, m/e 509.0 (M⁺) Analysis for $C_{26}H_{27}N_3O_6S$: Calc: C, 61.28; H, 5.34; N, 8.25; Found: C, 62.87; H, 5.67; N, 7.89.

EXAMPLE 55

Preparation of 2-(4-Isopropylbenzoylamino)-N-(4-methoxyphenyl)benzamide

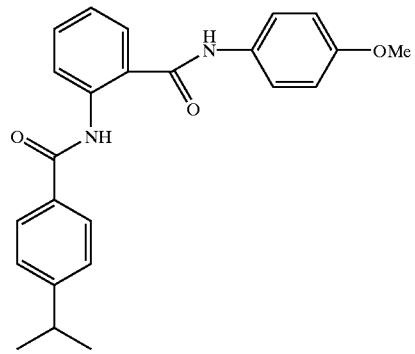

A. 2-Amino-N-(4-methoxyphenyl)benzamide

A mixture of isatoic anhydride (4.9 g, 30 mmol) and p-anisidine (3.7 g, 30 mmol) in toluene (60 mL) was heated to reflux for 5 h. After cooling, the supernatant was decanted and the solid was suspended in methylene chloride (500 mL). The resulting suspension was filtered. The filtrate was combined with the supernatant from above, partially concentrated, diluted with hexane, and decolorized with charcoal. The resulting crystallization provided 5.3 g (73%) of the title compound as a white solid;

mp 116–7° C. ¹H-NMR, IR MS-FD m/e 242 (p). Analysis for $C_{14}H_{14}N_2O_2$: Calc: C, 69.41; H, 5.83; N, 11.56; Found: C, 69.16; H, 5.71; N, 11.31.

B. 2-(4-Isopropylbenzoylamino)-N-(4-methoxyphenyl) benzamide

To a mixture of 4-isopropylbenzoic acid (191 mg, 1.16 mmol) and pyridine (0.12 mL, 1.5 mmol) in toluene (10 mL) was added thionyl chloride (0.11 mL, 1.5 mmol). After heating at 80° C. for 3 h, the reaction mixture was cooled and concentrated in vacuo to give 4-isopropylbenzoyl chloride. A solution of this material (1.16 mmol) in methylene chloride (10 mL) was added to a mixture of 2-amino-N-(4-methoxyphenyl)benzamide (200 mg, 0.83 mmol) and pyridine (0.07 mL, 0.87 mmol) in methylene chloride (15 mL) cooled to 0° C. The reaction mixture was warmed to room temperature and stirred for 1 h. The reaction was partitioned between methylene chloride (25 mL) and 1 N hydrochloric acid (10 mL). The organic layer was dried (magnesium sulfate), filtered, and concentrated in vacuo to give 262 mg (81%) of the title compound as a white solid.

$^1$H-NMR (CDCl$_3$): δ 8.70 (d, 1H, J=9.0 Hz), 8.22 (s, 1H, 7.58 (m, 3H), 7.93 (d, J=10.5, 2H), 7.46 (t, 1H, J=8.7 Hz), 7.35 (d, 2H, J=9.9 Hz), 6.95 (d, 2H, J=10.8 Hz), 7.04 (d, 1H, J=9.0 Hz), 2.98 (s, 1H), 1.28 (d, 6H, J=8.4 Hz); MS-FD m/e 388.1 (p); IR (CHCl$_3$) cm$^{-1}$: 1447, 1512, 1587, 1655. Analysis for C$_{24}$H$_{24}$N$_2$O$_3$: Calc: C, 74.21; H, 6.23; N, 7.21; Found: C, 74.46; H, 6.40; N, 7.35.

EXAMPLE 56

Preparation of 2-(4-Acetylbenzoylamino)-N-(4-methoxyphenyl)benzamide

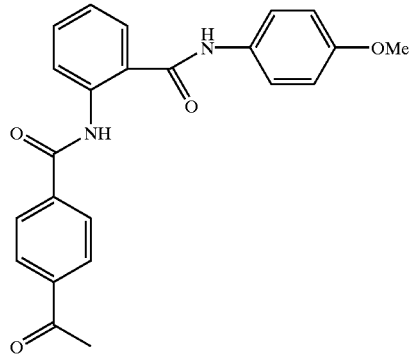

Using the procedure described in Example 55, Part B, 2-amino-N-(4-methoxyphenyl)benzamide (1.06 g, 4.36 mmol) was reacted with 4-acetylbenzoic acid to yield 292 mg (37%) of the title compound as a light yellow solid.

$^1$H-NMR (CDCl$_3$): δ 12.00 (s, 1H), 8.72 (d, 31H, J=9.9 Hz), 8.23 (s, 1H), 8.20 (m, 4H), 7.08 (t, 1H, J=8.4 Hz), 7.54 (m, 4H), 6.96 (d, 2H, J=11.1 Hz), 2.65 (s, 3H), 3.84 (s, 3H); MS-FD m/e 388 (p); IR (CHCl$_3$) cm$^{-1}$: 1249, 1448, 1511, 1683. Analysis for C$_{23}$H$_{20}$N$_2$O$_4$: Calc: C, 71.12; H, 5.19; N, 7.21; Found: C, 71.40; H, 5.36; N, 7.05.

EXAMPLE 57

Preparation of 2-[4-(1-Hydroxyethyl)benzoylamino]-N-(4-methoxyphenyl)benzamide

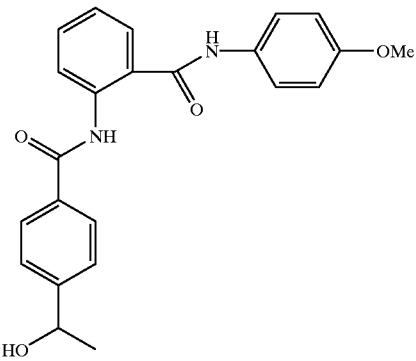

To a solution of 2-(4-acetylbenzoylamino)-N-(4-methoxyphenyl)benzamide (101 mg, 0.260 mmol) in methanol (5 mL) cooled to 0° C. was added sodium borohydride (17 mg, 0.46 mmol). After 20 min, the reaction mixture was quenched with saturated aqueous ammonium chloride solution (1 mL), diluted with methylene chloride (30 mL), and washed with water. The organic layer was dried (magnesium sulfate), filtered, and concentrated in vacuo. The residue was chromatographed (silica gel, 25% ethyl acetate/75% hexanes to 50% ethyl acetate/50% hexanes) to give 85 mg (84%) of the title compound as a yellow solid.

$^1$H-NMR (CDCl$_3$): δ 11.79 (s, 1H), 8.72 (d, 1H, J=9.9 Hz), 8.17 (s, 1H), 7.99 (d, 2H, J=9.9 Hz), 7.51 (m, 6H), 7.07 (t, 1H, J=9.0 Hz), 6.95 (d, 2H, J=10.5 Hz), 4.97 (q, 1H, J=7.8 Hz), 3.83 (s, 3H), 1.52 (d, 3H, J=7.5 Hz). Analysis for C$_{23}$H$_{22}$N$_2$O$_4$.0.25 H$_2$O: Calc: C, 69.96; H, 5.74; N, 7.09; Found: C, 69.84; H, 5.75; N, 7.08.

EXAMPLE 58

2-[4-(1-Hydroxy-1-methylethyl)benzoylamino]-N-(4-methoxyphenyl)benzamide

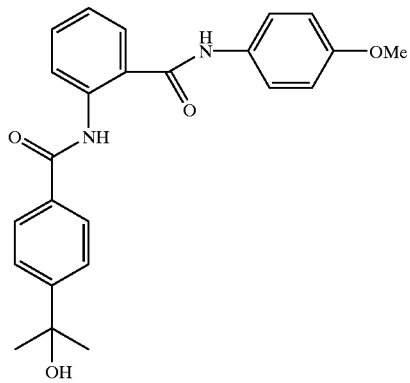

To a solution of 2-(4-acetylbenzoylamino)-N-(4-methoxyphenyl)benzamide (161 mg, 0.410 mmol) in tetrahydrofuran (10 mL) cooled to 0° C. was added 3 M methyl magnesium bromide in diethyl ether (0.2 mL, 0.6 mmol). After 1 h, the reaction mixture was quenched with saturated aqueous ammonium chloride solution (2 mL), diluted with ether, and washed with water. The organic layer was dried (magnesium sulfate), filtered, and concentrated in vacuo. The residue was chromatographed (silica gel, 15% ethyl acetate/85% hexanes to 35% ethyl acetate/65% hexanes) to give 24 mg (14%) of the title compound as a white solid.

$^1$H-NMR (CDCl$_3$): δ 8.78 (d, 1H, J=8.4 Hz), 8.17 (s, 1H), 8.02 (d, 2H, J=8.4 Hz), 7.55–7.67 (m, 6H), 7.13 (t, 1H, J=8.4 Hz), 6.99 (d, 2H, J=3.7 Hz), 3.88 (s, 3H), 1.64 (d, 6H, J=9.3 Hz); MS-FD m/e 404 (p).

EXAMPLE 59

Preparation of 2-(4-tert-Butylbenzoylamino)-5-methylsulfonylamino-N-(4-methoxyphenyl)benzamide

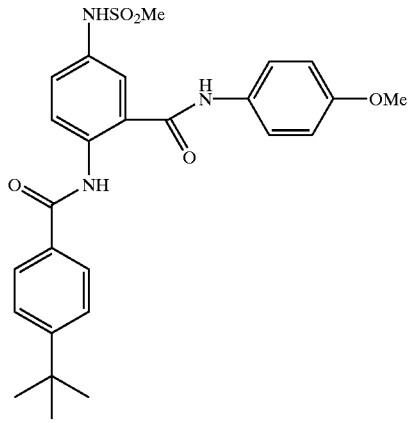

A. 2-(4-tert-Butylbenzoylamino)-5-nitrobenzoic Acid

To a mixture of 5-nitroanthranilic acid (24.6 g, 135 mmol) and pyridine (14.2 mL, 175 mmol) in N,N-dimethylformamide (140 mL) cooled to 0° C. was added tert-butylbenzoyl chloride (31.6 mL, 162 mmol). After stirring for 1 h, the reaction mixture was heated at 75° C. for 4 h, cooled, and poured into an ice/water mixture. The resulting solid was filtered, washed with water and a 1:2 mixture of diethyl ether/hexanes, and dried in vacuo at 150° C. for 2 h to give 37.1 g (80%) of the title compound as a light brown solid; mp 245–9° C. MS-FD m/e 342 (p) Analysis for C$_{18}$H$_{18}$N$_2$O$_5$: Calc: C, 63.15; H, 5.30; N, 8.18; Found: C, 62.85; H, 5.05; N, 8.48.

B. 6-Nitro-2-(4-tert-butylphenyl)-4H-3,1-benzoxazin-4-one

To a suspension of 2-(4-tert-butylbenzoylamino)-5-nitrobenzoic acid (37.1 g, 108 mmol) and N,N-dimethylformamide (0.4 mL, 5.4 mmol) in methylene chloride (200 mL) was added oxalyl chloride (10.4 mL, 119 mmol) in a dropwise manner. After stirring for 2 h, the mixture was filtered and the small amount of black solid was discarded. The filtrate was concentrated in vacuo to give 32.9 g (94%) of the title compound as a light brown solid; mp 159–61° C.

$^1$H-NMR, IR MS-FD m/e 324 (p) Analysis for C$_{18}$H$_{16}$N$_2$O$_4$: Calc: C, 66.66; H, 4.97; N, 8.64; Found: C, 66.54; H, 4.79; N, 8.55.

C. 2-(4-tert-Butylbenzoylamino)-5-nitro-N-(4-methoxyphenyl)benzamide

A mixture of 6-nitro-2-(4-tert-butylphenyl)-4H-3,1-benzoxazin-4-one (1.21 g, 3.73 mmol) and p-anisidine (551 mg, 4.47 mmol) in N,N-dimethylformamide (5 mL) was heated at 80° C. for 2.5 h. After cooling to room temperature, the reaction mixture was poured into an ice/water mixture and extracted twice with methylene chloride. The combined organic layers were washed with water, dried (sodium sulfate), and filtered. From the resulting solution crystallized 706 mg (42%) of the title product as a light brown solid. The mother liquor was chromatographed (silica gel, 20% diethyl ether/80% hexanes to 40% diethyl ether/60% hexanes) to give 242 mg (14%) of additional product; mp 210–11° C.

$^1$H-NMR, IR MS-FD m/e 447 (p) Analysis for C$_{25}$H$_{25}$N$_3$O$_5$: Calc: C, 67.10; H, 5.63; N, 9.39; Found: C, 67.09; H, 5.59; N, 9.17.

D. 2-(4-tert-Butylbenzoylamino)-5-amino-N-(4-methoxyphenyl)benzamide

A mixture of 2-(4-tert-butylbenzoylamino)-5-nitro-N-(4-methoxyphenyl)benzamide (895 mg, 2.00 mmol), 10% palladium-on-carbon (90 mg) and ethyl acetate (5 mL) in ethanol (5 mL) was hydrogenated at one atmospheric pressure for 5 h. The reaction was degassed and a suspension of 10% palladium-on-carbon (45 mg) and ethyl acetate (3 mL) was added. This mixture was hydrogenated for 2 days at one atmosphere. The reaction was filtered through diatomaceous earth assisted by ethyl acetate/ethanol washes. The filtrate was concentrated in vacuo and chromatographed (silica gel, 10% ethyl acetate/90% methylene chloride to 35% ethyl acetate/65% methylene chloride) to give 487 mg (58%) of the title compound as a white solid; mp 212–214.5° C.

$^1$H-NMR, IR MS-FD m/e 417 (p) Analysis for C$_{25}$H$_{27}$N$_3$O$_3$: Calc: C, 71.92; H, 6.52; N, 9.80; Found: C, 71.38; H, 6.56; N, 9.80.

E. 2-(4-tert-Butylbenzoylamino)-5-methylsulfonylamino-N-(4-methoxyphenyl)benzamide To a solution of 2-(4-tert-butylbenzoylamino)-5-amino-N-(4-methoxyphenyl)benzamide (150 mg, 0.36 mmol) in methylene chloride (5 mL) cooled to 0° C. was added pyridine (32 μl, 0.40 mmol) followed by-,methanesulfonyl chloride. (31 μl, 0.40 mmol). After 5 min, the reaction mixture was allowed to warm to room temperature and stirred for 30 min. The reaction mixture was diluted with methylene chloride and washed twice with water. The organic layer was dried (magnesium sulfate), filtered, and concentrated in vacuo. The residue was chromatographed (silica gel, 30% ethyl acetate/70% methylene chloride) to give 130 mg (73%) of the title compound.

$^1$H-NMR (DMSO-d$_6$): δ 11.24 (s, 1H), 9.81 (s, 1H), 10.47 (s, 1H), 8.31 (d, 1H, J=9.00 Hz), 7.80 (d, 2H, J=7,8 Hz), 7.61 (s, 1H), 7.56 (d, 4H, J=7.8 Hz), 7.39 (d, 1H, J=8.7 Hz), 6.93 (d, 2H, J=8.7 Hz), 3.73 (s, 3H), 3.04 (s, 3H), 1.29 (s, 9H); MS-FD m/e 495 (p); IR (CHCl$_3$) cm$^{-1}$: 1158, 1325, 1512, 1610, 1654. Analysis for C$_{26}$H$_{29}$N$_3$O$_5$S.0.50 H$_2$O: Calc: C, 61.90; H, 5.99; N, 8.33; Found: C, 61.99; H, 5.80; N, 7.89.

EXAMPLE 60a

Preparation of 2-(4-tert-Butylbenzoylamino)-4-ethylamino-N-(4-methoxyphenyl)benzamide

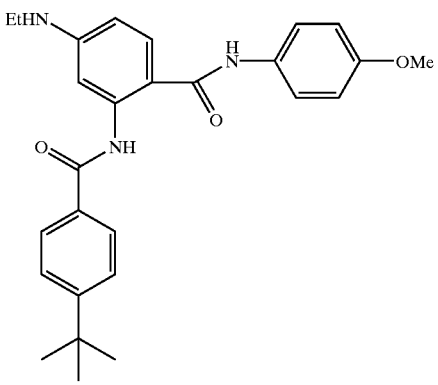

A. 2-Amino-4-nitro-N-(4-methoxyphenyl)benzamide

A mixture of 4-nitroisatoic anhydride (2.08 g, 10.0 mmol) and p-anisidine (1.35 g, 11.0 mmol) in N,N-dimethylformamide (10 mL) was heated at 80° C. for 2.5 h. After cooling, the reaction was poured into ice cold 3 N hydrochloric acid (60 mL). The resulting solid was filtered and washed with 1 N hydrochloric acid and water. Drying in vacuo gave 2.73 g (95%) of the title compound as a greenish yellow solid; mp 193–7° C.

$^1$H-NMR, IR MS-FD m/e 287 (p) Analysis for $C_{14}H_{13}N_3O_4$: Calc: C, 58.53; H, 4.56; N, 14.63; Found: C, 58.41; p, 4.58; N, 14.46.

B. 2-(4-tert-Butylbenzoylamino)-4-nitro-N-(4-methoxyphenyl)benzamide

To a mixture of 2-amino-4-nitro-N-(4-methoxyphenyl) benzamide (2.0 g, 7.0 mmol) and pyridine (0.62 mL, 7.7 mmol) in methylene chloride (40 mL) was added 4-tert-butylbenzoyl chloride (1.44 mL, 7.35 mmol). After stirring for 1.5 h, silica gel (30 g) was added and the solvent evaporated with a stream of nitrogen. The resulting material was chromatographed (silica gel, 5% hexanes/95% methylene chloride to 1.25% ethyl acetate/98.75% methylene chloride) to give 2.41 g (77%) of the title compound as a yellow solid; mp 221° C.

$^1$H-NMR, IR MS-FD m/e 287 (p) Analysis for $C_{14}H_{13}N_3O_4$: Calc: C, 58.53; H, 4.56; N, 14.63; Found: C, 58.41; H, 4.58; N, 14.46.

C. 2-(4-tert-Butylbenzoylamino)-4-ethylamino-N-(4-methoxyphenyl)benzamide and 2-(4-tert-Butylbenzoylamino)-4-amino-N-(4-methoxyphenyl)benzamide Using the procedure described in Example 59, Part D, and using a mixture of ethyl acetate (40 mL), ethanol (20 mL), and glacial acetic acid (4 mL, dried over activated molecular sieves) as solvent, 2-(4-tert-butylbenzoylamino)-4-nitro-N-(4-methoxyphenyl)benzamide (2.0 g, 4.5 mmol) yielded the title compounds:

2-(4-tert-Butylbenzoylamino)-4-ethylamino-N-(4-methoxyphenyl)benzamide (467 mg, 23%); mp 205–7.5° C. TLC: Rf=0.7 (10% ethyl acetate/90% methylene chloride)

$^1$H-NMR, IR MS-FD m/e 445 (p) Analysis for $C_{27}H_{31}N_3O_3$: Calc: C, 72.78; H, 7.01; N, 9.43; Found: C, 72.86; H, 7.10; N, 9.41

2-(4-tert-Butylbenzoylamino)-4-amino-N-(4-methoxyphenyl)benzamide (1.13 g, 61%); mp 137–40° C. TLC: Rf=0.2 (10% ethyl acetate/90% methylene chloride)

$^1$H-NMR, IR MS-FD m/e 417 (p) Analysis for $C_{25}H_{27}N_3O_3$: Calc: C, 71.92; H, 6.52; N, 10.06; Found: C, 72.04; R, 6.65; N, 9.87.

EXAMPLE 60b

Preparation of 2-(4-tert-Butylbenzoylamino)-4-phenylsulfonylamino-N-(4-methoxyphenyl)benzimide

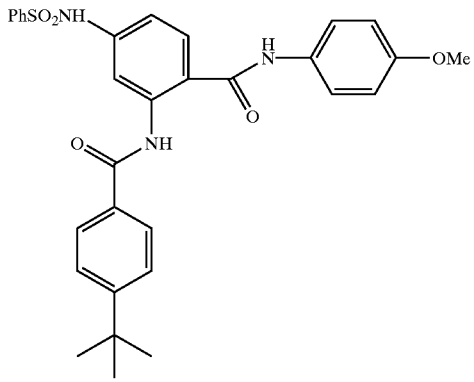

Using the procedure described in Example 59, Part E, 2-(4-tert-butylbenzoylamino)-4-amino-N-(4-methoxyphenyl)benzamide (150 mg, 0.36 mmol) was reacted with benzenesulfonyl chloride to yield 112 mg (56%) of the title compound as a white solid.

$^1$H-NMR (DMSO-$d_6$): δ 12.14 (s, 1H), 10.84 (s, 1H), 10.24 (s, 1H), 8.55 (s, 1H), 7.89 (d, 2H, J=8.4 Hz), 7.79 (m, 3H), 7.58 (m, 7H), 6.92 (m, 3H), 3.72 (s, 3H), 1.28 (s, 9H); MS-FD m/e 557 (p); IR (CHCl$_3$) cm$^{-1}$: 1156, 1512, 1610, 1651. Analysis for $C_{31}H_{31}N_3O_5S$: Calc: C, 66.77; H, 5.60; N, 7.54; Found: C, 66.67; H, 5.70; N, 7.33.

EXAMPLE 61

Preparation of 2-(4-tert-Butylbenzoylamino)-5-phenylsulfonylamino-N-(4-methoxyphenyl)benzamide

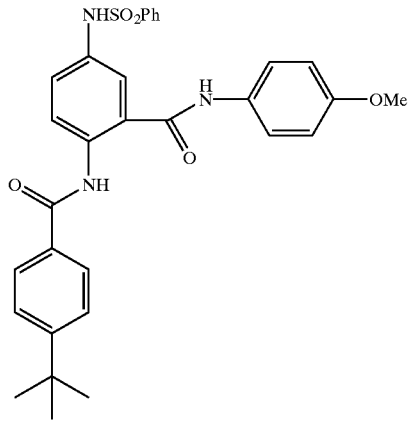

Using the procedure described in Example 59, Part E, benzenesulfonyl chloride (0.40 mmol) yielded 193 mg (96%) of the title compound as a white solid.

$^1$H-(DMSO-$d_6$): δ 11.14 (s, 1H), 10.45 (s, 1H), 10.43 (s, 1H), 8.16 (d, 1H, J=8.7 Hz), 7.55 (m, 8H), 7.77 (m, 4H), 7.21 (d, 1H, J=8.7 Hz), 6.93 (d, 2H, J=8.7 Hz), 3.74 (s, 3H), 1.29 (s, 9H); MS-FD m/e 557 (p); IR (CHCl$_3$) cm$^{-1}$: 1256, 1512, 1609, 1656. Analysis for $C_{31}H_{31}N_3O_5S \cdot 0.5\ H_2O$: Calc: C, 66.24; H, 5.65; N, 7.48; Found: C, 66.01; H, 5.70; N, 7.18.

EXAMPLE 62

Preparation of 2-(4-tert-Butylbenzoylamino)-4-[(L-phenylalanyl)amino]-N-(4-methoxyphenyl)benzamide Trifluoroacetic Acid Salt

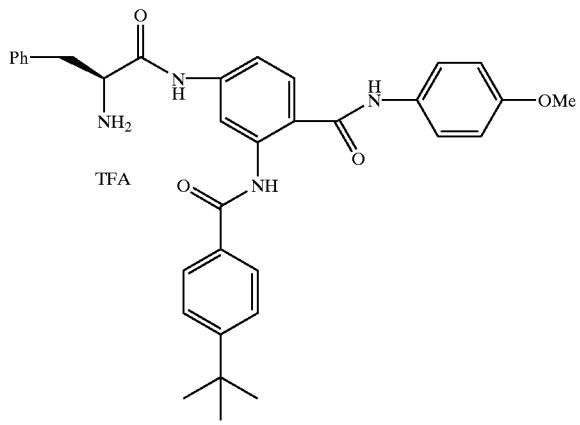

A. 2-(4-tert-Butylbenzoylamino)-4-[[N-(tert-butyloxycarbonyl)-L-phenylalanyl]amino]-N-(4-methoxyphenyl)benzamide To a solution of N-(tert-butoxycarbonyl)-L-phenylalanine (130 mg, 0.49 mmol) in N,N-dimethylformamide (5 mL) cooled to 0° C. was added 2-(4-tert-butylbenzoylamino)-4-amino-N-(4-methoxyphenyl)benzamide (240 mg, 0.49 mmol), dicyclohexylcarbodiimide (112 mg, 0.54 mmol), and 7-aza-1-hydroxybenzotriazole (71 mg, 0.52 mmol). After stirring for 1 h, the reaction mixture was allowed to warm to room temperature. After 12 h, the mixture was filtered and the filtrate diluted with ethyl acetate. The solution was washed with 1 N aqueous sodium carbonate solution, 1.5 N aqueous citric acid solution, and water. The organic layer was dried (magnesium sulfate), filtered, and concentrated in vacuo. The residue was chromatographed (silica gel, 10% ethyl acetate/90% methylene chloride) to give 195 mg (60%) of the title compound.

$^1$H-NMR (CDCl$_3$): δ 11.93 (s, 1H), 8.51 (s, 1H), 8.26–8.19 (m, 2H), 7.95 (d, 2H, J=8.4 Hz), 7.82 (d, 1H, J=9.6 Hz), 7.62 (d, 1H, J=9.3 Hz), 7.53–7.49 (m, 4H), 7.18–7.33 (m, 3H), 6.94 (d, 2H, J=9.0 Hz), 4.32–4.35 (m, 1H), 3.84 (s, 3H), 3.01–3.22 (m, 2H), 1.44 (s, 9H), 1.35 (s, 9H); MS-FD m/e 664 (p). Analysis for $C_{39}H_{44}N_4O_6$: Calc: C, 70.46; H, 6.67; N, 8.43; Found: C, 70.70; H, 6.90; N, 8.55.

B. 2-(4-tert-Butylbenzoylamino)-4-[(L-phenylalanyl)amino]-N-(4-methoxyphenyl)benzamide trifluoroacetic acid salt To a solution of 2-(4-tert-butylbenzoylamino)-4-[[N-(tert-butyloxycarbonyl)-L-phenylalanyl]amino]-N-(4-methoxyphenyl)benzamide (112 mg, 0.17 mmol) in methylene chloride (5 mL) was added trifluoroacetic acid (0.065 mL, 0.84 mmol). After 1.5 h, an additional portion of trifluoroacetic acid (0.50 mL, 6.5 mmol) was added and the resulting mixture stirred for 1 h. The mixture was concentrated in vacuo to give 144 mg (100%) of the title compound as a tan solid.

$^1$H-NMR (DMSO-$d_6$): δ 12.26 (s, 1H), 10.72 (s, 1H), 10.36 (s, 1H), 8.78 (s, 1H), 8.34–8.30 (m, 2H), 7.96 (d, 1H, J=8.4 Hz), 7.83 (d, 2H, J=8.7 Hz), 7.55–7.62 (m, 4H), 7.24–7.34 (m, 3H), 7.02 (d, 1H, J=9.0 Hz), 6.96–6.93 (m, 2H), 6.94 (d, 2H, J=9.0 Hz), 4.20 (m, 1H), 3.74 (s, 3H), 1.29 (s, 9H); MS-FD m/e 564 (p).

EXAMPLE 63

Preparation of 2-(4-tert-Butylbenzoylamino)-4-acetamido-N-(4-methoxyphenyl)benzamide

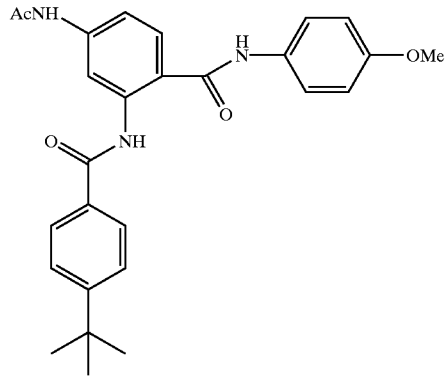

Using the procedure described in Example 59, Part E, 2-(4-tert-butylbenzoylamino)-4-amino-N-(4-methoxyphenyl)benzamide (100 mg, 0.25 mmol) was reacted with acetyl chloride to yield 82 mg (72%) of the title compound.

$^1$H-NMR (DMSO-$d_6$): δ 12.31 (s, 1H), 10.32 (s, 1H), 10.30 (s, 1H), 8.76 (s, 1H), 7.90 (d, 1H, J=8.4 Hz), 7.83 (d, 2H, J=7.8 Hz), 7.71 (d, 1H, J=8.4 Hz), 7.60–7.54 (m, 5 H), 6.93 (d, 2H, J=9.0 Hz), 3.74 (s, 3H), 2.08 (s, 3H), 1.30 (s, 9 H); MS-FD m/e 459 (p). Analysis for $C_{27}H_{29}N_3O_4$: Calc: C, 70.57; H, 6.36; N, 9.19; Found: C, 10.84; H, 6.54; N, 8.89.

EXAMPLE 64

Preparation of 2-(4-tert-Butylbenzoylamino)-4-methylsulfonylamino-N-(4-methoxyphenyl)benzamide

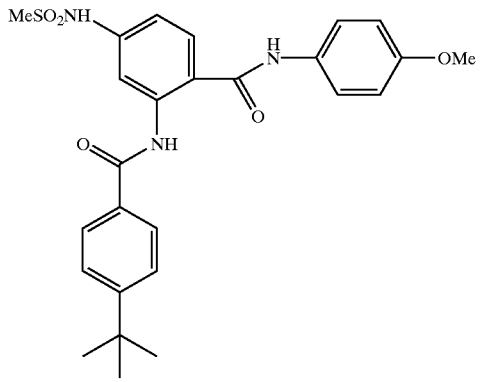

Using the procedure described in Example 59, Part E, 2-(4-tert-butylbenzoylamino)-4-amino-N-(4-methoxyphenyl)benzamide (150 mg, 0.37 mmol) yielded 124 mg (68%) of the title compound as a solid.

$^1$H-NMR (DMSO-d$_6$): δ 12.27 (s, 1H), 10.31 (s, 1H), 8.57 (s, 1H), 10.30 (s, 1H), 7.92 (d, 1H, J=8.7 Hz), 7.83 (d, 2H, J=8.4 Hz), 7.01 (d, 1H, J=8.7 Hz), 7.60–7.54 (m, 4 H), 6.93 (d, 2H, J=9.0 Hz), 3.73 (s, 3H), 1.29 (s, 9 H), 3.11 (s, 3H); MS-FD m/e 495 (p); IR (KBr) cm$^{-1}$: 1155, 1512, 1649, 3337. Analysis for C$_{26}$H$_{29}$N$_3$O$_5$S: Calc: C, 63.09; H, 5.90; N, 8.48; Found: C, 66.12; H, 6.08; N, 9.68.

EXAMPLE 65

Preparation of 2-(4-tert-Butylbenzoylamino)-5-isopropylsulfonylamino-N-(4-methoxyphenyl)benzamide

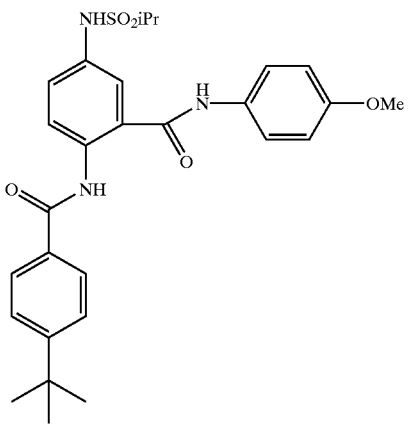

Using the procedure described in Example 59, Part E, isopropylsulfonyl chloride (0.55 mmol) yielded 32 mg (12%) of the title compound as a yellow solid.

$^1$H-NMR (CDCl$_3$): δ 11.69 (s, 1H), 8.65 (d, 1H, J=8.7 Hz), 8.46 (s, 1H), 7.93 (d, 2H, J=7.8 Hz), 7.70 (s, I), 7.57 (d, 2H, J=8.4 Hz), 7.51 (d, 2H, J=7.8 Hz), 6.94 (d, 2H, J=7.5 Hz), 6.78 (m, 1H), 3.26 (m, 1H), 3.83 (s, 3H), 1.37 (a, 6H, J=5.1 Hz), 1.35 (s, 9H); MS-FD m/e 523 (p). Analysis for C$_{28}$H$_{33}$N$_3$O$_5$S: Calc: C, 64.22; H, 6.35; N, 8.02; Found: C, 65.95; H, 6.17; N, 8.13.

EXAMPLE 66

Preparation of 2-(4-tert-Butylbenzoylamino)-5-[(3,5-dimethylisoxazol-4-yl)sulfonylamino]-N-(4-methoxyphenyl)benzamide

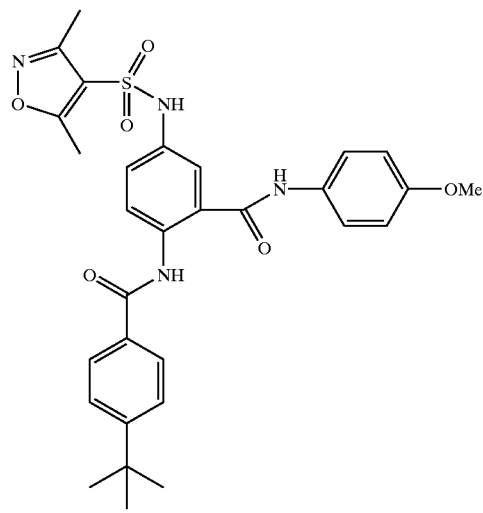

Using the procedure described in Example 59, Part E, 3,5-dimethylisoxazole-4-sulfonyl chloride (0.56 mmol) yielded 149 g (51%) of the title compound as a pale pink solid.

$^1$H-NMR (DMSO-d$_6$): δ 11.19 (s, 1H), 10.60 (s, 1H), 10.44 (s, 1H), 8.22 (d, 1H, J=9.0 Hz), 7.78 (d, 2H, J=8.1 Hz), 7.58–7.52 (m, 5 H), 7.22 (d, 1H, J=9.0 Hz), 6.91 (d, 2H, J=9.0) 3.72 (s, 3H), 2.47 (s, 1.5 H), 2.41 (s, 1.5 H), 2.24 (s, 1.5 H), 2.20 (s, 1.5 H), 1.28 (s, 9 H); MS-FD m/e 576 (p). Analysis for C$_{30}$H$_{32}$N$_4$O$_6$S: Calc: C, 62.48; H, 5.59; N, 9.71; Found: C, 58.27; H, 5.45; N, 8.88.

EXAMPLE 67

Preparation of 2-(4-tert-Butylbenzoylamino)-5-trifluoromethylsulfonylamino-N-(4-methoxyphenyl)benzamide

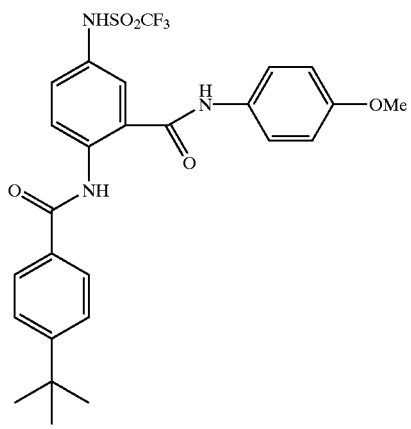

Using the procedure described in Example 59, Part E, trifluoromethanesulfonyl chloride (0.54 mmol) yielded 73 mg (27%) of the title compound as a solid.

$^1$H-NMR (DMSO-d$_6$): δ 10.94 (s, 1H); 10.29 (s, 1H), 7.99 (d, 1H, 8.7 Hz), 7.76 (d, 2H, J=8.4 Hz), 7.58 (d, 2H, J=9.0 Hz), 7.52 (d, 2H, J=8.4 Hz), 6.97 s, 1H), 6.90 (d, 2H, J=9.0 Hz), 6.76 (d, 1H, J=8.7 Hz), 5.24 (br s, 1H), 3.72 (s, 3H), 1.28 (s, 9H); MS-FD m/e 417.2 (M-133). Analysis for C$_{26}$H$_{26}$F$_3$N$_3$O$_5$S: Calc: C, 56.82; H, 4.77; N, 7.65; Found: C, 10.51; H, 6.40; N, 9.30.

EXAMPLE 68

Preparation of N$^1$-(4-Methoxybenzoyl)-N$^2$-(4-propylbenzyl)-4-hydroxy-1,2-benzenediamine

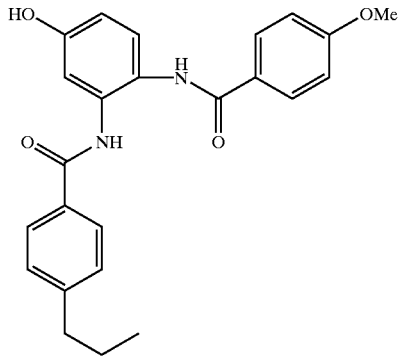

A. N$^1$-(4-Methoxybenzoyl)-N$^2$-(4-propylbenzoyl)-4-(tert-butyldimethylsilyloxy)-1,2-benzenediamine To a solution of N$^1$-(4-methoxybenzoyl)-4-(tert-butyldimethylsilyloxy)-1,2-benzenediamine (300 mg, 0.81 mmol) in methylene chloride (20 mL) was added pyridine (0.13 mL, 1.6 mmol) followed by 4-propylbenzoyl chloride (0.15 mL, 0.89 mmol). The reaction mixture was stirred for 4 h, diluted with methylene chloride, washed with saturated aqueous cupric sulfate solution, dried (magnesium sulfate), filtered, and concentrated in vacuo. The residue was chromatographed (silica gel, methylene chloride to 20% ethyl acetate/80% methylene chloride) to give 400 mg (95%) of the the title compound as a solid.

$^1$H-NMR (DMSO-d$_6$): δ 9.88 (d, 2 H, J=8.7 Hz), 7.92 (d, 2 H, J=9.0 Hz), 7.82 (d, 2 H, J=8.3 Hz), 7.41 (d, 1 H, J=8.7 Hz), 7.32 (d, 2 H, J=8.3 Hz), 7.28 (d, 1 H, J=2.6 Hz), 7.05 (d, 2 H, J=9.0 Hz), 6.76 (dd, 1 H, J=9.0, 3.0 Hz), 3.81 (s, 3 H), 2.60 (t, 2 H, J=7.2 Hz), 1.63–1.56 (m, 2 H), 0.97 (s, 9 H), 0.88 (t, 3 H, J=7.5 Hz), 0.22 (s, 6 H); MS(FAB): 519.3. Analysis for C$_{30}$H$_{38}$N$_2$O$_4$Si: Calc: C, 69.46; H, 7.38; N, 5.40; Found: C, 69.75; H, 7.45; N, 5.30.

B. N$^1$-(4-Methoxybenzoyl)-N$^2$-(4-propylbenzoyl)-4-hydroxy-1,2-benzenediamine To a solution of N$^1$-(4-methoxybenzoyl)-N$^2$-(4-propylbenzoyl)-4-(tert-butyldimethylsilyloxy)-1,2-benzenediamine (360 mg, 0.69 mmol) in tetrahydrofuran (20 mL) cooled to 0° C. was added a 1 M solution of tetra-n-butylammonium fluoride in tetrahydrofuran (1.4 mL, 1.4 mmol). After 15 min, the reaction mixture was diluted with water and partitioned with ethyl acetate. The organic layer was dried (magnesium sulfate), filtered, and concentrated in vacuo. The residue was chromatographed (silica gel, 10% ethyl acetate/90% methylene chloride to 40% ethyl acetate/60% methylene chloride) to give 239 mg (86%) of the title compound as a white solid.

$^1$H-NMR (DRSO-d$_6$): δ 9.84 (s, 1 H), 9.79 (s, 1 H), 9.53 (s, 1 H), 7.92 (d, 2 H, J=9.0 Hz), 7.80 (d, 2 H, J=7.9 Hz), 7.28–7.33 (m, 3 H), 7.20 (d, 1 H, J=2.6 Hz), 7.04 (d, 2 H, J=9.0 Hz), 6.65 (dd, 1H, J=8.7, 2.6 Hz), 3.81 (s, 3 H), 2.60 (t, 2 H, J=7.5 Hz), 1.63–1.55 (m, 2 H), 0.88 (t, 3 H, J=7.2 Hz); MS(FAB): 405.2 (M+1). Analysis for C$_{24}$H$_{24}$N$_2$O$_4$: Calc: C, 71.27; H, 5.98; N, 6.93; Found: C, 71.17; H, 6.11; N, 6.81.

EXAMPLE 69

Preparation of 2-(4-tert-Butylbenzoylamino)-5-hydroxy-N-(4-methyoxyphenyl)benzamide

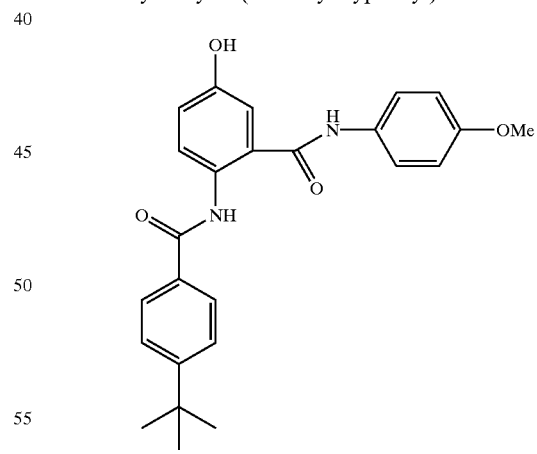

A. 5-Hydroxyisatoic anhydride

To a solution of 5-hydroxyanthranilic acid (46.0 g, 300 mmol) in p-dioxane was added 1.93 M phosgene in toluene (186 mL, 360 mmol) and the resulting mixture stirred for 30 min. The mixture was heated at 65° C. for 4 h. After cooling, 1 N aqueous hydrochloric acid (150 mL) was added and the mixture stirred vigorously. The resulting precipitate was filtered and vacuum dried at 70° C./0.1 mm for 14 h to give 40.7 g (76%) of the title compound as a gray solid.

$^1$H-NMR, IR MS-FD m/e 179 (p) Analysis for $C_8H_5NO_4$: Calc: C, 53.64; H, 2.81; N, 7.82; Found: C, 53.67; H, 2.84; N, 7.59.

B. 5-(tert-Butyldimethylsilyloxy)isatoic anhydride

To a mixture of 5-hydroxyisatoic anhydride (1.6 g, 9.0 mmol) and imidazole (670 mg, 9.9 mmol) in N,N-dimethylformamide (10 mL) was added tert-butyldimethylsilyl chloride N (1.42 g, 9.45 mmol). After stirring for 2 h, the reaction mixture was diluted with ice and water. After warming to room temperature, the resulting precipitate was filtered and washed with water and hexane. The solid was vacuum dried at 55° C./0.1 mm for 14 h to give 2.55 g (96%) of the title compound as a light gray solid; mp 198–200° C. (dec).

$^1$H-NMR, IR MS-FD m/e 293 (p) Analysis for $C_{14}H_{19}NO_4$: Calc: C, 57.31; H, 6.53; N, 4.77; Found: C, 57.38; H, 6.49; N, 4.48.

C. 2-Amino-5-(tert-butyldimethylsilyloxy)-N-(4-methoxyphenyl)benzamide

A mixture of 5-(tert-butyldimethylsilyloxy)isatoic anhydride (734 mg, 2.50 mmol) and p-anisidine (339 mg, 2.75 mmol) in toluene (6 mL) was heated at 80° C. for 3 h. The reaction mixture was cooled and silica gel (3.5 g) was added. The mixture was concentrated in vacuo and the resulting material was chromatographed (silica gel, 1% ethyl acetate/99% methylene chloride to 4% ethyl acetate/96% methylene chloride) to give 547 mg (59%) of the title compound as a light tan solid; mp 82.5–83.5° C. (dec).

$^1$H-NMR, IR MS-FD m/e 372 (p). Analysis for $C_{20}H_{28}N2O_3Si$: Calc: C, 64.48; H, 7.58; N, 7.52; Found: C, 64.52; H, 7.68; N, 7.45.

D. 2-(4-tert-Butylbenzoylamino)-5-(tert-butyldimethylsilyloxy)-N-(4-methoxyphenyl)benzamide Using the procedure described in Example 68, Part A, 2-amino-5-(tert-butyldimethylsilyloxy)-N-(4-methoxyphenyl)benzamide (460 mg, 1.23 mmol) was reacted with 4-tert-butylbenzoyl chloride (0.243 mL, 1.24 mmol) in N,N-dimethylformamide (10 mL). After quenching the reaction with saturated aqueous sodium carbonate, the resulting precipitate was filtered and washed with 2:1 diethyl ether/hexane. The solid was vacuum dried at 85° C./0.1 mm for 14 h to give 553 mg (84%) of the title compound as a white solid; mp 207° C.

$^1$H-NMR, IR MS-FD m/e 532 (p) Analysis for $C_{31}H_{40}N_2O_4Si$: Calc: C, 69.89; H, 7.57; N, 5.26; Found: C, 69.60; H, 7.53; N, 5.30.

E. 2-(4-tert-Butylbenzoylamino)-5-hydroxy-N-(4-methyoxyphenyl)benzamide

Using the procedure described in Example 68, Part B, 2-(4-tert-butylbenzoylamino)-5-(tert-butyldimethylsilyloxy)-N-(4-methoxyphenyl)benzamide (390 mg, 0.73 mmol) yielded 237 mg (78%) of the title compound as a solid.

$^1$H-NMR (DMSO-$d_6$): δ 11.22 (s, 1H), 10.33 (s, 1H), 9.66 (s, 1H), 8.17 (d, 1H, J=9.0 Hz),7.76 (d, 2H, J=8.4 Hz), 7.58–7.51 (m, 4 H), 7.20 (s, 1H), 6.95 (d, 1H, J=9.0 Hz), 6.89 (d, 2H, J=9.0 Hz), 1-26 (s, 9 H), 3.70 (s, 3H); MS-FD m/e 418 (p); IR (KBr) cm$^{-1}$: 1245, 1514, 1596, 1658, 3285. Analysis for $C_{25}H_{26}N_2O_4$: Calc: C, 71.75; H, 6.26; N, 6.69; Found: C, 71.89; H, 6.48; N, 6.57.

EXAMPLE 70

Preparation of $N^1$-(4-Methoxybenzoyl)-$N^2$-(4-methylsulfonylbenzoyl)-1,2-benzenediamine

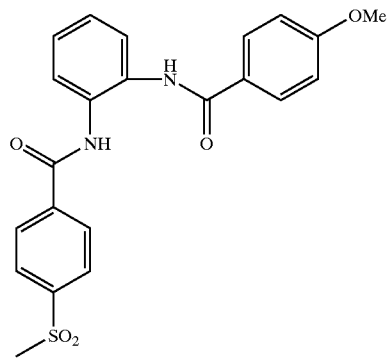

Using the procedure described in Example 55, Part B, $N^1$-(4-methoxybenzoyl)-1,2-benzenediamine (399 mg, 1.65 mmol) and 4-methylsulfonylbenzoic acid (463 mg, 2.31 mmol) yielded 591 mg (84%) of the title compound as a white solid.

$^1$H-NMR (CDCl$_3$): δ 9.75 (s, 1H), 8.51 (s, 1H), 8.15 (d, 2H, J=8.4 Hz), 8.04 (d, 2H, J=8.4 Hz), 7.91 (d, 2H, J=8.7 Hz), 7.71 (d, 1H, J=8.4 Hz), 7.32–7.12 (m, 3H), 7.00 (d, 2n, J=8.7 Hz), 3.88 (s, 3H), 3.08 (s, 3H); MS-FD m/e 424 (p); IR (KBr) cm$^{-1}$: 757, 1155, 1437, 1509, 1659, 3300. Analysis for $C_{22}H_{20}N_2O_5S$: Calc: C, 62.25; H, 4.75; N, 6.60; Found: C, 62.51; H, 5.04; N, 6.47.

EXAMPLE 71

Preparation of $N^1$-(4-Methoxybenzoyl)-$N^2$-[4-(1-methoxy-1-methylethyl)benzoyl]-1,2-benzenediamine

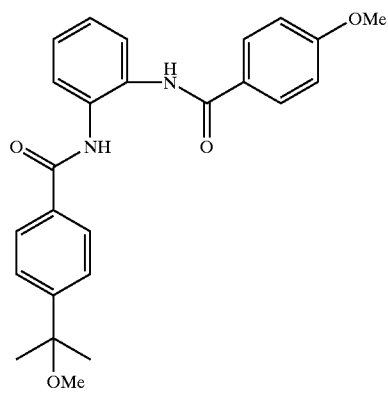

A. Methyl 4-(1-Methoxy-1-methylethyl)benzoate

To a solution of methyl 4-(1-hydroxy-1-methylethyl) benzoate (340 mg, 1.75 mmol) in methanol (20 mL) was added p-toluenesulfonic acid (70 mg, 0.37 mmol). The mixture was refluxed for 48 h, concentrated in vacuo, and the residue chromatographed (silica gel, 10% ethyl acetate/90%hexanes to 30% ethyl acetate/70% hexanes) to give 118 mg (32%) of the title compound.

$^1$H-NMR (CDCl$_3$): δ 8.03 (d, 2H, J=8.4 Hz), 7.49 (d, 2H, J=8.1 Hz), 3.93 (s, 3H): 3.10 (s, 3H), 1.55 (s, 6H); MS-FD:

208 (p). Analysis for $C_{12}H_{16}O_3 \cdot 0.10$ $H_2O$: Calc: C, 68.61; H, 7.77; Found: C, 68.23; H, 7.47.

B. 4-(1-Methoxy-1-methylethyl)benzoic Acid

To a solution of methyl 4-(1-methoxy-1-methylethyl) benzoate (120 mg, 0.57 mmol) in tetrahydrofuran (6 mL) and methanol (2 mL) was added 1 M aqueous lithium hydroxide (2 mL). After stirring for 2 h, the reaction mixture was diluted with diethyl ether and washed with 1 N hydrochloric acid (4 mL) and water (4 mL). The organic layer was dried (magnesium sulfate), filtered, and concentrated in vacuo to give 93 mg (84%) of the title compound.

$^1$H-NMR (CDCl$_3$): δ 1.58 (s, 6H), 3.13 (s, 3H), 7.55 (d, 2H, J=8.1 Hz), 8.11 (d, 2H, J=8.4 Hz); MS-FD m/e 194 (p).

C. $N^1$-(4-Methoxybenzoyl)-$N^2$-[4-(-methoxy-1-methylethyl)benzoyl]-1,2-benzenediamine Using the procedure described in Example 55, Part B. $N^1$-(4-methoxybenzoyl)-1,2-benzenediamine (125 mg, 0.52 mmol) was reacted with 4-[2-(2-methoxypropyl)]benzoic acid (93 mg, 0.48 mmol) to yield 107 mg (49%) of the title compound as a white solid.

$^1$H-NMR (CDCl$_3$): δ 9.36 (s, 1), 9.20 (s, 1H), 7.97–8.02 (m, 4H), 7.55 (d, 2H, J=8.4 Hz), 7.46–7.42 (m, 2H), 7.01 (d, 2H, J=9.0 Hz), 6.92–6.97 (m, 2H), 3.90 (s, 3H), 3.13 (s, 3H), 1.58 (s, 6H); MS-FD m/e 418 (p). Analysis for $C_{25}H_{26}N_2O_4$: Calc: C, 71.75; H, 6.26; N, 6.69; Found: C, 71.68; H, 6.36; N, 6.95.

EXAMPLE 72

Preparation of $N^1$-(4-Methoxybenzoyl)-$N^2$-(4-isopropylbenzoyl)-1,2-benzenediamine

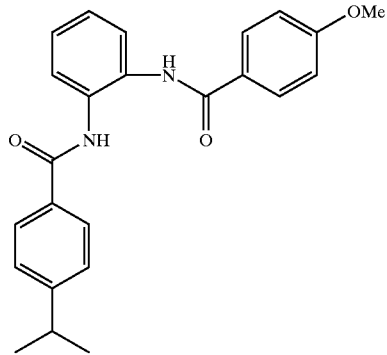

Using the procedure described in Example 55, Part B, $N^1$-(4-methoxybenzoyl)-1,2-benzenediamine (399 mg, 1.65 mmol) yielded 523 mg (82%) of the title compound as a white solid.

$^1$H-NMR (CDCl$_3$): δ 9.23 (s, 1H), 9.21 (s, 1H), 7.99 (d, 2H, J=9.0 Hz), 7.93 (d, 2H, J=8.4 Hz), 7.46–7.40 (m, 2H), 7.36 (d, 2H, J=8.1 Hz), 7.00 (d, 2H, J=8.7 Hz), 6.94–6.92 (m, 2H), 3.00 (m, 1H), 1.30 (d, 6H, J=6.9 Hz); MS-FD m/e 388 (p); IR (CHCl$_3$) cm$^{-1}$: 1256, 1507, 1608, 1646. Analysis for $C_{24}H_{24}N_2O_3$: Calc: C, 74.21; H, 6.23; N, 7.21; Found: C, 73.99; H, 6.37; N, 7.16.

EXAMPLE 73

Preparation of $N^1$-(4-Methoxybenzoyl)-$N^2$-[4-(methylthio))benzoyl]-1,2-benzenediamine

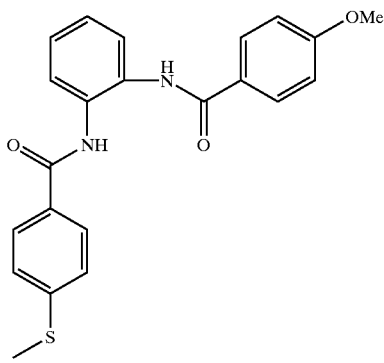

Using the procedure described in Example 55, Part B, $N^1$-(4-methoxybenzoyl)-1,2-benzenediamine (772 mg, 3.19 mmol) was reacted with 4-(methylthio)benzoic acid (772 mg, 4.59 mmol) to yield 1.13 g (91%) of the title compound as a white solid.

$^1$H-NMR (CDCl$_3$): δ 9.37 (s, 1H), 9.18 (s, 1H), 7.95 (d, 2H, J=10.5 Hz), 7.90 (d, 2H, J=10.2 Hz), 7.40–7.33 (m, 2H), 7.30 (d, 2H, J=10.8 Hz), 6.97 (d, 2H, J=10.5 Hz), 6.85 (m, 2H), 3.87 (s, 3H), 2.52 (s, 3H); MS-FD: 392 (p); IR (CHCl$_3$) cm$^{-1}$: 1256, 1508, 1599, 1644. Analysis for $C_{22}H_{20}N_2O_3S$: Calc: C, 67.33; H, 5.14; N, 7.14; Found: C, 67.07; H, 5.39; N, 7.11.

EXAMPLE 74

Preparation of $N^1$-(4-Methoxybenzoyl)-$N^2$-[4-(methylsulfinyl)benzoyl]-1,2-benzenediamine

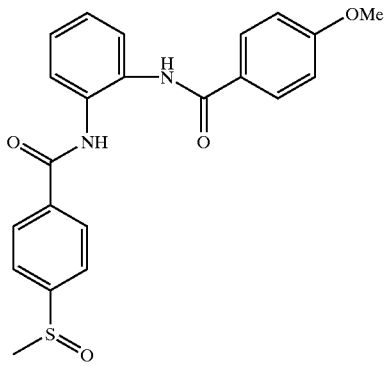

To a solution of $N^1$-(4-Methoxybenzoyl)-$N^2$-[4-(methylthio)benzoyl]-1,2-benzenediamine (417 mg, 0.60 mmol) in chloroform (20 mL), cooled to 0° C. was added m-chloroperoxybenzoic acid (346 mg, 1.16 mmol). After 30 min, the reaction mixture was warmed to room temperature and calcium hydroxide (123 mg, 1.66 mmol) was added. After 15 min, the reaction mixture was filtered and the filtrate concentrated in vacuo. The residue was chromatographed (silica gel, 50% ethyl acetate/50% hexanes to 80% ethyl acetate/20% hexanes) to give 360 mg (83%) of the title compound as a white solid.

$^1$H-NMR (CDCl$_3$): 9.79 (s, 1H), 9.12(s, 1H), 8.13 (d, 2H, J=8.7 Hz), 7.97 (d, 2H, J=8.7 Hz), 7.75 (d, 2H, J=8.7 Hz), 7.32 (m, 1H), 7.45 (m, 1H), 7.00 (d, 2H, J=8.7 Hz), 6.91 (m, 2H), 3.89 (s, 3H), 2.77 (s, 3H); MS-FD: 408 (p); IR (CHCl$_3$) cm$^{-1}$: 1257, 1508, 1607, 1651, 3008. Analysis for C$_{22}$H$_{20}$N$_2$O$_4$: Calc: C, 64.69; H, 4.93; N, 6.86; Found: C, 64.41; H, 5.12; N, 6.91.

EXAMPLE 75

Preparation of N$^1$-(4-Methoxybenzoyl)-N$^2$-[4-(dimethylaminosulfonyl)benzoyl]-1,2-benzenediamine

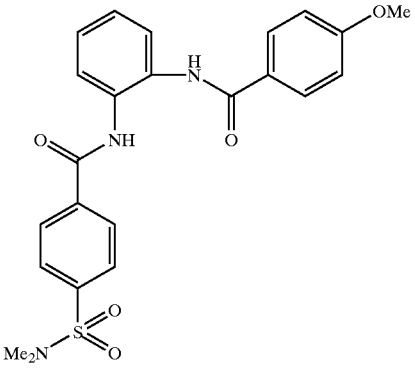

Using the procedure described in Example 55, Part B, N$^1$-(4-methoxybenzoyl)-1,2-benzenediamine (534 mg, 2.21 mmol) was reacted with 4-(dimethylaminosulfonyl)benzoic acid (534 mg, 2.33 mmol) to yield 349 mg (35%) of the title compound.

$^1$H-NMR (CDCl$_3$): δ 9.79 (s, 1H), 8.90 (s, 1H), 8.15 (d, 2H, J=8.4 Hz), 7.96 (d, 2H, J=8.7 Hz), 7.89 (d, 2H, J=8.4 Hz), 7.53 (d, 1H, J=9.3 Hz), 7.32 (d, 1H, J=9.6 Hz), 7.02 (d, 2H, J=9.0 Hz), 6.97 (m, 2H), 3.90 (s, 3H), 2.76 (s, 6H); MS-FD m/e 453 (p); IR (CHCl$_3$) cm$^{-1}$: 1166, 1257, 1508, 1607, 1652. Analysis for C$_{23}$H$_{23}$N$_3$O$_5$S: Calc: C, 60.91; H, 5.12; N, 9.26; Found: C, 61.20; H, 5.06; N, 9.41.

EXAMPLE 76

Preparation of N$^1$-(4-Methoxybenzoyl)-N$^2$-(4-ethylbenzoyl)-4-hydroxy-1,2-benzenediamine

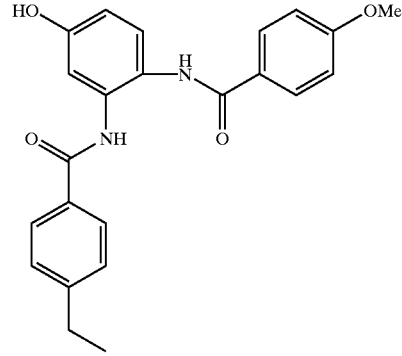

A. N$^1$-(4-Methoxybenzoyl)-N$^2$-(4-ethylbenzoyl)-4-(tert-butyldimethylsilyloxy)-1,2-benzenediamine Using the procedure described in Example 68, Part A, N$^1$-(4-methoxybenzoyl)-4-(tert-butyldimethylsilyloxy)-1,2-benzenediamine (300 mg, 0.81 mmol) was reacted with 4-ethylbenzoyl chloride (0.13 mL, 0.89 mmol) to yield 360 mg (88%) of the title compound as a white solid.

$^1$H-NMR (CDCl$_3$): δ 9.88 (d, 2 H, J=7.5 Hz), 7.93 (d, 2 H, J=9.0 Hz), 7.82 (d, 2 H, J=8.3 Hz), 7.40 (d, 1 H, J=8.7 Hz), 7.34 (d, 2 H, J=8.3 Hz), 7.29 (d, 1 H, J=2.6 Hz), 7.05 (d, 2 H, J=9.0 Hz), 6.76 (dd, 1 H, J=8.7, 3.0 Hz), 3.82 (s, 3 H), 2.65 (q, 2 H, J=7.5 Hz), 1.18 (t, 3 H, J=7.5 Hz), 0.97 (s, 9 H), 0.22 (s, 6 H); MS (G+FAB): 505.2. Analysis for C$_{29}$H$_{36}$N$_2$O$_4$Si.0.25 H$_2$O: Calc: C, 68.40; H, 7.23; N, 5.50; Found: C, 68.22; H, 7.14; N, 5.22.

B. N$^1$-(4-Methoxybenzoyl)-N$^2$-(4-ethylbenzoyl)-4-hydroxy-1,2-benzenediamine

Using the procedure described in Example 68, Part B, N$^1$-(4-methoxybenzoyl)-N$^2$-(4-ethylbenzoyl)-4-(tert-butyldimethylsilyloxy)-1,2-benzenediamine (300 mg, 0.59 mmol) yielded 200 mg (87%) of the title compound as a white solid.

$^1$H-NMR (DMSO-d$_6$): δ 9.84 (s, 1 H), 9.80 (s, 1 H), -9.53 (s, 1 H), 7.92 (d, 2 H, J=8.7 Hz), 7.81 (d, 2 H, J=8.3 Hz), 7.33 (d, 2 H, J=7.9 Hz), 7.29 (d, 1 H, J=9.0 Hz), 7.21 (d, 1 H, J=2.6 Hz), 7.04 (d, 2 H, J=8.7 Hz), 6.65 (dd, 1 H, J=8.7, 2.6 Hz), 3.81 (s, 3 H), 2.65 (q, 2 H, J=7.5 Hz), 1.18 (t, 3 H, J=7.5 Hz); MS-FAB: 391.1 (M+1). Analysis for C$_{23}$H$_{22}$N$_2$O$_4$: Calc: C, 70.75; H, 5.68; N, 7.17; Found: C, 70.48; H, 5.74; N, 7.04.

EXAMPLE 77

Preparation of N$^1$-(3-Carbamoylbenzoyl)-N$^2$-(4-tert-butylbenzoyl)-1,2-benzenediamine

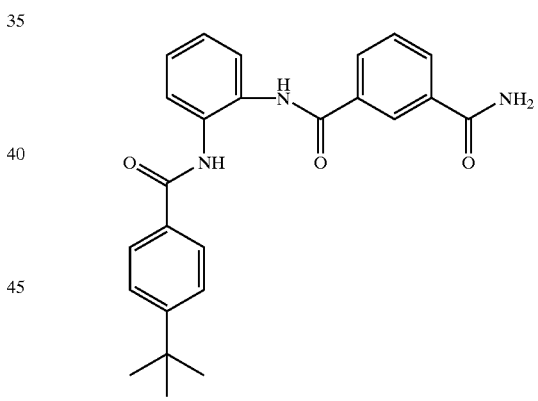

A. N-(3-Cyanobenzoyl)-2-nitroaniline

To a mixture of 3-cyanobenzoyl chloride (10.0 g, 60.4 mmol), triethylamine (12.6 mL, 90.6 mmol), and methylene chloride (120 mL) was added 2-nitroaniline (8.30 g, 60.4 mmol) followed by 4-(dimethylamino)pyridine (738 mg, 6.04 mmol). After stirring for 24 h, the reaction mixture was concentrated in vacuo. Chromatography (silica gel, 30% ethyl acetate/70% hexanes to 50% ethyl acetate/50% hexanes) yielded 17.1 g (99%) of the title compound as a yellow solid.

$^1$H-NMR (DMSO-d$_6$): δ 10.92 (s, 1H), 8.39 (s, 1H), 8.25 (dt, 1H, J=9.9, 1.5 Hz), 8.13 (dt, J=9.3, 1.2 Hz), 8.03 (dd, 1H, J=9.9, 1.8 Hz), 7.69–7.83 (m, 3H), 7.47 (dt, 1H, J=9.0, 2.4 Hz). Analysis for C$_{14}$H$_9$N$_3$O: Calc: C, 62.92; H, 3.39; N, 15.72; Found: C, 62.86; H, 3.44; N, 16.02.

B. $N^1$-(3-Cyanobenzoyl)-1,2-benzenediamine

A mixture of N-(3-cyanobenzoyl)-2-nitroaniline (1.0 g, 3.7 mmol), 10% palladium-on-carbon, and ethyl acetate (250 mL) was hydrogenated at one atmospheric pressure for 30 min. The mixture was filtered through diatomaceous earth and concentrated in vauco. Chromatography (silica gel, 50% ethyl acetate/50% hexanes) of the residue yielded 630 mg (72%) of the title compound as a yellow solid, mp 197–200° C.

$^1$H-NMR (DMSO-d$_6$): δ 9.81 (s, 1H), 8.44 (s, 1H), 8.27 (d, 1H, J=10.1 Hz), 8.05 (d, 1H, J=10.1 Hz), 7.73 (t, 1H, J=10.2 Hz), 7.17 (d, 1H, J=9.4 Hz), 6.98 (t, 1H, J=9.3 Hz), 6.79 (d, 1H, J=9.4 Hz), 6.59 (t, 1H, J=9.3 H), 5.00 (s, 2H); Analysis for C$_{14}$H$_{11}$N$_3$O; Calc: C, 70.87; H, 4.67; N, 17.71; Found: C, 70.68; H, 4.58; N, 17.52.

C. $N^1$-(3-Cyanobenzoyl)-$N^2$-(4-tert-butylbenzoyl)-1,2-benzenediamine

To a solution of $N^1$-(3-cyanobenzoyl)-1,2-benzenediamine (500 mg, 2.1 mmol), triethylamine (0.44 mL, 3.2 mmol) in methylene chloride (100 mL) was added 4-tert-butylbenzoyl chloride (0.41 mL, 2.1 mmol). After stirring for 20 hours, the reaction mixture was concentrated in vacuo. Chromatography (silica gel, 20% ethyl acetate/80% hexanes) yielded 730 mg (87%) of the title compound as a white solid.

$^1$H-NMR (DMSO-d$_6$): δ 10.24 (br s, 1H), 9.90 (br s, 1H), 8.36 (s, 1H), 8.23 (dd, 1H, J=9.6, 1.8 Hz), 8.06 (dd, 1H, J=7.8, 1.5 Hz), 7.88 (d, 2H, J=10.2 Hz), 7.75 (t, 1H, J=9.3 Hz), 7.86–7.72 (m, 1H), 7.61–7.64 (m, 1H), 7.53 (d, 2H, J=10.2 Hz), 7.27–7.32 (m, 2H), 1.27 (s, 9H). Analysis for C$_{25}$H$_{23}$N$_3$O$_2$: Calc: C, 75.54; H, 5.83; N, 10.57; Found: C, 75.69; H, 6.14; N, 10.57.

D. $N^1$-(3-Carbamoylbenzoyl)-$N^2$-(4-tert-butylbenzoyl)-1,2-benzenediamine

To a solution of $N^1$-(3-cyanobenzoyl)-$N^2$-(4-tert-butylbenzoyl)-1,2-benzenediamine (200 mg, 0.5 mmol) in methyl sulfoxide (10 mL) was added 30% hydrogen peroxide solution (0.5 mL, 5.8 mmol) and potassium carbonate (17 mg, 0.13 mmol). After stirring for 24 h, the reaction mixture was diluted with water (20 mL), filtered, washed with water, and dried to give 90 mg (43%) of the title compound as a white solid.

$^1$H-NMR (DMSO-d$_6$): δ 10.09 (s, 1 H), 9.84 (s, 1 H), 8.37 (s, 1 H), 8.06–7.94 (m, 3 H), 7.78 (d, 2 H, J=8.3 Hz), 7.70–7.67 (m, 1 H), 7.34–7.62 (m, 6 H), 7.18–7.21 (m, 2 H), 1.19 (s, 9 H); MS-FD: 415 (p). Analysis for C$_{25}$H$_{25}$N$_3$O$_3$.0.33 H$_2$O: Calc: C, 71.25; H, 6.14; N, 9.97; Found: C, 71.30; H, 6.45; N, 9.45;

EXAMPLE 78
Preparation of $N^1$-(3-Carbamoylbenzoyl)-$N^2$-(3-chlorobenzo[b]thiophen-2-ylcarbonyl)-1,2-benzenediamine

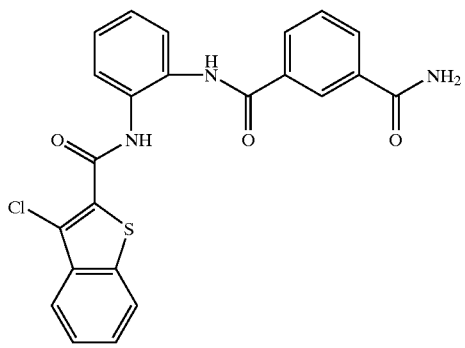

A. $N^1$-(3-Cyanobenzoyl)-$N^2$-(3-chlorobenzo[b]thiophen-2-ylcarbonyl)-1,2-benzenediamine To a mixture of $N^1$-(3-cyanobenzoyl)-1,2-benzenediamine (500 mg, 2.1 mmol) and triethylamine (0.44 mL, 3.2 mmol) in methylene chloride (100 mL) was added 3-chlorobenzo[b]thiophene-2-carbonyl chloride (490 mg, 2.1 mmol). After stirring for 20 h, the mixture was concentrated in vacuo and chromatographed (silica gel, 25% ethyl acetate/75% hexane) to give 660 mg (73%) of the title compound as a white solid.

$^1$H-NMR (DMSO-d$_6$): δ 10.47 (br s, 1 H), 9.75 (br s, 1 H), 8.48 (s, 1 H), 8.32 (d, 1 H, J=9.9 Hz), 8.14–8.08 (m, 2 H), 7.95–7.85 (m, 2 H), 7.78 (t, 1 H, J=9.3 Hz), 7.64–7.50 (m, 3 H), 7.42–7.29 (m, 2 H); MS-FD m/e 430.9 (M−1). Analysis for C$_{23}$H$_{14}$ClN$_3$O$_2$S: Calc: C, 63.96; H, 3.27; N, 9.73; Found: C, 63.62; H, 3.44; N, 10.38.

B. $N^1$-(3-Carbamoylbenzoyl)-$N^2$-(3-chlorobenzo[b]thiophen-2-ylcarbonyl)-1,2-benzenediamine Using the procedure described in Example 68, $N^1$-(3-cyanobenzoyl)-$N^2$-(3-chlorobenzo[b]thiophen-2-ylcarbonyl)-1,2-benzenediamine (300 mg, 0.69 mmol) yielded 100 mg (32%) of the title compound as a white solid.

$^1$H-NMR (DMSO-d$_6$): δ 10.44 (s, 1 H), 9.74 (s, 1 H), 8.55 (s, 1 H), 8.17–8.08 (m, 4 H), 7.98–7.95 (m, 1 H), 7.85–7.88 (m, 1 H), 7.67–7.51 (m, 5 H), 7.41–7.29 (m, 2 H); MS-FD m/e 449.0 (M+1). Analysis for C$_{23}$H$_{16}$ClN$_3$O$_3$S: Calc: C, 61.40; H, 3.58; N, 9.34; Found: C, 61.46; H, 3.85; N, 9.25.

EXAMPLE 79
Preparation of $N^1$-(4-tert-Butylbenzoyl)-4-methoxy-$N^2$-(4-methoxybenzoyl)-1,2-benzenediamine

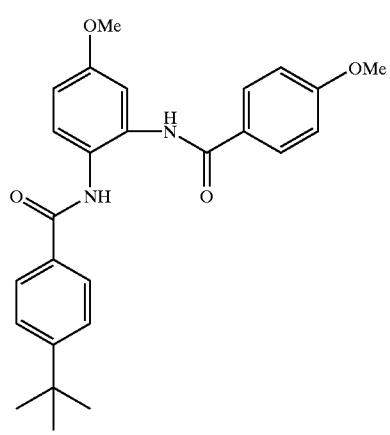

A. 4-Methoxy-2-nitro-N-(4-tert-butylbenzoyl)aniline

Using the procedure described in Example 68, Part A, 4-methoxy-2-nitroaniline (1.0 g, 3.4 mmol) was reacted with 4-tert-butylbenzoyl chloride to yield 1.45 g (100%) of the title compound as a yellow solid.

$^1$H-NMR (DMSO-d$_6$): δ 10.46 (s, 1 H), 7.88 (d, 2 H. J=9.9 Hz), 7.64 (d, 1 H. J=10.5 Hz), 7.57 (d, 2 H, J=9.9 Hz), 7.53 (d, 1 H, J=3.3 Hz), 7.35 (dd, 1 H, J=10.8, 3.3 Hz), 3.86 (s, 3 H), 1.32 (s, 9 H); MS-FD: 328 (p). Analysis for C$_{18}$H$_{20}$N$_2$O$_4$: Calc: C, 65.84; H, 6.14; N, 8.53; Found: C, 65.92; H, 6.21; N, 8.24.

B. 4-Methoxy-N$^1$-(4-tert-butylbenzoyl)-1,2-benzenediamine

Using the procedure described in Example 59, Part D, 4-methoxy-2-nitro-N-(4-tert-butylbenzoyl)aniline (3.32 g, 10.1 mmol) yielded 3.35 g (100%) of the title compound as a white solid.

$^1$H-NMR (DMSO-d$_6$): δ 9.46 (s, 1 H), 7.90 (d, 2 H, J=9.9 Hz), 7.51 (d, 2 H. J=9.9 Hz), 7.00 (d, 1 H, J=10.2 Hz), 6.35 (d, 1 H, J=3.0 Hz), 6.18 (dd, 1H, J=10.2, 3.0 Hz), 4.89 (s, 2H), 3.68 (dd, 1 H, J=10.2, 3.0 Hz), 1.32 (s, 9 H); MS-FD m/e 298 (p). Analysis for C$_{18}$H$_{22}$N$_2$O$_2$: Calc: C, 72.46; H, 7.43; N, 9.39; Found: C, 72.25; H, 7.35; N, 9.32.

C. N$^1$-(4-tert-Butylbenzoyl)-4-methoxy-N$^2$-(4-methoxybenzoyl)-1,2-benzenediamine Using the procedure described in Example 68, Part A, 4-methoxy-N$^1$-(4-tert-butylbenzoyl)-1,2-benzenediamine (3.35 g, 10.1 mmol) was reacted with 4-methoxybenzoyl chloride to yield 1.45 g (99%) of the title compound as a white solid.

$^1$H-NMR (DMSO-d$_6$): δ 9.92 (s, 2 H), 7.90 (t, 4 H, J=10.8 Hz), 7.53 (d, 2 H, J=10.2 Hz), 7.48 (d, 1 H, J=10.8 Hz), 7.31 (d, 1 H, J=3.3 Hz), 7.06 (d, 1 H, J=10.8 Hz), 6.87 (dd, 1 H, J=10.8, 3.6 Hz), 3.82 (s, 3 H), 3.79 (s, 3 H), 1.30 (s, 9 H); MS-FD m/e 6433 (M+1). Analysis for C$_{26}$H$_{28}$N$_2$O$_4$: Calc: C, 72.20; H, 6.53; N, 6.48; Found: C, 72.39, H, 6.55; N, 6.50.

EXAMPLE 80

Preparation of N$^2$-(4-tert-Butylbenzoyl)-[N$^1$-(3-vinylbenzoyl)-1,2-benzenediamine

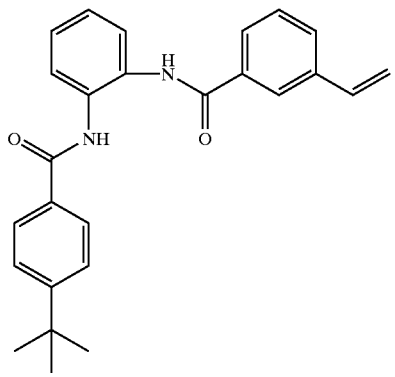

To a solution of 3-vinylbenzoic acid (200 mg, 1.35 mmol) in tetrahydrofuran (10 mL) was added thionyl chloride (241 mg, 2.02 mmol) and pyridine (214 mg, 2.7 mmol). The reaction was heated at 80° C. for 2 h and cooled to room temperature. N$^1$-(4-tert-Butylbenzoyl)-1,2-benzenediamine (362 mg, 1.35 mmol) was added. After stirring for 2 h, the reaction mixture was diluted with methylene chloride and washed once with saturated aqueous copper sulfate solution, once with saturated aqueous sodium chloride solution, dried (magnesium sulfate), filtered, and concentrated in vacuo. Chromatography (silica gel, 10% ethyl acetate/90% methylene chloride) provided 200 mg (37%) of the title compound as a white solid.

$^1$H-NMR (DMSO-d$_6$): δ 10.09 (s, 1 H), 10.01 (s, 1 H), 8.01 (s, 1 H), 7.91 (d, 2 H, J=8.4 Hz), 7.67–7.70 (m, 2 H), 7.84 (d, 1 H, J=7.8 Hz), 7.29–7.33 (m, 2 H), 7.52–7.56 (m, 2 H), 6.79 (dd, 1 H, J=10.9, 17.7 Hz), 5.94 (d, 1 H, J=17.7 Hz), 5.34 (d, 1 H, J=10.9 Hz), 1.32 (s, 9 H); MS-FAB 399(M+1). Analysis for C$_{26}$H$_{26}$N$_2$O$_2$: Calc: C, 78.36; H, 6.58; N, 7.03; Found: C, 78.32; H, 6.79; N, 7.13.

EXAMPLE 81

Preparation of N$^2$-(4-tert-butylbenzoyl)-N$^2$-(4-fluorobenzoyl)-1,2-benzenediamine

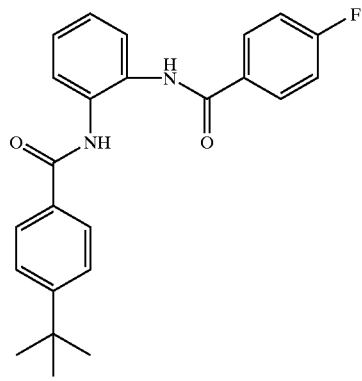

Using the procedure described in Example 80, 4-fluorobenzoic acid (0.71 mmol) yielded 260 mg (94%) of the title compound as a white amorphous solid.

$^1$H-NMR (DMSO-d$_6$): δ 10.08 (s, 1 H), 9.95 (s, 1 H), 8.00–8.04 (m, 2 H), 7.87 (d, 2 H, J=8.3 Hz): 7.68–7.61 (m, 2 H), 7.52 (d, 2 H, J=8.7 Hz), 7.36 (t, 2 H, J=8.3 Hz), 7.30–7.26 (m, 2 H), 1.29 (s, 9 H); MS-FD m/e 390. Analysis for C$_{24}$H$_{23}$FN$_2$O$_2$: Calc: C, 73.83; H, 5.94; N, 7.17; Found: C, 73.57;-H, 6.18; N, 7.06.

EXAMPLE 82

Preparation of N$^2$-(4-tert-butylbenzoyl)-N$^1$-(4-vinylbenzoyl)-1,2-benzenediamine

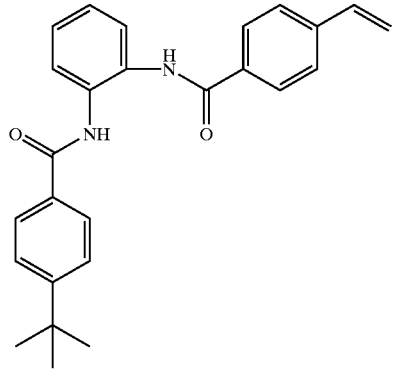

Using the procedure described in Example 80, 4-vinylbenzoic acid (0.67 mmol) yielded 210 g (79%) of the title compound as a white amorphous solid.

1H-NMR (DMSO-d$_6$): δ 10.07 (s, 1 H), 10.01 (s, 1 H), 7.94 (d, 2 H, J=10.2 Hz), 7.88 (d, 2 H, J=10.2 Hz), 7.68–7.61 (m, 4 H), 7.54 (d, 2 H, J=10.5 Hz), 7.31–7.27 (m, 2 H), 6.81 (dd, 1 H, J=21.3, 13.2 hz), 5.99 (d, 1 H, J=21.0 Hz), 5.40 (d, 1 H, J=13.5 Hz), 1.30 (s, 9 H); MS-FD m/e 398 (p). Analysis for C$_{26}$H$_{26}$N$_2$O$_2$: Calc: C, 78.36; H, 6.58; N, 7.03; Found: C, 78.10; H, 6.65; N, 7.02.

EXAMPLE 83

Preparation of N$^2$-(4-tert-Butylbenzoyl)-N$^2$-(3-cyanobenzoyl)-1,2-benzenediamine

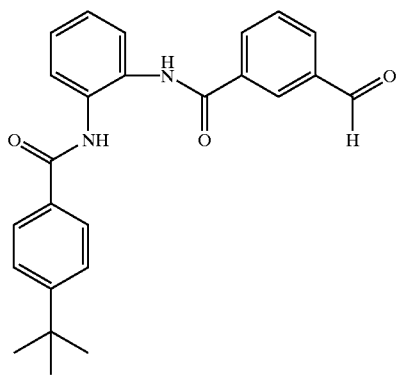

To a mixture of N$^2$-(4-tert-butylbenzoyl)-N$^1$-(3-cyanobenzoyl)-1,2-benzenediamine (1.0 g, 2.5 mmol), water (25 mL), and acetic acid (25 mL) in pyridine (50 mL) was added sodium hypophosphite monohydrate (270 mg, 5.0 mmol) and Raney nickel (400 mg). The reaction mixture was heated at 45° C. for 3 h, cooled to room temperature, and filtered through diatomaceous earth. The filtrate was concentrated in vacuo and chromatographed (silica gel, 5% ethyl acetate/95% methylene chloride) to give 56 mg (6%) of the title compound as a white amorphous solid.

$^1$H-NMR (DMSO-d$_6$): δ 10.29 (br s, 1 H), 10.10 (s, 1 H), 9.96 (br s, 1 H), 8.49 (s, 1 H), 8.27 (d, 1 H, J=7.5 Hz), 8.13 d,1 H, J=7.5Hz), 7.92 (d, 2 H, J=8.7 Hz), 7.79 (t, 1 H, J=7.5 Hz), 7.74–7.65 (m, 2 H), 7.54 (d, 2 H, J=8.3 Hz), 7.33–7.30 (m, 2 H), 1.31 (s, 9 H); MS-FD m/e 400 (p). Analysis for C$_{25}$H$_{24}$N$_2$O$_3$: Calc: C, 74.98; H, 6.04; N, 6.99; Found: C, 74.88; H, 6.07; N, 7.08.

EXAMPLE 84

Preparation of N$^2$-(4-tert-butylbenzoyl)-N$^1$-(3-hydroxymethylbenzoyl)-1,2-benzenediamine

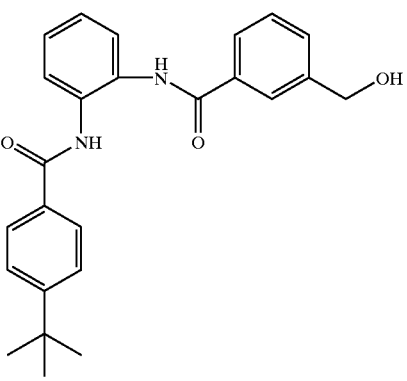

Using the procedure described in Example 57, N$^2$-(4-tert-butylbenzoyl)-N$^2$-(3-formylbenzoyl)-1,2-benzenediamine (230 mg, 0.57 mmol) was reacted in ethanol to yield 227 mg (99%) of the title compound as an off-white amorphous solid.

$^1$H-NMR (DMSO-d$_6$): δ 10.05 (s, 1 H), 9.96 (s, 1 H), 7.92–7.87 (m, 3 H), 7.80 (a, 1 H, J=8.4 Hz), 7.68–7.61 (m, 2 H), 7.55–7.44 (m, 4 H), 7.31–7.26 (m, 2 H), 5.32 (t, 1 H, J=5.5 Hz), 4.55 (d, 2 H, J=5.4 Hz), 1.29 (s, 9 H); MS-FD m/e 402 (p). Analysis for C$_{25}$H$_{26}$N$_2$O$_3$: Calc: C, 74.60; H, 6.51; N, 6.96; Found: C, 74.44; H, 6.70; N, 6.88.

EXAMPLE 85

Preparation of 2-(4-tert-Butylbenzoylamino)-4-dimethylaminosulfonylamino-N-(4-methoxyphenyl)benzamide

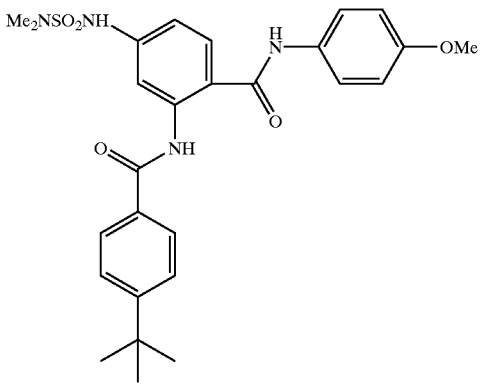

Using the procedure described in Example 59, Part E, 2-(4-tert-butylbenzoylamino)-4-amino-N-(4-methoxyphenyl)benzamide (500 mg, 1.20 mmol) was reacted with dimethylaminosulfonyl chloride to yield 190 mg (30%) of title compound as an orange solid.

$^1$H-NMR (DMSO-d$_6$): δ 12.28 (s, 1 H), 10.37 (s, 1 H), 10.30 (s, 1 H), 8.60 (d, 1 H, J=2.1 Hz), 7.91–7.83 (m, 3 H), 7.61–7.55 (m, 4 H), 7.03–6.93 (m, 3 H), 3.75 (s, 3 H), 2.79 (s, 6 H), 1.31 (s, 9 H). Analysis for C$_{27}$H$_{32}$N$_4$O$_5$S: Calc: C, 61.81; H, 6.14; N, 10.68; Found: C, 59.97; H, 5.57; N, 9.94.

EXAMPLE 86

Preparation of 2-(4-tert-Butylbenzoylamino)-4-butylsulfonylamino-N-(4-methoxyphenyl)benzamide

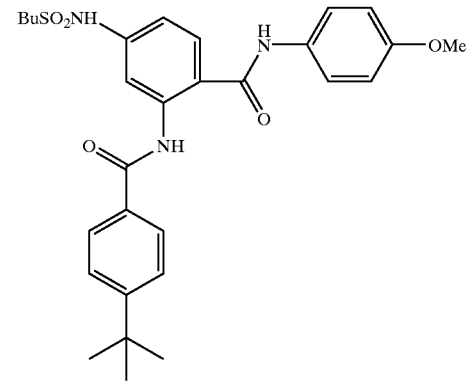

Using the procedure described in Example 59, Part E, 2-(4-tert-butylbenzoylamino)-4-amino-N-(4- methoxyphenyl)benzamide (500 mg, 1.20 mmol) was reacted with butylsulfonyl chloride in the presence of triethylamine to yield 130 mg (20%) of the title compound as an off-white solid.

$^1$H-NMR (DMSO-$d_6$): δ 12.26 (s, 1 H), 10.32 (s, 2 H), 8.58 (d, 1 H, J=2.4 Hz), 7.92 (d, 1 H, J=10.2 Hz), 7.84 (d, 2 H, J=10.2 Hz), 7.61–7.54 (m, 4 H), 7.04 (dd, 1 H, J=10.2, 2.4 Hz), 6.95 (d, 2 H, J=11.1 Hz), 3.75 (s, 3 H), 3.27–3.20 (m, 2 H), 1.70–1.61 (m, 2 H), 1.41–1.30 (m, 11 H), 0.84 (t, 3 H, J=8.7 Hz); MS-FD m/e 537 (p). Analysis for $C_{29}H_{35}N_3O_5S$: Calc: C, 64.78; H, 6.56; N, 7.82; Found: C, 64.52; H, 6.57; N, 7.78.

EXAMPLE 87

Preparation of 2-(4-tert-Butylbenzoylamino)-4-[2S-[2-(tert-butoxycarbonylamino)-4-methylsulfinyl-1-oxobutyl]amino]-N-(4-methoxyphenyl)benzamide

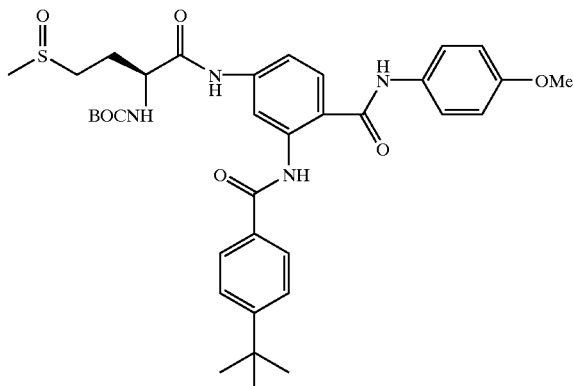

To a mixture of P-EPC resin (1.69 g, 1.44 mmol), N-(tert-butoxycarbonyl)-L-methionine sulfoxide (191 mg, 0.72 mmol) and 2-(4-tert-butylbenzoylamino)-4-amino-N-(4-methoxyphenyl)benzamide (150 mg, 0.36 mmol) was added chloroform (8 mL) and tert-butyl alcohol (2 mL). The resulting mixture was shaken at 300 rpm for 20 h. The reaction mixture was filtered, passed through an SCX cartridge, and concentrated in vacuo to give 239 g (100%) of the title compound as a solid.

MS-IS 665.3.

EXAMPLE 88

Preparation of 2-(4-tert-Butylbenzoylamino)-4-[(3-methoxycarbonyl-1-oxopropyl)amino]-N-(4-methoxyphenyl)benzamide

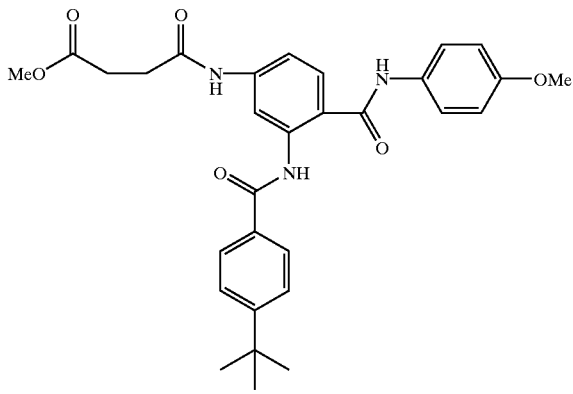

Using the procedure described in Example 87, monomethyl succinate (0.036 mmol) yielded 33 mg (86%) of the title compound as a solid.

MS-FD m/e 531 (p).

EXAMPLE 89

Preparation of 2-(4-tert-Butylbenzoylamino)-N-(4-methoxyphenyl)benzamide

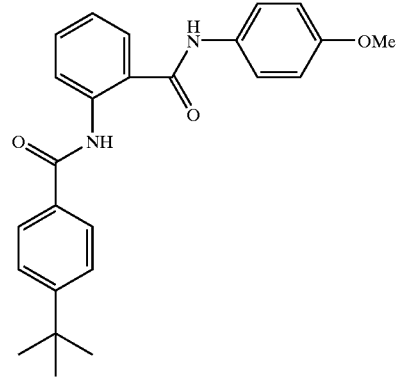

Using the procedure described in Example 55, Part B, 4-tert-butylbenzoyl chloride (4.0 mmol) yielded 809 mg (67%) of the title compound as a white solid; mp 208–210° C.

$^1$H-NMR, IR MS-FD m/e 402 (p). Analysis for $C_{25}H_{26}N_2O_3$: Calc: C, 74.61; H, 6.51; N, 6.69; Found: C, 74.38; H, 6.54; N, 7.05.

EXAMPLE 90

Preparation of $N^1$-(4-methoxybenzoyl)-$N^2$-[1,5-dioxo-5-(1-piperidinyl)pentyl]-1,2-benzenediamine

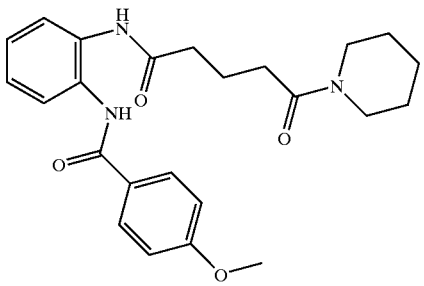

A. $N^1$-(4-Methoxybenzoyl)-$N^2$-(4-carboxy-1-oxobutyl)-1,2-benzenediamine $N^1$-(4-Methoxybenzoyl)-1,2-benzenediamine (3.0 g, 12 mmol), glutaric anhydride (1.7 g, 15 mmol), and pyridine (7 mL) were dissolved in methylene chloride (2 mL) and allowed to stir at ambient temperature for 5 h. The reaction mixture was quenched with water (2 mL) and concentrated in vacuo. The resultant residue was acidified with aqueous sulfuric acid. The resulting white solid was collected and dried at 60° C. in vacuo to yield 3.88 g (88%) of the title compound.

$^1$H-NMR, IR MS-FD m/e 356 (p) Analysis for $C_{19}H_{20}N_2O_5$: Calc: C, 64.04; H, 5.66; N, 7.86; Found: C, 64.19; H, 5.36; N, 7.77.

B. $N^3$-(4-methoxybenzoyl)-$N^2$-[1,5-dioxo-5-(1-piperidinyl) pentyl]-1,2-benzenediamine A solution of $N^1$-(4-methoxybenzoyl)-$N^2$-(4-carboxy-1-oxobutyl)-1,2-benzenediamine (1.0 g, 2.8 mmol), N-hydroxysuccinimide (320 mg, 2.8 mmol), and dicyclohexylcarbodiimide (580 mg, 2.8 mmol) in methylene chloride (10 mL) was stirred for 18 h at ambient temperature then filtered. The filtrate was concentrated in vacuo to provide the intermediate active ester as a white foam (1.31 g). A solution of the active ester (100 mg, 0.22 mmol) and piperidine (33 mL, 0.33 mmol) in tetrahydrofuran (0.5 mL) was allowed to stand for 60 h. The solution was concentrated under a stream of nitrogen and the residue dissolved in methylene chloride and chromatographed (silica gel, methylene chloride to 10% methanol/90% methylene chloride). The appropriate fractions were concentrated in vacuo, the residue dissolved in ethyl acetate, washed with dilute sulfuric acid, saturated aqueous sodium bicarbonate solution, dried (magnesium sulfate), filtered, and concentrated in vacuo to yield 47 mg (50%) of the title compound as a white amorphous solid.

$^1$H-NMR, IR MS-FD m/e 423 (p) Analysis for $C_{24}H_{29}N_3O_4$: Calc: C, 68.06; H, 6.90; N, 9.92; Found: C, 67;58; H, 7.58; N, 9.73.

EXAMPLE 91

Preparation of 2-[(4-tert-Butylbenzoyl)amino]-N-phenylbenzamide

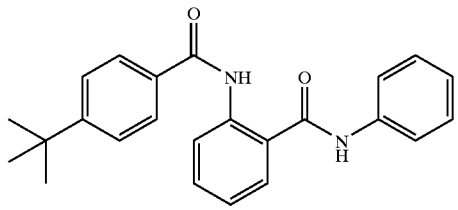

A. 2-(-tert-Butylphenyl)-4H-3,1-benzoxazin-4-one

To a stirred solution of anthranilic acid (34.3 g, 250 mmol) in pyridine (400 mL) was added 4-tert-butylbenzoyl chloride (94 mL, 500 mL) dropwise via an addition funnel. After stirring for 12 h, the solution was poured onto a slurry of ice and 2 N aqueous hydrochloric acid (100 mL). The mixture was extracted with dichloromethane and the organic extract was concentrated in vacuo. The residue was dissolved in fresh dichloromethane, washed once with 2 N aqueous hydrochloric acid, once with saturated aqueous sodium chloride solution, twice with saturated aqueous sodium bicarbonate solution, three times with water, dried (magnesium sulfate), filtered, and concentrated in vacuo. The residue was crystallized from ether/hexanes to give an initial crop of 15.2 g (22%) of the title compound as an off-white solid, followed by additional crops totalling 16.9 g (24%).

$^1$H-NMR (DMSO-$d_6$): δ 8.26 (m, 3 H), 7.83 (t, J=8.7 Hz, 1 H), 7.70 (d, J=8.7 Hz, 1 H), 7.52 (m, 3 H), 1.39 (s, 9 H).

B. 2-[(4-tert-Butylbenzoyl)amino]-N-phenylbenzamide

To a stirred solution of 2-(4-tert-butylphenyl)-4H-3,1-benzoxazin-4-one (1.0 g, 3.6 mmol) in toluene (15 mL) was added aniline (0.33 g, 3.6 mmol). After refluxing for 8 h, the solution was allowed to cool, diethyl ether was added, and the precipitate was filtered and dried In vacuo to give 120 mg (9%) of the title compound as an off-white solid.

$^1$H-NMR (DMSO-$d_6$): δ 11.70 (s, 1 H), 10.53 (s, 1 H), 8.51 (d, J=7.9 Hz, 1 H), 7.93 (dd, J=1.1, 7.5 Hz, 1 H), 7.84 (d, J=8.7 Hz, 2 H), 7.71 (d, J=7.9 Hz, 2 H), 7.61 (m, 1 H), 7.59 (d, J=8.7 Hz, 2 H), 7.37 (t, J=7.9 Hz, 2 H), 7.27 (dt, J=0.8, 7.9 Hz, 1 H), 7.14 (t, J=7.5 Ha, 1 H), 1.3 (s, 9 H); MS-FD m/e 372 (M$^+$). Anal. for $C_{24}H_{24}N_2O_2$: Calc: C, 77.39; H, 6.50; N, 7.52; Found: C, 77.54; H, 6.58; N, 7.57.

EXAMPLE 92

Preparation of 2-[(4-tert-Butylbenzoyl)amino]-N-(4-methylphenyl)benzamide

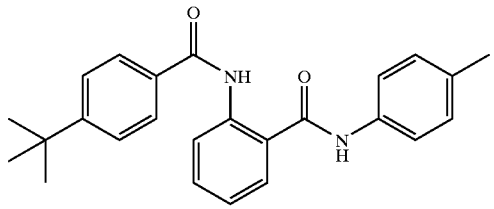

Using the procedure described in Example 91, Part B, p-toluidine (4.7 mmol) yielded 1.3 g, (72%) of the title compound.

$^1$H-NMR (DMSO-$d_6$): δ 11.80 (s, 1 H), 10.46 (s, 1 H), 8.54 (d, J=7.9 Hz, 1 H), 7.93 (dd, J=1.1, 7.9 Hz, 1 H), 7.84 (d, J=8.3 Hz, 2 H), 7.60 (m, 1 H), 7.58 (d, J=8.7 Hz, 4 H), 7.27 (t, J=8.3 Hz, 1 H), 7.18 (d, J=8.3 Hz, 2 H), 2.29 (s, 3 H), 1.31 (s, 9 H); MS-FD m/e 386.2 (M$^+$).

Anal. for $C_{25}H_{26}N_2O_2$: Calc: C, 77.69; H, 6.78; N, 7.25; Found: C, 77.73; H, 6.91; N, 7.21.

EXAMPLE 93

Preparation of 2-[(4-tert-Butylbenzoyl)amino]-N-(4-fluorophenyl)benzamide

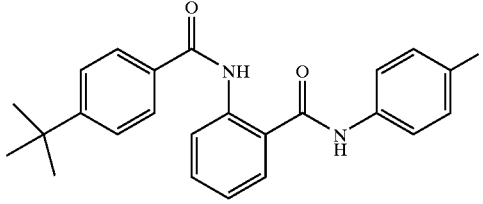

A. N-(4-Fluorophenyl)-2-nitrobenzamide

To a stirred solution of 4-fluoroaniline (2.4 mL, 25 mmol) and pyridine (6.1 mL, 75 mmol) in dichloromethane (30 mL) was added 2-nitrobenzoyl chloride (3.6 mL, 28 mmol). After 12 h, the mixture was diluted with dichloromethane and washed with 1 N aqueous citric acid, saturated aqueous sodium chloride solution, saturated aqueous sodium bicarbonate solution, dried (magnesium sulfate), filtered, and concentrated in vacuo. The resulting solid was suspended in diethyl ether, sonicated, filtered and dried in vacuo to give 5.1 g (79%) of the title compound as a tan solid.

MS-FD m/e 260 (M$^+$). Anal. for $C_{13}H_9FN_2O_3$: Calc: C, 60.00; H, 3.49; N, 10.76; Found: C, 60.02; H, 3.22; N, 10.49.

B. 2-Amino-N-(4-fluorophenyl)benzamide

To a stirred solution of N-(4-fluorophenyl)-2-nitrobenzamide (4.0 g, 15.4 mmol) in methanol (220 mL) and tetrahydrofuran (110 mL) was added nickel acetate tetrahydrate (7.7 g, 31 mmol). Sodium borohydride (2.3 g, 62 mmol) was added in small portions. After gas evolution had ceased, the solvent was removed in vacuo. The residue was partitioned between ethyl acetate and concentrated ammonium hydroxide, and the layers were separated. The organic phase was washed with concentrated ammonium hydroxide and saturated aqueous sodium chloride solution, dried (magnesium sulfate), filtered, and concentrated in vacuo to give 2.86 g (81%) of the title compound as an off-white solid.

MS-FD m/e 230.2 (M$^+$). Anal. for $C_{13}H_{11}FN_2O$: Calc: C, 67.82; H, 4.82; N, 12.17; Found: C, 67.52; H, 4.79; N, 12.06.

C. 2-[(4-tert-Butylbenzoyl)amino]-N-(4-fluorophenyl)benzamide

Using the procedure described in Example 93, Part A, 4-tert-butylbenzoyl chloride (4.8 mmol) yielded (1.03 g, 64%) of the title compound.

MS-FD m/e 230.2 (M$^+$). Anal. for $C_{24}H_{23}FN_2O_2$: Calc: C, 73.83; H, 5.94; N, 7.17; Found: C, 73.62; H, 5.87; N, 7.03.

EXAMPLE 94

Preparation of 2-[(4-tert-Butylbenzoyl)amino]-N-(4-chlorophenyl)benzamide

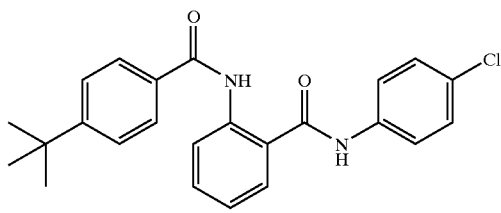

Using the procedure described in Example 91, Part B, 4-chloroaniline (3.0 mmol) provided 0.5 g (42%) of the title compound.

MS-FD m/e 406.3 (M$^+$). Anal. for $C_{24}H_{23}ClN_2O_2$: Calc: C, 70.84; H, 5.70; N, 6.88; Found: C, 70.59; H, 5.75; N, 6.63.

EXAMPLE 95

Preparation of 2-[(4-tert-Butylbenzoyl)amino]-N-(4-bromophenyl)benzamide

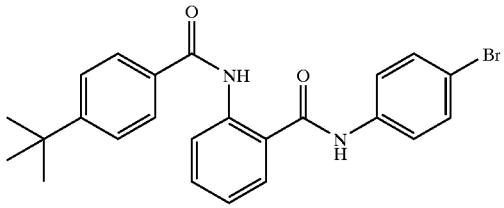

Using the procedure described in Example 91, Part B, 4-bromoaniline (2.98 mmol) provided 0.48 g (38%) of the title compound.

MS-FD m/e 450.2 (M$^+$). Anal. for $C_{24}H_{23}BrN_2O_2$: Calc: C, 63.86; H, 5.14; N, 6.21; Found: C, 63.71; H, 5.16; N, 6.03.

EXAMPLE 96

Preparation of 2-[(4-tert-Butylbenzoyl)amino]-N-(3-hydroxyphenyl)benzamide

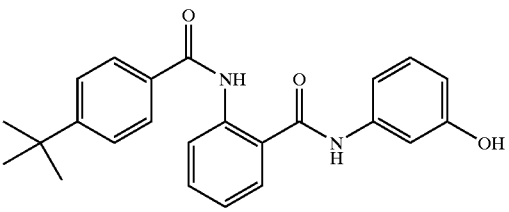

A. N-(3-Benzyloxyphenyl)-2-[(4-tert-butylbenzoyl)amino]-benzamide

Using the procedure described in Example 91, Part B, 3-benzyloxyaniline (1.8 mmol) provided 0.61 g (71%) of the title compound.

MS-FD m/e 478 (M$^+$).

B. 2-[(4-tert-Butylbenzoyl)amino]-N-(3-hydroxyphenyl)benzamide

To a stirred solution of N-(3-benzyloxyphenyl)-2-[(4-tert-butylbenzoyl)amino]benzamide (0.58 g, 1.2 mmol) in tetrahydrofuran (50 mL) was added 10% palladium-on-carbon (0.29 g). The vessel was placed under vacuum and the atmosphere was replaced with hydrogen (1 atm). After 12 h, the balloon was removed and the mixture was filtered through diatomaceous earth and concentrated in vacuo. The residue was dissolved in ethyl acetate and washed with saturated aqueous sodium chloride solution, dried (magnesium sulfate), filtered, and concentrated In vacuo to give 0.41 g (88%) of the title compound as an off-white solid.

$^1$H-NMR (DMSO-d$_6$): δ 11.67 (s, 1 H), 10.40 (s, 1 H), 9.45 (s, 1 H), 8.50 (dd, J=0.8, 8.3 Hz, 1 H), 7.89 (dd, J=1.1, 7.9 Hz, 1 H), 7.84 (d, J=8;5 Hz, 2 H), 7.59 (m, 1 H), 7.58 (d, J=8.5 Hz, 2 H), 7.26 (Abq, 2 H), 7.11 (Abq, 2 H), 6.54 (dt, J=7.2, 1.9 Hz, 1 H), 1.31 (s, 9 H); MS-FD m/e 388.3 (M$^+$). Anal. for $C_{24}H_{24}N_2O_3$: Calc: C, 74.21; H, 6.23; N, 7.21; Found: C, 74.29; H, 6.41; N, 6.97.

EXAMPLE 97

Preparation of N-(3-Aminophenyl)-2-[(4-tert-butylbenzoyl)amino]benzamide

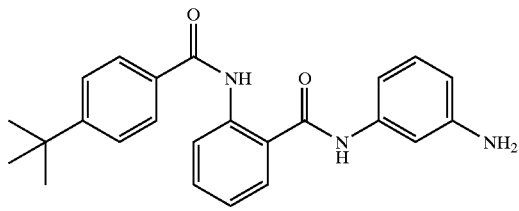

By methods substantially equivalent to those described in Example 96, the title compound (40 mg, 9% for two steps) was prepared from m-(benzyloxycarbonylamino)aniline 1.5 mmol) and 2-(4-tert-butylphenyl)-4H-3,1-benzoxazin-4-one (1.5 mmol).

MS-FD m/e 387.2 (M$^+$). Anal. for $C_{24}H_{25}N_3O_2 \cdot 0.9H_2O$: Calc: C, 71.41; H, 6.69; N, 10.40; Found: C, 71.58; H, 6.00; N, 10.15.

EXAMPLE 98

Preparation of N-(6-Aminopyridin-2-yl)-3-[(4-tert-butylbenzoyl)amino]benzamide

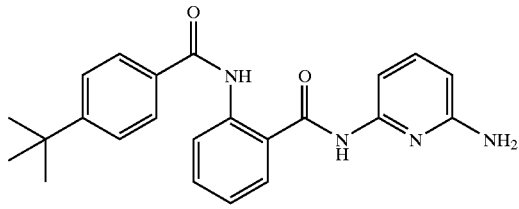

A. N-(6-Phthalimidopyridin-2-yl)-2-nitrobenzamide

Using the procedure described in Example 93, Part A, 2-nitrobenzoyl chloride (2.3 mmol) and 2-amino-6-phthalimidopyridine (2.1 mmol) yielded 654 mg (80%) of the title compound.

MS-FD m/e 388 (M$^+$). Anal. for $C_{20}H_{12}N_4O_5$: Calc: C, 61.86; H, 3.12; N, 14.43; Found: C, 61.61; H, 3.26; N, 14.17.

B. N-(6-Phthalimidopyridin-2-yl)-2-aminobenzamide

Using the procedure described in Example 96, Part B, N-(6-phthalimidopyridin-2-yl)-2-nitrobenzamide (0.6 mmol) yielded 170 mg (74%) of the title compound.

MS-FD m/e 359 (M$^+$).

C. N-(6-Phthalimidopyridin-2-yl)-2-[(4-tert-butylbenzoyl)amino]benzamide

Using the procedure described in Example 93, Part A, 4-tert-butylbenzoyl chloride (0.47 mmol) and N-(6-phthalimidopyridin-2-yl)-2-aminobenzamide (0.47 mmol) yielded 300 mg (100%) of the title product.

MS-FD m/e 518 (M$^+$).

D. N-(6-Aminopyridin-2-yl)-2-[(4-tert-butylbenzoyl)amino]benzamide

To a stirred solution N-(6-phthalimidopyridin-2-yl)-2-[(4-tert-butylbenzoyl)amino]benzamide (230 mg, 0.44 mmol) in ethanol (15 mL) was added hydrazine hydrate (0.22 g, 4.4 mmol). After refluxing the mixture for 30 min, the solvent was removed in vacuo and the residue was dissolved in ethyl acetate, washed twice with saturated aqueous sodium bicarbonate solution, twice with saturated aqueous sodium chloride solution, dried (magnesium sulfate), filtered, and concentrated in vacuo. The residue was dissolved in a minimal amount of chloroform and chromatographed (silica gel, eluting with a gradient of chloroform to 2% methanol/98% chloroform. The appropriate fractions were combined and concentrated In vacuo to give 51 mg (30%) of the title compound as a white solid.

MS-FD m/e 388 (M$^+$). Anal. for $C_{23}H_{24}N_4O_2$: Calc: C, 71.11; H, 6.23; N, 14.42; Found: C, 71.20; H, 6.31; N, 14.67.

EXAMPLE 99

Preparation of 2-[(4-tert-Butylbenzoyl)amino]-N-(3-hydroxy-4-methylphenyl)benzamide

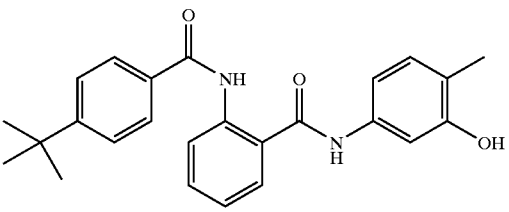

A. 3-Benzyloxy-4-methylnitrobenzene

To a stirred suspension of 2-methyl-5-nitrophenol (2.0 g, 13 mmol) and sodium carbonate (1.94 g, 18.3 mmol) in acetone was added benzyl bromide (1.7 mL, 14 mmol). The mixture was heated to reflux for 24 h, cooled, filtered, and the solid washed with acetone. The filtrate and acetone washings were combined and concentrated in vacuo. Recrystallization from ether/hexanes gave 1.06 g (33%) of the title product as an off-white solid.

MS-FD 243 m/e (M$^+$).

B. 3-Benzyloxy-4-methylaniline

To a stirred solution of 3-benzyloxy-4-methylnitrobenzene (1.1 g, 4.4 mmol) in tetrahydrofuran (25 mL) and methanol (50 mL) was added nickel acetate tetrahydrate (2.2 g, 8.7 mmol). The solution was cooled to 0° C. and sodium borohydride (0.66 g, 17.4 mmol) was added in small portions. After gas evolution had ceased, the solvents were removed in vacuo and the residue was partitioned between ethyl acetate and concentrated ammonium hydroxide. The layers were separated and the organic phase was washed with ammonium hydroxide followed by saturated aqueous sodium chloride solution, dried (magnesium sulfate), filtered, and concentrated In vacuo to give 0.9 g (97%) of the title product as an off-white solid.

MS-FD m/e (M$^+$).

C. N-(3-Benzyloxy-4-methylphenyl)-2-[(4-tert-butylbenzoyl)amino]benzamide

Using the procedure described in Example 91, Part B, 3-benzyloxy-4-methylaniline (4.2 mmol) yielded 1.4 g (68%) of the title compound.

MS-FD m/e 492.2 (M$^+$). Anal. for $C_{32}H_{32}N_2O_3$: Calc: C, 78.02; H, 6.55; N, 5.69; Found: C, 78.22; H, 6.79; N, 5.61.

D. 2-[(4-tert-Butylbenzoyl)amino]-N-(3-hydroxy-4-methylphenyl)benzamide

Using the procedure described in Example 96, Part B, N-(3-benzyloxy-4-methylphenyl)-2-[(4-tert-butylbenzoyl)amino]benzamide (2.0 mmol) yielded 701 mg (86%) of the title compound. MS-FD m/e 402.1 (M$^+$).

Anal. for C$_{25}$H$_{26}$N$_2$O$_3$: Calc: C, 74.60; H, 6.51; N, 6.96; Found: C, 74.41; H, 6.76; N, 6.88.

EXAMPLE 100

Preparation of N-(3-Amino-4-methoxyphenyl)-2-[(4-tert-butylbenzoyl)amino]benzamide

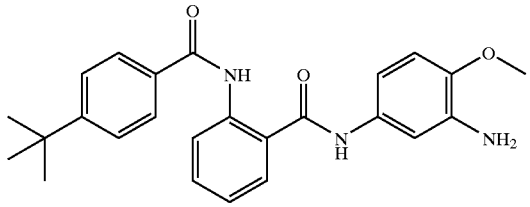

A. 3-Benzyloxycarbonylamino-4-methoxynitrobenzene To a stirred solution of 2-methoxy-5-nitroaniline (5.0 g, 30 mmol) and potassium carbonate (12 g, 90 mmol) in tetrahydrofuran (200 mL) and water (100 mL) was added benzyl chloroformate (6.1 g, 36 mmol). After 12 h, the mixture was diluted with ethyl acetate (200 mL) and the layers were separated. The organic phase was washed twice with 1 N aqueous hydrochloric acid, once with saturated aqueous sodium chloride solution, twice with saturated aqueous sodium bicarbonate solution, twice with saturated aqueous sodium chloride solution, dried (magnesium sulfate), filtered, and concentrated in vacuo. The resulting solid was suspended in diethyl ether and after sonication, the solid was filtered, washed with diethyl ether, and dried in vacuo to give 7.8 g (86%) of the title compound as a light yellow solid.

MS-FD m/e 302.1 (M$^+$) Anal. for C$_{15}$H$_{14}$N$_2$O$_5$: Calc: C, 59.60; H, 4.67; N, 9.27; Found: C, 59.88; H, 4.65; N, 9.35.

B. 3-Benzyloxycarbonylamino-4-methoxyaniline

Using the procedure described in Example 99, Part A, 3-benzyloxycarbonylamino-4-methoxynitrobenzene (9.9 mmol) yielded 2.1 g (78%) of the title compound.

MS-FD m/e 272.1 (M$^+$). Anal. for C$_{15}$H$_{16}$N$_2$O$_3$: Calc: C, 66.16; H, 5.92; N, 10.29; Found: C, 65.99; H, 5.97; N, 10.28.

C. N-(3-benzyloxycarbonylamino-4-methoxyphenyl)-2-[(4-tert-butylbenzoyl)amino]benzamide Using the procedure described in Example 91, Part B, 1-[N-(3-benzyloxycarbonylamino-4-methoxy)phenyl]-2-[N-(4-tert-butylbenzoyl)]anthranilamide (1.9 mmol) yielded 0.64 g (61%) of the title compound.

MS-FD m/e 551.2 (M$^+$). Anal. for C$_{33}$H$_{33}$N$_3$O$_5$: Calc: C, 71.85; H, 6.03; N, 7.62; Found: C, 72.10; H, 6.09; N, 7.76.

D. Preparation of 1-[N-(3-amino-4-methoxy)phenyl]-2-[N-(4-tert-butylbenzoyl)-3-anthranilamide Using the procedure described in Example 96, Part B, N-(3-benzyloxycarbonylamino-4-methoxyphenyl)-2-[(4-tert-butylbenzoyl)amino]benzamide (0.73 mmol) yielded 137 mg (45%) of the title product.

MS-FD m/e 417 (M$^+$). Anal. for C$_{25}$H$_{27}$N$_3$O$_3$: Calc: C, 71.92; H, 6.52; N, 10.06; Found: C, 71.63; H, 6.46; N, 9.76.

EXAMPLE 101

Preparation of 2-[(4-tert-Butylbenzoyl)amino]-N-(3-hydroxy-5-methoxyphenyl)benzamide

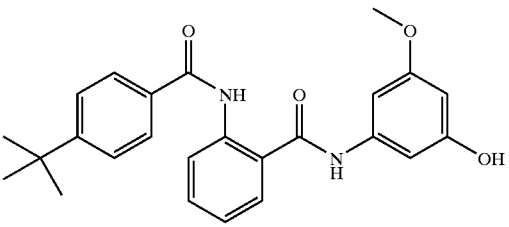

A. N-(3,5-Dimethoxyphenyl)-2-[(4-tert-butylbenzoyl) amino]benzamide

Using the procedure described in Example 91, Part B, 3,5-dimethoxyaniline (13.1 mmol) yielded 4.1 g (73%) of the title compound.

MS-FD m/e 432.1 (M$^+$). Anal. for C$_{26}$H$_{28}$N$_2$O$_4$: Calc: C, 72.20; H, 6.53; N, 6.48; Found: C, 72.25; H, 6.53; N, 6.53.

B. N-(3-Hydroxy-5-methoxyphenyl)-2-[(4-tert-butylbenzoyl)amino]benzamide

To a stirred suspension N-(3,5-dimethoxyphenyl)-2-[(4-tert-butylbenzoyl)amino]benzamide (1.0 g, 2.3 mmol) in dichloromethane (42 mL) was added a solution of boron tribromide (0.66 mL, 6.9 mmol) in dichloromethane (7 mL) via an addition funnel. After 30 min, a second portion of boron tribromide (0.66 mL, 6.9 mmol) in dichloromethane (7 mL) was added. After 30 min, saturated aqueous sodium bicarbonate solution was added and the solvents were removed in vacuo. The residue was dissolved in ethyl acetate and washed with saturated aqueous sodium bicarbonate solution, saturated aqueous sodium chloride solution, dried (magnesium sulfate), filtered, and concentrated in vacuo. Chromatography (silica gel, 30% ethyl acetate/70% hexanes) provided 96 mg (10%) of the title compound as a white solid.

MS-FD m/e 418 (M$^+$). Anal. for C$_{25}$H$_{26}$N$_2$O$_4$: Calc: C, 71.75; H, 6.26; N, 6.70; Found: C, 71.41; H, 6.24; N, 6.67.

EXAMPLE 102

Preparation of 2-[(4-tert-Butylbenzoyl)amino]-N-(4-methoxyphenyl)-5-methylbenzamide

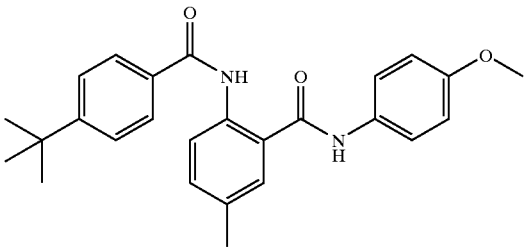

A. N-(4-Methoxyphenyl)-2-nitro-5-methylbenzamide

To a stirred solution of 4-methoxyaniline (1.4 g, 11 mmol) and 2-nitro-5-methylbenzoic acid (2.0 g, 11 mmol) in dimethylformamide (20 mL) was added 1-(3-dimethylaminopropyl)-3-ethylcarbodiimide hydrochloride (3.17 g, 16.5 mmol). After 12 h, the solvent was removed in vacuo. The residue was dissolved in ethyl acetate and washed twice with 1 M aqueous citric acid, once with water, twice with saturated aqueous sodium bicarbonate solution, once with water, and once with saturated aqueous sodium chloride solution. The organic phase was dried (magnesium sulfate), filtered, and concentrated in vacuo. The residue was triturated with diethyl ether, filtered, and dried in vacuo to give 1.57 g (50%) of the title compound as a yellow solid.

MS-FD m/e 286 (M$^+$). Anal. for $C_{15}H_{14}N_2O_4$: Calc: C, 62.93; H, 4.93; N, 9.78; Found: C, 63.13; H, 4.67; N, 9.69.

B. 2-Amino-N-(4-methoxyphenyl)-5-methylbenzamide

Using the procedure described in Example 93, Part B, N-(4-methoxyphenyl)-2-nitro-5-methylbenzamide (2.6 mmol) yielded 0.48 g (72%) of the title compound.

MS-FD m/e 256.1 (M$^+$). Anal. for $C_{15}H_{16}N_2O_2$: Calc: C, 70.29; H, 6.29; N, 10.93; Found: C, 70.29; H, 6.49; N, 10.71.

C. 2-[(4-tert-Butylbenzoyl)amino]-N-(4-methoxyphenyl)-5-methylbenzamide

Using the procedure described in Example 93, Part A, 4-tert-butylbenzoyl chloride (1.3 mmol) and 2-amino-N-(4-methoxyphenyl)-5-methylbenzamide (1.2 mmol) yielded 0.23 g (47%) of the title compound.

MS-FD m/e 416.2 (M$^+$). Anal. for $C_{26}H_{28}N_2O_3$: Calc: C, 74.97; H, 6.78; N, 6.73; Found: C, 75.01; H, 6.68; N, 6.52.

EXAMPLE 103

Preparation of 2-[(4-tert-Butylbenzoyl)amino]-N-(4-methoxyphenyl)-3-methylbenzamide

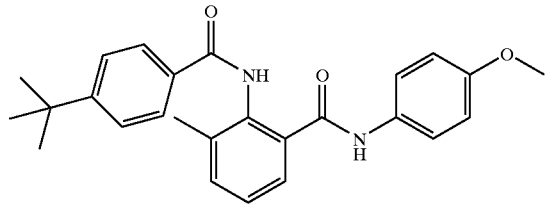

A. N-(4-methoxyphenyl)-2-nitro-3-methylbenzamide

Using the procedure described in Example 102, Part A, 2-nitro-3-methylbenzoic acid (11 mmol) yielded 1.78 g (56%) of the title compound.

MS-FD m/e 286.1 (M$^+$). Anal. for $C_{15}H_{14}N_2O_4$: Calc: C, 62.94; H, 4.93; N, 9.79; Found: C, 62.79; H, 4.82; N, 9.77.

B. 2-Amino-N-(4-methoxyphenyl)-3-methylbenzamide

Using the procedure described in Example 93, Part B, N-(4-methoxyphenyl)-2-nitro-3-methylbenzamide (2.6 mmol) yielded 0.41 g (61%) of the title compound.

MS-FD m/e 256.1 (M$^+$). Anal. for $C_{15}H_{16}N_2O_2$: Calc: C, 70.29; H, 6.29; N, 10.93; Found: C, 70.47; H, 6.10; N, 10.66.

C. 2-[(4-tert-Butylbenzoyl)amino]-N-(4-methoxyphenyl)-3-methylbenzamide

Using the procedure described in Example 93, Part A, 4-tert-butylbenzoyl chloride (1.76 mmol) and 2-amino-N-(4-methoxyphenyl)-3-methylbenzamide (1.6 mmol) yielded 0.30 g (45%) of the title compound.

MS-FD m/e 416 (M$^+$).

Anal. for $C_{26}H_{28}N_2O_3$: Calc: C, 74.98; H, 6.78; N, 6.73; Found: C, 74.76; H, 6.94; N, 6.90.

EXAMPLE 104

Preparation of 2-[(4-tert-Butylbenzoyl)amino]-3-methoxy-N-(4-methoxyphenyl)benzamide

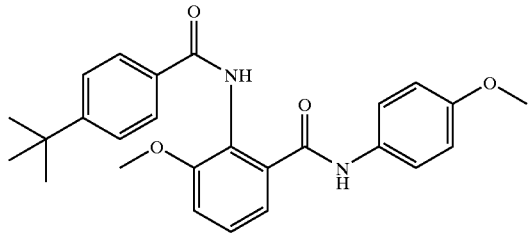

A. N-(4-Methoxyphenyl)]-2-nitro-3-methoxybenzamide

Using the procedure described in Example 102, Part A, 2-nitro-3-methoxy-benzoic acid (10.1 mmol) yielded 2.0 g (66%) of the title compound.

MS-FD m/e 302 (M$^+$). Anal. for $C_{15}H_{14}N_2O_5$: Calc: C, 59.60; H, 4.67; N, 9.28; Found: C,59.55; H, 4.53; N, 9.31.

B. 2-Amino-N-(4-ethoxyphenyl)-3-methoxybenzamide

Using the procedure described in Example 93, Part B, N-(4-methoxyphenyl)-2-nitro-3-methoxybenzamide (2.6 mmol) yielded 0.23 g (32%) of the title compound.

MS-FD m/e 272.1 (M$^+$). Anal. for $C_{15}H_{16}N_2O_3$: Calc: C, 66.16; H, 5.92; N, 10.29; Found: C, 65.91; H, 5.68; N, 10.29.

C. 2-[(4-tert-Butylbenzoyl)amino]-3-methoxy-N-(4-methoxyphenyl)benzamide

Using the procedure described in Example 93, Part A, 4-tert-butylbenzoyl chloride (0.81 mmol) and 2-amino-N-(4-methoxyphenyl)-3-methoxybenzamide (0.73 mmol) yielded 0.18 g (57%) of the title compound.

MS-FD m/e 432.1 (M$^+$). Anal. for $C_{26}H_{28}N_2O_4$: Calc: C, 72.20; H, 6.53; N, 6.48; Found: C, 72.48; H, 6.69; N, 6.42.

EXAMPLE 105

Preparation of 2-[(4-tert-Butylbenzoyl)amino]-N-(3-hydroxyphenyl)-4-(methylsulfonylamino)benzamide

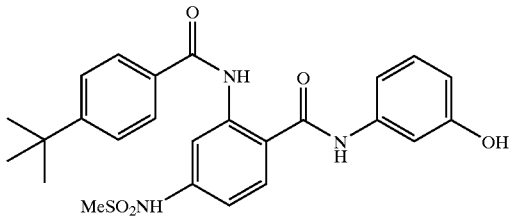

A. 2-Amino-N-(3-benzyloxyphenyl)-4-nitrobenzamide

Using the procedure described in Example 91, Part B, 3-benzyloxyaniline (4.4 mmol) and 4-nitroisatoic anhydride (4.8 mmol) yielded 1.2 g (81%) of the title product.

MS-FD m/e 363 (M$^+$).

B. N-(3-Benzyloxyphenyl)-2-[(4-tert-butylbenzoyl)amino]-4-nitrobenzamide

Using the procedure described in Example 93, Part A, 4-tert-butylbenzoyl chloride (3.5 mmol) and 2-amino-N-(3-benzyloxyphenyl)-4-nitrobenzamide (3.2 mmol) yielded 0.69 g (69%) of the title product.

MS-FD m/e 523 (M$^+$). Anal. for $C_{31}H_{29}N_3O_5$: Calc: C, 71.11; H, 5.58; N, 8.02; Found: C, 71.37; H, 5.72; N, 7.92.

C. 4-Amino-N-(3-benzyloxyphenyl)-2-[(4-tert-butylbenzoyl)amino]benzamide

Using the procedure described in Example 93, Part B. N-(3-benzyloxyphenyl)-2-[(4-tert-butylbenzoyl)amino]-4-nitrobenzamide (2.1 mmol) yielded 0.87 g (84%) of the title product.

MS-FD m/e 493 (M⁺). Anal. for $C_{31}H_{31}N_3O_3$: Calc: C, 75.43; H, 6.33; N, 8.51; Found: C, 75.59; H, 6.30; N, 8.26.

D. 2-[(4-tert-Butylbenzoyl)amino]-N-(3-benzyloxyphenyl)-4-(methylsulfonylamino)benzamide Using the procedure described in Example 59, Part E, 4-amino-N-(3-benzyloxyphenyl)-2-[(4-tert-butylbenzoyl) amino]benzamide (0.75 mmol) yielded 0.43 g (100%) of the title product.

MS-FD m/e 571 (M⁺). Anal. for $C_{32}H_{33}N_3O_5S$: Calc: C, 67.23; H, 5.82; N, 7.35; Found: C, 66.59; H, 5.84; N, 7.07.

E. 2-[(4-tert-Butylbenzoyl)amino]-N-(3-hydroxyphenyl)-4-(methylsulfonylamino)benzamide Using the procedure described in Example 96, Part B, 2-[(4-tert-butylbenzoyl)amino]-N-(3-benzyloxyphenyl)-4-(methylsulfonylamino)benzamide (0.7 mmol) yielded 0.25 g (74%) of the title product.

¹H-NMR (DMSO-d₆): δ 12.07 (s , 1 H), 10.29 (s, 2 H), 9.45 (s, 1 H), 8.55 (d, J=1.9 Hz, 1 H), 7.91 (d, J=8.7 Hz, 1 H), 7.86 (d, J=8.3 Hz, 2 H), 7.61 (d, J=8.3 Hz, 2 H), 7.23 (s, 1 H), 7.17–7.03 (m, 3 H), 6.54 (d, J=7.9 Hz, 1 H), 3.13 (s, 3 H), 1.31 (s, 9 H); MS-FD m/e 481 (M⁺). Anal. for $C_{25}H_{27}N_3O_5S$: Calc: C, 62.35; H, 5.65; N, 8.73; Found: C, 62.12; H, 5.72; N, 8.49.

EXAMPLE 106

Preparation of 2-[(2-Butoxy-4-methoxybenzoyl) amino]-N-(4-methoxyphenyl)benzamide

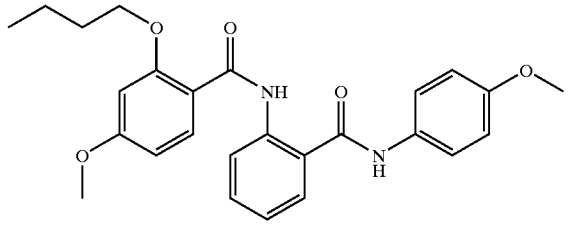

Using the procedure described in Example 102, Part A, 2-butoxy-4-methoxybenzoic acid (0.54 mmol) and 2-amino-N-(4-methoxyphenyl)benzamide (0.54 mmol) yielded 61 mg (25%) of the title compound.

MS-FD m/e 448.2 (M⁺). Anal. for $C_{26}H_{28}N_2O_5$: Calc: C, 69.63; H, 6.29; N, 6.25; Found: C, 69.90; H, 6.32; N, 6.51.

EXAMPLE 107

Preparation of N¹-Benzoyl-N²-(4-tert-butylbenzoyl)-1,2-benzenediamine

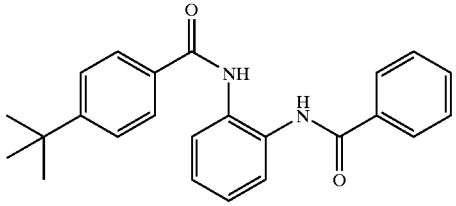

A. 2-Nitro-N-(4-tert-butylbenzoyl)aniline

Using the procedure described in Example 93, Part A, 4-tert-butylbenzoyl chloride (398 mmol) and 2-nitroaniline (362 mmol) yielded 21.6 g (100%) of the title compound.

¹H NMR

B. N¹-(4-tert-Butylbenzoyl)-1,2-benzenediamine

Using the procedure described in Example 96, Part B. 2-nitro-N-(4-tert-butylbenzoyl)aniline (91 mmol) yielded 19.9 g (79%) of the title compound.

¹H-NMR (DMSO-d₆): δ 9.58 (s, 1 H), 7.91 (d, J=8.3 Hz, 2 H), 7.52 (d, J=8.3 Hz, 2 H), 7.16 (d, J=8.0 Hz, 1 H), 6.97 (dt, J=1.4, 8.4 Hz, 1 H), 6.78 (d, J=1.3, 8.0 Hz, 1 H), 6.59 (dt, J=1.3, 8.4 Hz, 1 H), 4.88 (br s, 2 H), 1.32 (s, 9 H); MS-FD m/e 298.2 (M⁺).

C. N¹-Benzoyl-N²-(4-tert-butylbenzoyl)-1,2-benzenediamine

Using the procedure described in Example 93, Part A, benzoyl chloride (0.80 mmol) and N¹-(4-tert-butylbenzoyl)-1,2-benzenediamine (0.75 mmol) yielded 150 mg (54%) of the title compound.

MS-FD m/e 372.1 (M⁺). Anal. for $C_{24}H_{24}N_2O_2$: Calc: C, 77.39; H, 6.49; N, 7.52; Found: C, 77.19; H, 6.47; N, 7.26.

EXAMPLE 108

Preparation of N¹-(4-Methoxybenzoyl)-N²-(4-tert-butylbenzoyl)-1,2-benzenediamine

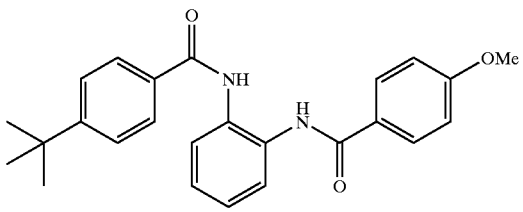

Using the procedure described in Example 93, Part A, 4-anisoyl chloride (2.2 mmol) and N¹-(4-tert-butylbenzoyl)-1,2-benzenediamine (1.8 mmol) yielded 441 mg (61%) of the title compound.

¹H-NMR (DMSO-d₆): δ 10.00 (br s, 2 H), 7.94 (d, J=8.5 Hz, 2 H), 7.88 (d, J=8.5 Hz, 2 H), 7.94 (d, J=8.5 Hz, 2 H), 7.88 (d, J=8.5 Hz, 2 H), 7.64 (m, 2 H), 7.54 (d, J=8.5 Hz, 2 H), 7.27 (m, 2 H), 7.07 (d, J=9.0 Hz, 2 H), 3.83 (s, 3 H), 1.30 (s, 9 H); MS-FD m/e 402.3 (M⁺). Anal. for $C_{25}H_{26}N_2O_3$: Calc: C, 74.61; H, 6.51; N, 6.96; Found: C, 74.74; H, 6.67; N, 6.77.

EXAMPLE 109

Preparation of N¹-(4-Hydroxybenzoyl)-N²-(4-tert-butylbenzoyl)-1,2-benzenediamine

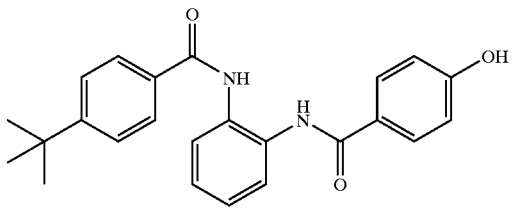

Using the procedure described in Example 101, Part B, N¹-(4-methoxybenzoyl)-N²-(4-tert-butylbenzoyl)-1,2-benzenediamine (0.98 mmol) yielded 220 mg (58%) of the title compound.

MS-FD m/e 388.1 (M⁺). Anal. for $C_{24}H_{24}N_2O_4$: Calc: C, 71.27; H, 5.98; N, 6.93; Found: C, 73.38; H, 5.97; N, 7.32.

EXAMPLE 110

Preparation of N¹-(4-Methylphenyl)-N²-(4-tert-butylbenzoyl)-1,2-benzenediamine

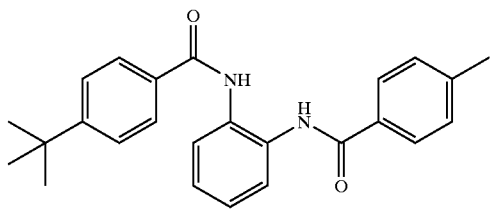

Using the procedure described in Example 93, Part A, 4-toluoyl chloride (1.1 mmol) and N¹-(4-tert-butylbenzoyl)-1,2-benzenediamine (0.93 mmol) yielded 360 mg (100%) of the title compound.

¹H-NMR (DMSO-$d_6$): δ 10.02 (br s, 2 H), 7.89 (d, J=8.3 Hz, 2 H), 7.85 (d, J=8.0 Hz, 2 H), 7.66 (m, 2 H), 7.54 (d, J 8.5 Hz, 2 H), 7.33 (d, J=8.0 Hz, 2 H), 7.28 (m, 2 H), 2.37 (s, 3 H), 1.30 (s, 9 H); MS-FD m/e 386.3 (M⁺). Anal. for $C_{25}H_{26}N_2O_2$: Calc: C, 77.69; H, 6.78; N, 7.25; Found: C, 77.59; H, 6.91; N, 7.48.

EXAMPLE 111

Preparation of N¹-(3-Methoxybenzoyl)-N²-(4-tert-butylbenzoyl)-1,2-benzenediamine

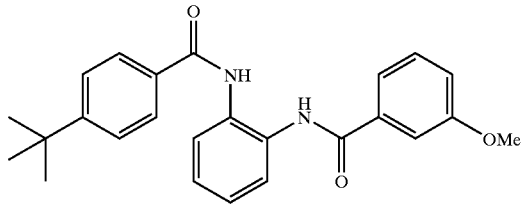

Using the procedure described in Example 102, Part A, 3-anisic acid (3.6 mmol) and N¹-(4-tert-butylbenzoyl)-1,2-benzenediamine (1.8 mmol) yielded 610 mg (84%) of the title compound.

MS-FD m/e 402.2(M⁺) Anal. for $C_{25}H_{26}N_2O_3$: Calc: C, 74.60; H, 6.51; N, 6.96; Found: C, 74.43; H, 6.39; N, 6.91.

EXAMPLE 112

Preparation of N¹-(3-Hydroxybenzoyl)-N²-(4-tert-butylbenzoyl)-1,2-benzenediamine

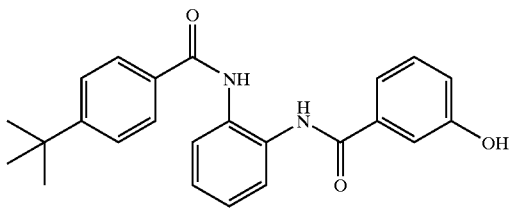

Using the procedure described in Example 101, Part B, N¹-(3-methoxybenzoyl)-N²-(4-tert-butylbenzoyl)-1,2-benzenediamine (0.19 mmol) yielded 70 mg (96%) of the title compound. MS-FD m/e 388.4 (M⁺). Anal. for $C_{24}H_{24}N_2O_3$: Calc: C, 74.21; H, 6.23; N, 7.21; Found: C, 73.82; H, 6.74; N, 6.80.

EXAMPLE 113

Preparation of N¹-(3-Methoxy-4-methylbenzoyl)-N²-(4-tert-butylbenzoyl)-1,2-benzenediamine

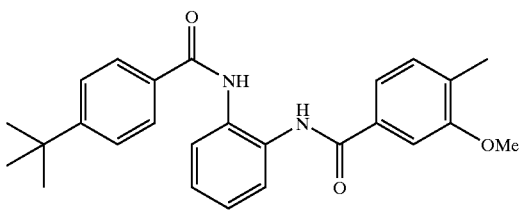

Using the procedure described in Example 102, Part A, 3-methoxy-4-methylbenzoic acid (3.6 mmol) and N¹-(4-tert-butylbenzoyl)-1,2-benzenediamine (1.8 mmol) yielded 210 mg (28%) of the title compound.

MS-FD m/e 416.3 (M⁺). Anal. for $C_{26}H_{28}N_2O_3$: Calc: C, 74.98; H, 6.78; N, 6.73; Found: C, 69.00; H, 6.30; N, 5.91.

EXAMPLE 114

Preparation of N¹-(3-Hydroxy-4-methylbenzoyl)-N²-(4-tert-butylbenzoyl)-1,2-benzenediamine

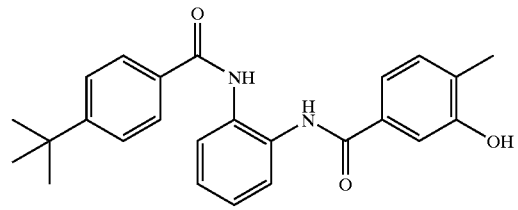

Using the procedure described in Example 101, Part B, N¹-(3-methoxy-4-methylbenzoyl)-N²-(4-tert-butylbenzoyl)-1,2-benzenediamine (0.18 mmol) yielded 51 mg (70%) of the title compound.

MS-FD m/e 402.2 (M+). Anal. for $C_{25}H_{26}N_2O_3$: Calc: C, 74.60; H, 6.51; N, 6.96; Found: C, 74.87; H, 6.28; N, 6.76.

EXAMPLE 115

Preparation of $N^1$-(4-Aminobenzoyl)-$N^2$-(4-tert-butylbenzoyl)-1,2-benzenediamine

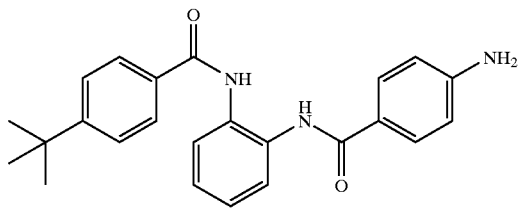

A. $N^1$-(4-Nitrobenzoyl)-$N^2$-(4-tert-butylbenzoyl)-1,2-benzenediamine

Using the procedure described in Example 102, Part A, $N^1$-(4-tert-butylbenzoyl)-1,2-benzenediamine (3.1 mmol) and 4-nitrobenzoic acid (3.0 mmol) yielded the title product, which was used directly in the next step without additional purification.

$^1$H NMR

B. $N^1$-(4-Aminobenzoyl)-$N^2$-(4-tert-butylbenzoyl)-1,2-benzenediamine

Using the procedure described in Example 96, Part B, $N^1$-(4-nitrobenzoyl)-$N^2$-(4-tert-butylbenzoyl)-1,2-benzenediamine (2.6 mmol) yielded 400 mg (36%) of the title compound.

MS-FD m/e 387 (M+). Anal. for $C_{24}H_{25}N_3O_2 \cdot 0.5$ $H_2O$: Calc: C, 72.71; H, 6.61; N, 10.59; Found: C, 72.41; H, 6.75; N, 10.25.

EXAMPLE 116

Preparation of $N^1$-(3-Aminobenzoyl)-$N^2$-(4-tert-butylbenzoyl)-1,2-benzenediamine

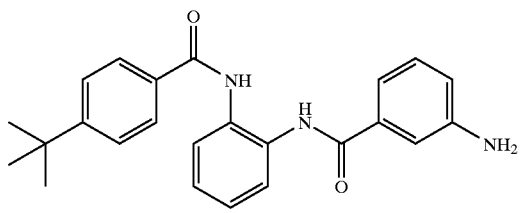

A. $N^1$-(3-Nitrobenzoyl)-$N^2$-(4-tert-butylbenzoyl)-1,2-benzenediamine

Using the procedure described in Example 93, Part A, 3-nitrobenzoyl chloride (2.2 mmol) and $N^1$-(4-tert-butylbenzoyl)-1,2-benzenediamine (1.8 mmol) yielded 427 mg (56%) of the title compound.

MS-FD m/e 417.2 (M+). Anal. for $C_{24}H_{23}N_3O_4$: Calc: C, 69.05; H, 5.55; N, 10.07; Found: C, 69.01; H, 5.59; N, 10.30.

B. $N^1$-(3-Aminobenzoyl)-$N^2$-(4-tert-butylbenzoyl)-1,2-benzenediamine

Using the procedure described in Example 96, Part B, $N^1$-(3-nitrobenzoyl)-$N^2$-(4-tert-butylbenzoyl)-1,2-benzenediamine (0.48 mmol) yielded 181 mg (97%) of the title compound.

MS-FD m/e 387 (M+). Anal. for $C_{24}H_{25}N_3O_2 \cdot 0.5$ $H_2O$: Calc: C, 72.71; H, 6.61; N, 10.59; Found: C, 72.84; H, 6.33; N, 10.32.

EXAMPLE 117

Preparation of $N^1$-(3-Amino-4-methoxybenzoyl)-$N^2$-(4-tert-butylbenzoyl)-1,2-benzenediamine

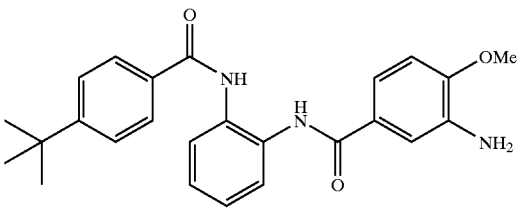

A. $N^1$-(3-Nitro-4-methoxybenzoyl)-$N^2$-(4-tert-butylbenzoyl)-1,2-benzenediamine Using the procedure described in Example 102, Part A, 3-nitro-4-methoxybenzoic acid (2.8 mmol) and $N^1$-(4-tert-butylbenzoyl)-1,2-benzenediamine (1.9 mmol) yielded 0.70 mg (84%) of the title compound.

MS-FD m/e 447 (M+). Anal. for $C_{25}H_{25}N_3O_5$: Calc: C, 67.10; H, 5.63; N, 9.39; Found: C, 67.29; H, 5.75; N, 9.22.

B. $N^1$-(3-Amino-4-methoxybenzoyl)-$N^2$-(4-tert-butylbenzoyl)-1,2-benzenediamine Using the procedure described in Example 96, Part B, $N^1$-(3-nitro-4-methoxybenzoyl)-$N^2$-(4-tert-butylbenzoyl)-1,2-benzenediamine (1.1 mmol) yielded 400 mg (85%) of the title compound.

MS-FD m/e 417.1 (M+). Anal. for $C_{25}H_{27}N_3O_3$: Calc: C, 71.92; H, 6.52; N, 10.06; Found: C, 71.88; H, 6.35; N, 9.97.

EXAMPLE 118

Preparation of $N^1$-(2-Aminothiazol-5-ylcarbonyl)-$N^2$-(4-tert-butylbenzoyl)-1,2-benzenediamine

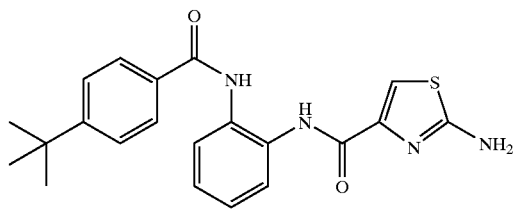

Using the procedure described in Example 102, Part A, 2-aminothiazole-5-carboxylic acid (1.0 mmol) and $N^1$-(4-tert-butylbenzoyl)-1,2-benzenediamine (1.5 mmol) yielded 50 mg (13%) of the title compound.

MS-FD m/e 394.1 (M+). Anal. for $C_{21}H_{22}N_4O_2S \cdot 0.5$ $H_2O$: Calc: C, 62.51; H, 5.75; N, 13.88; Found: C, 62.50; H, 5.72; N, 13.14.

EXAMPLE 119

Preparation of 3,6-Dimethoxy-$N^1,N^2$-bis(4-methoxybenzoyl)-1,2-benzenediamine

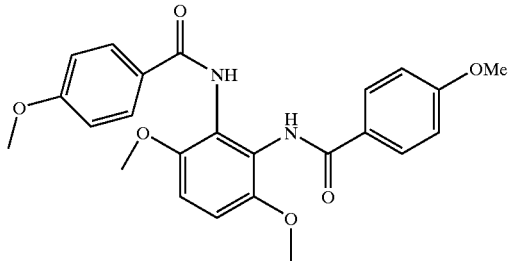

Using the procedure described in Example 93, Part A, 4-anisoyl chloride (4.9 mmol) and 3,6-dimethoxy-1,2-benzenediamine (2.0 mmol) yielded 555 mg (65%) of the title compound.

MS-FD m/e 435.9 ($M^+$). Anal. for $C_{24}H_{24}N_2O_6$: Calc: C, 66.05; H, 5.54; N, 6.42; Found: C, 66.30; H, 5.47; N, 6.36.

EXAMPLE 120

Preparation of 4-[(Amino)(hydroxyimino)methyl]-$N^1,N^2$-bis(4-methoxybenzoyl)-1,2-benzenediamine

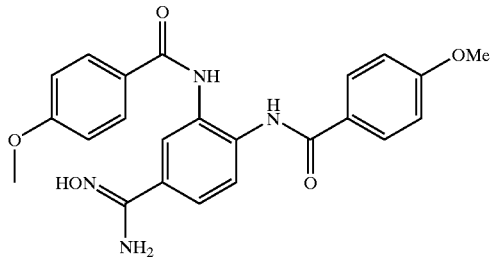

A. 4-Cyano-$N^1,N^2$-bis(4-methoxybenzoyl)-1,2-benzenediamine

Using the procedures described in Example 93, Part A and Example 96, Part B, 2-nitro-4-cyanoaniline (31 mmol) and 4-anisoyl chloride yielded 500 mg (21%, three steps) of the title compound.

MS-FD m/e 401 ($M^+$). Anal. for $C_{23}H_{19}N_3O_4$: Calc: C, 68.80; H, 4.79; N, 10.46; Found: C, 68.80; H, 4.93; N, 10.36.

B. 4-[(Amino)(hydroxyimino)methyl]-$N^1,N^2$-bis(4-methoxybenzoyl)-1,2-benzenediamine To a stirred solution of 4-cyano-$N^1,N^2$-bis(4-methoxybenzoyl)-1,2-benzenediamine (750 mg, 1.9 mmol) was added hydroxylamine hydrochloride (130 mg, 1.9 mmol) and N,N-diisopropylethylamine (0.30 mL, 1.9 mmol). After heating at reflux for 12 h, the solution was cooled and the solvent was removed in vacuo. The residue was suspended in ethyl acetate and water, stirred vigorously, filtered, and dried in vacuo to give 770 mg (95%) of the title product as a white solid.

MS-FD m/e 434.1 ($M^+$). Anal. for $C_{23}H_{22}N_4O_5 \cdot 1.1\, H_2O$: Calc: C, 60.82; H, 5.37; N, 12.33; Found: C, 60.47; H, 4.80; N, 12.10.

EXAMPLE 121

Preparation of 4-[(Amino)(imino)methyl]-$N^1,N^2$-bis(4-methoxybenzoyl)-1,2-benzenediamine

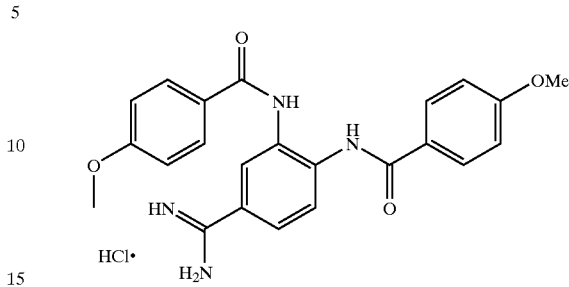

To a stirred solution 4-[(amino)(hydroxyimino)methyl]-$N^1,N^2$-bis(4-methoxybenzoyl)-1,2-benzenediamine (0.50 g, 1.2 mmol), tetrahydrofuran (5 mL), water (25 mL), and 1 N aqueous hydrochloric acid (1.4 mL) in ethanol (50 mL) was added 10% palladium-on-carbon (250 mg). The vessel was placed under vacuum and the atmosphere was replaced with hydrogen (1 bar). After 12 h, the balloon was removed and the mixture was filtered through diatomaceous earth and concentrated in vacuo. The residue was dissolved in ethyl acetate and washed with saturated aqueous sodium chloride solution, dried (magnesium sulfate), filtered, and concentrated in vacuo to give 180 mg (35%) of the title compound.

MS-FD m/e 419 ($M^+$). Anal. for $C_{23}H_{22}N_4O_4 \cdot HCl$: Calc: C, 57.97; H, 5.31; N, 11.76; Found: C, 57.73; H, 5.14; N, 12.06.

EXAMPLE 122

Preparation of $N^1$-(3-Aminobenzoyl)-$N^2$-(4-methoxybenzoyl)-1,2-benzenediamine

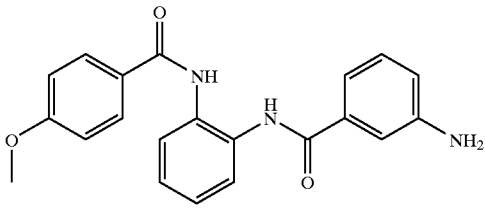

A. $N^1$-(3-Nitrobenzoyl)-$N^2$-(4-methoxybenzoyl)-1,2-benzenediamine

Using the procedure described in Example 93, Part A, 3-nitrobenzoyl chloride (2.3 mmol) and $N^1$-(4-methoxybenzoyl)-1,2-benzenediamine (2.1 mmol) yielded 708 mg (86%) of the title compound.

MS-FD m/e 391 ($M^+$). Anal. for $C_{21}H_{17}N_3O_5$: Calc: C, 64.45; H, 4.38; N, 10.74; Found: C, 64.21; H, 4.56; N, 10.51.

B. $N^1$-(3-Aminobenzoyl)-$N^2$-(4-methoxybenzoyl)-1,2-benzenediamine

Using the procedure described in Example 93, Part A, $N^1$-(3-nitrobenzoyl)-$N^2$-(4-methoxybenzoyl)-1,2-benzenediamine (1.3 mmol) yielded 130 mg (28%) of the title compound.

MS-FD m/e 361 ($M^+$). Anal. for $C_{21}H_{19}N_3O_3$: Calc: C, 69.79; H, 5.30; N, 11.63; Found: C, 69.83; H, 5.44; N, 11.49.

EXAMPLE 123

Preparation of N¹-(3-Amino-4-methoxybenzoyl)-N²-(4-methoxybenzoyl)-1,2-benzenediamine

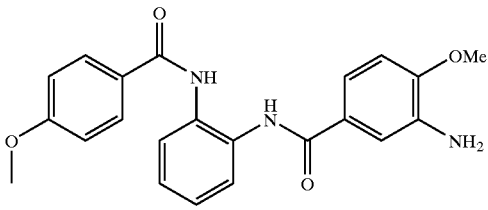

A. N¹-(3-Nitro-4-methoxybenzoyl)-N²-(4-methoxybenzoyl)-1,2-benzenediamine

Using the procedure described in Example 102, Part A, 3-nitro-4-methoxybenzoic acid (3.1 mmol) and N¹-(4-methoxybenzoyl)-1,2-benzenediamine (2.1 mmol) yielded 737 mg (83%) of the title compound.

MS-FD m/e 421 (M⁺). Anal. for $C_{22}H_{19}N_3O_6$: Calc: C, 62.71; H, 4.55; N, 9.97; Found: C, 62.91; H, 4.62; N, 9.97.

B. N¹-(3-Amino-4-methoxybenzoyl)-N²-(4-methoxybenzoyl)-1,2-benzenediamine

Using the procedure described in Example 96, Part B, N¹-(3-nitro-4-methoxybenzoyl)-N²-(4-methoxybenzoyl)-1,2-benzenediamine yielded 29 mg (6%) of the title compound.

MS-FD m/e 391 (M⁺).

EXAMPLE 124

Preparation of 2-[(4-t-Butylbenzoyl)amino]-N-(3,4-methylenedioxyphenyl)-4-[(methylsulfonyl)amino]benzamide

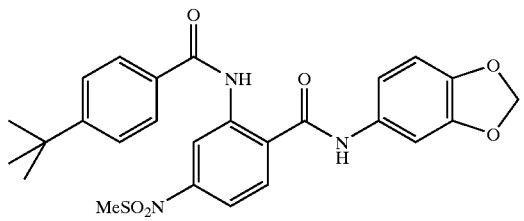

A. 2-[(4-t-Butylbenzoyl)amino]-N-(3,4-methylenedioxyphenyl)-4-nitrobenzamide

By methods substantially equivalent to those described in Example 59-C, 2-[(4-t-butylbenzoyl)amino]-N-(3,4-methylenedioxyphenyl)-4-nitrobenzamide (33%) was prepared from 7-nitro-2-(4-t-butylphenyl)-4H-3,1-benzoxazin-4-one and 3,4-methylenedioxyaniline.

¹H-NMR FD-MS, m/e 461 (M⁺) Analysis for $C_{25}H_{23}N_3O_6$: Calc: C, 65.07; H, 5.02; N, 9.11; Found: C, 66.48; H, 5.33; N, 9.15.

B. 4-Amino-2-[(4-t-butylbenzoyl)amino]-N-(3,4-methylenedioxyphenyl)benzamide

By methods substantially equivalent to those described in Example 1-B, 4-amino-2-[(4-t-butylbenzoyl)amino]-N-(3,4-methylenedioxyphenyl)benzamide (86%) was prepared from 2-[(4-t-butylbenzoyl)amino]-N-(3,4-methylenedioxyphenyl)-4-nitrobenzamide.

¹H-NMR FD-MS, m/e 431.2 (M⁺) Analysis for $C_{25}H_{25}N_3O_4 \cdot 0.1H_2O$: Calc: C, 69.30; H, 5.86; N, 9.70; Found: C, 69.34; H, 6.21; N, 9.09.

C. 2-[(4-t-Butylbenzoyl)amino]-N-(3,4-methylenedioxyphenyl)-4-[(methylsulfonyl)amino]benzamide By methods substantially equivalent to those described in Example 59-E, 2-[(4-t-butylbenzoyl)amino]-N-(3,4-methylenedioxyphenyl)-4-[(methylsulfonyl)amino]benzamide (83%) was prepared from 4-amino-2-[(4-t-butylbenzoyl)amino]-N-(3,4-methylenedioxyphenyl)benzamide.

¹H-NMR FD-MS, m/e 509.1 (M⁺) Analysis for $C_{26}H_{27}N_3O_6S$: Calc: C, 61.28; H, 5.34; N, 8.25; Found: C, 62.70; H, 5.93; N, 7.75.

Preparation of Examples 125–133a

The following procedure was use in Examples 125–133a:

To a small glass vial with a polytetrafluoroethylene lined cap was added an aryl-1,2-diamine (about 0.25 mmol) in tetrahydrofuran (3 mL), followed by poly(4-vinylpyridine) (250 mg, 1 mmol) and p-anisoyl chloride (0.625 mmol). After agitating this mixture for 24 h on a platform shaker; aminomethylated polystyrene (1 g, 1 mmol) was added and agitation continued for another 8 h. The solution was filtered and concentrated in vacuo, and the residue triturated with diethyl ether. The resulting solid was filtered and dried in vacuo to give approximately 50 mg of the title compound.

EXAMPLE 125

N¹,N²-bis(4-Methoxybenzoyl)naphthalene-1,2-diamine

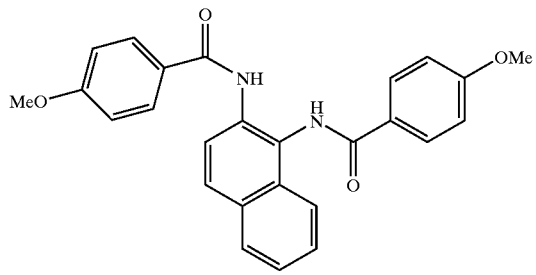

MS-FD m/e 426 (M⁺).

EXAMPLE 126

4-Methyl-N¹,N²-bis(4-methoxybenzoyl)-1,2-benzenediamine

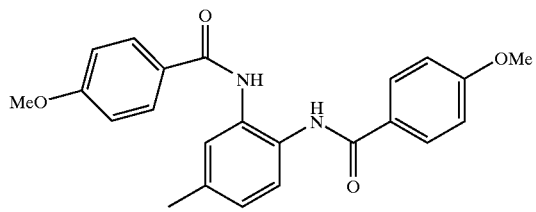

MS-FD m/e 391 (M⁺).

EXAMPLE 127

3-Methyl-$N^1$,$N^2$-bis(4-methoxybenzoyl)-1,2-benzenediamine

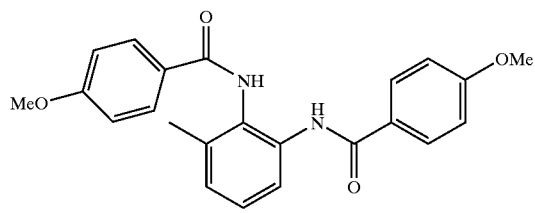

MS-FD m/e 390 (M$^+$).

EXAMPLE 128

4-Nitro-$N^1$,$N^2$-bis(4-methoxybenzoyl)-1,2-benzenediamine

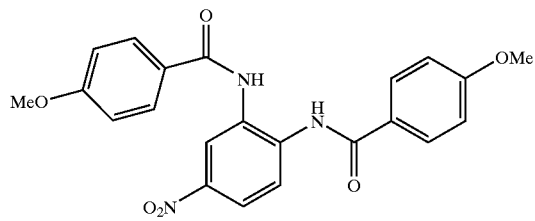

MS-FD m/e 421.2 (M$^+$).

EXAMPLE 129

4,5-Dichloro-$N^1$,$N^2$-bis(4-methoxybenzoyl)-1,2-benzenediamine

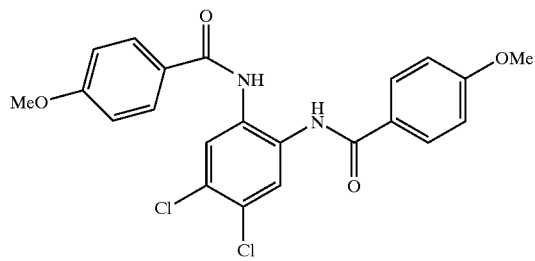

MS-FD m/e 444 (M$^+$).

EXAMPLE 130

4-Chloro-$N^1$,$N^2$-bis(4-methoxybenzoyl)-1,2-benzenediamine

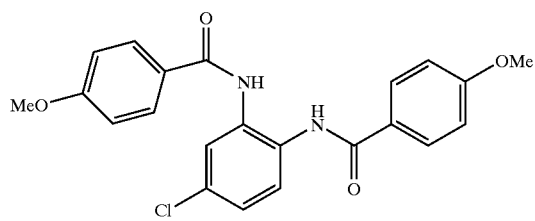

MS-FD m/e 409 (M$^+$).

EXAMPLE 131

4-Chloro-5-trifluoromethyl-$N^1$,$N^2$-bis(4-methoxybenzoyl)-1,2-benzenediamine

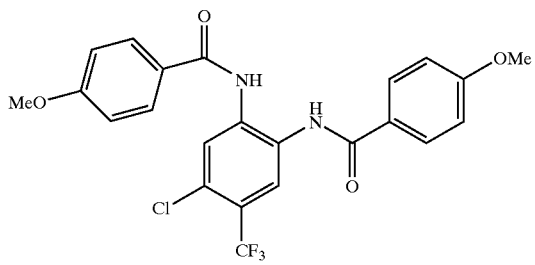

MS-FD m/e 478.1 (M$^+$)

EXAMPLE 132

4-Chloro-5-fluoro-$N^1$,$N^2$-bis(4-methoxybenzoyl)-1,2-benzenediamine

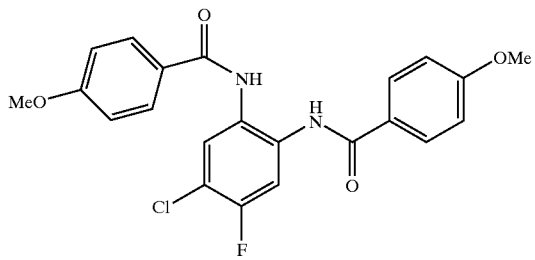

MS-FD m/e 428.1 (M$^+$).

EXAMPLE 133

4-Fluoro-$N^1$,$N^2$-bis(4-methoxybenzoyl)-1,2-benzenediamine

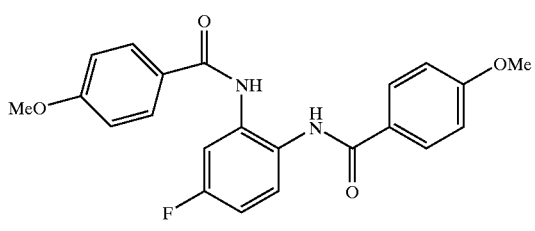

MS-FD m/e 394 (M$^+$).

EXAMPLE 133a

4-Methoxycarbonyl-$N^1,N^2$-bis(4-methoxybenzoyl)-1,2-benzenediamine

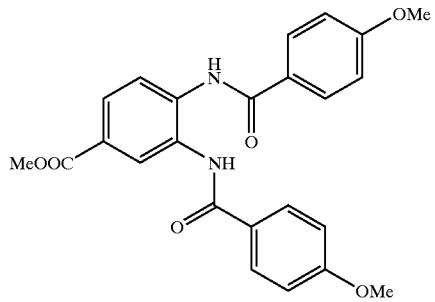

MS-FD m/e 434.1 (M⁺).

EXAMPLE 134

Preparation of 2-[(4-tert-Butylbenzoyl)amino]-N-(4-methoxyphenyl)-6-methylbenzamide

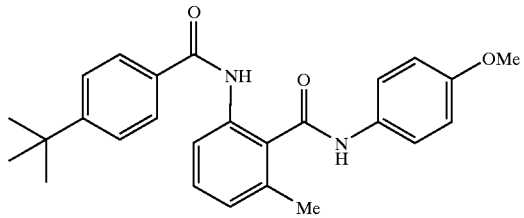

A. N-(4-Methoxyphenyl)-2-nitro-6-methylbenzamide

Using the procedure described in Example 102, Part A, 2-nitro-6-methylbenzoic acid (5.5 mmol) and 4-dimethylaminopyridine (1.1 mmol) yielded 0.44 g (28%) of the title compound.

MS-FD m/e 286.1 (M⁺). Anal. For $C_{15}H_{14}N_2O_4$: Calc: C, 62.93; H, 4.93; N, 9.78; Found: C, 62.47; H, 4.75; N, 9.27.

B. 2-[(4-tert-Butylbenzoyl)amino]-N-(4-methoxyphenyl)-6-methylbenzamide

Using the procedure described in Example 93, Part B, N-(4-methoxyphenyl)-2-nitro-6-methylbenzamide (1.05 mmol) was reduced to the corresponding amine. Using the procedure described in Example 93, Part A, the amine was reacted with 4-tert-butylbenzoyl chloride (1.05 mmol) to yield 72 mg (17%) of the title compound.

MS-FD m/e 416.4 (M⁺). Anal. For $C_{26}H_{28}N_2O_3$: Calc: C, 74.98; H, 6.78; N, 6.73; Found: C, 75.04; H, 6.82; N, 6.88.

EXAMPLE 135

Preparation of 2-[(4-tert-Butylbenzoyl)amino]-N-(4-methoxyphenyl)-6-fluorobenzamide

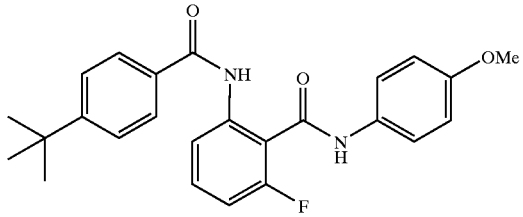

A. Preparation of 6-fluoroisatoic anhydride

Using the procedure described in Example 69, Part A, 6-fluoroanthranilic acid (31.5 mmol), yielded 5.2 g (91%) of the title compound.

MS-FD m/e 181.1 (M⁺). Anal. For $C_8H_4FNO_3$: Calc: C, 53.05; H, 2.23; N, 7.73; Found: C, 52.91; H, 2.31; N, 7.53.

B. N-(4-Methoxyphenyl)-2-amino-6-fluorobenzamide

Using the procedure described in Example 91, Part B, 6-fluoroisatoic anhydride (11 mmol) and 4-methoxyaniline (11 mmol) yielded 2.34 g (84%) of the title compound.

MS-FD m/e 260 (M⁺). Anal. For $C_{14}H_{13}FN_2O_2$: Calc: C, 64.61; H, 5.04; N, 10.76; Found: C, 63.33; H, 4.90; N, 10.34.

C. 2-[(4-tert-Butylbenzoyl)amino]-N-(4-methoxyphenyl)-6-fluorobenzamide

Using the procedure described in Example 93, Part A, N-(4-methoxyphenyl)-2-amino-6-fluorobenzamide (1.9 mmol) and 4-tert-butylbenzoyl chloride (2.1 mmol) yielded 530 mg (65%) of the title compound.

MS-FD m/e 420.3 (M⁺). Anal. For $C_{25}H_{25}FN_2O_3$: Calc: C, 71.41; H, 5.99; N, 6.66; Found: C, 71.58; H, 5.97; N, 6.55.

EXAMPLE 136

Preparation of 2-[(4-tert-Butylbenzoyl)amino]-N-(3-hydroxyphenyl)-5-(methylsulfonylamino)benzamide

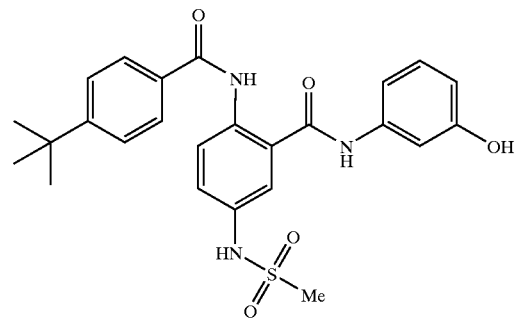

A. 2-[(4-tert-Butylbenzoyl)amino]-N-(3-benzyloxyphenyl)-5-nitrobenzamide

Using the procedure described in Example 91, Part B, 3-benzyloxyaniline (2.5 mmol) and 2-(4-tert-butylphenyl)-6-nitro-4H-3,1-benzoxazin-4-one (2.8 mmol) yielded 550 mg (42%) of the title compound.

MS-FD m/e 523 (M⁺) Anal. For $C_{31}H_{29}N_3O_5$: Calc: C, 71.11; H, 5.58; N, 8.03; Found: C, 71.34; H, 5.66; N, 8.16.

B. 2-[(4-tert-Butylbenzoyl)amino]-N-(3-benzyoxyphenyl)-5-aminobenzamide

Using the procedure described in Example 93, Part B, 2-[(4-tert-butylbenzoyl)amino]-N-(3-benzyloxyphenyl)-5-nitrobenzamide (1.03 mmol) yielded 270 mg (53%) of the title compound.

MS-FD m/e 493 (M+) Anal. For $C_{31}H_{31}N_3O_3$: Calc: C, 75.43; H, 6.33; N, 8.51; Found: C, 75.39; H, 6.41; N, 8.26.

C. 2-[(4-tert-Butylbenzoyl)amino]-N-(3-benzyloxyphenyl)-5-(methylsulfonylamino)benzamide Using the procedure described in Example 59, Part E, 2-[(4-tert-butylbenzoyl)amino]-N-(3-benzyoxyphenyl)-5-aminobenzamide (0.51 mmol) yielded 225 mg (77%) of the title compound.

MS-FD m/e 571.1 (M+). Anal. For $C_{32}H_{33}N_3O_5S$: Calc: C, 67.23; H, 5.82; N, 7.35; Found: C, 66.96; H, 5.96; N, 7.07.

D. 2-[(4-tert-Butylbenzoyl)amino]-N-(3-hydroxyphenyl)-5-(methylsulfonylamino)benzamide Using the procedure described in Example 96, Part B, 2-[(4-tert-butylbenzoyl)amino]-N-(3-benzyloxyphenyl)-5-(methylsulfonylamino)benzamide (0.35 mmol) yielded 160 mg (94%) of the title compound.

MS-FD m/e 481.2 (M+). Anal. For $C_{25}H_{27}N_3O_5S$: Calc: C, 62.35; H, 5.65; N, 8.73; Found: C, 62.47; H, 5.73; N, 8.60.

EXAMPLE 137

Preparation of 4-Acetylamino-N-(4-methoxyphenyl)-2-[[1-(4-pyridylmethyl)piperidin-4-ylcarbonyl]amino]benzamide

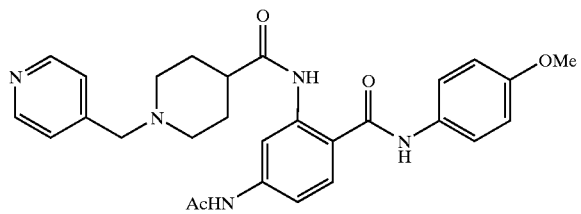

A. N-(4-Methoxyphenyl)-2,4-dinitrobenzamide

Using the procedure described in Example 93, Part A, 4-methoxyaniline (43.76 mmol) and 2,4-dinitrobenzoyl chloride (48.14 mmol) yielded 10.29 g (74%) of the title compound.

MS-FD m/e 317.1 (M+). Anal. For $C_{14}H_{11}N_3O_6$: Calc: C, 53.00; H, 3.50; N, 13.25; Found: C, 53.13; H, 3.57; N, 13.52.

B. N-(4-Methoxyphenyl)-2,4-diaminobenzamide

Using the procedure described in Example 96, Part B, N-(4-methoxyphenyl)-2,4-dinitrobenzamide (72 mmol), yielded 16.2 g (87%) of the title compound.

MS-FD m/e 257 (M+). Anal. For $C_{14}H_{15}N_3O_2$: Calc: C, 65.35; H, 5.88; N, 16.33; Found: C, 65.54; H, 5.92; N, 16.28.

C. 4-Acetylamino-2-amino-N-(4-methoxyphenyl)benzamide

To a stirred solution of N-(4-methoxyphenyl)-2,4-diaminobenzamide (19 g, 73.8 mmol) in N,N-dimethylformamide (250 mL) was added pyridine (6.6 mL, 81 mmol), followed by acetic anhydride (6.6 mL, 70 mmol). After stirring overnight, the solvents were removed in vacuo and the residue was chromatographed over a silica gel (10% tetrahydrofuran/90% chloroform). The appropriate fractions were combined and concentrated in vacuo to give 5.3 g (24%) of the title compound as an off-white solid.

MS-FD m/e (M+).

D. 4-Acetylamino-N-(4-methoxyphenyl)-2-[[1-(benzyloxycarbonyl)piperidin-4-ylcarbonyl]amino]benzamide To a stirred suspension of N-benzyloxycarbonylisonipecotic acid (8.0 g, 30.5mmol) in toluene (350 mL) was added oxalyl chloride (4.0 mL, 45.7 mmol) followed by a few drops of N,N-dimethylformamide. After stirring for 72 h, the solvents were removed in vacuo to give 8.4 g (94%) of an off-white solid. A portion of this solid (3.0 g) was dissolved dichloromethane (0 mL) and added to a stirred solution of 4-acetylamino-2-amino-N-(4-methoxyphenyl)benzamide (2.0 g, 6.68 mmol) in a mixture of dichloromethane (50 mL) and pyridine (50 mL). After 2 h, the solvent was removed in vacuo and the residue was dissolved in ethyl acetate and washed with water, followed by saturated aqueous sodium bicarbonate and brine. The organic phase was then dried (magnesium sulfate), filtered, and concentrated in vacuo to give a solid which was triturated from diethyl ether to give the title compound (2.79 g, 77%) as a white solid.

MS-FD m/e 544.1 (M+). Anal. For $C_{30}H_{32}N_4O_6$: Calc: C, 66.16; H, 5.92; N, 10.29; Found: C, 66.11; H, 6.07; N, 9.99.

E. 4-Acetylamino-N-(4-methoxyphenyl)-2-[(4-piperidinylcarbonyl)amino]benzamide

Using the procedure described in Example 96, Part B, 4-acetylamino-N-(4-methoxyphenyl)-2-[[1-(benzyloxycarbonyl)piperidin-4-ylcarbonyl]amino]benzamide (5.0 mmol), yielded 0.95 g (47%) of the title compound.

MS-FD m/e 410 (M+). Anal. For $C_{22}H_{26}N_4O_4 \cdot 1.2H_2O$: Calc: C, 61.15; H, 6.63; N, 12.97; Found: C, 61.43; H, 6.44; N, 12.59.

F. 4-Acetylamino-N-(4-methoxyphenyl)-2-[[1-(4-pyridylmethyl)piperidin-4-ylcarbonyl]amino]benzamide To a stirred suspension of 4-acetylamino-N-(4-methoxyphenyl)-2-[(4-piperidinylcarbonyl)amino]benzamide (0.4 g, 0.97 mmol), 4-pyridinecarboxaldehyde (0.11 mL, 1.17 mmol) and acetic acid (0.085 mL, 1.46 mmol) in 1,2-dichloroethane (20 mL) was added sodium triacetoxyborohydride (0.31 g, 1.46 mmol). After stirring overnight, the white solid was filtered off and the filtrate was concentrated in vacuo. The residue was suspended in diethyl ether, sonicated, and filtered. The combined solids were then washed with water, filtered and dried in vacuo to give 0.37 g (76%) of the title compound as a white solid.

MS-FD m/e 501.3 (M+). Anal. For $C_{28}H_{31}N_5O_4$: Calc: C, 67.05; H, 6.23; N, 13.96; Found: C, 67.06; H, 6.42; N, 13.81.

EXAMPLE 138

Preparation of N-(4-methoxyphenyl)-2-[[1-(4-pyridyl)piperidin-4-ylcarbonyl]amino]benzamide

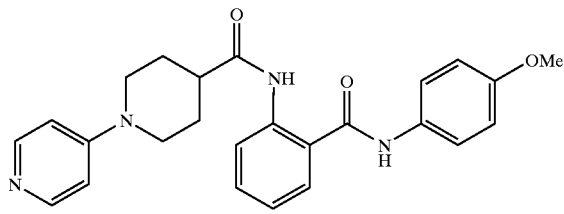

To a stirred suspension of N-(4-pyridyl)isonipecotic acid (0.2 g, 1 mmol) in dichloromethane (70 mL) was added thionyl chloride (0.11 mL, 1.5 mmol). After stirring overnight, the solvent was removed in vacuo and the residue was dissolved in dichloromethane (10 mL) and added to a stirred solution of 2-amino-N-(4-methoxyphenyl)benzamide (0.186 g, 0.77 mmol) and pyridine (0.19 g, 0.85 mmol) in dichloromethane (25 mL). After stirring for 72 h, the solution was transferred to a separatory funnel and washed with water, saturated aqueous sodium bicarbonate solution, and saturated aqueous sodium chloride solution. The organic phase was dried (magnesium sulfate), filtered, and concentrated in vacuo. The residue was suspended in a mixture of diethyl ether and hexanes, sonicated, and filtered. The resulting solid was washed with diethyl ether and dried in vacuo to give 0.10 g (30%) of the title compound as a pale tan solid.

$^1$H-NMR (DMSO-$d_6$): δ 10.79 (s, 1 H), 10.31 (s, 1 H), 8.25 (d, J=8.3 Hz, 1 H), 8.13 (d, J=5.7 Hz, 2 H), 7.80 (dd, J=1.1, 7.9 Hz, 1 H),7.60 (d, J=9.0 Hz, 2 H), 7.51 (dt, J=1.3, 8.3 Hz, 1 H), 7.21 (dt, J=1.3, 8.7 Hz, 1 H), 6.94 (d, J=9.0 Hz, 2 H), 6.82 (d, J=6.4 Hz, 2 H), 3.95 (dt, J=13.2, 3.4 Hz, 2 H), 2.92 (dt, J=2.3, 13.2 Hz, 2H), 2.63 (tt, J=4.1, 13.2 Hz, 1 H), 1.90 (dd, J=2.3, 12.8 Hz, 2 H), 1.61 (dq, J=3.8, 13.2 Hz, 2 H); MS-FD m/e 431 (M$^+$). Anal. For $C_{25}H_{26}N_4O_3$: Calc: C, 69.75; H, 6.09; N, 13.01; Found: C, 69.58; H, 6.36; N, 12.96.

EXAMPLE 139

Preparation of N$^1$-Benzyl-N$^2$-[[1-(4-pyridyl)piperidin-4-yl]methoxycarbonylamino]-1,2-benzenediamine hydrochloride hemihydrate

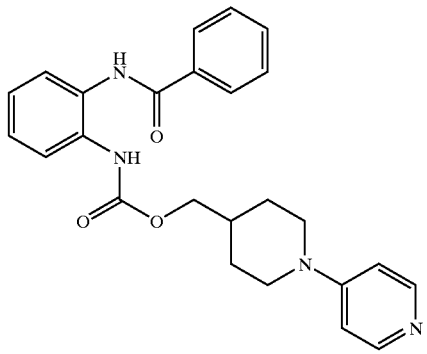

Using the procedure described in Example 48, Part C, N$^1$-[[1-(4-pyridyl)piperidin-4-yl]methoxycarbonylamino]- 1,2-benzenediamine (0.61 mmol) and benzoyl chloride (1.2 mmol) yielded 175 mg (61%) of the title compound.

MS-FD m/e 430.3 (M$^+$). Anal. For $C_{25}H_{26}N_4O_3$·1.1HCl·0.5H$_2$O: Calc: C, 62.61; H, 5.91; N, 11.68; Cl, 8.13; Found: C, 62.88; H, 5.75; N, 11.55; Cl, 7.89.

EXAMPLE 140

Preparation of N$^1$-(3-Fluorobenzoyl)-N$^2$-[[1-(4-pyridyl)piperidin-4-yl]methoxycarbonylamino]-1,2-benzenediamine hydrochloride hydrate

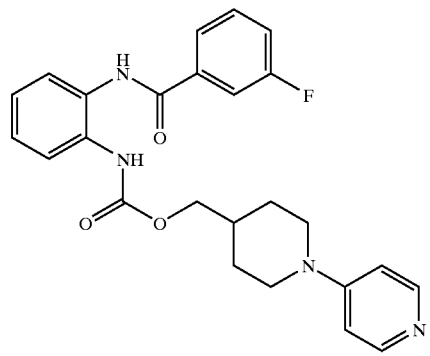

Using the procedure described in Example 48, Part C, N$^1$-[[1-(4-pyridyl)piperidin-4-yl]methoxycarbonylamino]- 1,2-benzenediamine (0.61 mmol) and 3-fluorobenzoyl chloride (1.2 mmol) yielded 152 mg (51%) of the title compound.

MS-FD m/e 448.1 (M$^+$). Anal. For $C_{25}H_{25}FN_4O_3$·1.25HCl·1.1H$_2$O: Calc: C, 60.68; H, 5.79; N, 11.32; Cl, 8.95; Found: C, 60.32; H, 5.39; N, 11.09; Cl, 8.89.

EXAMPLE 141

Preparation of N$^1$-(3-Chlorobenzoyl)-N$^2$-[[1-(4-pyridyl)piperidin-4-yl]methoxycarbonylamino]-1,2-benzenediamine hydrochloride hemihydrate

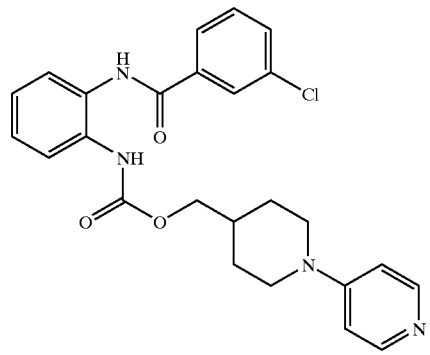

Using the procedure described in Example 48, Part C, N$^1$-[[1-(4-pyridyl)piperidin-4-yl]methoxycarbonylamino]- 1,2-benzenediamine (0.61 mmol) and 3-chlorobenzoyl chloride (1.2 mmol) yielded 211 mg (69%) of the title compound.

$^1$H-NMR (DMSO-$d_6$): δ 13.57 (br s, 1 H), 10.08 (s, 1 H), 9.00 (s, 1 H), 8.19 (t, J=6.2 Hz, 2 H), 8.06 (t, J=1.7 Hz, 1 H), 7.95 (d, J=7.9 Hz, 1 H), 7.68 (dd, J=1.5, 7.9 Hz, 1 H), 7.55–7.60 (m, 2 H), 7.48 (dd, J=1.5, 7.9 Hz, 1 H), 7.22 (dt, J=1.5, 7.5 Hz, 1 H), 7.17 (d, J=6.8 Hz, 2 H), 7.14 (m, 1 H), 4.21 (d, J=13.9 Hz, 2 H), 3.97 (d, J=6.4 Hz, 2 H), 3.14 (t, J=12.0 Hz, 2 H), 2.06 (m, 1 H), 1.81 (br d, J=12 Hz, 2 H), 1.23 (br q, J=12 Hz, 2 H); MS-FD m/e 464.1 (M$^+$). Anal. For C$_{25}$H$_{25}$ClN$_4$O$_3$.1.5HCl.0.5H$_2$O: Calc: C, 56.80; H, 5.24; N, 10.60; Cl, 16.77; Found: C, 56.62; H, 5.28; N, 10.53; Cl, 16.62.

EXAMPLE 142

Preparation of N$^1$-(3-Bromobenzoyl)-N$^2$-[[1-(4-pyridyl)piperidin-4-yl]methoxycarbonylamino]-1,2-benzenediamine hydrochloride hydrate

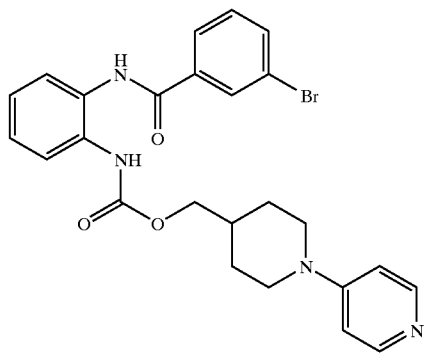

Using the procedure described in Example 48, Part C, N$^1$-[[1-(4-pyridyl)piperidin-4-yl]methoxycarbonylamino]-1,2-benzenediamine (0.61 mmol) and 3-bromobenzoyl chloride (1.2 mmol) yielded 202 mg (60%) of the title compound.

MS-FD m/e 508.2 (M$^+$). Anal. For C$_{25}$H$_{25}$BrN$_4$O$_3$.1.4HCl.0.75H$_2$O: Calc: C, 52.32; H, 4.90; N, 9.76; Cl, 8.64; Found: C, 51.99; H, 4.52; N, 9.54; Cl, 8.69.

EXAMPLE 143

Preparation of N$^1$-(4-Methylbenzoyl)-N$^2$-[[1-(4-pyridyl)piperidin-4-yl]methoxycarbonylamino]-1,2-benzenediamine hydrochloride

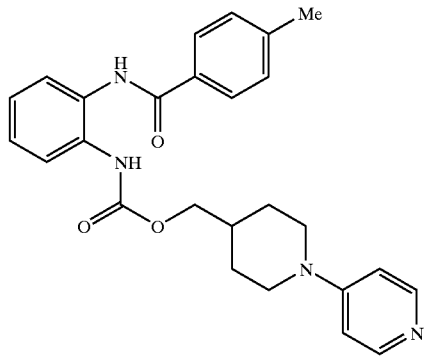

Using the procedure described in Example 48, Part C, N$^1$-[[1-(4-pyridyl)piperidin-4-yl]methoxycarbonylamino]-1,2-benzenediamine (0.61 mmol) and 4-methylbenzoyl chloride (1.2 mmol) yielded 164 mg (56%) of the title compound.

$^1$H-NMR (DMSO-d$_6$): δ 13.50 (br s, 1 H), 9.90 (s, 1 H), 8.90-(s, 1 H), 8.19 (br t, J=5.8 Hz, 2 H), 7.89 (d, J=8.3 Hz, 2 H), 7.49–7.56 (m, 2 H), 7.34 (d, J=8.3 Hz, 2 H), 7.13–7.23 (m, 4 H), 4.21 (d, J=13.6 Hz, 2 H), 3.97 (d, J=6.4 Hz, 2 H), 3.14 (t, J=12.4 Hz, 2 H), 2.05 (m, 1 H), 1.80 (d, J=13.2 Hz, 2 H), 1.23 (q, J=12.4 Hz, 2 H); MS-FD m/e 444.2 (M$^+$). Anal. For C$_{26}$H$_{28}$N$_4$O$_3$.1.4HCl: Calc: C, 63.01; H, 5.98; N, 11.31; Cl, 10.02; Found: C, 63.30; H, 6.06; N, 11.18; Cl, 9.80.

EXAMPLE 144

Preparation of N$^1$-(4-Methoxybenzoyl)-N$^2$-(4-ethoxybenzoyl)-1,2-benzenediamine

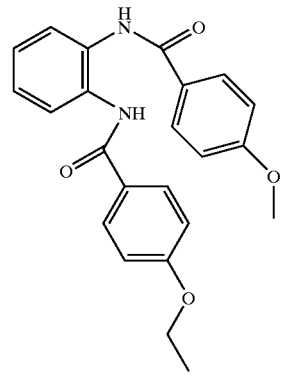

To a mixture of 4-ethoxybenzoic acid (0.332 g, 2.00 mmol) and a few drops of N,N-dimethylformamide in methylene chloride (50 mL) cooled to 0° C. was added oxayl chloride (0.21 mL, 2.2 mmole). After 30 min reaction the mixture was warmed to room temperature and stirred for an additional 10 min. The mixture was concentrated in vacuo, and the residue dissolved in methylene chloride (10 mL), and the resulting solution added in two portions to a mixture of N$^1$-(4-methoxybenzoyl)-1,2-benzenediamine (0.455 g, 2.00 mmol) and triethylamine (0.281 mL, 2.00 mmol) in methylene chloride (40 mL) cooled to 0° C. After 4 h, the mixture was allowed to warm to room temperature and stirred for an additional 12 h. The reaction was quenched with cold dilute aqueous hydrochloric acid (50 mL), diluted with hexane, and shaken in a separatory funnel. The organic layer was washed with cold dilute aqueous hydrochloric acid and saturated aqueous sodium bicarbonate solution. The solution was dried (magnesium sulfate), filtered, and concentrated in vacuo. Recrystallization of the residue from methylene chloride/hexane provided 317 mg (41%) of title compound.

$^1$H-NMR (DMSO-d$_6$) δ 9.97 (s, 2H), 7.86 (d, 4H), 7.6 (m, 2H), 7.3 (m, 2H), 7.08 (d, 2H), 7.05 (d, 2H), 4.10 (g, 2H), 3.82 (s, 3H), 1.37 (t,3H); IR (KBr) cm$^{-1}$: 1606, 1646, 3259;

MS-FD m/e 390 (M$^+$). Analysis for C$_{23}$H$_{23}$N$_2$O$_4$: Calc: C, 70.75; H, 5.68; N, 7.17; Found: C, 66.03; H, 5.36; N, 6.58.

EXAMPLE 145

Preparation of N¹-(4-methoxybenzoyl)-N²-[4-(1-methylethoxy)benzoyl]-1,2-benzenediamine

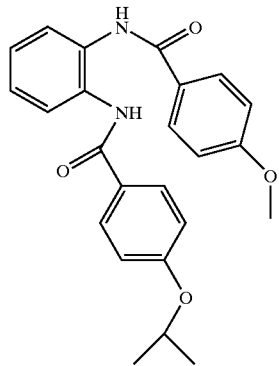

Using the procedure described in Example 144, 4-(1-methylethoxy)benzoic acid (2.00 mmol) yielded, after recrystallization from methylene chloride/hexane, 272 mg (34%) of the title compound.

¹H-NMR (DMSO-$d_6$) δ 9.96 (s, 2H), 7.91 (d, 2H), 7.86 (d, 2H), 7.6 (m, 2H), 7.2 (m, 2H), 7.02 (d, 2H), 6.99 (d, 2H), 4.68 (septet, 1H), 3.78 (s, 3H), 1.24 (d, 6H); IR (KBr) cm⁻¹: 1607, 1648, 3300; MS-FD m/e 404 (M⁺). Analysis for $C_{24}H_{24}N_2O_4$: Calc: C, 71.27; H, 5.98; N, 6.93; Found: C, 71.37; H, 5.99; N, 7.07.

EXAMPLE 146

Preparation of 3-[(4-Methoxybenzoyl)amino]-4-[(4-tert-butylbenzoyl)amino]benzoic Acid

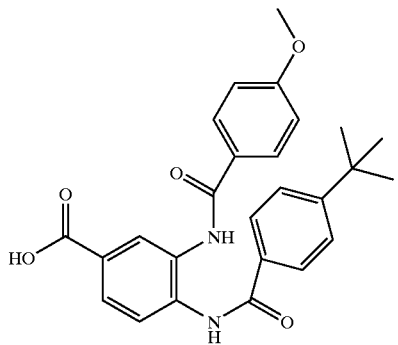

A. Methyl 3-[(4-Methoxybenzoyl)amino]-4-aminobenzoate

A solution of methyl 3,4-diaminobenzoate hydrochloride (1.43 g, 6.00 mmol) in acetonitrile (100 mL) was cooled to 0° C. and treated with water (15 mL), pyridine (0.97 mL, 12 mmol), and a solution of p-anisoyl chloride (1.03 g, 6.00 mmol) in acetonitrile (25 mL). The reaction mixture was allowed to slowly warm to room temperature over 16 h. The resulting precipitate was collected and washed with acetonitrile to provide 1.07 g (59%) of the title compound.

¹H-NMR (DMSO-$d_6$) δ 10.12 (s, 1 H), 10.08 (s, 1 H), 8.18 (s, 1H), 7.95 (d, 2H), 7.9 (m, 4H), 7.8–7.9 (m, 4H), 7.53 (d, 2H), 7.05 (d, 2H), 3.81 (s, 3H), 1.28 (s, 9H).

B. Methyl 3-[(4-Methoxybenzoyl)amino]-4-[(4-tert-butylbenzoyl)amino]benzoate

A solution of methyl 3-[(4-methoxybenzoyl)amino]-4-aminobenzoate (0.800 g, 2.67 mmol) in 1:1 acetonitrile/chloroform (100 mL) was cooled to 0° C. and treated with triethylamine (0.41 mL, 2.9 mmol), and a solution of 4-tert-butylbenzoyl chloride (0.58 mL) in acetonitrile (25 µL). The reaction mixture was allowed to warm to room temperature over 16 h, concentrated in vacuo, diluted with ethyl acetate, washed with cold dilute aqueous hydrochloric acid and cold saturated aqueous sodium bicarbonate solution. The organic layer was dried (magnesium sulfate), filtered, and concentrated in vacuo. Crystallization of the residue from methylene chloride/hexane provided 1.0 g (81%) of the title compound.

¹H-NMR (DMSO-$d_6$) δ 10.16 (s, 2H), 8.27 (s, 1H), 7.8–8.0 (m, 6H), 7.58 (d, 2H), 7.09 (d, 2H), 3.87 (s, 3H), 3.80 (s, 3H), 1.30 (s, 9H); MS-FD m/e 460 (M⁺). Analysis for $C_{27}H_{28}N_2O_5$: Calc: C, 70.42; H, 6.13; N, 6.08; Found: C, 70.15; H, 6.09; N, 6.27.

C. 3-[(4-Methoxybenzoyl)amino]-4-[(4-tert-butylbenzoyl)amino]benzoic Acid

To a solution of methyl 3-(4-methoxybenzoyl)amino]-4-[(4-tert-butylbenzoyl)amino]benzoate (0.487 g, 1.00 mmol) in tetrahydrofuran (32 mL) and methanol (8 mL) was added 5 N aqueous sodium hydroxide (0.6 mL). The resulting mixture was stirred for 16 h, a second portion of 5 N aqueous sodium hydroxide (0.6 mL) added, and the mixture stirred for an additional 16 h. The solvent was concentrated in vacuo and the crude product acidified with dilute aqueous hydrochloric acid and diluted with ethyl acetate. The mixture was extracted with saturated aqueous potassium carbonate solution. The aqueous layer was acidified and extracted with ethyl acetate. The organic layer was dried (magnesium sulfate), filtered, and concentrated in vacuo. Crystallization of the residue from methylene chloride/hexane provided 376 mg (100%) of the title product.

¹H NMR (DMSO-$d_6$) δ 10.12 (s, 1H) 10.08 (s, 1H), 8.18 (s, 1H), 7.87 (d, 1H), 7.86 (d, 2H), 7.82 (d, 1H), 7.53 (d, 2H), 7.05 (d, 2H), 3.81 (s, 3H), 1.28 (s, 9H); MS-FD m/e 446 (M⁺); IR (KBr) cm⁻¹: 1608, 1659, 1687, 2963. Analysis for $C_{26}H_{26}N_2O_5$: Calc: C, 69.94; H, 5.87; N, 6.27; Found: C, 70.90; H, 6.06; N, 6.29.

EXAMPLE 147

Preparation of 3-[(4-tert-Butylbenzoyl)amino]-4-[(4-methoxybenzoyl)aminobenzoic Acid

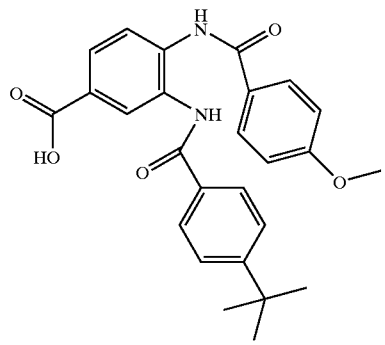

A. Methyl 4-Amino-3-[(4-tert-butylbenzoyl)amino]benzoate

Using the procedure described in Example 146, Part A, 4-tert-butylbenzoyl chloride (6.00 mmol) was reacted with methyl 3,4-diaminobenzoate dihydrochloride. As the product did not precipitate directly, the reaction mixture was concentrated in vacuo, diluted with ethyl acetate, and washed with saturated aqueous sodium bicarbonate solution. The organic layer was dried (magnesium sulfate), filtered, and concentrated in vacuo to provide 0.885 g (44%) of the title compound as a crystalline solid.

$^1$H-NMR (DMSO-d$_6$) δ 7.89 (d, 2H), 7.75 (s, 1H), 7.49 (d, 2H), 6.74 (d, 2H), 5.78 (s, 2H), 3.72 (s, 3H), 1.29 (s, 9H); MS-FD m/e 326 (M$^+$); IR (KBr) cm$^{-1}$: 1634, 1654, 1700, 1334. Analysis for C$_{19}$H$_{22}$N$_2$O$_3$: Calc: C, 69.92; H, 6.79; N, 8.58; Found: C, 69.34; H, 6.61; N, 8.57.

B. Methyl 3-[(4-tert-Butylbenzoyl)amino]-4-[(4-methoxybenzoyl)amino]benzoate

Using p-anisoyl chloride and the procedure described in Example 146, Part B, methyl 4-amino-3-[(4-tert-butylbenzoyl)amino]benzoate (2.71 mmol) yielded, after recrystallization from methylene chloride/hexane, 0.862 g (69%) of the title compound as a crystalline solid.

$^1$H NMR (DMSO-d$_6$) δ 10.14 (s, 2H), 8.28 (s, 1H), 7.97 (d, 2H), 7.9 (m, 4H), 7.57 (d, 2H), 7.10 (d, 2H), 3.87 (s, 3H), 3.82 (s, 3H), 1.33 (s, 9H); IR (KBr) cm$^{-1}$: 1606, 1647, 1721, 3200. Analysis for C$_{27}$H$_{28}$N$_2$O$_5$: Calc: C, 70,42; H, 6.13; N, 6.08; Found: C, 70.34; H, 6.08; N, 6.01.

C. 3-[(4-tert-Butylbenzoyl)amino]-4-[(4-methoxybenzoyl)amino]benzoic Acid

Using the procedure described in Example 146, Part C, methyl 3-[(4-tert-butylbenzoyl)amino]-4-[(4-methoxybenzoyl)amino]benzoate (1.00 mmol) yielded, after acidification of the aqueous layer, 318 mg (71%) of the title compound as a crystalline solid.

$^1$H NMR (DMSO-d$_6$) δ 10.19 (s, 1H), 10.11 (s, 1H), 8.19 (s, 1H), 7.94 (d, 1H), 7.89 (d, 1H), 7.81 (s, 1H), 7.52 (d, 2H), 7.05 (d, 2H), 3.80 (s, 3H), 1.28 (s, 9H); IR (KBr) cm$^{-1}$: 1645, 1690, 3256; MS-FD m/e 446 (M$^+$). Analysis for C$_{26}$H$_{26}$N$_2$O$_5$: Calc: C, 69.49; H, 5.87; N, 6.27; Found: C, 69.74; H, 5.72; N, 6.16.

EXAMPLE 148

Preparation of N-[2-(4-Methoxybenzoyloxy)phenyl]-4-methoxybenzamide

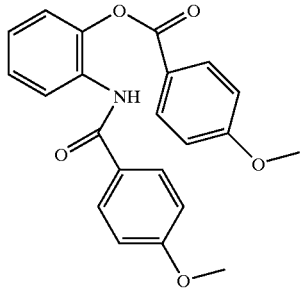

A solution of 2-aminophenol (6.54 g, 60.0 mmol) was dissolved in methylene chloride (200 mL) and cooled to 0° C. Triethylamine (16.7 mL, 120 mmol) was added, followed by the dropwise addition of a solution of p-anisoyl chloride (20.5 g, 120 mmol) in methylene chloride (50 mL). The reaction mixture was allowed to slowly warm to room temperature over 16 h. The reaction mixture was poured over a 1:1 mixture of concentrated hydrochloric acid/crushed ice. The organic layer was diluted with ethyl acetate, washed with cold saturated aqueous sodium bicarbonate solution, dried (magnesium sulfate), filtered, and concentrated in vacuo. Crystallization of the residue from methylene chloride/hexane provided 18.8 g (83%) of the title compound.

$^1$H NMR (DMSO-d$_6$) δ 3.76 (s, 3H), 3.81 (s, 3H), 6.95 (d, 2H), 7.3 (m, 3H), 7.60 (t, 1H), 7.81 (d, 2H), 8.02 (d, 2H); MS-FD m/e 377 (M$^+$); IR (KBr) cm$^{-1}$: 1670, 1715, 3400. Analysis for C$_{22}$H$_{19}$NO$_5$; Calc: C, 70.02; H, 5.07, N, 3.71; Found: C, 69.85; H, 5.00; N, 3.44.

EXAMPLE 149

Preparation of N-[2-(4-tert-Butylbenzoyloxy)phenyl]-4-methoxybenzamide

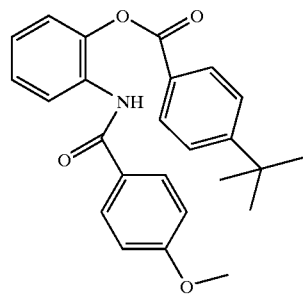

A. N-(2-Hydroxyphenyl)-4-methoxybenzamide

A solution of N-[2-(4-methoxybenzoyloxy)phenyl]-4-methoxybenzamide (3.0 g, 8.0 mmol) in methanol (50 mL) was treated with 5 N aqueous sodium hydroxide (4.78 mL) at room temperature for 16 h. The solution was concentrated to one-half volume in vacuo, 5 N aqueous sodium hydroxide was added, and the resulting mixture stirred for an additional 16 h. The mixture was concentrated in vacuo and acidified with dilute hydrochloric acid. The resulting precipitate was collected by filtration, dissolved in ethyl acetate, and extracted with saturated aqueous potassium carbonate solution. The aquous layer was acidified with dilute hydrochloric acid and extrated with ethyl acetate. The organic layer was dried (magnesium sulfate), filtered, and concentrated in vacuo to provide 1.75 g (90%) the title product as a crystalline solid.

$^1$H NMR (DMSO-d$_6$) δ 9.70 (s, 1H), 9.41 (s, 1H), 7.93 (d, 2H), 7.63 (d, 1H), 7.04 (d, 2H), 7.00 (t, 1H), 6.88 (d, 1H), 6.80 (t, 1H), 3.81 (s, 3H); MS-FD m/e 243 (M$^+$); IR (CHCl$_3$) cm$^{-1}$; 1607, 1645, 3500.

B. N-[2-(4-tert-Butylbenzoyloxy)phenyl]-4-methoxybenzamide

A solution of N-(2-hydroxyphenyl)-4-methoxybenzamide (0.486 g, 2.00 mmol) in methylene chloride (35 mL) was cooled to 0° C. Triethylamine (0.281 mL, 2.00 mmol) was added followed by the dropwise addition of a solution of 4-tert-butylbenzoyl chloride (0.393 mL, 2.00 mmol) in methylene chloride (15 mL). The reaction mixture was allowed to warm to room temperature over 16 h and washed with cold water, dried (magnesium sulfate), filtered, and concentrated in vacuo. Crystallization of the residue from diethyl ether provided 0.563 g (70%) of the title compound.

$^1$H NMR (CDCl$_3$) δ 8.36 (d, 1H), 8.18 (d, 2H), 8.04 (s, 1H), 7.75 (d, 2H), 7.57 (d, 2H), 7.34 (t, 1H), 7.29 (d, 1H), 7.22 (t, 1H), 6.80 (d, 2H), 3.84 (s, 3H), 1.39 (s, 9H); MS-FD m/e 403 (M$^+$); IR (KBr) cm$^{-1}$: 1606, 1679, 1717, 3363. Analysis for C$_{25}$H$_{25}$NO$_4$: Calc: C, 74.42; H, 6.25; N, 3.47; Found: C, 74.65; H, 6.24; N, 3.60.

EXAMPLE 150

Preparation of N-[2-(4-Methoxybenzoyloxy) phenyl]-4-tert-butylbenzamide

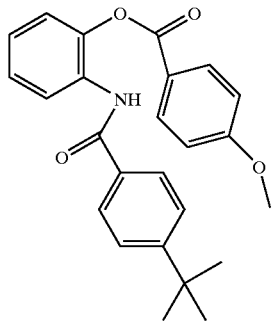

A. N-[2-(4-tert-Butybenzoyloxy)phenyl]-4-tert-butylbenzamide

Using the procedure described in Example 148, 2-aminophenol (30.0 mmol) was reacted with 4-tert-butylbenzoyl chloride to provide, after recrystallization from diethyl ether, 9.48 g (73%) of the title compound.

$^1$H NMR (DMSO-d$_6$) δ 9.59 (s, 1H), 8.01 (d, 2H), 7.65 (t, 1H), 7.55 (d, 2H), 7.42 (d, 2H), 7.3 (m, 3H), 1.27 (s, 9H), 1.24 (s, (H), MS-FD m/e 429 (M$^+$); IR (KBr) cm$^{-1}$: 1607, 1663, 1679, 1751, 2961, 3372. Analysis for C$_{28}$H$_{31}$NO$_3$: Calc: C, 78.17; H, 7.92; N, 3.14; Found: C, 78.82; H, 7.17; N, 3.44.

B. N-(2-Hydroxyphenyl)-4-tert-butylbenzamide

Using the procedure described in Example 149, Part A, N-[2-(4-tert-butybenzoyloxy)phenyl]-4-tert-butylbenzamide (10 mmol) yielded, after crystallization from methylene chloride, 2.08 g (48%) of the title compound.

C. N-[2-(4-Methoxybenzoyloxy)phenyl]-4-tert-butylbenzamide

Using the procedure described in Example 149, Part B, N-(2-hydroxyphenyl)-4-tert-butylbenzamide (2.00 mmol) was reacted with p-anisoyl chloride to yield 494 mg (61%) of the title compound as a crystalline solid.

EXAMPLE 151

No Example for this Number

EXAMPLE 152

Preparation of N-(4-Methoxyphenyl)-2-(4-tert-butylbenzoyloxy)benzamide

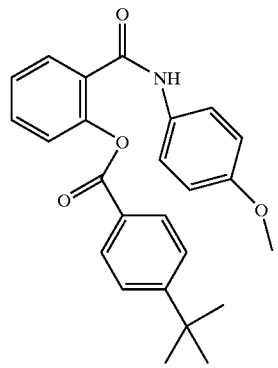

A. N-(4-Methoxyphenyl)-2-hydroxybenzamide

To a solution of salicylic acid (1.38 g, 10.0 mmol) in methylene chloride (100 mL) cooled to 0° C. was added a few drops of dry N,N-dimethylformamide, followed by oxalyl chloride (1.41 mL). After 39 min, the ice bath was removed, and the reaction mixture allowed to warm to room temperature over 2 h. The solvent was removed in vacuo, and the residue dissolved in dry methylene chloride (125 mL). After cooling the solution to 0° C., triethylamine (2.81 mL, 20.0 mmol) was added, followed by the dropwise addition of a solution of p-anisoyl chloride (2.46 g, 20.0 mmol) in methylene chloride (25 mL). After 1 h, the reaction mixture was washed twice with 1 N aqueous hydrochloric acid and once with cold saturated aqueous sodium bicarbonate solution. The organic layer was dried (magnesium sulfate), filtered, and concentrated in vacuo. Trituration with hexane, produced 1.95 g (80%) of the title compound as a crystalline solid.

$^1$H NMR (DMSO-d$_6$) δ 12.00 (s, 1H), 10.25 (s, 1H), 7.95 (d, 1H), 7.51 (d, 2H), 7.44 (t, 1H), 6.9 (m, 4H), 3.75 (s, 3H); MS-FD m/e 243 (M$^+$); IR (KBr) cm$^{-1}$: 1600, 1648, 3500. Analysis for C$_{14}$H$_{13}$NO$_3$: Calc: C, 69.12; H, 5.39; N, 5.76; Found: C, 68.95; H, 5.31; N, 5.84.

B. N-(4-Methoxyphenyl)-2-(4-tert-butylbenzoyloxy) benzamide

To a solution of N-(4-methoxyphenyl)-2-hydroxybenzamide (0.484 g, 2.00 mmol) in methylene chloride (35 mL) cooled to 0° C. was added 0.28 mL triethylamine (0.28 mL, 2.0 mmol), followed by the dropwise addition of a solution of 4-tert-butylbenzoyl chloride (0.393 mL, 2.00 mmol) in methylene chloride (15 mL). The reaction mixture was allowed to warm to room temperature over 16 h and washed with cold water. The organic layer was dried (magnesium sulfate), filtered, and concentrated in vacuo. Trituration with hexane provided 0.488 g (61%) of the title compound.

$^1$H NMR (DMSO-d$_6$) δ 10.23 (s, 1H), 8.01 (d, 2H), 7.71 (d, 1H), 7.64 (t, 1H), 7.57 (d, 2H), 7.52 (d, 2H), 7.43 (t, 1H), 7.38 (d, 1H), 6.84 (d, 2H), 3.80 (s, 3H), 1.40 (s, 9H); MS-FD m/e 403 (M$^+$); IR (KBr) cm$^{-1}$: 1672, 1747, 3500. Analysis for $C_{25}H_{25}NO_2$: Calc: C, 74.42; H, 6.25; N, 3.47; Found: C, 74.28; H, 6.23; N, 3.56.

EXAMPLE 153

Preparation of N-Phenyl-2-(4-tert-butylbenzoyloxy)benzamide

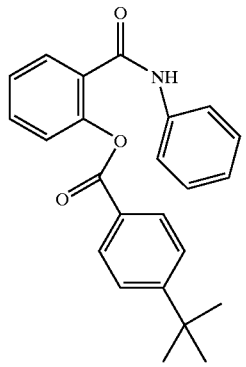

Using the procedure described in Example 152, Part B, N-phenylsalicylamide (5.00 mmol) yielded 1.2 g (64%) of the title compound.

$^1$H NMR (DMSO-d$_6$) δ 10.38 (s, 1H), 8.00 (d, 2H), 7.75 (d, 1H), 7.6 (m, 5H), 7.49 (d, 1H), 7.40 (d, 1H), 7.25 (t, 2H), 7.05 (t, 1H), 1.30 (s, 9H); MS-FD m/e 373 (M$^+$); IR (KBr) cm$^{-1}$: 1601, 1651, 1738, 3300. Analysis for $C_{25}H_{25}NO_4$: Calc: C, 77.19; H, 6.21; N, 3.75; Found: C, 77.24; H, 6.23; N, 3.76.

EXAMPLE

Preparation of N$^1$,N$^2$-bis(4-Methoxybenzoyl)-1,2-benzenediamine

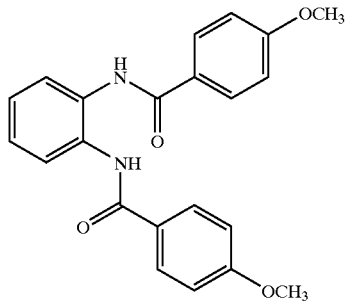

To a solution of o-phenylenediamine (2.16 g, 19.8 mmol) in methylene chloride (200 mL) was added 0.5 N aqueous sodium hydroxide (84 mL), and the resulting mixture was cooled in an ice-water bath. p-Anisoyl chloride (6.2 g, 40 mmol) was added slowly with vigorous stirring. The mixture was allowed to warm slowly to room temperature and stirred for 18 h. The organic layer was separated and washed with dilute aqueous sodium bicarbonate solution, dilute aqueous hydrochloric acid, and water. The organic layer was dried (sodium sulfate), filtered, and concentrated in vacuo to provide 5.2 g (70%) of the title compound.

$^1$H NMR

EXAMPLE 155

Preparation of 4-Methoxy-N$^1$,N$^2$-bis(4-methoxybenzoyl)-1,2-benzenediamine

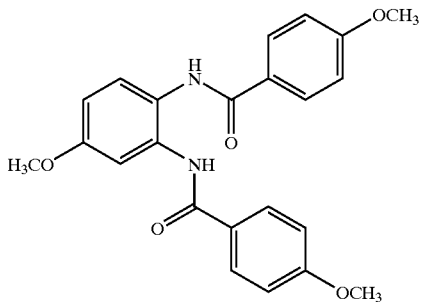

Using the procedure described in Example 154, 4-methoxy-1,2-benzenediamine dihydrochloride (3.60 g, 25.9 mmol) yielded, after recrystallization from methylene chloride, 5.0 g (48%) of the title compound. mp 238–239° C.

$^1$H NMR Anal. for $C_{23}H_{22}N_2O_5$: Calc: C, 67.96; H, 5.46; N, 6.89; Found: C, 67.81; H, 5.51, N, 7.01.

EXAMPLE 156

Preparation of N$^1$-(2,4-Dimethoxybenzoyl)-N$^2$-(4-methoxybenzoyl)-1,2-benzenediamine

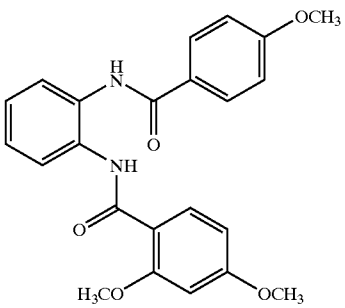

To a solution N$^1$-(4-methoxybenzoyl)-1,2-benzenediamine hydrochloride (558 mg, 2.08 mmol) in methylene chloride (100 mL) was added 0.5 N aqueous sodium hydroxide (8 mL) and the resulting mixture was cooled in an ice-water bath. 2,4-Dimethoxybenzoyl chloride (0.40 g, 2.0 mmol) was added slowly with vigorous stirring. The mixture was allowed to warm slowly to room temperature and stirred for 18 h. The organic layer was separated and washed with dilute aqueous sodium bicarbonate solution, dilute aqueous hydrochloric acid, and water. The organic layer was dried (sodium sulfate), filtered, and concentrated in vacuo to provide 0.52 g (64%) of the title compound.

$^1$H NMR Anal. for $C_{23}H_{22}N_2O_5$: Calc: C, 67.96; H, 5.46; N, 6.89; Found: C, 67.88; H, 5.52, N, 7.18.

EXAMPLE 157

Preparation of $N^1$-(2-Chloro-4-methoxybenzoyl)-$N^2$-(4-methoxybenzoyl)-1,2-benzenediamine

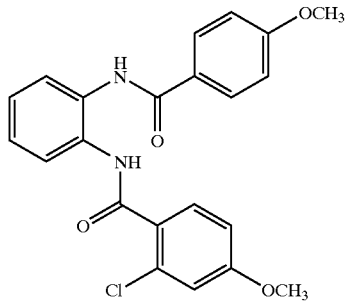

Using the procedure described in Example 156, 2-chloro-4-methoxybenzoyl chloride (410 mg, 2.42 mmol) yielded 770 mg (77%) of the title compound.

$^1$H NMR Anal. for $C_{22}H_{19}ClN_2O_4$: Calc: C, 64.32; H, 4.66; N, 6.82; Found: C, 64.29; H, 4.71; N, 6.75.

EXAMPLE 158

Preparation of 2,3-bis[(4-Methoxybenzoyl)amino]phenol

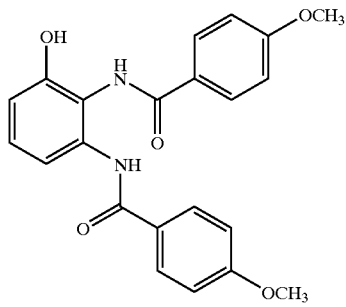

A. 2,3-bis[(4-Methoxybenzoyl)amino]phenoxy 4-Methoxybenzoate 2,3-Diaminophenol (2.48 g, 20 mmol) was dissolved in methylene chloride (200 mL) and the solution was cooled to ice-water bath temperature. Aqueous 5 N sodium hydroxide solution (126 mL) was added followed by 4-methoxybenzoyl chloride (8.6 mL, 63 mmol). The mixture was allowed to warm to room temperature and stirred for 18 h. The organic layer was separated and washed with dilute aqueous sodium hydroxide solution, dilute aqueous hydrochloric acid, and saturated aqueous sodium chloride solution. The organic layer was dried (sodium sulfate), filtered, and concentrated in vacuo to give 7.75 g (74%) of the title compound as a brown foam. This material was used without further purification.

B. 2,3-bis[(4-methoxybenzoyl)amino]phenol

A solution of 2,3-bis[(4-methoxybenzoyl)amino]phenoxy 4-methoxybenzoate (7.75 g, 14.7 mmol) in methanol (100 mL) was cooled to ice-water bath temperature and 5 N aqueous sodium hydroxide solution (3.0 mL) was added. The reaction mixture was allowed to warm to room temperature and stirred for 72 hr. The reaction mixture was concentrated in vacuo and the resulting solid was dissolved in methylene chloride and washed with dilute aqueous hydrochloric acid, water, and saturated sodium chloride solution. The organic layer was dried (sodium sulfate), filtered, and concentrated in vacuo. Recrystallization of the residue from diethyl ether/hexane gave 2.3 g (40%) of the title product. mp 208–209° C.

$^1$H NMR Anal. for $C_{22}H_{20}N_2O_5$: Calc: C, 67.34; H, 5.14, N, 7.14, Found: C, 67.48; H, 5.14; N, 7.19.

EXAMPLE 159

Preparation of $N^1$-(2-Butoxy-4-methoxybenzoyl)-$N^2$-(4-methoxybenzoyl)-1,2-benzenediamine

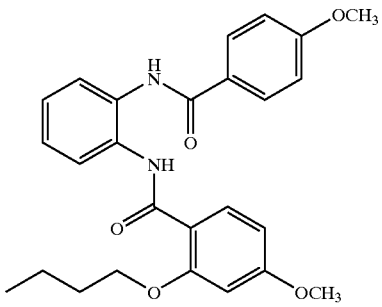

Using the procedure described in Example 156, 2-butoxy-4-methoxybenzoyl chloride (437 mg, 1.80 mmol) yielded 355 mg (45%) of the title compound.

$^1$H NMR Anal. for $C_{26}H_{28}N_2O_5$: Calc: C, 69.63; H, 6.29; N, 6.25; Found: C, 69.82; H, 6.14; N, 6.20.

EXAMPLE 160

Preparation of $N^1$-(2-Benzyloxy-4-methoxybenzoyl)-$N^2$-(4-methoxybenzoyl)-1,2-benzenediamine

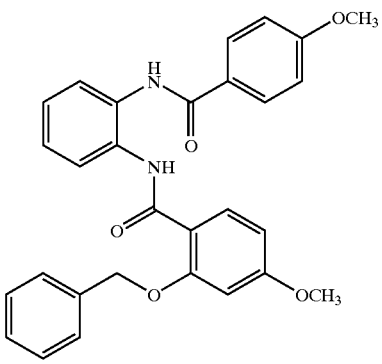

Using the procedure described in Example 156, 2-benzyloxy-4-methoxybenzoyl chloride (437 mg, 1.80 mmol) yielded 190 mg (22%) of the title compound.

$^1$H NMR

EXAMPLE 161

Preparation of $N^1$-(4-Methoxybenzoyl)-$N^2$-(5-chlorobenzofuran-2-ylcarbonyl)-1,2-benzenediamine

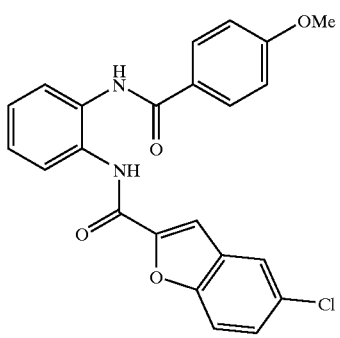

To a solution of $N^1$-(4-methoxybenzoyl)-1,2-benzenediamine (200 mg, 0.826 mmol) in methylene chloride (5 mL) was added 5-chlorobenzofuran-2-carboxylic acid (162 mg, 0.826 mmol), 1-(3-dimethylaminopropyl)-3-ethylcarbodiimide hydrochloride (316 mg, 1.65 mmol), and 4-dimethylaminopyridine (10 mg, 0.083 mmol), The resulting solution was stirred at room temperature for 6 h. The resulting precipitate was collected via vacuum filtration to provide 209 mg (60%) of the title compound as an amorphous off-white solid.

$^1$H-NMR, IR MS-FD m/e 420 (p) Analysis for $C_{23}H_{17}ClN_2O_4$: Calc: C, 65.64; H, 4.07; N, 6.66; Found: C, 64.01; H, 4.19; N, 7.31.

EXAMPLE 162

Preparation of $N^1$-(4-Methoxybenzoyl)-$N^2$-(5-methoxybenzofuran-2-ylcarbonyl)-1,2-benzenediamine

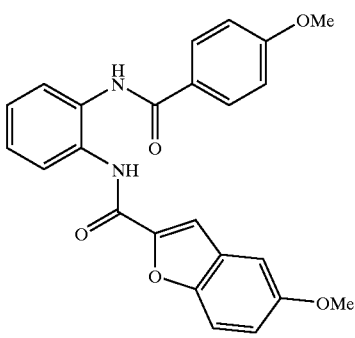

Using the procedure described in Example 161, 5-methoxybenzofuran-2-carboxylic acid (159 mg, 0.826 mmol) yielded 228 mg (66%) of the title compound as an off-white solid.

$^1$H-NMR, IR MS-FD m/e 416 (p) Analysis for $C_{24}H_{20}N_2O_5$: Calc: C, 69.22; H, 4.84; N, 6.73; Found: C, 68.13; H, 4.87; N, 7.03.

EXAMPLE 163

Preparation of $N^1$-(4-methoxybenzoyl)-$N^2$-(1,5-dioxo-5-morpholinopentyl)-1,2-benzenediamine

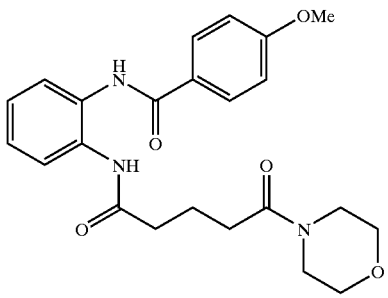

Using the procedure described in Example 161, 5-oxo-5-morpholinopentanoic acid (166 mg, 0.826 mmol) was reacted with $N^1$-(4-methoxybenzoyl)-1,2-benzenediamine. The reaction mixture was diluted with additional methylene chloride and washed with 1 N aqueous sodium hydroxide. The organic phase was washed with 1 N aqueous hydrochloric acid, dried (sodium sulfate), filtered, and concentrated in vacuo to provide 300 mg (85%) of the title compound as an amorphous white solid.

$^1$H-NMR, IR MS-FD m/e 425 (p) Analysis for $C_{23}H_{27}N_3O_5$: Calc: C, 64.93; H, 6.40; N, 9.88; Found: C, 64.68, H, 6.41; N, 9.75.

EXAMPLE 164

Preparation of $N^1$-(4-Methoxybenzoyl)-$N^2$-[4-(4-pyridylthio)benzoyl]-1,2-benzenediamine

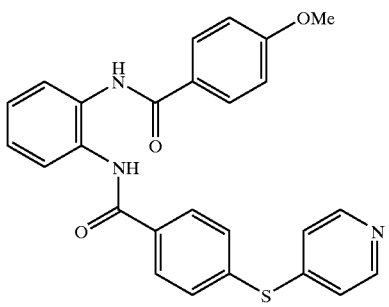

A. Ethyl 4-(4-Pyridylthio)benzoate

A mixture of ethyl 4-fluorobenzoate (3.30 g, 29.8 mmol), 4-mercaptopyridine (5.00 g, 29.8 mmol), 36% w/w potassium fluoride-on-alumina (3.5 g), and 18-crown-6 (0.787 g, 2.98 mmol) in methyl sulfoxide (20 mL) was heated at 120° C. for 24 h. The mixture was cooled to room temperature, filtered, and diluted with diethyl ether. The organic layer was washed with water, dried (sodium sulfate), filtered, and concentrated in vacuo. Chromatography (silica gel, ethyl acetate/hexanes) of the residue provided 400 mg (7%, based on recovered starting material) of the title product.

$^1$H-NMR, IR MS-FD (m/e) 259 (p) Analysis for $C_{14}H_{13}NO_2S$: Calc: C, 64.84; H, 5.05; N, 5.40; Found: C, 64.66; H, 5.21; N, 5.12.

B. 4-(4-Pyridylthio)benzoic Acid

A mixture of ethyl 4-(4-pyridylthio)benzoate (400 mg, 1.54 mmol) and 5 N aqueous sodium hydroxide (2 mL) in 1:1 tetrahydrofuran/methanol (2 mL) was stirred at room temperature for 18 h. The mixture was diluted with water and washed with diethyl ether. The aqueous layer was acidified to pH 6 with concentrated hydrochloric acid. The resulting precipitate was collected via vacuum filtration to provide 280 mg (78%) of the title compound as a pale yellow solid.

$^1$H-NMR, IR MS-FD (m/e) 231 (p) Analysis for $C_{12}H_9NO_2S$: Calc: C, 62.32; H, 3.92; N, 6.06; Found: C, 62.17; H, 3.97; N, 6.07.

C. $N^1$-(4-Methoxybenzoyl)-$N^2$-[4-(4-pyridylthio)benzoyl]-1,2-benzenediamine

Using the procedure described in Example 161, 4-(4-pyridylthio)benzoic acid (191 mg, 0.826 mmol) yielded, after chromatography (silica gel, 75% ethyl acetate/25% hexanes), 180 mg (48%) of the title compound as a pale yellow solid.

$^1$H-NMR, IR MS-FD (m/e) 455 (p) Analysis for $C_{26}H_{21}N_3O_2S$: Calc: C, 68.55; H, 4.65; N, 9.22; Found: C, 69.38; H, 4.71; N, 9.19.

EXAMPLE 165

Preparation of N-(4-Methoxyphenyl)-2-[(1,5-dioxo-5-morpholinopentyl)amino]benzamide

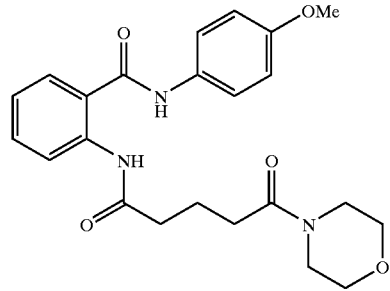

Using the procedure described in Example 161, 5-oxo-5-morpholinopentanoic acid (166 mg, 0.826 mmol) and 2-amino-N-(4-methoxyphenyl)benzamide yielded, after recrystallization from ethyl acetate/hexanes, 220 mg (63%) of the title compound as a white amorphous solid.

$^1$H-NMR, IR MS-FD (m/e) 425 (p) Analysis for $C_{23}H_{27}N_3O_5$: Calc: C, 64.93; H, 6.40; N, 9.88; Found: C, 65.20; H, 6.48; N, 9.97.

EXAMPLE 166

Preparation of N-(4-Methoxybenzoyl)-2-(1-oxo-1,3-dihydro-2H-benz[f]isoindol-2-yl)benzeneamine

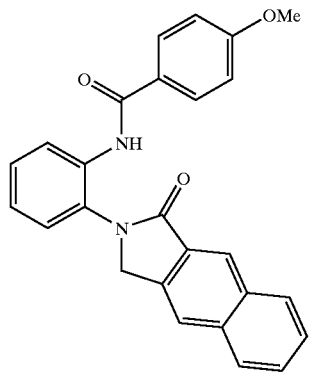

To a solution of N-(4-methoxybenzoyl)-2-(1-ethoxy-1,3-dihydro-3-oxo-2H-benz[f]isoindol-2-yl)benzeneamine (140 mg, 0.31 mmol) in methylene chloride (2 mL) was added triethylsilane (0.5 mL) and trifluoroacetic acid (0.5 mL). After standing at room temperature for 16 h, the mixture was concentrated in vacuo. The residue was dissolved in methylene chloride and washed with saturated aqueous sodium bicarbonate solution, dried (magnesium sulfate), filtered, and concentrated in vacuo to yield 120 mg (95%) of the title compound.

$^1$H-NMR, IR MS-FD m/e 408 (p) Analysis for $C_{26}H_{20}N_2O_3$: Calc: C, 76.46; H, 4.94; N, 6.86; Found: C, 76.32; H, 5.07; N, 6.62.

EXAMPLE 167

Preparation of $N^1$-(4-Chlorobenzoyl)-$N^2$-[1-(4-pyridyl)piperidin-4-ylmethoxycarbonyl]-4-hydroxy-1,2-benzenediamine

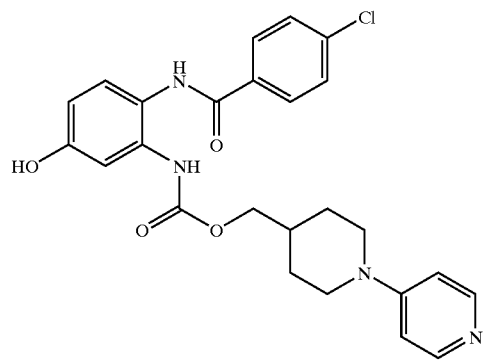

A. 4-(tert-Butyldimethylsilyloxy)-2-nitroaniline

To a mixture of 4-amino-3-nitrophenol (10.07 g, 65.3 mmol) and DMF (20 mL) was added imidazole (11.15 g, 163.8 mmol) followed by t-butyldimethylsilyl chloride (11.82 g, 78.4 mmol) in several portions. After 5 h the reaction was diluted with EtOAc (150 mL) and washed with water (5×20 mL). The organic layer was MgSO$_4$, dried, filtered, and concentrated. The residue was chromatographed (10% EtOAc/hexanes to 20% EtOAc/hexanes) to give the title compound as a solid (17.06 g, 97%); mp 80–83° C.; IR (CHCl$_3$): 3399, 2932, 1519, 1242, 866 cm$^{-1}$; NMR (300 MHz, CDCl$_3$): δ 0.19 (s, 6H), 0.97 (s, 9H), 6.70 (d, 1H, J=9.0), 6.95 (d, 1H, J=3.0), 7.56 (d, 1H, J=2.7); MS(FD): 268.2.

Analysis for C$_{12}$H$_{20}$N$_2$O$_3$Si: Calc: C 53.70, H 7.51, N 10.44; Found: C 53.47, H 7.50, N 10.31.

B. 5-(tert-Butyldimethylsilyloxy)-2-phthalimido-1-nitrobenzene

A mixture of 2-nitro-4-(tert-butyldimethylsilyloxy)aniline (10.3 g, 38.5 mmol) and phthalic anhydride (6.50 g, 41.5 mmol) in toluene (30 mL) was refluxed for 18 h. A Dean-Stark apparatus was fitted to the flask, diisopropylethylamine (0.1 mL) was added and water was removed azeotropically over the next 24 h. About 20 mL of solvent was removed by distillation and the resultant solution allowed to cool to room temperature. The residue was diluted with methylene chloride and passed through a plug of silica gel eluting with methylene chloride. The desired fractions were combined and concentrated in vacuo. Recrystallization from methylene chloride-hexane provided 12.2 g (80%) of the title compound in two crops.

Analysis for C$_{20}$H$_{22}$N$_2$O$_5$Si: Calc: C, 60.28; H, 5.56; N, 7.03; Found: C, 60.35; H, 5.67; N, 6.98.

C. 5-(tert-Butyldimethylsilyloxy)-2-phthalimidoaniline

A suspension of 5-(tert-butyldimethylsilyloxy)-2-phthalimido-1-nitrobenzene (5.00 g, 12.5 mmol) and 10% palladium-on-carbon (2.5 g) in ethyl acetate (60 mL) was stirred under 1 atm of hydrogen for 16 h. The mixture was filtered through a pad of diatomaceous earth and concentrated in vacuo to yield 4.1 g (89%) of the title compound.

D. 5-(tert-Butyldimethylsilyloxy)-2-phthalimido-N-[[1-(4-pyridyl)piperidin-4-yl]methoxycarbonyl]aniline A solution of 5-(tert-butyldimethylsilyloxy)-2-phthalimidoaniline (1.02 g, 2.77 mmol) in toluene (15 mL) was treated with a solution of 20% phosgene in toluene (2 mL) at reflux for 20 min. The volatile materials were removed in vacuo to give a tan solid, which was dissolved in dry methylene chloride (20 mL) and treated with 1-(4-pyridyl)piperidine-4-methanol (0.53 g, 2.77 mmol). The resulting suspension was stirred for 90 min then diluted with hexane. The mixture was allowed to stand overnight and the resulting precipitate collected by vacuum filtration and dried to yield 1.46 g (90%) of the title compound as a tan powder.

MS-FD, m/e 587 (M+). Analysis for C$_{32}$H$_{38}$N$_4$O$_5$Si: Calc: C, 65.50; H, 6.53; N, 9.55; Found: C, 65.23; H, 6.47; N, 9.38.

E. 4-(tert-Butyldimethylsilyloxy)-N$^2$-[[1-(4-pyridyl) piperidin-4-yl]methoxycarbonyl-1,2-benzenediamine A solution of 5-(tert-butyldimethylsilyloxy)-2-phthalimido-N-[[1-(4-pyridyl)piperidin-4-yl] methoxycarbonyl]aniline (1.34 g, 2.28 mmol) in 1 M hydrazine in methanol (6 mL) was stirred at ambient temperature for 40 h during which time a white precipitate formed. The mixture was further diluted with methylene chloride and cooled with an ice bath then filtered. The filtrate was washed once with saturated sodium chloride solution, dried over anhydrous sodium sulfate, filtered, and concentrated in vacuo to yield 890 mg (86%) of the title compound as a tan powder.

MS-FD, m/e 456 (M).

F. N$^1$-(4-Chlorobenzoyl)-N$^2$-[1-(4-pyridyl)piperidin-4-ylmethoxycarbony]-4-(tert-butyldimethylsilyloxy)-1,2-benzenediamine A mixture of N$^1$-[1-(4-pyridyl)piperidin-4-ylmethoxy carbony]-4-(tert-butyldimethylsilyloxy)-1,2-benzenediamine (80 mg, 0.175 mmol) and 4-chlorobenzoylchloride (0.045 mL, 0.35 mmol) in methylene chloride (2 mL) was stirred in the presence of excess potassium carbonate for 10 min. The mixture was diluted with saturated sodium hydrogen carbonate solution, stirred 20 min, partitioned between water and methylene chloride, dried (magnesium sulfate), filtered, and concentrated in vacuo to give 97 mg (93%) of the title compound.

G. N$^1$-(4-Chlorobenzoyl)-N$^2$-[1-(4-pyridyl)piperidin-4-ylmethoxycarbony]-4-hydroxy-1,2-benzenediamine A solution of N$^1$-(4-chlorobenzoyl)-N$^2$-[1-(4-pyridyl) piperidin-4-ylmethoxycarbony]-4-(tert-butyldimethylsilyloxy)-1,2-benzenediamine (97 mg, 0.16 mmol) in tetrahydrofuran (2 mL) was treated with 5 N aqueous hydrochloric acid (0.5 mL) and allowed to stand at ambient temperature for 18 h. Volatile solvents were removed in vacuo and the residue diluted with dilute sodium hydrogen carbonate solution, hexane, and methylene chloride. The mixture was sonicated 5 min then filtered. The resultant material was vacuum dried to yield 48 mg (61%) of the title compound as a white solid.

MS-FD, m/e 481 (p). Analysis for C$_{25}$H$_{25}$ClN$_4$O$_4$: Calc.: C, 62.43; H, 5.24; N, 11.65; Found: C, 62.51; H, 5.52; N, 11.42.

EXAMPLE 168

Preparation of N$^1$-(4-Difluoromethoxybenzoyl)-N$^2$-[1-(4-pyridyl)piperidin-4-ylmethoxycarbonyl]-1,2-benzenediamino Hydrochloride

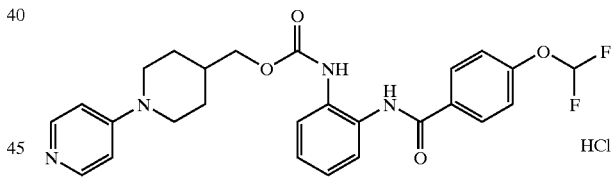

To a solution of N$^1$-[1-(4-pyridyl)piperidin-4-ylmethoxycarbonyl]-1,2-benzenediamine (0.2 g, 0.6 mmol) and 4-difluoromethoxybenzoic acid (0.23 g, 1.2 mmol) in DMF (10 mL) was added 1-(3-dimethylaminopropyl)-3-ethylcarbodiimide hydrochloride (0.24 g, 1.2 mmol). After stirring overnight, the solvent was removed in vacuo and the residue was partitioned between ethyl acetate (300 mL) and 1 N NaOH (150 ml). The layers were separated and the organic phase was washed with brine, dried with MgSO$_4$, filtered and concentrated in vacuo. The residue was purified by RPHPLC method A and the fractions containing pure product were combined and lypholized to give 123 mg (38%) of the title product as a white solid.

$^1$H-NMR MS-FD,m/e 497 (M+) Analysis for C$_{26}$H$_{26}$F$_2$N$_4$O$_4$·1.0HCl·0.9H$_2$O: Calc: C, 56.89; H, 5.28; N, 10.20; Found: C, 56.92; H, 5.22; N, 9.98.

EXAMPLE 169

Preparation of $N^1$-(5-Chlorofuran-2-ylcarbonyl)-$N^2$-[1-(4-pyridyl)piperidin-4-ylmethoxycarbonyl]-1,2-benzenediamine Hydrochloride

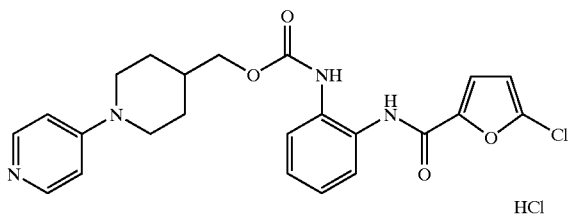

Using the procedure described in Example 168, $N^1$-[1-(4-pyridyl)piperidin-4-ylmethoxycarbonyl]-1,2-benzenediamine (0.61 mmol) and 5-chloro-2-furancarboxylic acid (1.2 mmol), purifying with RPHPLC Method A, yielded 57 mg (22%) of the title compound.

$^1$H-NMR MS-FD, m/e 455 (M+) Analysis for $C_{23}H_{23}ClN_4O_4 \cdot 1.0HCl \cdot 1.75H_2O$: Calc: C, 52.83; H, 5.30; N, 10.71; Found: C, 52.83; H, 5.02; N, 10.59.

EXAMPLE 170

Preparation of $N^1$-(5-Methylthiophen-2-ylcarbonyl)-$N^2$-[1-(4-pyridyl)piperidin-4-ylmethoxycarbonyl]-1,2-benzenediamine Hydrochloride

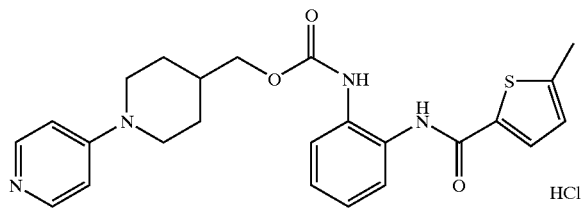

Using the procedure described in Example 168, $N^1$-[1-(4-pyridyl)piperidin-4-ylmethoxycarbonylamino]-1,2-benzenediamine (0.61 mmol) and 5-methylthiophene-2-carboxylic acid (1.2 mmol), purifying with RPHPLC Method A, yielded 45 mg (17%) of the title compound.

$^1$H-NMR MS-FD, m/e 451 (M+) Analysis for $C_{24}H_{26}N_4O_3S \cdot 2.0HCl \cdot 0.5H_2O$: Calc: C, 54.13; H, 5.49; N, 10.52; Found: C, 53.94; H, 5.47; N, 10.55.

EXAMPLE 171

Preparation of $N^1$-(3,4-Dichlorobenzoyl)-$N^2$-[1-(4-pyridyl)piperidin-4-ylmethoxycarbonyl-1,2-benzenediamine Hydrochloride

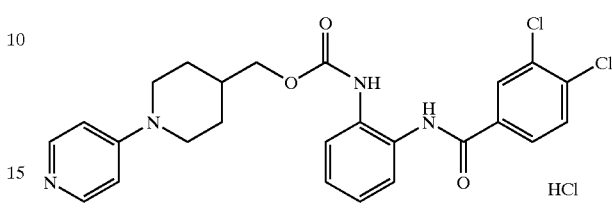

Using the procedure described in Example 48, Part C, $N^1$-[1-(4-pyridyl)piperidin-4-ylmethoxycarbonylamino]-1,2-benzenediamine (0.61 mmol).and 3,4-dichlorobenzoyl chloride (1.2 mmol), purifying with RPHPLC Method B, yielded 120 mg (40%) of the title compound.

$^1$H-NMR MS-FD, m/e 498 (M+) Analysis for $C_{25}H_{24}Cl_2N_4O_3 \cdot 1.25HCl$: Calc: C, 55.09; H, 4.67; N, 10.28; Found: C, 55.09; H, 4.62; N, 10.15.

EXAMPLE 172

Preparation of $N^1$-(5-Chlorothiophen-2-ylcarbonyl)-$N^2$-[1-(4-pyridyl)piperidin-4-ylmethoxycarbonyl]-1,2-benzenediamine Hydrochloride

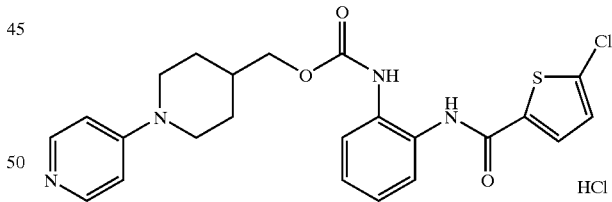

Using the procedure described in Example 168, $N^1$-[1-(4-pyridyl)piperidin-4-ylmethoxycarbonylamino]-1,2-benzenediamine (0.61 mmol) and 5-chlorothiophene-2-carboxylic acid (1.2 mmol) yielded 260 mg of the title compound which was purified with RPHPLC Method C.

$^1$H-NMR MS-IS, m/e 471.1 (MH+) Analysis for $C_{23}H_{23}ClN_4O_3S \cdot 1.5HCl \cdot 1.0H_2O$: Calc: C, 50.81; H, 4.91; N, 10.31; Found: C, 50.81; H, 4.84; N, 10.33.

EXAMPLE 173

Preparation of $N^1$-(1,2-Dihydrobenzofuran-5-ylcarbonyl)-$N^2$-[1-(4-pyridyl)piperidin-4-ylmethoxycarbonyl)-1,2-benzenediamine Hydrochloride

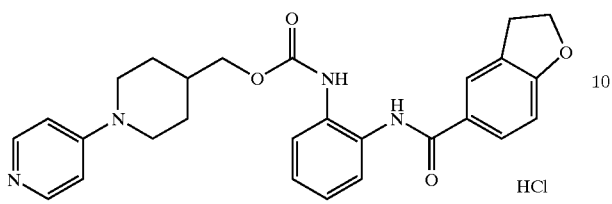

Using the procedure described in Example 168, $N^1$-[1-(4-pyridyl)piperidin-4-ylmethoxycarbonylamino]-1,2-benzenediamine (0.61 mmol) and 1,2-dihydrobenzofuran-5-carboxylic acid (1.2 mmol), purifying with RPHPLC Method A, yielded 57 mg (20%) of the title compound.

$^1$H-NMR MS-FD, m/e 472.1 (M+) Analysis for $C_{27}H_{28}N_4O_4 \cdot 1.0HCl \cdot 0.6H_2O$: Calc: C, 62.34; H, 5.86; N, 10.78; Found: C, 62.32; H, 5.79; N, 10.74.

EXAMPLE 174

Preparation of $N^1$-(3-Fluoro-4-methoxybenzoyl)-$N^2$-[1-(4-pyridyl)piperidin-4-ylmethoxycarbonyl]-1,2-benzenediamine Hydrochloride

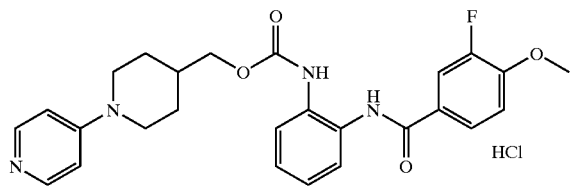

Using the procedure described in Example 168, N-1-[1-(4-pyridyl)piperidin-4-ylmethoxycarbonylamino]-1,2-benzenediamine (0.61 mmol) and 3-fluoro-4-methoxybenzoic acid (1.2 mmol), purifying with RPHPLC Method A, yielded 36 mg (13%) of the title compound.

$^1$H-NMR MS-FD, m/e 478.0 (M+) Analysis for $C_{26}H_{27}FN_4O_4 \cdot 1.0HCl \cdot 1.4H_2O$: Calc: C, 57.81; H, 5.75; N, 10.37; Found: C, 57.78; H, 5.70, N, 10.31.

EXAMPLE 175

Preparation of $N^1$-(3-Chloro-4-methylbenzoyl)-$N^2$-[1-(4-pyridyl)piperidin-4-ylmethoxycarbonyl]-1,2-benzenediamine Hydrochloride

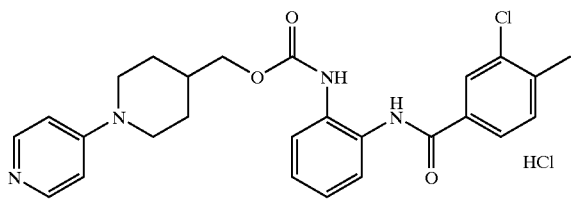

Using the procedure described in Example 168, $N^1$-[1-(4-pyridyl)piperidin-4-ylmethoxycarbonylamino]-1,2-benzenediamine (0.61 mmol) and 3-chloro-4-methylbenzoic acid (1.2 mmol), purifying with RPHPLC Method A, yielded 90 mg (31%) of the title compound.

$^1$H-NMR MS-FD, m/e 478.1 (M+) Analysis for $C_{26}H_{27}ClN_4O_3 \cdot 1.0HCl \cdot 0.95H_2O$: Calc: C, 58.64; H, 5.65; N, 10.52; Found: C, 58.74; H, 5.39; N, 10.47.

EXAMPLE 176

Preparation of $N^1$-(3-Fluoro-4-methylbenzoyl)-$N^2$-[1-(4-pyridyl)piperidin-4-ylmethoxycarbonyl]-1,2-benzenediamine Hydrochloride

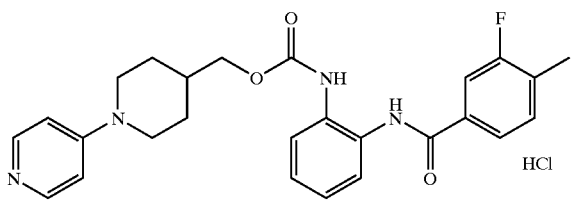

Using the procedure described in Example 168, $N^1$-[1-(4-pyridyl)piperidin-4-ylmethoxycarbonylamino]-1,2-benzenediamine (0.61 mmol) and 3-fluoro-4-methylbenzoic acid (1.2 mmol), purifying with RPHPLC Method A, yielded 61 mg (22%) of the title compound.

$^1$H-NMR MS-FD, m/e 463 (M+) Analysis for $C_{26}H_{27}FN_4O_3 \cdot 1.0HCl \cdot 1.4H_2O$: Calc: C, 57.81; H, 5.75; N, 10.37; Found: C, 57.96; H, 6.02; N, 10.49.

EXAMPLE 177

Preparation of $N^1$-(1-Cyclohexenylcarbonyl)-$N^2$-[1-(4-pyridyl)piperidin-4-ylmethoxycarbonyl]-1,2-benzenediamine Hydrochloride

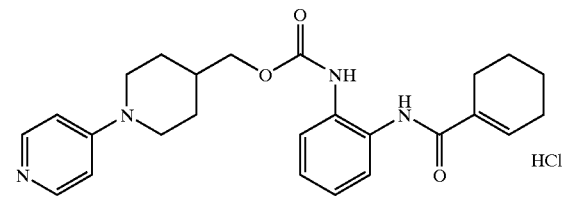

Using the procedure described in Example 168, $N^1$-[1-(4-pyridyl)piperidin-4-ylmethoxycarbonylamino]-1,2-benzenediamine (0.61 mmol) and 1-cylcohexenecarboxylic acid (1.2 mmol), purifying with RPHPLC Method B. yielded the title compound.

$^1$H-NMR MS-FD, m/e 434.8 (M+) Analysis for $C_{25}H_{30}N_4O_3 \cdot 1.3HCl$: Calc: C, 62.31; H, 6.55; N, 11.63; Cl, 9.56; Found: C, 62.20; H, 6.70; N, 11.21; Cl, 9.47.

EXAMPLE 178

Preparation of N¹-(1-Cyclopentenylcarbonyl)-N²-[1-(4-pyridyl)piperidin-4-ylmethoxycarbonyl]-1,2-benzenediamine Hydrochloride

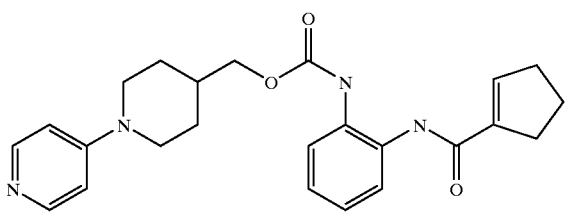

Using the procedure described in Example 168, N¹-[1-(4-pyridyl)piperidin-4-ylmethoxycarbonylamino]-1,2-benzenediamine (0.61 mmol) and 1-cyclopentenecarboxylic acid (1.2 mmol), purifying with RPHPLC Method A, yielded 28 mg (12%) of the title compound.

¹H-NMR MS-FD, m/e 421.1 (M+) Analysis for $C_{24}H_{28}N_4O_3 \cdot 1.2HCl \cdot 2.0H_2O$: Calc: C, 57.62; H, 6.69; N, 11.20; Found: C, 57.69; H, 6.41; N, 11.29.

EXAMPLE 179

Preparation of 6-Fluoro-2-[[1-(4-pyridyl)piperidin-4-ylcarbonyl]amino]-N-(4-methoxyphenyl)benzamide Hydrochloride

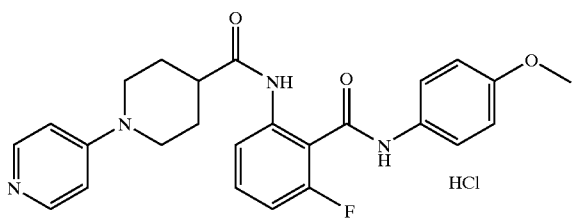

Using the procedure described in Example 138, N-(4-methoxyphenyl)-2-amino-6-fluorobenzamide (1.8 mmol) and N-(4-pyridyl)isonipecotoyl chloride (3.6 mmol), purifying with RPHPLC Method A, yielded 570 mg (66%) of the title compound.

¹H-NMR MS-FD, m/e 448.8 (M+) Analysis for $C_{25}H_{25}FN_4O_3 \cdot 1.4HCl$: Calc: C, 60.11; H, 5.33; N, 11.22; Cl, 9.94; Found: C, 60.44; H, 5.43; N, 11.16; Cl, 10.02.

EXAMPLE 180

Preparation of 4,5-Difluoro-2-[[1-(4-pyridyl)piperidin-4-ylcarbonyl]amino]-N-(4-methoxyphenyl)benzamide Hydrochloride

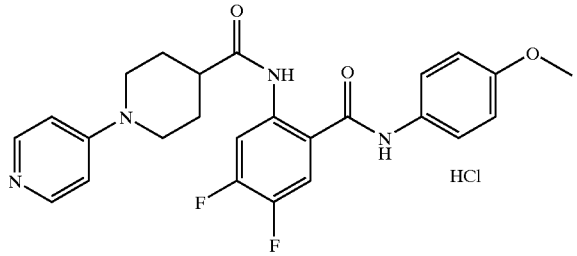

A. 4,5-Difluoroisotoic anhydride

Using the procedure described in Example 69, Part A, 4,5-difluoroanthranilic acid (27.4 mmol) yielded 4.5 g (82%) of the title compound.

¹H-NMR MS-FD, m/e 199 (M+) Analysis for $C_8H_3F_2NO_3$: Calc: C, 48.26; H, 1.52; N, 7.03; Found: C, 48.07; H, 1.63; N, 6.98.

B. 2-Amino-4,5-difluoro-N-(4-methoxyphenyl)benzamide

Using the procedure described in Example 69, Part C, 4,5-difluoroisotoic anhydride (10 mmol) and p-anisidine (10 mmol) in DMF (10 mL) at 80° C. yielded 2.1 g (76%) of the title compound.

¹H-NMR MS-FD, m/e 278 (M+)

C. 4,5-Difluoro-2-[[1-(4-pyridyl)piperidin-4-ylcarbonyl]amino]-N-(4-methoxyphenyl)benzamide hydrochloride Using the procedure described in Example 138, N-(4-methoxyphenyl)-2-amino-4,5-difluorobenzamide (1.8 mmol) and N-(4-pyridyl)isonipecotoyl chloride (3.6 mmol), purifying with RPHPLC Method A, yielded 505 mg (57%) of the title compound.

¹H-NMR MS-FD, m/e 467 (M+) Analysis for $C_{25}H_{24}F_2N_4O_3 \cdot 1.0HCl \cdot 0.5H_2O$: Calc: C, 58.66; H, 5.11; N, 10.94; Found: C, 58.48; H, 5.08; N, 10.93.

EXAMPLE 181

Preparation of 4-Fluoro-2-[[1-(4-pyridyl)piperidin-4-ylcarbonyl]amino]-N-(4-methoxyphenyl)benzamide Hydrochloride

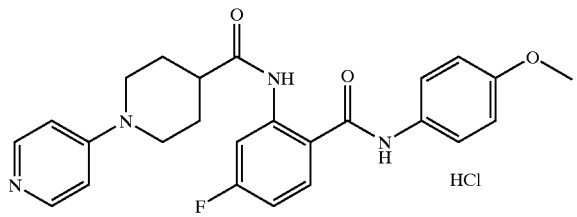

A. 4-Fluoroisotoic anhydride

Using the procedure described in Example 69, Part A, 4-fluoroanthranilic acid (31.5 mmol) yielded 5.23 g (92%) of the title compound.

¹H-NMR MS-FD, m/e 181.1 (M+) Analysis for $C_8H_4FNO_3$: Calc: C, 53.05; H, 2.23; N, 7.73; Found: C, 53.30; H, 2.43; N, 7.63.

B. 2-Amino-4-fluoro-N-(4-methoxyphenyl)benzamide

Using the procedure described in Example 69, Part C, 4-fluoroisotoic anhydride (11 mmol) and p-anisidine (11 mmol) in 3MF (10 mL) at 80° C. yielded 1.5 g (52%) of the title compound.

$^1$H-NMR MS-FD, m/e 260 (M+) Analysis for $C_{14}H_{13}FN_2O_2$: Calc: C, 64.61; H, 5.04; N, 10.76; Found: C, 64.49; H, 5.07; N, 11.02.

C. 4-Fluoro-2-[[1-(4-pyridyl)piperidin-4-ylcarbonyl]amino]-N-(4-methoxyphenyl)benzamide Hydrochloride Using the procedure described in Example 138, N-(4-methoxyphenyl)-2-amino-4-fluorobenzamide (1.8 mmol) and N-(4-pyridyl)isonipecotoyl chloride (3.6 mmol), purifying with RPHPLC Method A, yielded 677 mg (78%) of the title compound.

$^1$H-NMR MS-FD, m/e 448.6 (M+)

EXAMPLE 182

Preparation of 5-Fluoro-2-[[1-(4-pyridyl)piperidin-4-ylcarbonyl]amino]-N-(4-methoxyphenyl)benzamide Hydrochloride

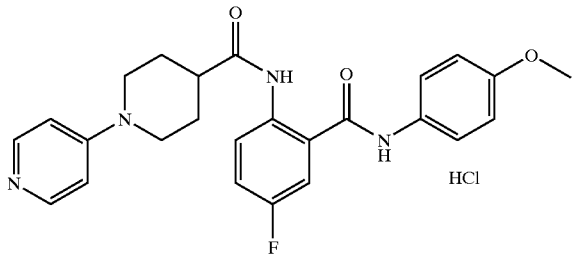

A. 5-Fluoroisotoic anhydride

Using the procedure described in Example 69, Part A, 5-fluoroanthranilic acid (31.5 mmol) yielded 2.72 g (48%) of the title compound.

$^1$H-NMR MS-FD, m/e 181.2 (M+) Analysis for $C_8H_4FNO_3$: Calc: C, 53.05; H, 2.23; N, 7.73; Found: C, 53.22; H, 2.20; N, 7.58.

B. 2-Amino-5-fluoro-N-(4-methoxyphenyl)benzamide

Using the procedure described in Example 69, Part C, 5-fluoroisotoic anhydride (11 mmol) and p-anisidine (11 mmol) in DMF (10 mL) at 80° C. yielded 2.1 g (73%) of the title compound.

$^1$H-NMR MS-FD, m/e 260.2 (M+)

C. 5-Fluoro-2-[[1-(4-pyridyl)piperidin-4-ylcarbonyl]amino]-N-(4-methoxyphenyl)benzamide Hydrochloride Using the procedure described in Example 138, N-(4-methoxyphenyl)-2-amino-5-fluorobenzamide (1.8 mmol) and N-(4-pyridyl)isonipecotoyl chloride (3.6 mmol), purifying with RPHPLC Method A, yielded 500 mg (58%) of the title compound.

$^1$H-NMR MS-FD, m/e 448.8 (M+)

EXAMPLE 183

Preparation of 2-[[1-(4-Pyridyl)piperidin-4-ylcarbonyl]amino]-N-phenylbenzamide Hydrochloride

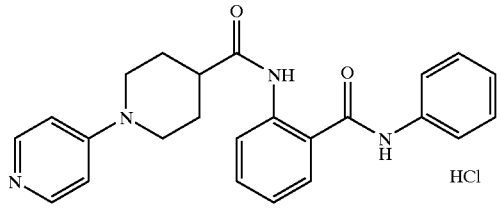

A. 2-Nitro-N-phenylbenzamide

Using the procedure described in Example 93, Part A, aniline (11 mmol) and 2-nitrobenzoyl chloride (12.1 mmol) yielded 2.14 g (80%) of the title compound.

$^1$H-NMR MS-FIA, m/e 242.2 (MH+) Analysis for $C_{13}H_{10}N_2O_3$: Calc: C, 64.46; H, 4.16; N, 11.56; Found: C, 64.57; H, 4.14; N, 11.45.

B. 2-Amino-N-phenylbenzamide

Using the procedure described in Example 99, Part B. 2-nitro-N-phenylbenzamide (6.9 mmol) yielded 1.2 g (92%) of the title compound.

$^1$H-NMR MS-FIA, m/e 212.8 (MH+) Analysis for $C_{13}H_{12}N_2O$: Calc: C, 73.57; H, 5.70; N, 13.20; Found: C, 73.53; H, 5.78; N, 13.27.

C. 2-[[1-(4-pyridyl)piperidin-4-ylcarbonyl]amino]-N-phenylbenzamide Hydrochloride Using the procedure described in Example 138, N-phenyl-2-aminobenzamide (0.97 mmol) and N-(4-pyridyl)isonipecotoyl chloride (1.9 mmol), purifying with RPHPLC Method A, yielded 233 mg (55%) of the title compound.

$^1$H-NMR MS-FD, m/e 401.3 (MH+) Analysis for $C_{24}H_{24}N_4O_2 \cdot 1.0HC \cdot 2.2H_2O$: Calc: C, 60.49; H, 6.22; N, 11.75; Cl, 7.44; Found: C, 60.56; H, 5.93; N, 11.72; Cl, 7.82.

EXAMPLE 184

Preparation of 2-[[1-(4-Pyridyl)piperidin-4-ylcarbonyl]amino]-N-(4-fluorophenyl)benzamide Hydrochloride

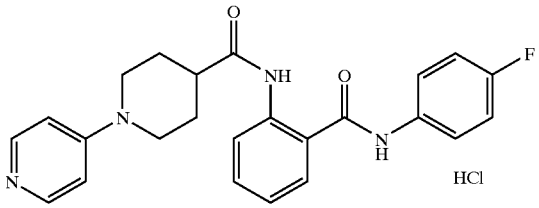

Using the procedure described in Example 138, N-(4-fluorophenyl)-2-aminobenzamide (0.92 mmol) and N-(4-pyridyl)isonipecotoyl chloride (1.8 mmol), purifying with RPHPLC Method A, yielded 146 mg (35%) of the title compound.

$^1$H-NMR MS-FIA, m/e 419.0 (MH+) Analysis for $C_{24}H_{23}FN_4O_2 \cdot 1.05HCl \cdot 1.0H_2O$: Calc: C, 60.72; H, 5.53; N, 11.80; Cl, 7.84; Found: C, 60.86; H, 5.09; N, 11.88; Cl, 7.73.

EXAMPLE 185

Preparation of 2-[[1-(4-Pyridyl)piperidin-4-ylcarbonyl]amino3-N-(4-chlorophenyl)benzamide hydrochloride

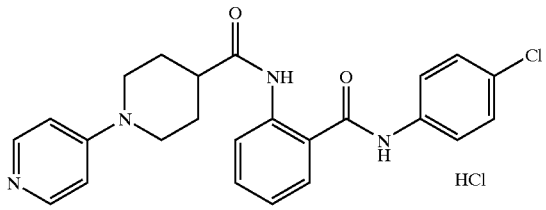

A. 2-Nitro-N-(4-chlorophenyl)benzamide

Using the procedure described in Example 93, Part A, 4-chloroaniline (11.8 mmol) and 2-nitrobenzoyl chloride (12.9 mmol) yielded 2.07 g (64%) of the title compound.

$^1$H-NMR MS-FIA, m/e 277.0 (M+) Analysis for $C_{13}H_9ClN_2O_3$: Calc: C, 56.43; H, 3.28; N, 10.12; Found: C, 56.66; H, 3.24; N, 10.09.

B. 2-Amino-N-(4-chlorophenyl)benzamide

Using the procedure described in Example 99, Part B, 2-nitro-N-(4-chlorophenyl)benzamide (5.4 mmol) yielded 0.79 g (59%) of the title compound.

$^1$H-NMR MS-FIA, m/e 247.2 (M+) Analysis for $C_{13}H_{11}ClN_2O$: Calc: C, 63.29; H, 4.49; N, 11.36; Found: C, 63.43; H, 4.73; N, 11.14.

C. 2-[[1-(4-Pyridyl)piperidin-4-ylcarbonyl]amino]-N-(4-chlorophenyl)benzamide Hydrochloride Using the procedure described in Example 138, N-(4-chlorophenyl)-2-aminobenzamide (0.97 mmol) and N-(4-pyridyl)isonipecotoyl chloride (1.8 mmol), purifying with RPHPLC Method A, yielded 334 mg (37%) of the title compound.

$^1$H-NMR MS-FD, m/e 435.2 (M+) Analysis for $C_{24}H_{23}ClN_4O_2 \cdot 1.1HCl \cdot 1.2H_2O$: Calc: C, 58.04; H, 5.37; N, 11.28; Cl, 14.99; Found: C, 58.41; H, 5.02; N, 11.09; Cl, 15.18.

EXAMPLE 186

Preparation of 2-[[1-(4-Pyridyl)piperidin-4-ylcarbonyl]amino]-N-(4-methylphenyl)benzamide Hydrochloride

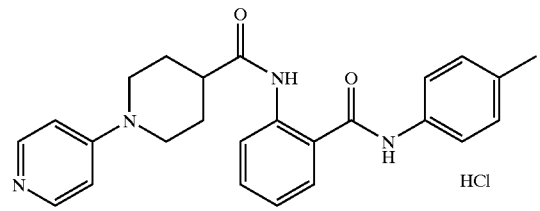

A. 2-Nitro-N-(4-methylphenyl)benzamide

Using the procedure described in Example 93, Part A, 4-methylaniline (9.3 mmol) and 2-nitrobenzoyl chloride (10.3 mmol) yielded 1.55 g (65%) of the title compound.

$^1$H-NMR MS-FIA, m/e 256.3 (MH+) Analysis for $C_{14}H_{12}N_2O_3$: Calc: C, 65.62; H, 4.72; N, 10.93; Found: C, 65.87; H, 5.00; N, 10.94.

B. 2-Amino-N-(4-methylphenyl)benzamide

Using the procedure described in Example 99, Part B, 2-nitro-N-(4-methylphenyl)benzamide (4.9 mmol) yielded 0.29 g (26%) of the title compound.

$^1$H-NMR MS-FIA, m/e 227.2 (MH+) Analysis for $C_{14}H_{14}N_2O$: Calc: C, 74.31; H, 6.24; N, 12.38; Found: C, 74.44; H, 6.38; N, 12.58.

C. 2-[[1-(4-Pyridyl)piperidin-4-ylcarbonyl]amino]-N-(4-methylphenyl)benzamide hydrochloride Using the procedure described in Example 138, N-(4-methylphenyl)-2-aminobenzamide (0.97 mmol) and N-(4-pyridyl)isonipecotoyl chloride (1.9 mmol), purifying with RPHPLC Method A, yielded 147 mg (34%) of the title compound.

$^1$H-NMR MS-FD, m/e 415.4 (MH+) Analysis for $C_{25}H_{26}N_4O_2 \cdot 1.1HCl \cdot 2.0H_2O$: Calc: C, 61.20; H, 6.39; N, 11.41; Cl, 7.95; Found: C, 61.02; H, 5.99; N, 11.66; Cl, 8.07.

EXAMPLE 187

Preparation of 2-[[1-(4-Pyridyl)piperidin-4-ylcarbonyl]amino]-N-(3-hydroxyphenyl)benzamide Hydrochloride

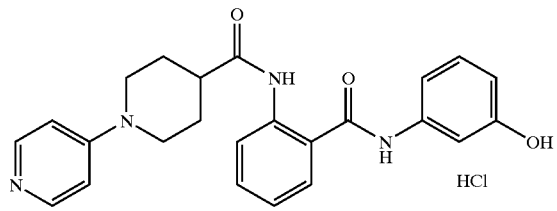

A. 2-Nitro-N-(3-benzyloxyphenyl)benzamide

Using the procedure described in Example 93, Part A, 3-benzyloxyaniline (10 mmol) and 2-nitrobenzoyl chloride (11 mmol) yielded 3.1 g (89%) of the title compound.

$^1$H-NMR MS-FIA, m/e 349.2 (MH+) Analysis for $C_{20}H_{16}N_2O_4$: Calc: C, 68.96; H, 4.63; N, 8.04; Found: C, 68.67; H, 4.58; N, 8.31.

B. 2-Amino-N-(3-benzyloxyphenyl)benzamide

Using the procedure described in Example 99, Part B, 2-nitro-N-(3-benzyloxyphenyl)benzamide (7.2 mmol) yielded 1.5 g (66%) of the title compound.

$^1$H-NMR MS-FIA, m/e 319.0 (MH+) Analysis for $C_{20}H_{18}N_2O_2$: Calc: C, 75.45; H, 5.70; N, 8.80; Found: C, 75.39; H, 5.72; N, 9.02.

C. 2-[[1-(4-Pyridyl)piperidin-4-ylcarbonyl]amino]-N-(3-benzyloxyphenyl)benzamide Using the procedure described in Example 138, N-(3-benzyloxyoxyphenyl)-2-aminobenzamide (0.97 mmol) and N-(4-pyridyl)isonipecotoyl chloride (1.9 mmol), yielded 405 mg (82%) of the title compound.

$^1$H-NMR

D. 2-[[1-(4-Pyridyl)piperidin-4-ylcarbonyl]amino]-N-(3-hydroxyphenyl)benzamide Hydrochloride Using the procedure described in Example 96, Part A, and purifying with RPHPLC Method A, 2-[[1-(4-pyridyl)piperidin-4-ylcarbonyl]amino]-N-(3-benzyloxyphenyl)benzamide (0.39 mmol) yielded 22 mg (12%) of the title compound.

$^1$H-NMR MS-FD, m/e 416.2 (M+) Analysis for $C_{24}H_{24}N_4O_3 \cdot 1.2HCl \cdot 1.6H_2O$: Calc: C, 58.95; H, 5.85; N., 11.45; Cl, 8.70; Found: C, 59.00; H, 5.57; N, 11.37; Cl, 8.30.

EXAMPLE 188

Preparation of 2-[[1-(4-Pyridyl)piperidin-4-ylcarbonyl]amino]-N-(2-fluorophenyl)benzamide Hydrochloride

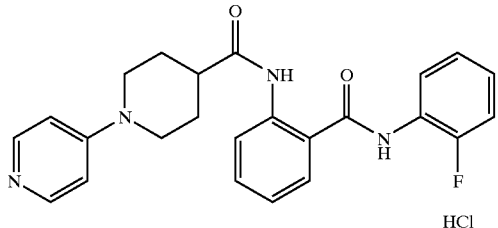

A. 2-Nitro-N-(2-fluorophenyl)benzamide

Using the procedure described in Example 93, Part A, 2-fluoroaniline (20.7 mmol) and 2-nitrobenzoyl chloride (22.8 mmol) yielded 3.78 g (70%) of the title compound.

$^1$H-NMR MS-FIA, m/e 261.0 (MH+) Analysis for $C_{13}H_9FN_2O_3$: Calc: C, 60.00; H, 3.48; N, 10.77; Found: C, 60.07; H, 3.64; N, 10.78.

B. 2-Amino-N-(2-fluorophenyl)benzamide

Using the procedure described in Example 99, Part B, 2-nitro-N-(2-fluorophenyl)benzamide (11.5 mmol) yielded 1.9 g (72%) of the title compound.

$^1$H-NMR MS-FIA, m/e 231.2 (MH+) Analysis for $C_{13}H_{11}FN_2O$: Calc: C, 67.82; H, 4.82; N, 12.17; Found: C, 68.08; H, 5.03; N, 12.22.

C. 2-[[1-(4-Pyridyl)piperidin-4-ylcarbonyl]amino]-N-(2-fluorophenyl)benzamide Hydrochloride Using the procedure described in Example 138, N-(2-fluorophenyl)-2-aminobenzamide (0.89 mmol) and N-(4-pyridyl)isonipecotoyl chloride (2.23 mmol), purifying with RPHPLC Method A, yielded 141 mg (35%) of the title compound.

$^1$H-NMR MS-FIA, m/e 419.2 (MH+) Analysis for $C_{24}H_{23}FN_4O_2 \cdot 1.1HCl \cdot 1.8H_2O$: Calc: C, 58.79; H, 5.49; N, 11.43; Cl, 8.03; Found: C, 58.35; H, 4.93; N, 11.30; Cl, 7.68.

EXAMPLE 189

Preparation of 2-[[1-(4-Pyridyl)piperidin-4-ylcarbonyl]amino]-N-(4-bromophenyl)benzamide hydrochloride.

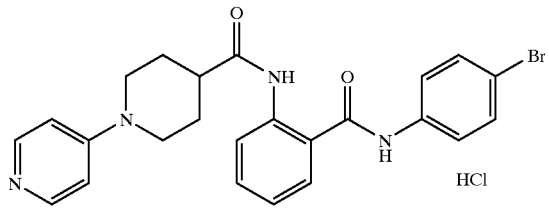

A. 2-Nitro-N-(4-bromophenyl)benzamide

Using the procedure described in Example 93, Part A, 4-bromoaniline (11.6 mmol) and 2-nitrobenzoyl chloride (12.8 mmol) yielded 3.46 g (93%) of the title compound.

$^1$H-NMR MS-FIA, m/e 321.0 (MH+) Analysis for $C_{13}H_9BrN_2O_3$: Calc: C, 48.62; H, 2.82; N, 8.72; Found: C, 48.90; H, 2.81; N, 8.63.

B. 2-Amino-N-(4-bromophenyl)benzamide

Using the procedure described in Example 99, Part B, 2-nitro-N-(4-bromophenyl)benzamide (9.3 mmol) yielded 2.17 g (80%) of the title compound.

$^1$H-NMR MS-FIA, m/e 291.0 (MH+) Analysis for $C_{13}H_{11}BrN_2O$: Calc: C, 53.63; H, 3.81; N, 9.62; Found: C, 53.89; H, 3.85; N, 9.82.

C. 2-[[1-(4-Pyridyl)piperidin-4-ylcarbonyl]amino]-N-(4-bromophenyl)benzamide hydrochloride Using the procedure described in Example 138, N-(4-bromophenyl)-2-aminobenzamide (0.97 mmol) and N-(4-pyridyl)isonipecotoyl chloride (1.9 mmol), purifying with RPHPLC Method A, yielded 383 mg (77%) of the title compound.

$^1$H-NMR MS-FIA, m/e 479.2 (MH+) Analysis for $C_{24}H_{23}BrN_4O_2 \cdot 1.2HCl \cdot 1.6H_2O$: Calc: C, 52.22; H, 5.00; N, 10.15; Cl, 7.71; Found: C, 52.09; H, 4.49; N, 10.01; Cl, 7.41.

EXAMPLE 190

Preparation of 2-[[1-(4-Pyridyl)piperidin-4-ylcarbonyl]amino]-N-(3-chlorophenyl)benzamide Hydrochloride

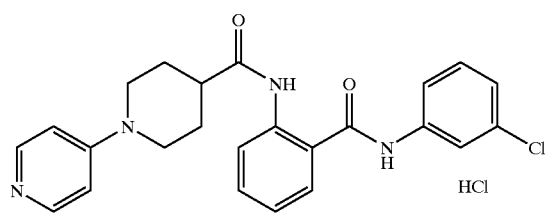

A. 2-Nitro-N-(3-chlorophenyl)benzamide

Using the procedure described in Example 93, Part A, 3-chloroaniline (9.4 mmol) and 2-nitrobenzoyl chloride (10.4 mmol) yielded 2.55 g (98%) of the title compound.

$^1$H-NMR MS-FIA, m/e 277.0 (MH+)

B. 2-Amino-N-(3-chlorophenyl)benzamide

Using the procedure described in Example 99, Part B, 2-nitro-N-(3-chlorophenyl)benzamide (7.2 mmol) yielded 0.84 g (47%) of the title compound.

$^1$H-NMR MS-FIA, m/e 247.2 (MH+) Analysis for $C_{13}H_{11}ClN_2O$: Calc: C, 63.29; H, 4.49; N, 11.35; Found: C, 64.12; H, 4.35; N, 11.36.

C. 2-[[1-(4-Pyridyl)piperidin-4-ylcarbonyl]amino]-N-(3-chlorophenyl)benzamide Hydrochloride Using the procedure described in Example 138, N-(3-chlorophenyl)-2-aminobenzamide (1.8 mmol) and N-(4-pyridyl)isonipecotoyl chloride (3.6 mmol), purifying with RPHPLC Method A, yielded 220 mg (48%) of the title compound.

$^1$H-NMR MS-FIA, m/e 435.3 (M+) Analysis for $C_{24}H_{23}ClN_4O_2 \cdot 1.1HCl \cdot 1.4H_2O$: Calc: C, 57.62; H, 5.42; N, 11.20; Cl, 14.88; Found: C, 57.74; H, 5.04; N, 11.15; Cl, 14.91.

EXAMPLE 191

Preparation of 2-[[1-(4-Pyridyl)piperidin-4-ylcarbonyl]amino]-N-(3-fluorophenyl)benzamide hydrochloride

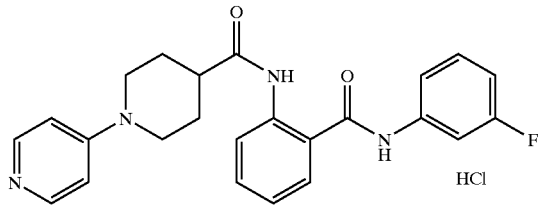

A. 2-Nitro-N-(3-fluorophenyl)benzamide

Using the procedure described in Example 93, Part A, 3-fluoroaniline-15.6 mmol) and 2-nitrobenzoyl chloride (17.2 mmol) yielded 3.09 g (76%) of the title compound.

$^1$H-NMR MS-FIA, m/e 261.1 (MH+) Analysis for $C_{13}H_9FN_2O_3$: Calc: C, 60.00; H, 3.49; N, 10.77; Found: C, 60.30; H, 3.52; N, 10.74.

B. 2-Amino-N-(3-fluorophenyl)benzamide

Using the procedure described in Example 99, Part B, 2-nitro-N-(3-fluorophenyl)benzamide (11.3 mmol) yielded 1.15 g (43%) of the title compound.

$^1$H-NMR MS-FIA, m/e 231.2 (MH+) Analysis for $C_{13}H_{11}FN_2O$: Calc: C, 67.82; H, 4.82; N, 12.17; Found: C, 68.09; H, 5.09; N, 12.00.

C. 2-[[1-(4-Pyridyl)piperidin-4-ylcarbonyl]amino]-N-(3-fluorophenyl)benzamide hydrochloride Using the procedure described in Example-138, N-(3-fluorophenyl)-2-aminobenzamide (1.3 mmol) and N-(4-pyridyl)isonipecotoyl chloride (2.6 mmol), purifying with RPHPLC Method D, yielded 402 mg (68%) of the title compound.

$^1$H-NMR MS-FIA, m/e 419.2 (MH+) Analysis for $C_{24}H_{23}FN_4O_2 \cdot 1.0HCl \cdot 0.9H_2O$: Calc: C, 61.19; H, 5.52; N, 11.89; Cl, 7.52; Found: C, 61.18; H, 5.34; N, 11.70; Cl, 7.19.

EXAMPLE 192

Preparation of 2-[[4-(4-Pyridyl)benzoyl]amino]-N-(4-methoxyphenyl)benzamide Hydrochloride

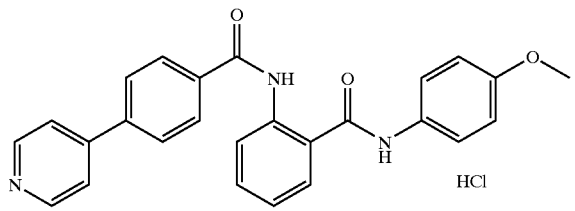

To a stirring suspension of 4-(4-pyridyl)benzoic acid (0.2 g, 1 mmol) in toluene (35 mL) was added thionyl chloride (0.55 mL, 7.5 mmol) and the mixture was heated to reflux. After 1 h the solution was cooled and added to a solution of 2-amino-N-(4-methoxyphenyl)benzamide (0.176 g, 0.73 mmol) in pyridine (2 mL) and toluene (5 mL). After stirring for 48 h, the solvent was removed in vacuo and the residue was partitioned between ethyl acetate and water. The organic phase was separated and washed with sat. NaHCO$_3$, brine and dried (MgSO$_4$), filtered and concentrated to give 103 mg of brown solid which was chromatographed by RPHPLC Method B. Upon standing, a sample of the title compound (14 mg, 4%) crystalized from one of the product containing fractions.

MS-FD, m/e 424.2 (MH+) Analysis for $C_{26}H_{21}N_3O_3 \cdot 2.1HCl$: Calc: C, 62.45; H, 4.66; N, 8.40; Found: C, 62.66; H, 4.01; N, 7.93.

EXAMPLE 193

Preparation of 2-[[1-Methyl-3,4-didehydropiperidin-4-ylcarbonyl]amino]-N-(4-chlorophenyl)benzamide Hydrochloride

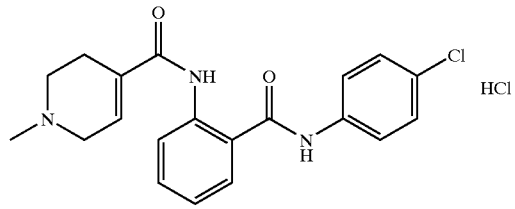

A. 2-(4-Pyridylcarbonyl)amino-N-(4-chlorophenyl)benzamide

Using the procedure described in Example 93, Part A, 2-amino-N-(4-chlorophenyl)benzamide (5 g, 20.3 mmol) and isonicotinoyl chloride hydrochloride (3.97 g, 22.3 mmol) yielded 6.48 g (91%) of the title compound.

$^1$H-NMR MS-FIA, m/e 352.4 (MH+) Analysis for $C_{19}H_{14}ClN_3O_2$: Calc: C, 64.87; H, 4.01; N, 11.94; Found: C, 64.48; H, 3.89; N, 11.58.

B. 2-[[(1-Methylpyridinium-4-yl)carbonyl]amino]-N-(4-chlorophenyl)benzamide Iodide To a stirring solution of 2-(4-pyridinecarbonyl)amino-N-(4-chlorophenyl)benzamide (500 mg, 1.42 mmol) in DMF (10 mL) was added methyl iodide (3 mL, 48 mmol). After 48 h, the precipitate was filtered, washed with diethyl ether and dried in vacuo to give 416 mg (59%) of the title compound.

$^1$H-NMR MS-FIA, m/e 366.1 (MH+) Analysis for $C_{20}H_{17}ClN_3O_2$: Calc: C, 48.66; H, 3.47; N, 8.51; Found: C, 48.46; H, 3.56; N, 8.35.

C. 2-[[1-Methyl-3,4-didehydropiperidin-4-ylcarbonyl]amino]-N-(4-chlorophenyl)benzamide Hydrochloride To a stirring suspension of 2-[[1-methylpyridinium-4-carbonyl]amino]-N-(4-chlorophenyl)benzamide iodide (247 mg, 0.5 mmol) in ethanol was added NaBH$_4$ (20 mg, 0.5 mmol). After 30 min, the solvent was removed and the residue was partitioned between ethyl acetate and water. The organic phase was separated, washed with brine and concentrated in vacuo. The residue was triturated from ether and filtered. The resulting solid was purified by RPHPLC Method 1 to give 40 mg (20%) of white solid.

$^1$H-NMR MS-FIA, m/e 370.1 (MH+) Analysis for $C_{20}H_{20}ClN_3O_2 \cdot 1.2HCl \cdot 2.5H_2O$: Calc: C, 52.37; H, 5.76; N, 9.16; Cl, 17.01; Found: C, 52.15; H, 4.95; N, 9.40; Cl, 15.56.

EXAMPLE 194

Preparation of 2-[[1-Benzyl-3,4-didehydropiperidin-4-ylcarbonyl]amino]-N-(4-chlorophenyl)benzamide Hydrochloride

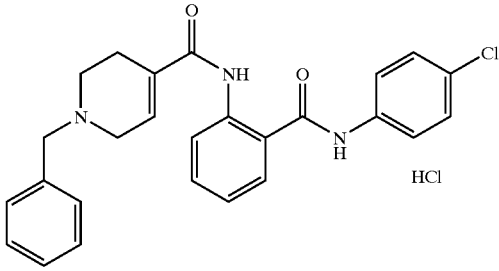

A. 2-[[(1-Benzylpyridinium-4-yl)carbonyl]amino]-N-(4-chlorophenyl)benzamide Bromide Using the procedure described in Example 26, Part B, 2-(4-pyridinecarbonyl)amino-N-(4-chlorophenyl)benzamide (500 mg, 1.42 mmol) and benzyl bromide (0.25 mL, 2.13 mmol) yielded 538 mg (73%) of the title compound.

$^1$H-NMR MS-FIA, m/e 442.2 (MH+) Analysis for $C_{26}H_{21}BrClN_3O_2$: Calc: C, 59.73; H, 4.05; N, 8.04; Found: C, 59.54; A, 4.06; N, 8.16.

B. 2-[[1-Benzyl-3,4-didehydropiperidin-4-ylcarbonyl]amino]-N-(4-chlorophenyl)benzamide Hydrochloride Using the procedure described in Example 26, Part C, 2-[[1-benzylpyridinium-4-carbonyl]amino]-N-(4-chlorophenyl)benzamide bromide (345 mg, 0.66 mmol) yielded 23 mg (7%) of the title compound.

$^1$H-NM ES-MS, m/e 446.1 (MH+) Analysis for $C_{26}H_{24}ClN_3O_2 \cdot 1.1HCl \cdot 1.0H_2O$: Calc: C, 61.95; H, 5.42; N, 8.34; Cl, 14.77; Found: C, 61.86; H, 5.05; N, 8.26; Cl, 14.54.

EXAMPLE 195

Preparation of $N^1$-(4-Chlorobenzoyl)-4-hydroxy-$N^2$-[1-(4-pyridyl)piperidin-4-ylcarbonyl]-1,2-benzenediamine

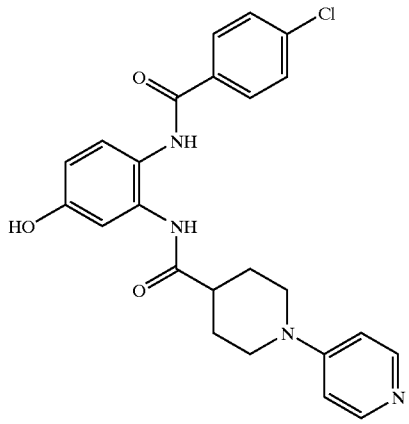

A. 5-tert-Butyldimethylsilyloxy-2-(phthalimido)-N-[1-(4-pyridyl)piperidin-4-ylcarbonyl]aniline 1-(4-Pyridyl)piperidine-4-carboxylic acid (176 mg, 0.85 mmol) and thionyl chloride (93 mL, 1.28 mmol) in 5 mL methylene chloride were heated under reflux for 2 h. The mixture was allowed to cool, concentrated in vacuo to a white foam and dried under vacuum. The foam was suspended in dry methylene chloride (5 mL) then added were 5-tert-butyldimethylsilyloxy-2-(phthalimido)aniline (314 mg; 0.85 mmol)(see Example 167, step C, above) as a solution in 5 mL methylene chloride and 1 mL pyridine in several portions. The cloudy mixture was stirred 45 min then passed through a 35×80 mm plug of silica gel eluting first with methylene chloride then with 9:1:0.1 methylene chloride/methanol/ammonium hydroxide. Appropriate fractions were combined, concentrated in vacuo and dried under vacuum to yield 360 mg (76%) of the desired intermediate phthalimide.

MS, FD+, m/e 557(p+1).

B. $N^1$-(4-Chlorobenzoyl)-4-hydroxy-$N^2$-[1-(4-pyridyl)piperidin-4-ylcarbonyl]-1,2-benzenediamine The phthalimide (350 mg, 0.63 mmol) from step A above was dissolved in 2 mL 1M hydrazine in methanol and allowed to stand 16 h at ambient temperature after which the mixture had solidified. The mixture was diluted with 10 mL 1:1 methylene chloride/methanol and stirred vigorously for 1 h. The mixture was filtered and concentrated in vacuo to yield 276 mg (103%) of the desired intermediate aniline as a white solid.

A mixture of the aniline (80 mg, 0.188 mmol), 4-chlorobenzoyl chloride (48 μL, 0.375 mmol) and excess potassium chloride was stirred 30 min in 8 mL 3:1 methylene chloride/tetrahydrofuran. The resultant mixture was treated with additional 4-chlorobenzoyl chloride (48 μL, 0.375 mmol) and stirred 20 min. The resultant mixture was treated with saturated sodium hydrogen carbonate and stirred vigorously for 15 min. The mixture was partitioned with methylene chloride, the organic portion separated and dried over magnesium sulfate. Solvent was removed in vacuo to yield 145 mg of a yellow foam. The yellow foam was dissolved in methylene chloride and precipitated with hexane, sonicated 5 min then filtered to yield 87 mg (86%) of the silyl ether as a yellow powder.

The crude silyl ether (87 mg, 0.162 mmol) was stirred in a solution of 2 mL tetrahydrofuran and 0.5 mL 5 N HCl at ambient temperature for 16 h. Volatile solvents were removed in vacuo then the residue suspended in excess saturated sodium hydrogen carbonate and 5 mL 1:1 methylene chloride/hexane. The suspension was sonicated about 10 min. The solid was collected by filtration, washed with water and hexane, and dried under vacuum to yield 45 mg (62%) of the title compound as a tan solid.

MS, FD+, m/e 450 (p).

EXAMPLE 196

Preparation of N¹-(4-tert-Butylbenzoyl)-N²-(4-chlorobenzoyl)-1,2-benzenediamine

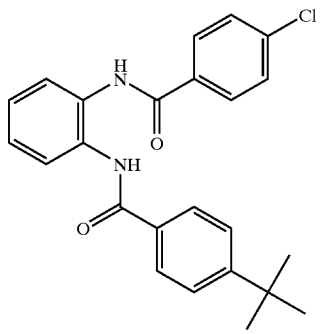

To a solution of N¹-(4-tert-butylbenzoyl)-1,2-benzenediamine (100 mg, 0.37 mmol) in 3 mL methylene chloride was added 4-chlorobenzoyl chloride (95 µL, 0.74 mmol) and excess potassium carbonate. The mixture was stirred 30 min then a 1:1 solution of tetrahydrofuran and 5 N NaOH was added. The resultant mixture was stirred an additional 20 min and diluted with ether. The mixture was washed twice with water, dried over magnesium sulfate, filtered and concentrated in vacuo. The residue was sonicated with hexane causing a precipitate to form which was collected by filtration and dried under vacuum to yield 100 mg (66%) of the title compound.

MS, FD+, m/e 406(p). Analysis for $C_{24}H_{23}ClN_2O_2$: Calc.: C, 69.82; H, 5.70; N, 6.88; Found: C, 69.82; H, 5.71; N, 7.00.

EXAMPLE 197

Preparation of N¹-[(4-Dimethylamino)benzoyl]-N²-(4-methoxybenzoyl)-1,2-benzenediamine

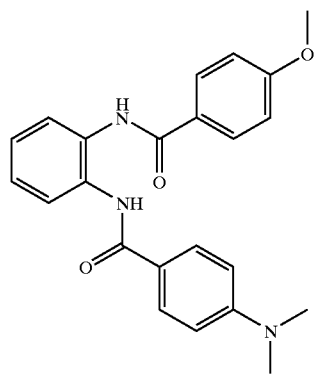

A mixture of N¹-(4-methoxybenzoyl)-1,2-benzenediamine (242 mg, 1.00 mmol), 4-(dimethylamino)benzoic acid (200 mg, 1.24 mmol), 1-(3-dimethylaminopropyl)-3-ethylcarbodiimide hydrochloride (2040 mg, 1.26 mmol), and 1-hydroxybenzotriazole (135 mg, 1.00 mmol) in 3 mL methylene chloride was stirred 48 h at ambient temperature. The mixture was partitioned between ethyl acetate and 10% citric acid. The organic portion was washed with water and saturated sodium hydrogen carbonate then dried over magnesium sulfate, filtered and concentrated in vacuo. The residue was purified on silica gel with 40% ethyl acetate in hexane to yield the title compound (77 mg, 20%) as a white powder.

MS, FD+, m/e 389(p). Analysis for $C_{23}H_{23}N_3O_3$: Calc.: C, 70.93; H, 5.95; N, 10.79; Found: C, 70.74; H, 5.97; N, 10.86.

EXAMPLE 198

Preparation of N²-[(4-Dimethylamino)benzoyl]-4-hydroxy-N¹-(4-methoxybenzoyl)-1,2-benzenediamine

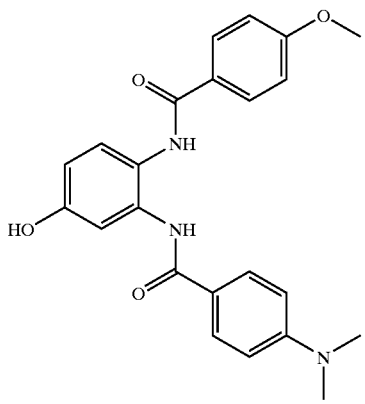

A. 4-(Dimethylamino)benzoyl chloride

A solution of 4-(dimethylamino)benzoic acid and thionyl chloride in methylene chloride was refluxed 4 h. Volatile solvents were removed in vacuo to yield 1.10 g of 4-(dimethylamino)benzoyl chloride. This material was used in subsequent reactions without purification.

B. N²-[(4-Dimethylamino)benzoyl]-4-hydroxy-N¹-(4-methoxybenzoyl)-1,2-benzenediamine To a mixture of 4-tert-butyldimethylsilyloxy-N¹-(4-methoxybenzoyl)-1,2-benzenediamine (200 mg, 1.20 mmol) and 4-(dimethylamino)benzoyl chloride (200 mg) in methylene chloride (5 mL) was added excess N-methylmorpholine and a catalytic amount of 4-dimethylaminopyridine. The mixture was stirred 16 h at ambient temperature then was partitioned between ethyl acetate and saturated sodium hydrogen carbonate. The organic portion was washed with brine, dried over magnesium sulfate and concentrated in vacuo. The residue was taken up in ethyl acetate and hexane added until cloudy. The mixture was sonicated causing a precipitate to form. The solid silyl ether was collected by filtration then dissolved in 3 mL tetrahydrofuran. The solution was treated with 1 mL 5N HCl and allowed to stand for 60 h then neutralized with saturated sodium hydrogen carbonate solution. Hexane was added and the mixture sonicated. The resultant solid was collected by filtration and dried under vacuum to yield the title bisamide phenol.

MS, Ion spray, m/e 406(p+1). Analysis for $C_{23}H_{23}N_3O_4$: Calc.: C, 68.13; H, 5.72; N, 10.36; Found: C, 68.52; H, 5.96; N, 9.72.

EXAMPLE 199

Preparation of 2-(4-tert-Butylbenzoylamino)-4-(2-methoxyacetylamino)-N-(4-methoxyphenyl)benzamide

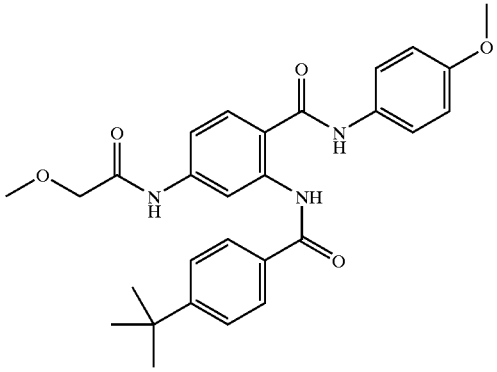

Using the procedure described in Example 59, Part E, 2-(4-tert-butylbenzoylamino)-4-amino-N-(4-methoxyphenyl)benzamide was reacted with methoxyacetyl chloride (0.55 mmol) to yield 175 mg (74%) of the title compound as a solid.

$^1$H-NMR(300 MHz, DMSO-$d_6$): δ 12.24(s, 1H); 10.32(s, 1H); 10.16(s, 1H); 8.88(s, 1H); 7.91(d, J=8.7 Hz, 1H); 7.83(d, J=8.4 Hz, 2H); 7.66(d, J=8.4 Hz, 2H); 7.58(m, 4H); 6.93(d, J=9.0 Hz, 2H); 4.04(s, 2H); 3.74(s, 3H); 3.37(s, 1H); 1.29(s, 9H); MS-FD m/e: 489 (p). Analysis for $C_{20}H_{31}N_3O_5 \cdot 0.5$ $CH_2Cl_2 \cdot 0.5$ $H_2O$: Calc: C, 63.56; H, 6.25; N, 7.67; Found: C, 63.53; H, 5.98; N, 8.01.

EXAMPLE 200

Preparation of 2-(4-tert-Butylbenzoylamino)-4-(ethylsulfonylamino)-N-(4-methoxyphenyl)benzamide

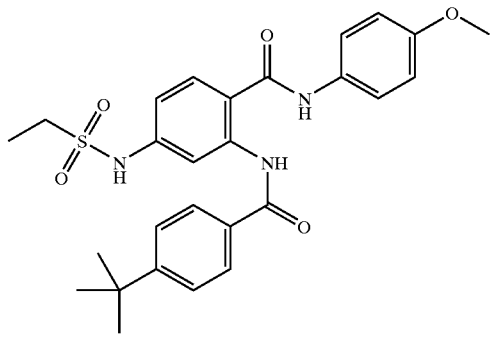

Using the procedure described in Example 59, Part E, 2-(4-tert-butylbenzoylamino)-4-amino-N-(4-methoxyphenyl)benzamide was reacted with ethanesulfonyl chloride (0.47 mmol) to yield 127 mg (52%) of the title compound as a solid.

$^1$H-NMR(300 MHz, DMSO-$d_6$): δ 12.24(s, 1H); 10.30(s, 2H); 8.58(s, 1H).; 7.91(d, J=8.7 Hz, 1H); 7.83(d, J=8.4 Hz, 2H); 7.57(t, J=8.4 Hz, 4H); 7.04(d, J=8.7 Hz, 1H); 6.93(d, J=9.0 Hz, 2H); 3.73(s, 3H); 3.22(q, J=7.5 Hz, 2H); 1.29(s, 9H); 1.21(t, J=7.5 Hz, 3H); IR(CHCl$_3$): 1651, 1512, 1463, 1147; MS-FD m/e: 509 (p). Analysis for $C_{27}H_{31}N_3O_5S$: Calc: C, 63.63; H, 6.13; N, 8.24; Found: C, 65.08; H, 5.95; N, 8.10.

EXAMPLE 201

Preparation of 2-(4-tert-Butylbenzoylamino)-4-(ethoxycarbonylamino)-N-(4-methoxyphenyl)benzamide

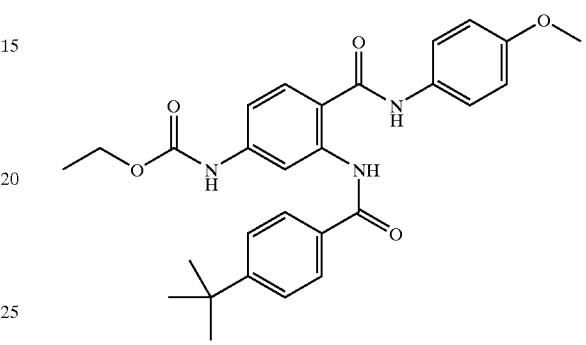

Using the procedure described in Example 59, Part E, 2-(4-tert-butylbenzoylamino)-4-amino-N-(4-methoxyphenyl)benzamide was reacted with ethyl chloroformate (0.52 mmol) to yield 129 mg (55%) of the title compound as a solid.

$^1$H-NMR(300 MHz, DMSO-$d_6$): δ 12.28(s, 1H); 10.26(s, 1H); 10.02(s, 1H); 8.81(s, 1H); 7.88(d, J=8.7 Hz, 1H); 7.83(d, J=8.4 Hz, 2H); 7.57(t, J=8.1 Hz, 4H); 7.36(d, J=8.7 Hz, 1H); 6.93(d, J=8.7 Hz, 2H); 4.15(q, J=6.9 Hz, 2H); 3.73(s, 3H); 1.29(s, 9H); 1.25(t, J=7.2 Hz, 3H): MS-FD m/e: 489 (p). Analysis for $C_{28}H_{31}N_3O_5$: Calc: C, 68.69; H, 6.38; N, 8.58; Found: C, 69.99; H, 6.77; N, 8.78.

EXAMPLE 202

Preparation of 2-(4-tert-Butylbenzoylamino)-4-(2-dimethylacetylamino)-N-(4-methoxyphenyl)benzamide

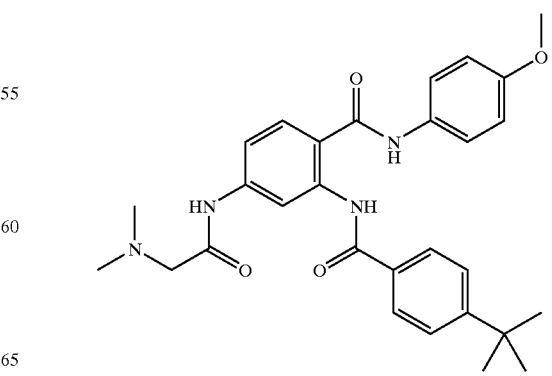

2-Dimethylaminoacetyl chloride was prepared using the procedure described in Example 55, Part B, but using 2-dimethylaminoacetic acid. Using the procedure described in Example 59, Part E, 2-(4-tert-butylbenzoylamino)-4-amino-N-(4-methoxyphenyl)benzamide was reacted with 2-dimethylaminoacetyl chloride (9.77 mmol) to yield 27 mg (7%) of the title compound as a solid.

$^1$H-NMR(300 MHz, DMSO-d$_6$): δ 12.27(s, 1H); 10.31(s, 1H); 10.11(s, 1H); 8.87(s, 1H); 7.92(d, J=8.7 Hz, 1H); 7.83(d, J=8.4 Hz, 2H); 7.65(d, J=8.4 Hz, 1H); 7.58(m, 4H); 6.93(d, J=9.0 Hz, 2H); 3.74(s, 3H); 3.31(s, 2H); 2.30(s, 6H); 1.29(s, 9H); MS-FD m/e: 502 (p). Analysis for $C_{29}H_{34}N_4O_4$: Calc: C, 69.30; H, 6.82; N, 11.15; Found: C, 71.15; H, 7.25; N, 10.73.

EXAMPLE 203

Preparation of 2-(4-Dimethylaminobenzoylamino)-N-(4-methoxyphenyl)benzamide

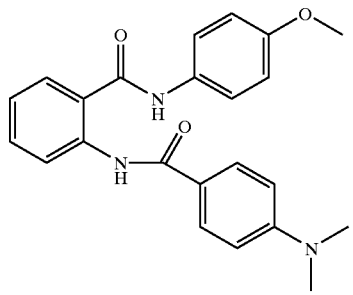

Using the procedure described in Example 55, Part B, 4-dimethylaminobenzoic acid and 2-amino-N-(4-methoxyphenyl)benzamide (1.25 mmol), yielded 444 mg (91%) of the title compound as a white solid.

IR(CHCl$_3$): 1607, 1510, 1443. 1306; $^1$H-NMR(300 MHz, DMSO-d$_6$): δ 11.74(s, 1H); 10.39(s, 1H); 8.57(d, J=8.1 Hz, 1H); 7.88(d, J=7.5 Hz, 1H); 7.72(d, J=9.0 Hz, 2H); 7.59–7.54(m, 3H); 7.17(m, 1H); 6.92(d, J=8.7 Hz, 2H); 6.76(d, J=9.0 Hz, 2H); 3.72(s, 3H); 2.96(s, 6H); MS-IS m/e: 390.2 (p+1). Analysis for $C_{23}H_{23}N_3O_3$: Calc: C, 70.93; H, 5.95; N, 10.79; Found: C, 71.95; H, 5.78; N, 10.93.

EXAMPLE 204

Preparation of N-(4-Methoxyphenyl)-2-[1-(4-pyridinyl)piperidin-4-yloxycarbonyl]aminobenzamide

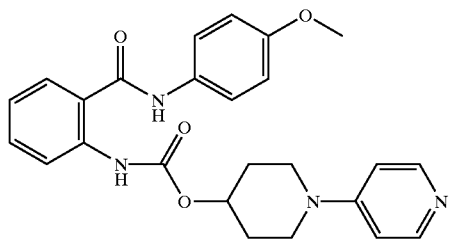

To a mixture of 1-(4-pyridyl)-4-hydroxypiperidine (536 mg, 3.01 mmol) and methylene chloride (45 mL) was added methanesulfonic acid (0.2 ml, 3.1 mmol). After stirring for 15 seconds, quinoline (0.45 mL, 3.8 mmol) was added, immediately followed by 1.93 M phosgene in toluene (2 mL, 3.9 mmol). After 5 minutes, the reaction was placed in a 35° C. oil bath for 45 minutes. The reaction was cooled to room temperature and N-(4-methoxyphenyl)-2-aminobenzamide (728 mg, 3.0 mmol) and quinoline(0.45 mL, 3.8 mmol) were added. After stirring overnight, the reaction was diluted with CH$_2$Cl$_2$(150 mL) and washed with sat'd sodium carbonate (2×25 mL). The organic layer was concentrated and the crude residue was chromatographed to give 617 mg (46%) of the title compound as a white solid.

IR(CHCl$_3$): 1724, 1598, 1511, 1237; $^1$H-NMR(300 MHz, DMSO-d$_6$): δ 10.30(s, 1H); 10.25(s, 1H); 8.11–8.07(m, 3H); 7.78(d, J=8.1 Hz, 1H); 7.57–7.48(m, 3H); 7.14(t, J=7.5 Hz, 1H); 6.89(d, J=9.0 Hz, 2H); 6.82(d, J=5.4 Hz, 2H); 4.85(m, 1H); 4.85(m, 5H); 3.68–3.65(m, 2H); 1.90(m, 2H); 1.60(m, 2H); MS-IS m/e: 447.2 (p+1). Analysis for $C_{25}H_{26}N_4O_4 \cdot 0.5$ $H_2O$: Calc: C, 65.92; H, 5.97; N, 12.30; Found: C, 65.85; H, 5.50; N, 11.87.

EXAMPLE 205

Preparation of N-(4-Methoxyphenyl)-2-[1-(4-pyridyl)pyrrolidin-3-yloxycarbonyl]aminobenzamide

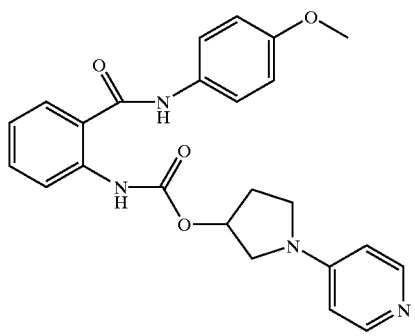

Using the procedure described in Example 204, 1-(4-pyridyl)-3-hydroxypyrrolidine (3.03 mmol), yielded 189 mg 114%) of the title compound as a white solid.

IR(CHCl$_3$): 1728, 1650, 1600, 1512 cm$^{-1}$; $^1$H-NMR(300 MHz, DMSO-d$_6$): δ 10.28 (s, 1H); 10.26 (s, 1H); 8.10 (br s, 2H); 8.03 (d, J=8.1 Hz, 1H); 7.76 (d, J=7.8 Hz, 1H); 7.55–7.47 (m, 3H); 7.15 (t, J=7.5 Hz, 1H); 6.87 (d, J=8.7 Hz, 2H); 6.54 (d, J=5.1 Hz, 2H); 5.35 (s, 1H); 3.69 (S. 3H); 3.66–3.34 (m, 4H); 2.27–2.19 (m, 2H); MS-IS m/e: 433.5 (p+1). Analysis for $C_{24}H_{24}N_4O_4 \cdot 1.25$ $H_2O$: Calc: C, 63.35; H, 5.87; N, 12.31; Found: C, 63.23; H, 5.38; N, 12.07.

EXAMPLE 206

Preparation of $N^1$-(3-Hydroxybenzoyl)-$N^2$-[1-(4-pyridyl)piperidin-4-ylmethoxycarbonyl]-1,2-benzenediamine

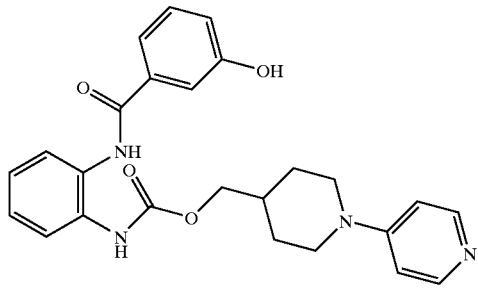

A. 3-Benzyloxybenzoic acid

A solution of methyl 3-hydroxybenzoate (1.00 g, 6.56 mmol) in THF was treated with sodium hydride (60% by wt in oil, 276 mg, 6.90 mmol). After 20 minutes, the mixture was treated with benzyl bromide (0.78 mL, 6.56 mmol) and then heated at reflux. The mixture was cooled, treated with saturated ammonium chloride and EtOAc. The layers were separated and the aqueous layer was washed with EtOAc (3×). The combined organic extracts were washed with saturated NaCl, dried over $MgSO_4$ and concentrated. A solution of the crude material in dioxane (20 mL) was treated with 2.5 N NaOR (13 mL) and stirred vigorously. The mixture was acidified by addition of 5 N HCl and partitioned with EtOAc. The aqueous layer was washed with EtOAc (3×) and the combined extracts were dried ($MgSO_4$) and concentrated yielding the title compound.

$^1$H-NMR MS-FD m/e 227 (p)

B. $N^1$-(3-Benzyloxybenzoyl)-$N^2$-[1-(4-pyridyl)piperidin-4-ylmethoxycarbonyl]-1,2-benzenediamine Using a similar procedure to that described in Example 48, Part C, $N^1$-[1-(4-pyridyl)piperidin-4-ylmethoxycarbonyl]-1,2-benzenediamine (300 mg, 0.920 mmol) yielded 230 mg (46%) of the title compound.

$^1$H-NMR

C. $N^1$-(3-Hydroxybenzoyl)-1-$N^2$-[1-(4-pyridyl)piperidin-4-ylmethoxycarbonyl]-1,2-benzenediamine A mixture of $N^1$-(3-benzyloxybenzoyl)-$N^2$-[1-(4-pyridyl) piperidin-4-ylmethoxycarbonyl]-1,2-benzenediamine (75 mg, 0.14 mmol) and 5% palladium-on-carbon (200 mg) in ethanol (4 mL) was placed under an atmosphere of hydrogen (1 atm). After consumption of the starting material, the mixture was filtered through diatomaceous earth and the filtrate concentrated in vacuo yielding 30 mg (48%) of the title compound.

$^1$H-NMR MS-FD m/e 447 (p+1) Analysis for $C_{25}H_{26}N_4O_4$: Calc: C, 67.25; H, 5.87; N, 12.55; Found: C, 67.38; H, 5.81; N, 10.93.

EXAMPLE 207

Preparation of $N^1$-(3-Methylbenzoyl)-$N^2$-[1-(4-pyridyl)piperidin-4-ylmethoxycarbonyl]-1,2-benzenediamine hydrochloride hydrate

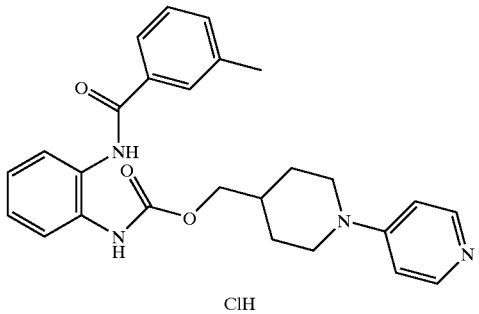

Using a similar procedure to that described in Example 48, Part C, $N^1$-[1-(4-pyridyl)piperidin-4-ylmethoxycarbonyl]-1,2-benzenediamine (300 mg, 0.920 mmol) yielded, after treatment with excess HCl and lyophilization, 300 mg (68%) of the title compound as the HCl salt.

$^1$H-NMR, IR MS-FD m/e 445 (p) Analysis for $C_{26}H_{30}Cl_2N_4O_3 \cdot H_2O$: Calc: C, 62.58; H, 6.26; N, 11.23; Found: C, 62.92; H, 6.34; N, 10.81.

EXAMPLE 208

Preparation of $N^1$-(4-Fluorobenzoyl)-$N^2$-[1-(4-pyridyl)piperidin-4-ylmethoxycarbonyl]-1,2-benzenediamine hydrochloride

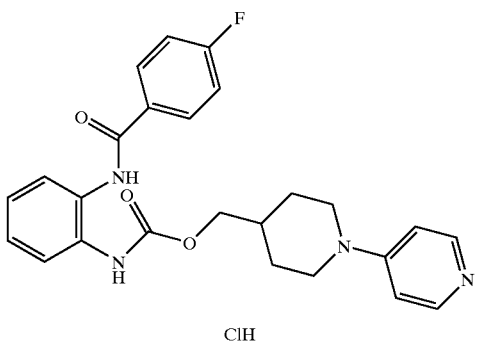

Using a similar procedure to that described in Example 48, Part C, $N^1$-[1-(4-pyridyl)piperidin-4-ylmethoxycarbonyl]-1,2-benzenediamine (300 mg, 0.920 mmol) yielded, after treatment with excess HCl and lyophilization, 289 mg (70%) of the title compound.

$^1$H-NMR, IR MS-FD m/e 449 (p+1) Analysis for $C_{25}H_{26}ClFN_4O_3$: Calc: C, 61.92; H, 5.40; N, 11.55; Found: C, 61.77; H, 5.21; N, 11.33.

EXAMPLE 209

Preparation of N¹-(4-Chlorobenzoyl)-N²-[1-(4-pyridyl)piperidin-4-ylmethoxycarbonyl]-1,2,4-benzenetriamine

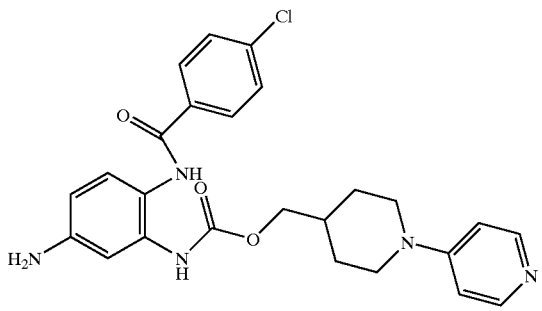

A. 2-Amino-4-(N-tert-butoxycarbonylamino)nitrobenzene

A solution of 2,4-diamino-nitrobenzene (500 mg, 3.26 mmol) in 30 mL of THF at −10° C. was treated with potassium hexamethyldisilazide (6.86 mL, 0.5M in toluene, 3.43 mmol). After 0.2 h, the mixture was treated with di-tert-butyl dicarbonate (749 mg, 3.43 mmol) and stirred for 2 h. The mixture was poured into EtOAc and saturated NaCl (aq). The organic layer was dried (MgSO$_4$), concentrated, and the residue purified by chromatography (19:1 CH$_2$Cl$_2$:EtOAc) yielding 370 mg (45%) of the title compound.

$^1$H-NMR MS-FD m/e 253 (p)

B. 4-(N-tert-Butoxycarbonylamino)-2-[1-(4-pyridyl)piperidin-4-ylmethoxycarbonylamino]nitrobenzene A solution of 2-amino-4-(N-tert-butoxycarbonylamino) nitrobenzene (2.1 g, 8.3 mmol) in toluene (50 mL) was treated with phosgene (1.93M in toluene, 12.9 mL, 24.9 mmol) and the mixture-was heated at 50° C. After 2 h, the mixture was concentrated, the residue was dissolved in CH$_2$Cl$_2$ and treated with triethylamine (2.31 mL, 16.6 mmol) and 1-(4-pyridyl)piperidine-4-methanol (1.59 g, 8.29 mmol). After 16 h, the mixture was concentrated and the residue purified by chromatography (9:1 CH$_2$Cl$_2$:MeOH) affording 1.78 g (46%) of the title compound.

$^1$H-NMR MS-FD m/e 472 (p+1)

C. N⁴-(N-tert-Butoxycarbonyl)-N²-[1-(4-pyridyl)piperidin-4-ylmethoxycarbonyl]-1,2,4-benzenetriamine A solution of 4-(N-tert-butoxycarbonylamino)-2-[1-(4-pyridyl)piperidin-4-ylmethoxycarbonylamino]nitrobenzene (500 mg, 1.06 mmol) and 5% palladium on carbon (250 mg) in 1:1 EtOAc:EtOH was placed under an atmosphere of hydrogen. Upon consumption of starting material, the mixture was filtered, concentrated, and the residue purified by chromatography (4:1 CH$_2$Cl$_2$:MeOH) affording 390 mg (83%) of the title compound.

$^1$H-NMR MS-FD m/e 442 (p+1)

D. N¹-(4-Chlorobenzoyl)-N²-[1-(4-pyridyl)piperidin-4-ylmethoxycarbonyl]-N⁴-(tert-butoxycarbonyl)-1,2,4-benzenetriamine Using a similar procedure to that described in Example 48, Part C, N⁴-(tert-butoxycarbonyl)-N²-[1-(4-pyridylpiperidin-4-ylmethoxycarbonyl]-1,2,4-benzenetriamine (380 mg, 0.86 mmol) and 4-chlorobenzoyl chloride (0.12 mL, 0.95 mmol) yielded 360 mg (72%) of the title compound.

$^1$H-NMR MS-FD m/e 580 (p)

E. N¹-(4-Chlorobenzoyl)-N²-[1-(4-pyridyl)piperidin-4-ylmethoxycarbonyl]-1,2,4-benzenetriamine N¹-(4-Chlorobenzoyl)-N²-[1-(4-pyridyl)piperidin-4-ylmethoxycarbonyl]-N⁴-tert-butoxycarbonylamino-1,2,4-benzenetriamine (150 mg, 0.26 mmol) was dissolved in trifluoroacetic acid (2 mL). After 2 h, the mixture was concentrated and the residue partitioned between EtOAc and 1N NaOH and sat'd NaHCO$_3$ (aq). The aqueous layer was washed with EtOAc (2×) and the combined extracts were dried (MgSO$_4$) and concentrated. The residue was purified by chromatography (9:1 CH$_2$Cl$_2$:MeOH) affording 110 mg (89%) of the title compound.

$^1$H-NMR MS-FD m/e 479 (p)

EXAMPLE 210

Preparation of N¹-(4-Chlorobenzoyl)-N²-[1-(4-pyridyl)piperidin-4-ylmethoxycarbonyl]-N⁴-(methylsulfonyl)-1,2,4-benzenetriamine

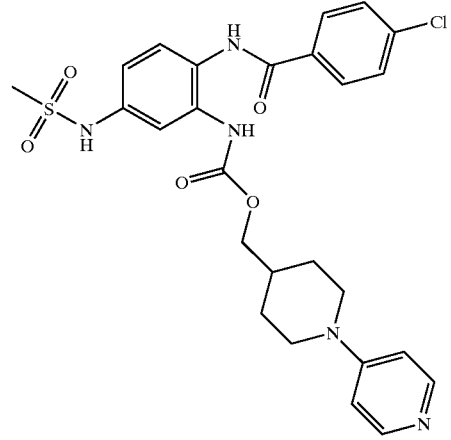

A solution of N¹-(4-chlorobenzoyl)-N²-[1-(4-pyridyl) piperidin-4-ylmethoxycarbonyl]-1,2,4-benzenetriamine (40 mg, 0.08 mmol) in 5 mL of CH$_2$Cl$_2$ was treated with pyridine (1 mL) and methanesulfonyl chloride (0.008 mL, 0.09 mmol). After 16 h, the mixture was treated with MeOH (1 mL) and then concentrated. The residue was partitioned between EtOAc and NaOH (aq). The organic layer was dried (MgSO$_4$) concentrated, and purified by chromatography (17:3 CH$_2$Cl$_2$:MeOH) affording 20 mg (40%) of the title compound.

$^1$H-NMR MS-FAB m/e 558 (p+1)

EXAMPLE 211

Preparation of $N^4$-Acetyl-$N^1$-(4-chlorobenzoyl)-$N^2$-[1-(4-pyridyl)piperidin-4-ylmethoxycarbonyl]-1,2,4-benzenetriamine

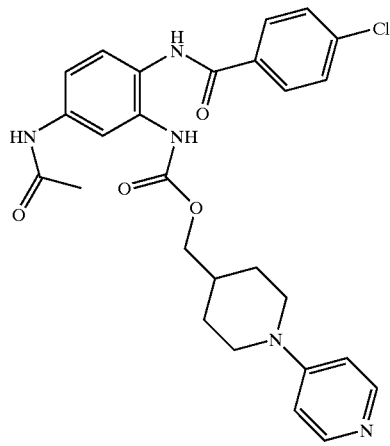

A solution of $N^1$-(4-chlorobenzoyl)-$N^2$-[1-(4-pyridyl)piperidin-4-ylmethoxycarbonyl]-1,2,4-benzenetriamine (40 mg, 0.08 mmol) in 5 mL of $CH_2Cl_2$ was treated with pyridine (1 mL) and acetyl chloride (0.006 mL, 0.09 mmol). After 16 h, the mixture was treated with MeOH (1 mL) and then concentrated. The residue was partitioned between EtOAc and NaOH (aq). The organic layer was dried ($MgSO_4$), concentrated, and purified by chromatography (17:3 $CH_2Cl_2$:MeOR), affording 32 mg (76%) of the title compound.

$^1$H-NMR MS-FAB m/e 522 (p+1)

EXAMPLE 212

Preparation of $N^1$-(4-Chlorobenzoyl)-$N^2$-[1-(4-pyridyl)piperidin-4-ylmethoxycarbonyl]-1,2,5-benzenetriamine

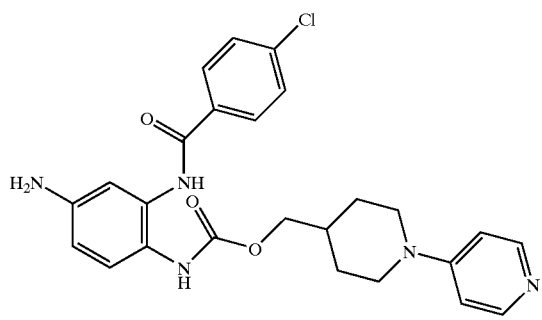

A. 2-Amino-5-(N-tert-butoxycarbonylamino)nitrobenzene

Using a procedure similar to that described in Example 209, part A, 2,5-diamino-nitrobenzene (1.00 g, 6.53 mmol) yielded 1.31 g (79%) of the title compound.

$^1$H-NMR MS-FD m/e 253 (p)

B. 5-(tert-Butoxycarbonylamino)-2-[1-(4-pyridyl)piperidin-4-ylmethoxycarbonyl]amino-nitrobenzene Using a procedure similar to that described in Example 209, part S, 2-amino-5-(N-tert-butoxycarbonylamino) nitrobenzene (1.16 g, 4.58 mmol) and 1-(4-pyridyl) piperidine-4-methanol (0.88 g, 4.58 mmol) yielded 1.33 g (62%) of the title compound.

$^1$H-NMR MS-FD m/e 471 (p)

C. $N^5$-(N-tert-Butoxycarbonyl)-$N^2$-[1-(4-pyridyl)piperidin-4-ylmethoxycarbonyl]-1,2,5-benzenetriamine Using a procedure similar to that described in Example 209, part B, 5-(tert-butoxycarbonylamino)-2-[1-(4-pyridyl) piperidin-4-ylmethoxycarbonyl]amino-nitrobenzene (500 mg, 1.06 mmol) and 5% palladium on carbon. (250 mg) yielded 450 mg (96%) of the title compound.

$^1$H-NMR MS-FD m/e 442 (p+1)

D. $N^1$-(4-Chlorobenzoyl)-$N^2$-[1-(4-pyridyl)piperidin-4-ylmethoxycarbonyl]-$N^5$-(tert-butoxycarbonyl)-1,2,5-benzenetriamine Using a similar procedure to that described in Example 48, Part C, $N^5$-(N-tert-butoxycarbonyl)-$N^2$-[1-(4-pyridyl) piperidin-4-ylmethoxycarbonyl]-1,2,5-benzenetriamine (380 mg, 0.86 mmol) and 4-chlorobenzoyl chloride (0.12 mL, 0.95 mmol) yielded 400 mg (80%) of the title compound.

$^1$H-NMR MS-FD m/e 580 (p)

E. $N^1$-(4-Chlorobenzoyl)-$N^2$-[1-(4-pyridyl)piperidin-4-ylmethoxycarbonyl]-1,2,5-benzenetriamine Using a procedure similar to that described in Example 209, part E, $N^1$-(4-chlorobenzoyl)-$N^2$-[1-(4-pyridyl) piperidin-4-ylmethoxycarbonyl]-$N^5$-(tert-butoxycarbonyl)-1,2,5-benzenetriamine (150 mg, 0.26 mmol) yielded 115 mg (93%) of the title compound.

$^1$H-NMR MS-FD m/e 480 (p)

EXAMPLE 213

Preparation of $N^1$-(4-Chlorobenzoyl)-$N^2$-[1-(4-pyridyl)piperidin-4-ylmethoxycarbonyl]-$N^5$-(methylsulfonyl)-1,2,5-benzenetriamine

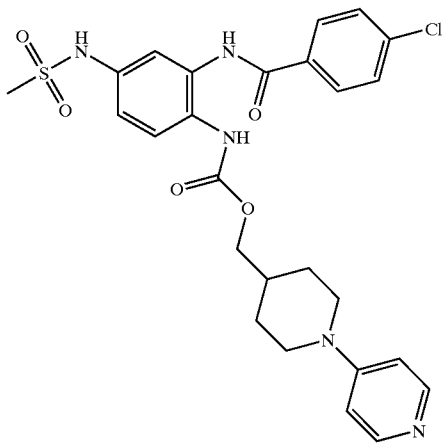

Using a procedure similar to that described in Example 210, $N^1$-(4-chlorobenzoyl)-$N^2$-[1-(4-pyridyl)piperidin-4-ylmethoxycarbonyl]-1,2,5-benzenetriamine (35 mg, 0.07 mmol) yielded 15 mg (38%) of the title compound.

$^1$H-NMR MS-FAB m/e 558 (p)

EXAMPLE 214

Preparation of $N^5$-Acetyl-$N^1$-(4-chlorobenzoyl)-$N^2$-[1-(4-pyridyl)piperidin-4-ylmethoxycarbonyl]-1,2,5-benzenetriamine

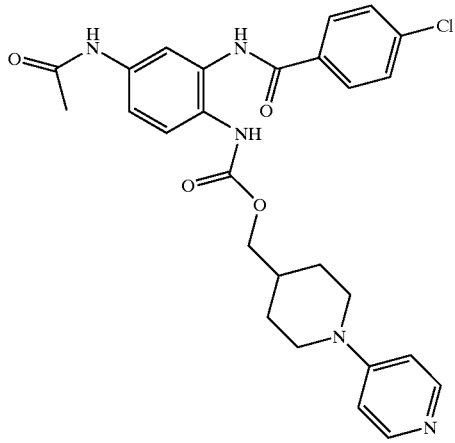

Using a procedure similar to that described in Example 211, $N^1$-(4-chlorobenzoyl)-$N^2$-[1-(4-pyridyl)piperidin-4-ylmethoxycarbonyl]-1,2,5-benzenetriamine (40 mg, 0.08 mmol) yielded 30 mg (71%) of the title compound.

$^1$H-NMR MS-FAB m/e 522 (p+1)

EXAMPLE 215

Preparation of $N^1$-(4-Chlorobenzoyl)-$N^2$-[1-(4-pyridyl)piperidin-4-ylmethoxycarbonyl]-$N^5$-trifluoroacetyl-1,2,5-benzenetriamine

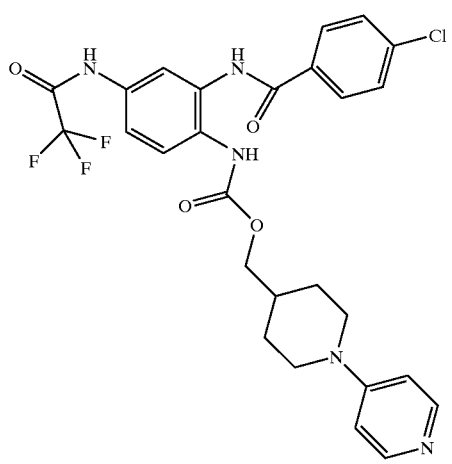

Using a procedure similar to that described in Example 210, $N^1$-(4-chlorobenzoyl)-$N^2$-[1-(4-pyridyl)piperidin-4-ylmethoxycarbonyl]-1,2,5-benzenetriamine (40 mg, 0.07 mmol) yielded 30 mg (65%) of the title compound.

$^1$H-NMR MS-FAB m/e 576 (p)

EXAMPLE 216

Preparation of $N^1$-(4-Chlorobenzoyl)-$N^2$-[1-(4-pyridyl)piperidin-4-ylmethylaminocarbonyl]-1,2-benzenediamine

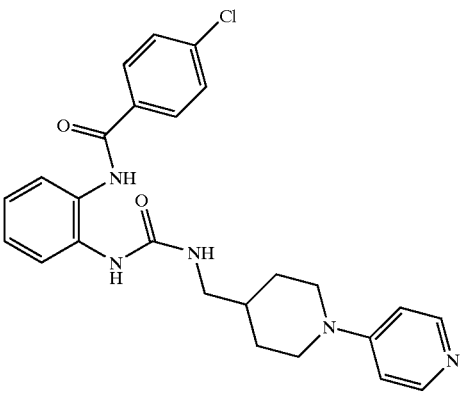

A. 1-(4-Pyridyl)piperidine-4-methylamine

A solution of 1-(4-pyridyl)piperidine-4-methanol (5.87 g, 30.6 mmol), phthalimide (4.59 g, 31.2 mmol), and triphenylphosphine (8.10 g, 30.9 mmol) in 125 mL of THF at −5° C. was treated with a solution of diethyl azodicarboxylate (5.38 g, 30.9 mmol) in THF (40 mL). After 16 h, the mixture was poured into EtOAc and 1N HCl. The aqueous layer was washed with EtOAc (2×), pH adjusted to 12 by addition of 5N NaOH, and washed with EtOAc (3×). The combined organic extracts were dried ($K_2CO_3$) and concentrated yielding 8.45 g (86%) of the substituted phthalimide. The crude material (5.47 g, 17.0 mmol) was then treated with hydrazine hydrate (3.5mL, 60.0 mmol) in EtOH (50 mL). The mixture was heated at 75° C. for 5 h, cooled, diluted with $CH_2Cl_2$ (100 mL), and cooled to 0° C. The solid was removed by filtration and the filtrate was concentrated yielding 3.32 g of the title compound which was used without further purification.

$^1$H-NMR

B. 2-[1-(4-Pyridyl)piperidin-4-ylmethylaminocarbonyl]amino-nitrobenzene

Using a similar procedure to that described for Example 48, Part A, 1-(4-pyridyl)piperidine-4-methylamine (1.34 g, 7.01 mmol) and 2-nitrophenyl isocyanate (1.21 g, 7.40 mmol) yielded 1.59 g (64%) of the title compound.

$^1$H-NMR, IR MS-FD m/e 355 (p) Analysis for $C_{18}H_{21}N_5O_3$: Calc: C, 60.83; H, 5.96; N, 19.71; Found: C, 60.66; H, 5.90; N, 19.50.

C. $N^1$-[1-(4-Pyridyl)piperidin-4-ylmethylaminocarbonyl]-1,2-benzenediamine

Using a similar procedure to that described for Example 48, Part B, 2-[1-(4-pyridyl)piperidin-4-ylmethylaminocarbonyl]amino-nitrobenzene (1.02 g, 2.87 mmol) yielded 930 mg (99%) of the title compound.

$^1$H-NMR, IR MS-FD m/e 326 (p+1) Analysis for $C_{18}H_{23}N_5O$: Calc: C, 66.44; H, 7.12; N, 21.52; Found: C, 65.39; H, 7.02; N, 20.76.

D. $N^1$-(4-Chlorobenzoyl)-$N^2$-[1-(4-pyridyl)piperidin-4-ylmethylaminocarbonyl]-1,2-benzenediamine Using a similar procedure to that described in Example 48, Part C, $N^1$-[1-(4-pyridyl)piperidin-4-ylmethylaminocarbonyl]-1,2-benzenediamine (43 mg, 0.13 mmol) yielded 51 mg (84%) of the title compound.

$^1$H-NMR, IR MS-FD m/e 464 (p) Analysis for $C_{25}H_{26}ClN_5O_2$: Calc: C, 64.72; H, 5.65; N, 15.09; Found: C, 64.52; H, 5.62; N, 14.84.

EXAMPLE 217

Preparation of $N^1$-(4-Methoxybenzoyl)-$N^2$-[1-(4-pyridyl)piperidin-4-ylmethylaminocarbonyl]-1,2-benzenediamine

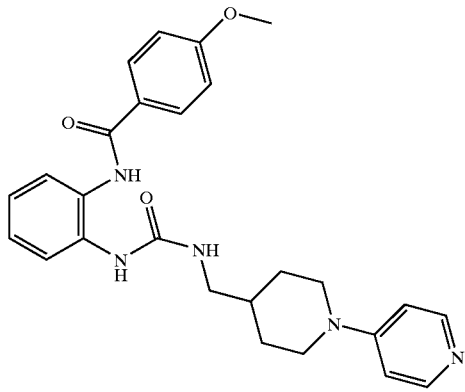

Using a similar procedure to that described in Example 48, Part C, $N^1$-[1-(4-pyridyl)piperidin-4-ylmethylaminocarbonyl]-1,2-benzenediamine (68 mg, 0.21 mmol) yielded 68 mg (70%) of the title compound.

$^1$H-NMR, IR MS-FD m/e 460 (p) Analysis for $C_{26}H_{29}N_5O_3$: Calc: C, 67.95; H, 6.36; N, 15.24; Found: C, 67.45; H, 6.45; N, 14.88.

EXAMPLE 218

Preparation of $N^1$-(3,4-Dichlorobenzoyl)-$N^2$-[1-(4-pyridyl)piperidin-4-ylmethylaminocarbonyl]-1,2-benzenediamine

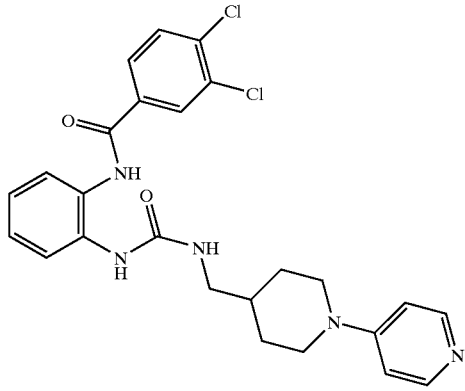

Using a similar procedure to that described in Example 48, Part C, $N^1$-[1-(4-pyridyl)piperidin-4-ylmethylaminocarbonyl]-1,2-benzenediamine (106 mg, 0.327 mmol) yielded 72.8 mg (45%) of the title compound.

$^1$H-NMR, IR MS-FD m/e 498 (p)

EXAMPLE 219

Preparation of $N^1$-(2,4-Dichlorobenzoyl)-$N^2$-[1-(4-pyridyl)piperidin-4-ylmethylaminocarbonyl]-1,2-benzenediamine

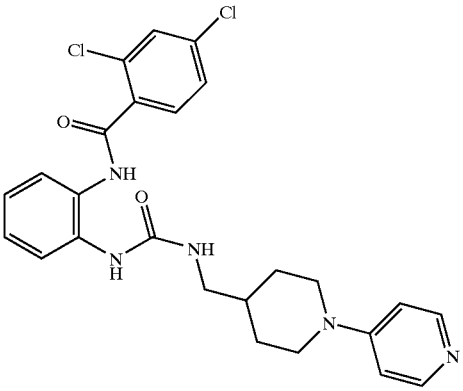

Using a similar procedure to that described in Example 48, Part C, $N^1$-[1-(4-pyridyl)piperidin-4-ylmethylaminocarbonyl]-1,2-benzenediamine (113 mg, 0.347 mmol) yielded 111.4 mg (64%) of the title compound.

$^1$H-NMR. MS-IS m/e 498 (p+1)

EXAMPLE 220

Preparation of $N^1$-(2-Naphthalenylcarbonyl)-$N^2$-[1-(4-pyridyl)piperidin-4-ylmethylaminocarbonyl]-1,2-benzenediamine

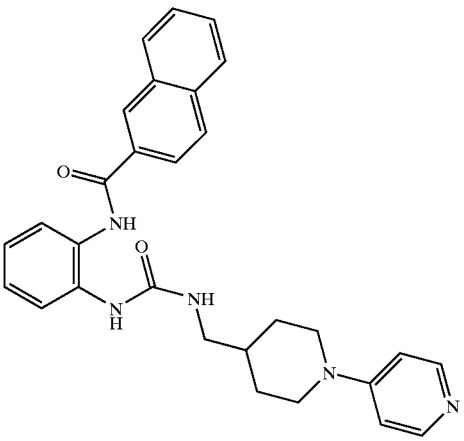

Using a similar procedure to that described in Example 48, Part C, $N^1$-[1-(4-pyridyl)piperidin-4-ylmethylaminocarbonyl]-1,2-benzenediamine (113 mg, 0.347 mmol) yielded 48.9 mg (29%) of the title compound.

$^1$H-NMR MS-IS m/e 480 (p+1)

EXAMPLE 221

Preparation of N¹-(4-Chlorabenzoyl)-N²-[1-(4-pyridyl)piperidin-4-ylaminocarbonyl]-1,2-benzenediamine

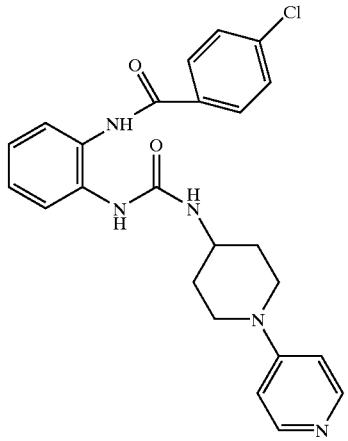

A. 4-Hydroxy-1-(4-pyridyl)piperidine

A solution of 4-hydroxypiperidine (7.80 g, 77 mmol), 4-bromopyridine (15.0 g, 77 mmol), and triethylamine (32 mL, 231 mmol) in 90 mL of EtOH and 30 mL of H$_2$O was heated at 150° C. in a sealed tube for 4 days. The mixture was concentrated and the residue partitioned between CH$_2$Cl$_2$ and H$_2$O. The organic layer was washed with 1 N NaOH (2x), diluted with EtOAc and the resulting solid collected by filtration affording 7.30 g (53%) of the title compound.
$^1$H-NMR

B. 4-(Phthalimido)-1-(4-pyridyl)piperidine

Using a procedure similar to that described in Example 216, Part A, 4-hydroxy-1-(4-pyridyl)piperidine (5.00 g) yielded 5.08 g (60%) of the title compound.
$^1$H-NMR

C. 4-Amino-[1-(4-pyridyl)piperidine

Using a procedure similar to that described in Example 216, Part B, 4-(phthalimido)-[1-(4-pyridyl)piperidine (1.00 g) yielded 470 mg (81%) of the title compound.
$^1$H-NMR MS-FD m/e 178. (p+1)

D. 2-[1-(4-Pyridyl)piperidin-4-ylaminocarbonyl]aminonitrobenzene

Using a similar procedure to that described for Example 48, Part A, 4-amino-1-(4-pyridyl)piperidine (220 mg, 1.24 mmol) yielded 340 mg (80%) of the title compound.
$^1$H-NMR MS-FD m/e 342 (p+1)

E. N¹-[1-(4-Pyridyl)piperidin-4-ylaminocarbonyl]-1,2-benzenediamine

Using a similar procedure to that described for Example 48, Part B, 2-[1-(4-pyridyl)piperidin-4-ylaminocarbonyl]amino-nitrobenzene (200 mg, 1.00 mmol) yielded 200 mg (64%) of the title compound.
$^1$H-NMR MS-FD, m/e 312 (p+1) Analysis for C$_{17}$H$_{21}$N$_5$O: Calc: C, 65.57; H, 6.80; N, 22.49; Found: C, 65.31; H, 6.55; N, 22.29.

F. N¹-(4-Chlorobenzoyl)-N²-[1-(4-pyridyl)piperidin-4-ylaminocarbonyl]-1,2-benzenediamine Using a similar procedure to that described in Example 48, Part C, N¹-[1-(4-pyridyl)piperidin-4-ylaminocarbonyl]-1,2-benzenediamine (82 mg, 0.26 mmol) yielded 32 mg (27%) of the title compound.

$^1$H-NMR MS-FD m/e 451 (p+1) Analysis for C$_{24}$H$_{24}$ClN$_5$O$_2$: Calc: C, 64.07; H, 5.38; N, 15.56; Found: C, 63.93; H, 5.39; N, 15.35.

EXAMPLE 222

Preparation of N¹-(4-Methoxybenzoyl)-N²-[1-(4-pyridyl)piperidin-4-ylaminocarbonyl]-1,2-benzenediamine

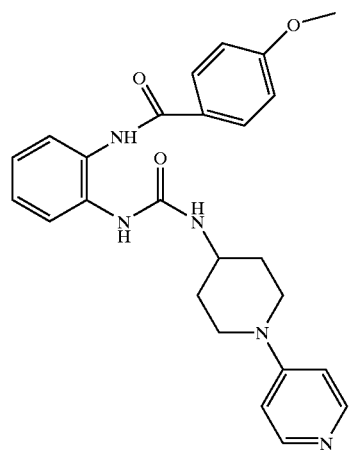

Using a similar procedure to that described in Example 48, Part C, N¹-[1-(4-pyridyl)piperidin-4-ylaminocarbonyl]-1,2-benzenediamine (82 mg, 0.26 mmol) yielded 45 mg (38%) of the title compound.
$^1$H-NMR MS-FD m/e 446 (p+1) Analysis C$_{25}$H$_{27}$N$_5$O$_3$: Calc: C, 67.40; H, 6.11; N, 15.72; Found: C, 67.30; H, 6.07; N, 15.42.

EXAMPLE 223

Preparation of 2-(4-Methoxybenzoyl)amino-N-[1-(4-pyridyl)piperidin-4-ylmethyl]beznzeneacetamide

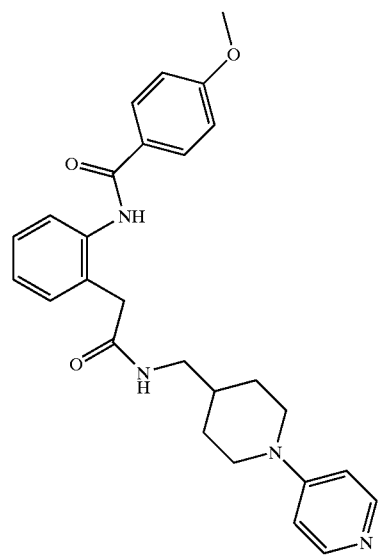

A. 2-Amino-N-[1-(4-pyridyl)piperidin-4-ylmethyl]-benzeneacetamide

A solution of 1-(4-pyridyl)piperidine-4-methylamine (156 mg, 0.817 mmol), 2-nitrophenylacetic acid (159 mg, 0.875 mmol), and 1-[3-(dimethylaminopropyl]-3-ethylcarbodiimide hydrochloride (168 mg, 0.875 mmol) in DMF was stirred 16 h; and the mixture was poured into EtOAc and H₂O. The aqueous layer was washed with EtOAc (2×) and the combined extracts were dried (K₂CO₃) and concentrated. The under an atmosphere of hydrogen gas. After 2.5 h, the mixture was filtered and the filtrate concentrated. The residue was dissolved in 5% HOAc in MeOH and loaded onto a SCX Column (Varian). The column was eluted with MeOH followed by 2 M NH₃ in MeOH. The latter fractions were concentrated yielding 158.6 mg (60%) of the title compound.

¹H-NMR, IR MS-FD m/e 324 (p)

B. 2-(4-Methoxybenzoyl)amino-N-[1-(4-pyridyl)piperidin-4-ylmethyl]benzeneacetamide.

Using a similar procedure to that described in Example 48, Part C, 2-amino-N-[1-(4-pyridyl)piperidin-4-ylmethyl]benzeneacetamide (60 mg, 0.19 mmol) yielded 26 mg (31%) of the title compound.

¹H-NMR MS-FD m/e 446 (p+1) Analysis for C₂₇H₃₀N₄O₃: Calc: C, 70.72; H, 6.59; N, 12.22; Found: C, 70.66; H, 6.79; N, 11.99.

EXAMPLE 224

Preparation of 2-(4-Chlorobenzoyl)amino-N-[1-(4-pyridyl)piperidin-4-ylmethyl]benzeneacetamide

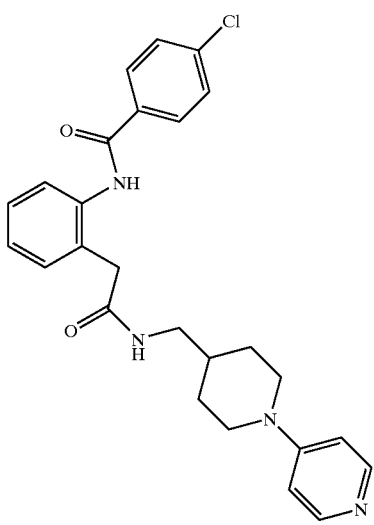

Using a similar procedure to that described in Example 48, Part C, 2-amino-N-[1-(4-pyridyl)piperidin-4-ylmethyl]benzeneacetamide (60 mg, 0.19 mmol) yielded 51 mg (60%) of the title compound.

¹H-NMR MS-FD m/e 446 (p+1) Analysis for C₂₆H₂₇ClN₄O₂: Calc: C, 67.45; H, 5.88; N, 12.10; Found: C, 67.53; H, 5.99; N, 11.70.

EXAMPLE 225

Preparation of 2-(4-Chlorophenylaminocarboyl)-N-[1-(4-pyridyl)piperidin-4-ylmethyl]benzeneacetamide

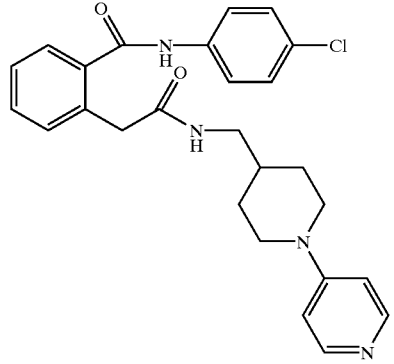

A. 2-(4-chlorophenylaminocarbonyl)phenyl acetic acid in 250 mL of homophthalic anhydride (4.0 g, 24.7 mmol) and 1 N NaOH. The aqueous layer was washed with EtOAc, then brought to a pH of 2–3 by addition of 1 N HCl. The aqueous layer was washed with EtOAc (2×), and the combined extracts were dried (MgSO₄) and concentrated. Recrystallization of the residue from EtOAc/hexanes yielded 3.41 g (48%) of the title compound.

¹H-NMR, IR MS-FD m/e 290 (p+1) Analysis for C₁₅H₁₂ClNO₃: Calc: C, 62.19; H, 4.17; N, 4.84; Found: C, 62.03; H, 4.26; N, 4.83.

B. 2-(4-Chlorophenylaminocarbonyl)-N-[1-(4-pyridyl)piperidin-4-ylmethyl]benzeneacetamide.

Using a similar procedure to that described in Example 223, Part A, 2-(4-chlorophenylaminocarbonyl)phenyl acetic acid (362 mg, 1.25 mmol) yielded 122.1 mg (22%) of the title compound.

¹H-NMR, IR MS-FD m/e 290 (p+1) Analysis for C₂₆H₃₁ClN₄O₂: Calc: C, 67.45; H, 5.88; N, 12.10; Found: C, 67.47; H, 5.74; N, 12.06.

EXAMPLE 226

Preparation of 5-Chloro-2[(1-isopropyl-3,4-didehydropiperidin-4-ylcarbonyl)amino]-N-(2-pyridinyl)benzamide hydrochloride

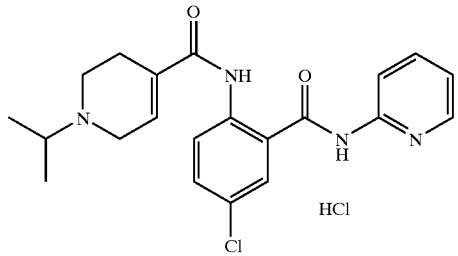

A. 5-Chloro-2-nitro-N-(2-pyridyl)benzamide

To a stirring solution of 5-chloro-2-nitrobenzoic acid (15 g, 74 mmol) in dichloromethane (300 mL) was added DMF (a few drops) followed by oxalyl chloride (11.3 g, 89 mmol). After stirring for 2 h, the solvent was removed in vacuo and the residue was redissolved in dichloromethane (300 mL). To this stirring solution was added pyridine (17.5 g, 222 mmol), followed by 2-aminopyridine (7 g, 74 mmol). After 24 h, the solvent was removed in vacuo and the residue was partitioned between ethyl acetate and water. The organic phase was separated and washed twice with 1 M citric acid, once with brine, twice with satd aq $NaHCO_3$, and once with brine. The organic phase was then dried ($MgSO_4$), filtered and concentrated in vacuo to a volume of about 25 mL, then diluted with diethyl ether, and sonicated. The resulting precipitate was filtered and dried in vacuo to give 8.63 g (42%) of an off-white solid.

$^1$H-NMR MS-FIA, m/e 278.0 (MH+) Analysis for $C_{12}H_8ClN_3O_3$: Calc: C, 51.91; H, 2.90; N, 15.13; Found: C, 52.53; H, 2.85; N, 15.05.

B. 2-Amino-5-chloro-N-(2-pyridyl)benzamide

To a solution of 5-chloro-2-nitro-N-(2-pyridyl)benzamide (4 g, 14.4 mmol) in THF (50 mL) and ethyl acetate (50 mL) was added Raney nickel (0.5 g). The mixture was placed under an atmosphere of hydrogen (4.1 bar) overnight. The mixture was then filtered and the filtrate was flushed through a pad of silica gel, eluting with ethyl acetate, and then concentrated in vacuo. The crude solid was suspended in diethyl ether, sonicated, filtered and dried in vacuo to give 2.4 g (67%) of a faint green solid.

$^1$H-NMR MS-FIA, m/e 248.3 (MH+) Analysis for $C_{12}H_{10}ClN_3O$: Calc: C, 58.18; H, 4.07; N, 16.96; Found: C, 58.39; H, 4.07; N, 17.08.

C. 1-Boc-4-trifluoromethylsulfonyloxy-3,4-didehydropiperidine

To a stirring solution of diisopropylamine (38.7 mL, 275 mmol) in THF (900 mL) at 0° C. was added dropwise via an addition funnel a solution of n-BuLi in hexanes (1.6 MN 171.5 mL, 276 mmol). After 25 min, the solution was cooled to −78° C. To this solution was added dropwise via an addition funnel a solution of 1-Boc-4-piperidinone (50 g, 250.9 mmol) in THF (300 mL). After 30 min, a solution of N-phenyltrifluoromethanesulfonamide (95.9 g, 268.5 mmol) in THF (300 mL) was added and the solution was warmed to 0° C. After 3 h, the solvents were evaporated in vacuo and the residue was loaded into a silica gel column with a minimal amount of dichloromethane and eluted with 5% ethyl acetate/hexanes. The product containing fractions were combined and concentrated in vacuo to give 74.84 g (90%) of a light yellow oil.

$^1$H-NMR

D. 1-Boc-4-methoxycarbonyl-3,4-didehydropiperidine

To a stirring solution of 1-Boc-4-trifluoromethylsulfonyloxy-3,4-didehydropiperidine (74.8 g, 226 mmol) in acetonitrile (900 mL) was added triethylamine (63 mL, 452 mmol), palladium(II)acetate (1.53 g, 6.8 mmol), triphenylphosphine (3.57 g, 13.6 mmol) and methanol (366 mL). Carbon monoxide gas was bubbled through the solution for 15 min and then the system was placed under an atmosphere of carbon monoxide and stirred for an additional 48 h. The solvent was then removed in vacuo and the residue was chromatographed over silica gel, eluting with ethyl acetate. The product containing fractions were combined and concentrated in vacuo to give 50.04 g (92%) of a yellow oil.

$^1$H-NMR MS-FD, m/e 240.2 (M+) Analysis for $C_{12}H_{19}NO_4$: Calc: C, 59.74; H, 7.94; N, 5.81; Found: C, 59.60; H, 8.07; N, 5.85.

E. 1-Boc-4-carboxy-3,4-didehydropiperidine

To a stirring solution of 1-Boc-4-methoxycarbonyl-3,4-didehydropiperidine (28.81 g, 119 mmol) in methanol (300 mL) was added 1 N aqueous sodium hydroxide (300 mL). After stirring overnight, the solvent was removed by rotary evaporation and the residue was partitioned between water and diethyl ether. The aqueous phase was separated and washed with diethyl ether, acidified to pH 2.5 with conc. HCl, then extracted with diethyl ether. The organic extract was then washed with brine, dried with $MgSO_4$, filtered and concentrated in vacuo to give 25.16 g (93%) of a light yellow solid.

$^1$H-NMR MS-IS, m/e 226.1 (M−) Analysis for $C_{11}H_{17}NO_4$: Calc: C, 58.14; H, 7.54; N, 6.16; Found: C, 57.41; H, 7.48; N, 6.19.

F. 5-Chloro-2-[1-Boc-3,4-didehydropiperidin-4-ylcarbonyl]amino-N-(2-pyridinyl)benzamide To a stirring solution of 1-Boc-4-carboxy-3,4-didehydropiperidine (5 g, 22 mmol) in THF (100 mL) was added NaOEt (1.5 g, 22 mmol). After 30 min, the solvent was removed in vacuo and the residue was suspended in dichloromethane 40 mL). To this stirring suspension was added DMF (a few drops), followed by oxalyl chloride (2.1 mL, 24.2 mmol). After 1 h, the solvent was removed in vacuo and the residue was dissolved in dichloromethane (22 mL). A portion of this solution (4 mL) was then taken via syringe and added to a stirring solution of 2-amino-5-chloro-N-(2-pyridyl)benzamide (495 mg, 2 mmol) in pyridine (3 mL). After stirring overnight, the solvents were removed in vacuo and the residue was partitioned between ethyl acetate and water. The organic phase was separated and washed twice with 1 M citric acid, once with brine, twice with satd aq sodium bicarbonate and twice with brine. The organic phase was then dried with $MgSO_4$, filtered, concentrated in vacuo and chromatographed over silica gel, eluting with a step gradient of dichloromethane through 20% ethyl acetate/dichloromethane. The product containing fractions were combined and concentrated in vacuo to give 390 mg (43%) of a white solid.

$^1$H-NMR MS-FIA, m/e 457.4 (MH+) Analysis for $C_{23}H_{25}ClN_4O_4$: Calc: C, 60.46; H, 5.51; N, 12.26; Found: C, 60.27; H, 5.51; N, 12.26.

G. 5-Chloro-2-[3,4-didehydropiperidin-4-ylcarbonyl]amino-N-(2-pyridinyl)benzamide bis(trifluoroacetate)

To a stirring solution of 5-chloro-2-[1-Boc-3,4-didehydropiperidin-4-ylcarbonyl]amino-N-(2-pyridinyl)benzamide (330 mg, 0.72 mmol) in dichloromethane (25 mL) was added anisole (1 mL), followed by TFA (25 mL). After 1 h, the solvent was evaporated in vacuo and the residue was suspended in diethyl ether, sonicated, filtered and dried in vacuo to give 300 mg (88%) of an off-white solid.

$^1$H-NMR MS-FIA, m/e 357.3 (MH+) Analysis for $C_{18}H_{17}ClN_4O_2 \cdot 2.2TFA$: Calc: C, 44.27; H, 3.18; N, 9.22; Found: C, 44.03; H, 3.18; N, 9.47.

H. 5-Chloro-2-[1-isopropyl-3,4-didehydropiperidin-4-ylcarbonyl]amino-N-(2-pyridinyl)benzamide hydrochloride To a stirring suspension of 5-chloro-2-[3,4-didehydropiperidin-4-ylcarbonyl]amino-N-(2-pyridinyl)benzamide bis(trifluoroacetate) (275 mg, 0.58 mmol) in 1,2-dichloroethane (8 mL) was added acetone (8 mL), followed by acetic acid (0.14 mL, 2.34 mmol) and sodium triacetoxyborohydride (0.5 g, 2.34 mmol). After stirring for 17 h, the mixture was loaded onto an SCX column, washed with methanol, and then eluted with 2 M ammonia in methanol. The product containing fractions were combined and concentrated in vacuo, and the residue was purified by RPHPLC method A to give 180 mg (70%) of white solid.

$^1$H-NMR MS-FIA, m/e 399.2 (MH+) Analysis for $C_{21}H_{23}ClN_4O_2 \cdot 1.3HCl \cdot 0.5H_2O$: Calc: C, 55.40; H, 5.60; N, 12.31; Cl, 17.91; Found: C, 55.28; H, 5.57; N, 12.11; Cl, 17.93.

What is claimed is:
1. A novel compound of formula I

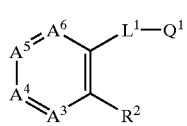

wherein
$A^3$, $A^4$, $A^5$ and $A^6$, together with the two carbons to which they are attached, complete a substituted benzene in which $A^3$ is $CR^3$, $A^4$ is $CR^4$, $A^5$ is $CR^5$, and $A^6$ is $CR^6$;

wherein
$R^3$ is hydrogen, hydroxy, [(1–2C)alkyl]carbonyloxy (which may bear an ω-carboxy substituent), benzoyloxy (which may bear one or more halo, hydroxy, methoxy or methyl substituents), methyl or methoxy;
one of $R^4$ and $R^5$ is hydrogen, methyl, halo, trifluoromethyl, nitro, amino(imino)methyl, amino(hydroxyimino)methyl, $R^fO$—, $R^fO_2C$—, $R^fO_2C$—$CH_2$—, $R^fO_2C$—$CH_2$—O—, 3-methoxycarbonyl-1-oxopropyl, $R^gNH$— or bis(methylsulfonyl)amino;
the other of $R^4$ and $R^5$ is hydrogen, halo or methyl; and
$R^6$ is hydrogen, fluoro, hydroxy, [(1–2C)alkyl]-carbonyloxy (which may bear an ω-carboxy substituent), benzoyloxy (which may bear one or more halo, hydroxy, methoxy or methyl substituents), methyl or methoxy;
in which $R^f$ is hydrogen, (1–4C)alkyl or benzyl; $R^g$ is hydrogen, [(1–4C)alkyl]carbonyl, acetyl, trifluoroacetyl, methoxyacetyl, dimethylaminoacetyl, phenylalanyl, 2-(t-butoxycarbonylamino)-4-methylsulfinyl-1-oxobutyl, 3-[[(1–2C)alkoxy]carbonyl]-1-oxopropyl or $R^hSO_h$— (wherein h is 1 or 2); and $R^h$ is (1–4C)alkyl, trifluoromethyl, phenyl, 3,5-dimethylisoxazol-4-yl or dimethylamino; or
two adjacent residues selected from $R^3$, $R^4$ $R^5$ and $R^6$ together form a benz ring; and the other two are each hydrogen;
$L^1$ is —NH—CO—, —O—CO— or —CO—NH— such that —$L^1$—$Q^1$ is —NH—CO—$Q^1$—O—CO—$Q^1$ or —CO—NH—$Q^1$;
$Q^1$ is 2-furanyl, 4-thiazolyl, 2-pyridyl, 2-naphthyl, 1,2-dihydrobenzofuran-5-yl, 1,2-dihydrobenzofuran-6-yl or 1,2-benzisoxazol-6-yl in which the 2-furanyl may bear a chloro or methyl substituent at the 5-position, the 4-thiazolyl may bear an amino substituent at the 2-position, the 2-pyridyl may bear an amino substituent at the 6-position, and the 1,2-benzisoxazol-6-yl may bear a chloro or methyl substituent at the 3-position;
$R^2$ is —$L^{2A}$—$Q^{2A}$, —$L^{2B}$—$Q^{2B}$, —$L^{2C}$—$Q^{2C}$, —$L^{2D}$—$Q^{2D}$ or —$L^{2E}$—$Q^{2E}$ wherein $L^{2A}$ is a direct bond; and
$Q^{2A}$ is

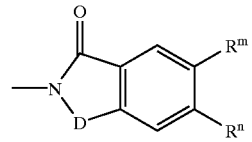

in which D is carbonyl or —$CHR^k$— in which $R^k$ is hydrogen, hydroxy, (1–6C)alkoxy, or —$CH_2$—$R^j$ in which $R^j$ is carboxy, [(1–4C)alkoxy]carbonyl or carbamoyl which may bear one or two (1–2C)alkyl substituents on the nitrogen; and one of $R^m$ and $R^n$ is hydrogen and the other is amino, bromo, (1–4C)alkyl or (1–4C)alkoxy, or $R^m$ and $R^n$ together form a benz ring;
$L^{2B}$ is —NH—CO—, —O—CO—, —$CH_2$—O— or —O—$CH_2$— such that —$L^{2B}$—$Q^{2B}$ is —NH—CO—$Q^{2B}$, —O—CO—$Q^{2B}$, —$CH_2$—O—$Q^{2B}$ or —O—$CH_2$—$Q^{2B}$; and
$Q^{2B}$ is

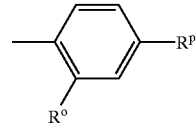

in which $R^o$ is hydrogen, halo, (1–6C)alkyl, (1–4C)alkoxy, benzyloxy or (1–4C)alkylthio; and $R^p$ is 1-hydroxyethyl, 1-hydroxy-1-methylethyl, 1-methoxy-1-methylethyl, 4-piperidinyl, 4-pyridinyl, dimethylaminosulfonyl or —J—$R^q$ in which J is a single bond, methylene, carbonyl, oxo, —$S(O)_q$— (wherein q is 0, 1 or 2), or —$NR^r$— (wherein $R^r$ is hydrogen or methyl); and $R^q$ is (1–6C)alkyl, phenyl, 3-pyridyl or 4-pyridyl;
$L^{2C}$ is —$NR^v$—CO—X—, —$NR^v$—CS—Y—, —$CH_2$—CO—$NR^w$—$CH_2$—, —O—CO—, —O—$CH_2$—, —S—$CH_2$— or —$CH_2$—$NR^x$—$CH_2$— such that —$L^{2C}$—$Q^{2C}$ is —$NR^v$—CO—X—$Q^{2C}$, —$NR^v$—CS—Y—$Q^{2C}$, —$CH_2$—CO—$NR^w$—$CH_2$—$Q^{2C}$, —O—CO—$Q^{2C}$, —O—$CH_2$—$Q^{2C}$, —S—$CH_2$—$Q^{2C}$ or —$CH_2$—$NR^x$—$CH_2Q^{2C}$ in which X is —$(CH_2)_x$— (wherein x is 0, 1 or 2), —$NR^w$—, —$NR^w$—$CH_2$, —O—, —O—$CH_2$— or —S—$CH_2$—; Y is —$NR^w$—$CH_2$— or —O—$CH_2$—; each of $R^v$ and $R^w$ is independently hydrogen, benzyl or (1–6C)alkyl which is not branched at the α-position; and $R^x$ is hydrogen, benzyloxycarbonyl or [(1–4C)alkoxy]carbonyl; and
$Q^{2C}$ is 1-(4-pyridyl)piperidin-4-yl, 1-(4-pyridyl) piperidin-3-yl or 1-(4-pyridyl)pyrrolidin-3-yl in which the pyridyl may bear a substituent at its 2-position selected from cyano, aminomethyl, carboxy, hydroxymethyl and (1–2C)alkyl;
$L^{2D}$ is —NH—CO— such that —$L^{2D}$—$Q^{2D}$ is —NH—CO—$Q^{2D}$; and
$Q^{2D}$ is selected from 4-(4-pyridinyl)benzyloxy, 9-oxo-9H-fluoren-3-yl, benzo[b]thiophen-2-yl (which may bear a chloro, methyl or methoxy substituent), benzofuran-2-yl (which may bear a chloro, methyl or methoxy substituent), 4-(4-morpholinyl)-4-oxobutyl, and 4-piperidinyl or 3,4-didehydropiperidin-4-yl (either one bearing a substituent at the 1-position selected from methylsulfonyl, phenylsulfonyl, (1–5C)alkyl, (4–7C)cycloalkyl, tetrahydropyran-4-yl, 4-thiacyclohexyl and —CH$_2$—R$^z$ in which R$^z$ is isopropyl, cyclopropyl, phenyl, pentafluorophenyl, furyl, thienyl, 2-thiazolyl, or pyridyl in which the phenyl may bear one or two substituents independently selected from halo, cyano, hydroxy, methoxy, acetoxy, benzyloxy, amino, acetylamino, nitro and 3,4-methylenedioxy, and the thienyl or furyl may bear a methyl or nitro substituent);

L$^{2E}$ is —NH—CO—O—(CH$_2$)$_n$— (wherein n is 0, 1 or 2) or —NH—CO—O—(CH$_2$)$_2$—O— such that —L$^{2E}$—Q$^{2E}$ is —NH—CO—O—(CH$_2$)$_n$—Q$^{2E}$ or —NH—CO—O—(CH$_2$)$_2$—O—Q$^{2E}$; and Q$^{2E}$ is 4-piperidinyl or 1-benzylpiperidin-4-yl;

or a prodrug of the compound of formula I;

or a pharmaceutically acceptable salt of the compound of formula I or prodrug thereof;

and provided that when L$^1$ is —CO—NH— such that —L$^1$—Q$^1$ is —CO—NH—Q$^1$ and Q$^1$ is 2-pyridyl which may bear an amino substituent at the 6-position, then Q$^{2D}$ is other than benzo[b]thiophen-2-yl (which may bear a chloro, methyl or methoxy substituent).

2. A method of inhibiting factor Xa in a mammal comprising administering to a mammal in need thereof a factor Xa inhibiting amount of a compound of formula I

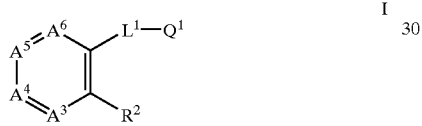

as claimed in claim 1.

3. The novel compound of formula I of claim 1 wherein

A$^3$, A$^4$, A$^5$ and A$^6$, together with the two carbons to which they are attached, complete a substituted benzene in which A$^3$ is CR$^3$, A$^4$ is CR$^4$, A$^5$ is CR$^5$, and A$^6$ is CR$^6$;

wherein

R$^3$ is hydrogen, hydroxy, [(1–2C)alkyl]carbonyloxy (which may bear an ω-carboxy substituent), benzoyloxy (which may bear one or more halo, hydroxy, methoxy or methyl substituents), methyl or methoxy;

one of R$^4$ and R$^5$ is hydrogen, methyl, halo, trifluoromethyl, nitro, amino(imino)methyl, amino(hydroxyimino)methyl, R$^f$O—, R$^f$O$_2$C—, R$^f$O$_2$C—CH$_2$—, R$^f$O$_2$C—CH$_2$—O—, 3-methoxycarbonyl-1-oxopropyl, R$^g$NH— or bis(methylsulfonyl)amino;

the other of R$^4$ and R$^5$ is hydrogen, halo or methyl; and

R$^6$ is hydrogen, hydroxy, [(1–2C)alkyl]carbonyloxy (which may bear an ω-carboxy substituent), benzoyloxy (which may bear one or more halo, hydroxy, methoxy or methyl substituents), methyl or methoxy;

in which R$^f$ is hydrogen, (1–4C)alkyl or benzyl;

R$^g$ is hydrogen, acetyl, trifluoroacetyl, phenylalanyl, 2-(t-butoxycarbonylamino)-4-methylsulfinyl-1-oxobutyl, 3-[[(1–2C)alkoxy]carbonyl]-1-oxopropyl or R$^h$SO$_2$—; and R$^h$ is (1–4C)alkyl, trifluoromethyl, phenyl, 3,5-dimethylisoxazol-4-yl or dimethylamino; or two adjacent residues selected from R$^3$, R$^4$, R$^5$ and R$^6$ together form a benz ring; and the other two are each hydrogen;

L$^1$ is —NH—CO—, —O—CO— or —CO—NH— such that —L$^1$—Q$^1$ is —NH—CO—Q$^1$, —O—CO—Q$^1$ or —CO—NH—Q$^1$;

Q$^1$ is 4-thiazolyl, 2-pyridyl, 2-naphthyl or 1,2-benzisoxazol-6-yl in which the 4-thiazolyl may bear an amino substituent at the 2-position, the 2-pyridyl may bear an amino substituent at the 6-position, and the 1,2-benzisoxazol-6-yl may bear a chloro or methyl substituent at the 3-position;

R$^2$ is —L$^{2A}$—Q$^{2A}$, L$^{2B}$—Q$^{2B}$, L$^{2C}$—Q$^{2C}$, —L$^{2D}$—Q$^{2D}$ or —L$^{2E}$—Q$^{2E}$ wherein L$^{2A}$ is a direct bond; and Q$^{2A}$ is

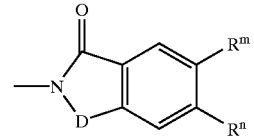

in which D is carbonyl or —CHR$^k$— in which R$^k$ is hydrogen, hydroxy, (1–6C)alkoxy or —CH$_2$—R$^j$ in which R$^j$ is carboxy, [(1–4C)alkoxy]carbonyl or carbamoyl which may bear one or two (1–2C)alkyl substituents on the nitrogen; and one of R$^m$ and R$^n$ is hydrogen and the other is amino, bromo, (1–4C)alkyl or (1–4C)alkoxy, or R$^m$ and R$^n$ together form a benz ring;

L$^{2B}$ is —NH—CO—, —O—CO—, —CH$_2$—O— or —O—CH$_2$— such that —L$^{2B}$—Q$^{2B}$ is —NH—CO—Q$^{2B}$, —O—CO—Q$^{2B}$, —CH$_2$—O—Q$^{2B}$ or —O—CH$_2$—Q$^{2B}$; and Q$^{2B}$ is

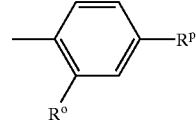

in which R$^o$ is hydrogen, halo, (1–6C)alkyl, (1–4C)alkoxy, benzyloxy or (1–4C)alkylthio; and R$^p$ is 1-hydroxyethyl, 1-hydroxy-1-methylethyl, 1-methoxy-1-methylethyl, 4-piperidinyl, 4-pyridinyl, dimethylaminosulfonyl or —J—R$^q$ in which J is a single bond, methylene, carbonyl, oxo, —S(O)$_q$— (wherein q is 0, 1 or 2), or —NR$^r$— (wherein R$^r$ is hydrogen or methyl); and R$^q$ is (1–6C)alkyl, phenyl, 3-pyridyl or 4-pyridyl;

L$^{2C}$ is —NR$^v$—CO—X—, —NR$^v$—CS—Y—, —CH$_2$—CO—NR$^w$—CH$_2$—, —O—CO—, —O—CH$_2$—, —S—CH$_2$— or —CH$_2$—NR$^x$—CH$_2$—, such that —L$^{2C}$—Q$^{2C}$ is —NR$^v$—CO—X—Q$^{2C}$, —NR$^v$—CS—Y—Q$^{2C}$, —CH$_2$—CO—NR$^w$—CH$_2$—Q$^{2C}$, —O—CO—Q$^{2C}$, —O—CH$_2$—Q$^{2C}$, —S—CH$_2$—Q$^{2C}$ or —CH$_2$—NR$^x$—CH$_2$—Q$^{2C}$ in which X is —(CH$_2$)$_x$— (wherein x is 0, 1 or 2), —NR$^w$—CH$_2$—, —O—CH$_2$— or —S—CH$_2$—; Y is —NR$^w$—CH$_2$— or —O—CH$_2$—;

each of R$^v$ and R$^w$ is independently hydrogen, benzyl or (1–6C)alkyl which is not branched at the α-position; and R$^x$ is hydrogen, benzyloxycarbonyl or [(1–4C)alkoxy]carbonyl; and Q$^{2C}$ is 1-(4-pyridyl)piperidin-4-yl in which the pyridyl may bear a substituent at its 2-position selected from cyano, aminomethyl, carboxy, hydroxymethyl and (1–2C)alkyl;

$L^{2D}$ is —NH—CO— such that —$L^{2D}$—$Q^{2D}$ is —NH—CO—$Q^{2D}$; and $Q^{2D}$ is selected from 4-(4-pyridinyl)benzyloxy, 9-oxo-9H-fluoren-3-yl, benzo[b]thiophen-2-yl (which may bear a chloro, methyl or methoxy substituent), benzofuran-2-yl (which may bear a chloro, methyl or methoxy substituent), 4-(4-morpholinyl)-4-oxobutyl, and 4-piperidinyl bearing a substituent at the 1-position selected from methylsulfonyl, phenylsulfonyl and —CH$_2$—R$^z$ in which R$^z$ is isopropyl, cyclopropyl, phenyl, pentafluorophenyl, furyl, thienyl, 2-thiazolyl, or pyridyl in which the phenyl may bear one or two substituents independently selected from halo, cyano, hydroxy, methoxy, acetoxy, benzyloxy, amino, acetylamino, nitro and 3,4-methylenedioxy, and the thienyl or furyl may bear a methyl or nitro substituent;

$L^{2E}$ is —NH—CO—O—(CH$_2$)$_n$— (wherein n is 0, 1 or 2) or —NH—CO—O—(CH$_2$)$_2$—O— such that —$L^{2E}$—$Q^{2E}$ is —NH—CO—O—(CH$_2$)$_n$—$Q^{2E}$ or —NH—CO—O—(CH$_2$)$_2$—O—$Q^{2E}$; and $Q^{2E}$ is 4-piperidinyl or 1-benzylpiperidin-4-yl;

or a prodrug of the compound of formula I;

or a pharmaceutically acceptable salt of the compound of formula I or prodrug thereof.

4. The compound of claim 1 wherein the compound of formula I is one in which each of A$^3$, A$^5$ and A$^6$ is CH.

5. The compound of claim 1 wherein R$^2$ is (4-t-butylbenzoyl) amino, (4-methoxybenzoyl) amino, or ]1-(4-pyridyl) piperidin-4-yl]methoxycarbonylamino.

6. A pharmaceutical composition comprising a compound of formula I, or prodrug or pharmaceutically acceptable salt thereof, as claimed in claim 1 in association with a pharmaceutically acceptable carrier, excipient or diluent.

7. A process for preparing a compound of formula I (or a pharmaceutically acceptable salt thereof) as provided in claim 1 which is selected from (A) for a compound of formula I in which the linkage of R$^2$ to the ring terminates in —NH—CO—, —NR$^v$—CO— or —NR$^v$—CS—, acylating an amine of formula II,

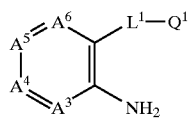

II or a corresponding amine in which the nitrogen bears the group R$^v$, using a corresponding acid which terminates with the group HO—CO— or HO—CS—, or an activated derivative thereof;

(B) for a compound of formula I in which —L$^1$—Q$^1$ is —NH—CO—Q$^1$, acylating an amine of formula III

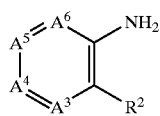

III using an acid of formula HO—CO—Q$^1$, or an activated derivative thereof;

(C) for a compound of formula I in which —L$^1$—Q$^1$ is —CO—NH—Q$^1$ and R$^2$ is of the form —NH—CO—Q$^2$, acylating an amine of formula H$_2$N—Q$^1$ using a [1,3]oxazine of formula IV,

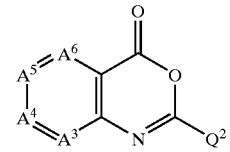

IV wherein Q$^2$ represents Q$^2$B, Q$^2$C or Q$^2$D;

(D) for a compound of formula I in which R$^2$ is —L$^{2A}$—Q$^{2A}$ and D is carbonyl, diacylating a compound of formula II using an anhydride of formula V;

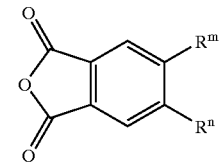

V (E) for a compound of formula I in which R$^2$ is —O—CO—Q$^{2B}$, acylating an alcohol of formula VI

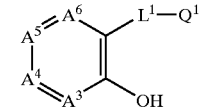

VI using an acid of formula HO—CO—Q$^{2B}$, or an activated derivative thereof;

(F) for a compound of formula I in which R$^4$ or R$^5$ is amino, reducing the nitro group of a corresponding compound of formula I in which R$^4$ or R$^5$ is nitro; and (G) for a compound of formula I in which R$^4$ or R$^5$ is R$^g$NH— and R$^g$ is R$^h$SO$_2$—, substituting the amino group of a corresponding compound of formula I in which R$^4$ or R$^5$ is amino using an activated derivative of the sulfonic acid R$^h$SO$_2$—OH;

whereafter, for any of the above procedures, when a functional group is protected using a protecting group, removing the protecting group; and whereafter, for any of the above procedures, when a pharmaceutically acceptable salt of a compound of formula I is required, it is obtained by reacting the basic form of a basic compound of formula I with an acid affording a physiologically acceptable counterion or the acidic form of an acidic compound of formula I with a base affording a physiologically acceptable counterion or by any other conventional procedure; and wherein, unless otherwise specified, L$^1$, Q$^1$, R$^2$, R$^m$, R$^n$, A$^3$, A$^4$, A$^5$ and A$^6$ have any of the values defined in claim 1.

8. The compound of claim 3 wherein the compound of formula I is one in which each of A$^3$, A$^5$ and A$^6$ is CH.

9. The compound of claim 3 wherein R$^2$ is (4-t-butylbenzoyl) amino, (4-methoxybenzoyl) amino, or [1-(4-pyridyl)piperidin-4-yl]methoxycarbonylamino.

10. The compound of claim 4 wherein R$^2$ is (4-t-butylbenzoyl) amino, (4-methoxybenzoyl) amino, or [1-(4-pyridyl)piperidin-4-yl]methoxycarbonylamino.

11. The compound of claim 8 wherein R² is (4-t-butylbenzoyl) amino, (4-methoxybenzoyl) amino, or [1-(4-pyridyl)piperidin-4-yl]methoxycarbonylamino.

12. The compound of any one of claims 1, 3, 4, 5, 8, 9, 10, or 11 wherein L¹—Q¹ is —NH—CO—Q¹.

13. The compound of any one of claims 1, 3, 4, 5, 8, 9, 10, or 11 wherein L¹—Q¹ is —CO—NH—Q¹.

14. The compound of claim 12 wherein for an alkyl group or the alkyl portion of an alkyl containing group, (1–2C) alkyl is methyl or ethyl;

(1–4C)alkyl is methyl, ethyl, propyl, isopropyl, butyl, isobutyl, or t-butyl;

(1–6C)alkyl is methyl, ethyl, propyl, butyl, pentyl or hexyl, and halo is bromo or chloro.

15. The compound of claim 14 wherein for an alkyl group or the alkyl portion of an alkyl containing group, (–2C)alkyl is methyl or ethyl;

(1–4C)alkyl is methyl, isopropyl, butyl or t-butyl;

(1–6C)alkyl is methyl, butyl, or hexyl, and halo is chloro.

16. The compound of claim 13 wherein for an alkyl group or the alkyl portion of an alkyl containing group, (1–2C) alkyl is methyl or ethyl;

(1–4C)alkyl is methyl, ethyl, propyl, isopropyl, butyl, isobutyl, or t-butyl; (1–6C)alkyl is methyl, ethyl, propyl, butyl, pentyl or hexyl, and halo is bromo or chloro.

17. The compound of claim, 16 wherein for an alkyl group or the alkyl portion of an alkyl containing group, (1–2C) alkyl is methyl or ethyl;

(1–4C)alkyl is methyl, isopropyl, butyl or t-butyl;

(1–6C)alkyl is methyl, butyl, or hexyl, and halo is chloro.

* * * * *